US011459340B2

(12) United States Patent
Fu et al.

(10) Patent No.: US 11,459,340 B2
(45) Date of Patent: Oct. 4, 2022

(54) TRI-SUBSTITUTED HETEROARYL DERIVATIVES AS SRC HOMOLOGY-2 PHOSPHATASE INHIBITORS

(71) Applicant: Nikang Therapeutics, Inc., Wilmington, DE (US)

(72) Inventors: Jiping Fu, Wilmington, DE (US); Yan Lou, Wilmington, DE (US); Yigang He, Wilmington, DE (US)

(73) Assignee: NIKANG THERAPEUTICS, INC., Wilmington, DE (US)

( * ) Notice: Subject to any disclaimer, the term of this patent is extended or adjusted under 35 U.S.C. 154(b) by 0 days.

(21) Appl. No.: 17/277,293

(22) PCT Filed: Sep. 17, 2019

(86) PCT No.: PCT/US2019/051590
§ 371 (c)(1),
(2) Date: Mar. 18, 2021

(87) PCT Pub. No.: WO2020/061101
PCT Pub. Date: Mar. 26, 2020

(65) Prior Publication Data
US 2021/0380604 A1    Dec. 9, 2021

Related U.S. Application Data

(60) Provisional application No. 62/733,061, filed on Sep. 18, 2018, provisional application No. 62/749,655, filed on Oct. 23, 2018, provisional application No. 62/810,911, filed on Feb. 26, 2019, provisional application No. 62/883,120, filed on Aug. 6, 2019, provisional application No. 62/883,121, filed on Aug. 6, 2019.

(51) Int. Cl.
| | | |
|---|---|---|
| *C07D 498/14* | (2006.01) | |
| *A61K 31/5383* | (2006.01) | |
| *C07D 519/00* | (2006.01) | |
| *A61P 35/00* | (2006.01) | |
| *C07D 401/14* | (2006.01) | |
| *C07D 471/10* | (2006.01) | |
| *C07D 491/107* | (2006.01) | |

(52) U.S. Cl.
CPC ........ *C07D 519/00* (2013.01); *A61K 31/5383* (2013.01); *A61P 35/00* (2018.01); *C07D 401/14* (2013.01); *C07D 471/10* (2013.01); *C07D 491/107* (2013.01)

(58) Field of Classification Search
CPC ............... C07D 498/14; C07D 401/14; A61K 31/5383; A61K 31/497; A61P 35/00
USPC .................. 544/101, 405; 514/230.2, 205.05
See application file for complete search history.

(56) References Cited

U.S. PATENT DOCUMENTS

| | | |
|---|---|---|
| 4,169,846 A | 10/1979 | Inagaki et al. |
| 4,261,989 A | 4/1981 | Sasaki et al. |
| 4,775,612 A | 10/1988 | Abe et al. |
| 4,828,973 A | 5/1989 | Hirano et al. |
| 4,931,434 A | 6/1990 | Broom et al. |
| 5,266,573 A | 11/1993 | Croci et al. |
| 5,360,459 A | 11/1994 | Kolp et al. |
| 5,621,002 A | 4/1997 | Bosslet et al. |
| 5,977,134 A | 11/1999 | Ciccarone et al. |
| 6,225,052 B1 | 5/2001 | Batz et al. |
| 6,465,467 B1 | 10/2002 | Nilsson et al. |
| 6,514,964 B1 | 2/2003 | Chen et al. |
| 6,528,460 B2 | 3/2003 | Kawata et al. |
| 6,544,725 B2 | 4/2003 | Morimoto |
| 6,599,917 B1 | 7/2003 | Okada et al. |
| 6,620,946 B2 | 9/2003 | Dershem et al. |
| 6,670,377 B1 | 12/2003 | Mekouar et al. |
| 6,699,873 B1 | 3/2004 | Maguire et al. |
| 6,699,994 B1 | 3/2004 | Babu et al. |
| 6,780,996 B2 | 8/2004 | Boschelli et al. |
| 6,812,225 B2 | 11/2004 | Pierson et al. |
| 6,831,175 B2 | 12/2004 | Li et al. |
| 6,953,857 B2 | 10/2005 | Nazaré et al. |
| 6,963,001 B2 | 11/2005 | Dershem et al. |
| 7,026,314 B2 | 4/2006 | Chapdelaine et al. |
| 7,071,355 B2 | 7/2006 | Leban et al. |
| 7,125,879 B2 | 10/2006 | Arts et al. |
| 7,148,237 B2 | 12/2006 | Fuji et al. |
| 7,183,313 B2 | 2/2007 | Makriyannis et al. |
| 7,229,943 B2 | 6/2007 | Gibson et al. |

(Continued)

FOREIGN PATENT DOCUMENTS

| | | |
|---|---|---|
| CN | 108794485 A | 11/2018 |
| CN | 108863982 A | 11/2018 |

(Continued)

OTHER PUBLICATIONS

CAS No. 1029872-29-4 (updated CAS Registry No. 934660-93-2), retrieved from web on May 18, 2020, 5 pages.
CAS No. 1133385-83-7 (updated CAS Registry No. 896466-04-9), retrieved from web on May 18, 2020, 4 pages.
CAS No. 915296-00-3, retrieved from web on May 18, 2020, 6 pages.
CAS No. 934235-44-6, retrieved from web on May 18, 2020, 5 pages.
CAS No. 942487-16-3, retrieved from web on May 18, 2020, 3 pages.
International Search Report and Written Opinion received for PCT Patent International Application No. PCT/US19/51590, dated Nov. 4, 2019, 11 pages.

(Continued)

*Primary Examiner* — Charanjit Aulakh
(74) *Attorney, Agent, or Firm* — Wilson Sonsini Goodrich & Rosati

(57) ABSTRACT

The present disclosure provides certain tri-substituted heteroaryl derivatives that are Src Homology-2 phosphatase (SHP2) inhibitors and are therefore useful for the treatment of diseases treatable by inhibition of SHP2. Also provided are pharmaceutical compositions containing such compounds and processes for preparing such compounds.

8 Claims, No Drawings

(56) References Cited

U.S. PATENT DOCUMENTS

| | | |
|---|---|---|
| 7,244,739 B2 | 7/2007 | Cheng et al. |
| 7,342,004 B2 | 3/2008 | Potter et al. |
| 7,442,842 B2 | 10/2008 | Jaekel et al. |
| 7,632,865 B2 | 12/2009 | Kato et al. |
| 7,700,620 B2 | 4/2010 | Sutton et al. |
| 7,728,008 B2 | 6/2010 | Qiao et al. |
| 7,763,739 B2 | 7/2010 | Kadyrov et al. |
| 7,842,638 B2 | 11/2010 | Gibson et al. |
| 7,897,607 B2 | 3/2011 | Gyorkos et al. |
| 7,910,741 B2 | 3/2011 | Nishizawa et al. |
| 7,919,046 B2 | 4/2011 | Delapierre et al. |
| 7,956,020 B2 | 6/2011 | Negoro et al. |
| 7,989,565 B2 | 8/2011 | Gibson et al. |
| 8,039,674 B2 | 10/2011 | Habashita et al. |
| 8,067,328 B2 | 11/2011 | Gibson et al. |
| 8,143,276 B2 | 3/2012 | Yang et al. |
| 8,288,425 B2 | 10/2012 | Edwards et al. |
| 8,304,553 B2 | 11/2012 | Liu et al. |
| 8,362,181 B2 | 1/2013 | Hogan et al. |
| 8,414,983 B2 | 4/2013 | Parri et al. |
| 8,501,955 B2 | 8/2013 | Bhuniya et al. |
| 8,545,720 B2 | 10/2013 | Goetz et al. |
| 8,575,283 B1 | 11/2013 | Fang et al. |
| 8,585,925 B2 | 11/2013 | Czanta et al. |
| 8,598,164 B2 | 12/2013 | Hadida-Ruah et al. |
| 8,642,278 B2 | 2/2014 | Sebti et al. |
| 8,673,911 B2 | 3/2014 | Mallais et al. |
| 8,686,009 B2 | 4/2014 | Blumberg et al. |
| 8,710,233 B2 | 4/2014 | Lee et al. |
| 8,791,136 B2 | 7/2014 | Goff et al. |
| 8,796,280 B2 | 8/2014 | Page et al. |
| 8,815,918 B2 | 8/2014 | Fernandez et al. |
| 8,822,513 B2 | 9/2014 | Lu et al. |
| 8,859,581 B2 | 10/2014 | Heinrich et al. |
| 8,877,930 B2 | 11/2014 | Bedore et al. |
| 8,883,793 B2 | 11/2014 | Chen et al. |
| 8,907,091 B2 | 12/2014 | Raeppel et al. |
| 8,951,890 B2 | 2/2015 | Yamamoto et al. |
| 8,969,349 B2 | 3/2015 | Campbell et al. |
| 8,987,271 B2 | 3/2015 | Cardone et al. |
| 8,999,459 B2 | 4/2015 | Bernatz et al. |
| 9,005,720 B2 | 4/2015 | Goetz et al. |
| 9,012,498 B2 | 4/2015 | Manoharan et al. |
| 9,073,801 B2 | 7/2015 | Hoveyda et al. |
| 9,090,633 B2 | 7/2015 | Kasina et al. |
| 9,212,311 B2 | 12/2015 | Lee et al. |
| 9,217,050 B2 | 12/2015 | Fornof et al. |
| 9,234,136 B2 | 1/2016 | Archetti et al. |
| 9,290,528 B1 | 3/2016 | Glazer et al. |
| 9,295,754 B2 | 3/2016 | Boden et al. |
| 9,326,926 B2 | 5/2016 | Pressly et al. |
| 9,334,242 B2 | 5/2016 | Lu et al. |
| 9,340,506 B2 | 5/2016 | Bhuniya et al. |
| 9,340,528 B2 | 5/2016 | Bader et al. |
| 9,347,002 B2 | 5/2016 | Klasen-memmer et al. |
| 9,376,425 B2 | 6/2016 | Bartberger et al. |
| 9,394,290 B2 | 7/2016 | Hartmann et al. |
| 9,399,623 B2 | 7/2016 | Karra et al. |
| 9,410,105 B2 | 8/2016 | Desantis et al. |
| 9,421,274 B2 | 8/2016 | Robillard et al. |
| 9,427,482 B2 | 8/2016 | Rossin et al. |
| 9,458,308 B1 | 10/2016 | Park et al. |
| 9,463,256 B2 | 10/2016 | Lub et al. |
| 9,464,065 B2 | 10/2016 | Schultz et al. |
| 9,487,472 B2 | 11/2016 | Betley et al. |
| 9,520,565 B2 | 12/2016 | Wang et al. |
| 9,550,000 B2 | 1/2017 | Robinson et al. |
| 9,556,166 B2 | 1/2017 | Foley et al. |
| 9,580,400 B2 | 2/2017 | Makriyannis et al. |
| 9,580,653 B2 | 2/2017 | Archetti et al. |
| 9,586,947 B2 | 3/2017 | Lu et al. |
| 9,593,115 B2 | 3/2017 | Barawkar et al. |
| 9,617,291 B2 | 4/2017 | Li et al. |
| 9,676,757 B2 | 6/2017 | Sherer et al. |
| 9,714,381 B2 | 7/2017 | Archetti et al. |
| 9,725,479 B2 | 8/2017 | Manoharan et al. |
| 9,802,965 B2 | 10/2017 | Fürstner et al. |
| 9,815,859 B2 | 11/2017 | Duan et al. |
| 9,818,959 B2 | 11/2017 | Li et al. |
| 9,862,789 B2 | 1/2018 | Asandei |
| 9,908,884 B2 | 3/2018 | Gray et al. |
| 9,913,921 B2 | 3/2018 | Robillard et al. |
| 9,932,305 B2 | 4/2018 | List et al. |
| 9,938,234 B2 | 4/2018 | Evans et al. |
| 9,947,876 B2 | 4/2018 | Kawamura et al. |
| 9,963,452 B2 | 5/2018 | Grueneberg et al. |
| 9,963,637 B2 | 5/2018 | Lee et al. |
| 10,017,520 B2 | 7/2018 | Koehler et al. |
| 10,023,800 B2 | 7/2018 | Kim et al. |
| 10,069,079 B2 | 9/2018 | Stoessel et al. |
| 10,072,017 B2 | 9/2018 | Zawistoski et al. |
| 10,076,581 B2 | 9/2018 | Marik et al. |
| 10,087,151 B2 | 10/2018 | Tsvetkov et al. |
| 10,120,281 B2 | 11/2018 | Takahashi et al. |
| 10,125,126 B2 | 11/2018 | Braun et al. |
| 10,131,841 B2 | 11/2018 | Archetti et al. |
| 10,164,200 B2 | 12/2018 | Hwang et al. |
| 10,180,626 B2 | 1/2019 | Fujiwara et al. |
| 10,199,583 B1 | 2/2019 | Hang et al. |
| 10,201,531 B2 | 2/2019 | Saitoh et al. |
| 10,205,190 B2 | 2/2019 | Lee et al. |
| 10,240,085 B2 | 3/2019 | Ihn et al. |
| 10,243,149 B2 | 3/2019 | Kang et al. |
| 10,280,171 B2 | 5/2019 | Jones et al. |
| 10,329,270 B2 | 6/2019 | Qiu et al. |
| 10,336,772 B2 | 7/2019 | Ishii et al. |
| 10,376,594 B2 | 8/2019 | Robillard et al. |
| 10,435,369 B2 | 10/2019 | Marcoux et al. |
| 10,463,661 B2 | 11/2019 | Long et al. |
| 10,478,445 B2 | 11/2019 | Bae et al. |
| 10,894,797 B2 * | 1/2021 | Fu .................. C07D 401/14 |
| 11,034,705 B2 * | 6/2021 | Fu .................. C07D 519/00 |
| 2002/0012960 A1 | 1/2002 | Schallner et al. |
| 2002/0173524 A1 | 11/2002 | Collins et al. |
| 2003/0187026 A1 | 10/2003 | Li et al. |
| 2004/0110745 A1 | 6/2004 | Chapdelaine et al. |
| 2005/0009894 A1 | 1/2005 | Babin et al. |
| 2005/0107268 A1 | 5/2005 | Negoro et al. |
| 2005/0247001 A1 | 11/2005 | Gouliaev et al. |
| 2006/0156481 A1 | 7/2006 | Lim |
| 2007/0010529 A1 | 1/2007 | Takahashi et al. |
| 2007/0088040 A1 | 4/2007 | Hinman et al. |
| 2007/0135437 A1 | 6/2007 | Benjamin et al. |
| 2007/0244133 A1 | 10/2007 | Bower et al. |
| 2007/0260062 A1 | 11/2007 | Goetz |
| 2008/0134938 A1 | 6/2008 | Negoro et al. |
| 2008/0194821 A1 | 8/2008 | Johannes et al. |
| 2008/0255183 A1 | 10/2008 | Arnould et al. |
| 2009/0118146 A1 | 5/2009 | Negoro et al. |
| 2010/0004284 A1 | 1/2010 | Farina et al. |
| 2010/0190766 A1 | 7/2010 | Moser et al. |
| 2010/0197687 A1 | 8/2010 | Pelcman et al. |
| 2012/0040977 A1 | 2/2012 | Li et al. |
| 2012/0046301 A1 | 2/2012 | Frank et al. |
| 2012/0059179 A1 | 3/2012 | Yu |
| 2012/0077959 A1 | 3/2012 | Zhang et al. |
| 2012/0108819 A1 | 5/2012 | Hashmi et al. |
| 2012/0149663 A1 | 6/2012 | Brown et al. |
| 2012/0232108 A1 | 9/2012 | Huang et al. |
| 2012/0238546 A1 | 9/2012 | Zhu et al. |
| 2012/0245158 A1 | 9/2012 | Huang et al. |
| 2012/0283175 A1 | 11/2012 | Patten et al. |
| 2013/0183252 A1 | 7/2013 | Li et al. |
| 2013/0202652 A1 | 8/2013 | Manoharan et al. |
| 2014/0031547 A1 | 1/2014 | Sheridan et al. |
| 2014/0131628 A1 | 5/2014 | D'lavari et al. |
| 2014/0163229 A1 | 6/2014 | Barany et al. |
| 2015/0036095 A1 | 2/2015 | Jeong et al. |
| 2015/0087673 A1 | 3/2015 | Hitoshi et al. |
| 2015/0221878 A1 | 8/2015 | Rai et al. |
| 2015/0297741 A1 | 10/2015 | Robillard |
| 2015/0340627 A1 | 11/2015 | Jatsch et al. |
| 2015/0344514 A1 | 12/2015 | Robillard et al. |
| 2015/0376198 A1 | 12/2015 | Roberts et al. |

(56) References Cited

U.S. PATENT DOCUMENTS

| | | |
|---|---|---|
| 2016/0093812 A1 | 3/2016 | Stoessel et al. |
| 2016/0151505 A1 | 6/2016 | Robillard et al. |
| 2016/0190482 A1 | 6/2016 | Jeon et al. |
| 2016/0197289 A1 | 7/2016 | Sado et al. |
| 2016/0211466 A1 | 7/2016 | Ogiwara et al. |
| 2016/0229866 A1 | 8/2016 | Dousson et al. |
| 2016/0257657 A1 | 9/2016 | Wipf et al. |
| 2016/0268519 A1 | 9/2016 | Choi et al. |
| 2017/0029366 A1 | 2/2017 | Cole et al. |
| 2017/0054083 A1 | 2/2017 | Lee |
| 2017/0054095 A1 | 2/2017 | Choi et al. |
| 2017/0121606 A1 | 5/2017 | Tong et al. |
| 2017/0170405 A1 | 6/2017 | Cho et al. |
| 2017/0174826 A1 | 6/2017 | Ye et al. |
| 2017/0179395 A1 | 6/2017 | Kim et al. |
| 2017/0179401 A1 | 6/2017 | Kim et al. |
| 2017/0186964 A1 | 6/2017 | Cho et al. |
| 2017/0186975 A1 | 6/2017 | Kim et al. |
| 2017/0213987 A1 | 7/2017 | Kim et al. |
| 2017/0256721 A1 | 9/2017 | Kim et al. |
| 2017/0294613 A1 | 10/2017 | Cho et al. |
| 2018/0002604 A1 | 1/2018 | Yoon et al. |
| 2018/0044591 A1 | 2/2018 | Jeong et al. |
| 2018/0053898 A1 | 2/2018 | Kim et al. |
| 2018/0119010 A1 | 5/2018 | Klasen-memmer et al. |
| 2018/0273562 A1 | 9/2018 | Choi et al. |
| 2018/0305334 A1 | 10/2018 | Larsen et al. |
| 2018/0312511 A1 | 11/2018 | Liu et al. |
| 2018/0340002 A1 | 11/2018 | Park et al. |
| 2018/0362567 A1 | 12/2018 | Hwang et al. |
| 2019/0013485 A1 | 1/2019 | Li et al. |
| 2019/0036042 A1 | 1/2019 | Kim et al. |
| 2019/0040028 A1 | 2/2019 | Diness et al. |
| 2019/0077792 A1 | 3/2019 | Volkmann et al. |
| 2019/0079095 A1 | 3/2019 | Gee et al. |
| 2019/0092784 A1 | 3/2019 | Wu et al. |
| 2019/0099748 A1 | 4/2019 | Ritter et al. |
| 2019/0100546 A1 | 4/2019 | Balk et al. |
| 2019/0152943 A1 | 5/2019 | Lain et al. |
| 2019/0157579 A1 | 5/2019 | Jeon et al. |
| 2019/0192517 A1 | 6/2019 | Burrows et al. |
| 2019/0218240 A1 | 7/2019 | Yoo et al. |
| 2019/0218459 A1 | 7/2019 | Song et al. |
| 2019/0259952 A1 | 8/2019 | Sasada et al. |
| 2019/0280064 A1 | 9/2019 | Kim et al. |
| 2019/0280215 A1 | 9/2019 | Kim et al. |
| 2019/0290649 A1 | 9/2019 | Xie et al. |
| 2019/0300523 A1 | 10/2019 | Liu et al. |
| 2019/0343836 A1 | 11/2019 | Alghalandis et al. |
| 2020/0002330 A1 | 1/2020 | Chen et al. |
| 2020/0115389 A1 | 4/2020 | Fu et al. |
| 2020/0277308 A1 | 9/2020 | Fu et al. |
| 2021/0040122 A1 | 2/2021 | Fu et al. |

FOREIGN PATENT DOCUMENTS

| | | |
|---|---|---|
| EP | 2098226 A1 | 9/2009 |
| EP | 2524918 A1 | 11/2012 |
| EP | 3229290 A1 | 10/2017 |
| EP | 3525253 A1 | 8/2019 |
| JP | S62135830 A | 6/1987 |
| JP | S62135834 A | 6/1987 |
| JP | S62135835 A | 6/1987 |
| JP | S62136650 A | 6/1987 |
| JP | S62136651 A | 6/1987 |
| JP | S62136654 A | 6/1987 |
| JP | H05181221 A | 7/1993 |
| JP | H05196976 A | 8/1993 |
| JP | 2000072695 A | 3/2000 |
| JP | 2005170939 A | 6/2005 |
| JP | 2008007634 A | 1/2008 |
| JP | 2009013314 A | 1/2009 |
| JP | 2010217692 A | 9/2010 |
| JP | 4749000 B2 | 5/2011 |
| JP | 2014232188 A | 12/2014 |
| JP | 5782836 B2 | 7/2015 |
| JP | 2015163671 A | 9/2015 |
| JP | 5814141 B2 | 10/2015 |
| JP | 6215674 B2 | 10/2017 |
| JP | 6309834 B2 | 3/2018 |
| JP | 2019050369 A | 3/2019 |
| JP | 6522313 B2 | 5/2019 |
| KR | 1020120045905 A | 5/2012 |
| KR | 1020150016140 A | 2/2015 |
| KR | 101537860 B1 | 7/2015 |
| KR | 1020170138614 A | 12/2017 |
| WO | 93/15047 A1 | 8/1993 |
| WO | 93/16684 A1 | 9/1993 |
| WO | 98/02438 A1 | 1/1998 |
| WO | 98/06709 A1 | 2/1998 |
| WO | 00/76984 A2 | 12/2000 |
| WO | 01/02369 A2 | 1/2001 |
| WO | 01/10842 A2 | 2/2001 |
| WO | 02/00651 A2 | 1/2002 |
| WO | 02/10192 A2 | 2/2002 |
| WO | 02/066470 A1 | 8/2002 |
| WO | 03/003008 A1 | 1/2003 |
| WO | 03/003009 A1 | 1/2003 |
| WO | 03/064383 A2 | 8/2003 |
| WO | 03/075836 A2 | 9/2003 |
| WO | 2004/017922 A2 | 3/2004 |
| WO | 2005/028443 A2 | 3/2005 |
| WO | 2006/028958 A2 | 3/2006 |
| WO | 2006/038594 A1 | 4/2006 |
| WO | 2006/061094 A1 | 6/2006 |
| WO | 2006/122806 A2 | 11/2006 |
| WO | WO-2006122806 A2 | 11/2006 |
| WO | 2007/011721 A1 | 1/2007 |
| WO | 2007/011759 A2 | 1/2007 |
| WO | 2007/064869 A2 | 6/2007 |
| WO | 2008/024423 A2 | 2/2008 |
| WO | 2008/118626 A2 | 10/2008 |
| WO | 2008/118626 A9 | 12/2008 |
| WO | 2009/036082 A2 | 3/2009 |
| WO | WO-2009036082 A2 | 3/2009 |
| WO | 2009/055730 A1 | 4/2009 |
| WO | WO-2009055730 A1 | 4/2009 |
| WO | 2009/155386 A1 | 12/2009 |
| WO | WO-2009155386 A1 | 12/2009 |
| WO | 2010/011666 A2 | 1/2010 |
| WO | 2010/012363 A1 | 2/2010 |
| WO | 2010/048149 A2 | 4/2010 |
| WO | 2010/075273 A1 | 7/2010 |
| WO | 2010/148422 A1 | 12/2010 |
| WO | 2011/093603 A1 | 8/2011 |
| WO | 2011/101644 A1 | 8/2011 |
| WO | 2011/109059 A1 | 9/2011 |
| WO | 2011/111930 A1 | 9/2011 |
| WO | 2011/115378 A1 | 9/2011 |
| WO | 2012/016133 A2 | 2/2012 |
| WO | 2012/020215 A1 | 2/2012 |
| WO | 2012/020357 A1 | 2/2012 |
| WO | 2012/056419 A1 | 5/2012 |
| WO | 2013/190212 A1 | 12/2013 |
| WO | 2014/031872 A2 | 2/2014 |
| WO | 2014/068893 A1 | 5/2014 |
| WO | 2014/081299 A1 | 5/2014 |
| WO | 2014/081300 A1 | 5/2014 |
| WO | 2014/122933 A1 | 8/2014 |
| WO | 2014/157267 A1 | 10/2014 |
| WO | 2014/176488 A1 | 10/2014 |
| WO | 2015/003094 A1 | 1/2015 |
| WO | 2015/008097 A1 | 1/2015 |
| WO | 2015/107493 A1 | 7/2015 |
| WO | 2015/107494 A1 | 7/2015 |
| WO | 2015/107495 A1 | 7/2015 |
| WO | 2016/022645 A1 | 2/2016 |
| WO | 2016/049565 A1 | 3/2016 |
| WO | WO-2016049565 A1 | 3/2016 |
| WO | 2016/145383 A1 | 9/2016 |
| WO | 2016/164675 A1 | 10/2016 |
| WO | 2016/168540 A1 | 10/2016 |
| WO | WO-2016164675 A1 | 10/2016 |
| WO | WO-2016168540 A1 | 10/2016 |

(56) References Cited

FOREIGN PATENT DOCUMENTS

| | | |
|---|---|---|
| WO | 2016/203404 A1 | 12/2016 |
| WO | 2016/203405 A1 | 12/2016 |
| WO | 2016/203406 A1 | 12/2016 |
| WO | 2016/207261 A1 | 12/2016 |
| WO | 2017/015562 A1 | 1/2017 |
| WO | WO-2017015562 A1 | 1/2017 |
| WO | 2017/027357 A1 | 2/2017 |
| WO | 2017/027358 A1 | 2/2017 |
| WO | 2017/058092 A1 | 4/2017 |
| WO | 2017/058728 A1 | 4/2017 |
| WO | 2017/058768 A1 | 4/2017 |
| WO | 2017/058805 A1 | 4/2017 |
| WO | 2017/058807 A1 | 4/2017 |
| WO | 2017/058902 A1 | 4/2017 |
| WO | 2017/058915 A1 | 4/2017 |
| WO | 2017/070256 A2 | 4/2017 |
| WO | WO-2017058792 A1 | 4/2017 |
| WO | 2017/087528 A1 | 5/2017 |
| WO | 2017/100546 A1 | 6/2017 |
| WO | 2017/170263 A1 | 10/2017 |
| WO | 2017/172979 A1 | 10/2017 |
| WO | 2017/201161 A1 | 11/2017 |
| WO | 2017/210134 A1 | 12/2017 |
| WO | 2017/211303 A1 | 12/2017 |
| WO | 2017/216706 A1 | 12/2017 |
| WO | 2018/013597 A1 | 1/2018 |
| WO | 2018/057884 A1 | 3/2018 |
| WO | 2018/064510 A1 | 4/2018 |
| WO | 2018/068017 A1 | 4/2018 |
| WO | 2018/081091 A1 | 5/2018 |
| WO | 2018/119183 A2 | 6/2018 |
| WO | 2018/119263 A1 | 6/2018 |
| WO | 2018/136264 A1 | 7/2018 |
| WO | 2018/136265 A1 | 7/2018 |
| WO | 2018/146469 A1 | 8/2018 |
| WO | 2018/146471 A1 | 8/2018 |
| WO | 2018/161033 A1 | 9/2018 |
| WO | 2018/172984 A1 | 9/2018 |
| WO | 2018/218133 A1 | 11/2018 |
| WO | 2018/230595 A1 | 12/2018 |
| WO | 2019/002173 A1 | 1/2019 |
| WO | 2019/018119 A1 | 1/2019 |
| WO | 2019/020828 A1 | 1/2019 |
| WO | 2019/051084 A1 | 3/2019 |
| WO | 2019/051469 A1 | 3/2019 |
| WO | 2019/020828 A9 | 4/2019 |
| WO | 2019/063585 A1 | 4/2019 |
| WO | 2019/067843 A1 | 4/2019 |
| WO | 2019/075265 A1 | 4/2019 |
| WO | 2019/118909 A1 | 6/2019 |
| WO | 2019/126730 A1 | 6/2019 |
| WO | 2019/136442 A1 | 7/2019 |
| WO | 2019/144764 A1 | 8/2019 |
| WO | 2019/144765 A1 | 8/2019 |
| WO | 2019/158019 A1 | 8/2019 |
| WO | 2019/165073 A1 | 8/2019 |
| WO | 2019/167000 A1 | 9/2019 |
| WO | 2019/182960 A1 | 9/2019 |
| WO | 2019/183364 A1 | 9/2019 |
| WO | 2019/183367 A1 | 9/2019 |
| WO | 2019/213318 A1 | 11/2019 |
| WO | 2019/218968 A1 | 11/2019 |
| WO | 2020/022323 A1 | 1/2020 |
| WO | 2020/033286 A1 | 2/2020 |
| WO | 2020/033828 A1 | 2/2020 |
| WO | 2020/061101 A1 | 3/2020 |
| WO | 2020/061103 A1 | 3/2020 |
| WO | 2020/065452 A1 | 4/2020 |
| WO | 2020/065453 A1 | 4/2020 |
| WO | 2020/076723 A1 | 4/2020 |

OTHER PUBLICATIONS

International Search Report and Written Opinion received for PCT Patent International Application No. PCT/US19/51592, dated May 11, 2019, 8 pages.
Bagdanoff et al. (Jan. 28, 2019) "Optimization of Fused Bicyclic Allosteric SHP2 Inhibitors", Journal of Medicinal Chemistry, 62(4);1781-1792.
Chen et al. (Jul. 7, 2016) "Allosteric Inhibition of SHP2 Phosphatase Inhibits Cancers Driven by Receptor Tyrosine Kinases", Nature, 535(7610):148-152.
Dardaei et al. (Mar. 5, 2018) "SHP2 Inhibition Restores Sensitivity in ALK-rearranged Non-Small-Cell Lung Cancer Resistant to ALK Inhibitors", Nature Medicine, 24(4):8 pages.
Fedele et al. (Jul. 25, 2018) "SHP2 Inhibition Prevents Adaptive Resistance to MEK Inhibitors in Multiple Cancer Models", Cancer discovery, 8(10):1237-1249.
Grossmann et al. (2010) "The Tyrosine Phosphatase Shp2 in Development and Cancer", Advances in Cancer Research, 106:53-89.
Gura Trisha (Nov. 7, 1997) "Cancer Models: Systems for Identifying New Drugs are Often Faulty", Science, 278(5340):5 pages.
Hinman et al. (Jul. 11, 2006) "Novel Antibacterial Class: A Series of Tetracyclic Derivatives", Journal of Medicinal Chemistry, 49(16):4842-4856.
Johnson et al. (2001) "Relationships Between Drug Activity in NCI Preclinical in Vitro and in Vivo Models and Early Clinical Trials", British Journal of Cancer, 84(10):1424-1431.
Li et al. (2014) "Discovery of AMG 925, a FLT3 and CDK4 Dual Kinase Inhibitor with Preferential Affinity for the Activated State of FLT3", Journal of Medicinal Chemistry, 57(8):3430-3449.
Maeshima et al. (2016) "Abnormal PTPN11 Enhancer Methylation Promotes Rheumatoid Arthritis Fibroblast-like Synoviocyte Aggressiveness and Joint Inflammation", JCI Insight, 1(7):14 pages.
Mainardi et al. (May 28, 2018) "SHP2 Is Required for Growth of KRAS-Mutant Non-Small-Cell Lung Cancer in Vivo", Nature Medicine, 24:961-967.
Massari et al. (Sep. 8, 2016) "Polymerase Acidic Protein-Basic Protein 1 (PA-PB1) Protein-Protein Interaction as a Target for Next-Generation Anti-influenza Therapeutics", Journal of Medicinal Chemistry, 59(17):7699-7718.
Nichols et al. (Sep. 2018) "RAS nucleotide cycling underlies the SHP2 phosphatase dependence of mutant BRAF-, NF1- and RAS-driven cancers", Nature Cell Biology, 20(9):1064-1073.
Pearce et al. (2008) "Failure Modes in Anticancer Drug Discovery and Development", Cancer Drug Design and Discovery, 18:424-435.
Prahallad et al. (2015) "PTPN11 Is a Central Node in Intrinsic and Acquired Resistance to Targeted Cancer Drugs", Cell Reports, 12:1978-1985.
Ruess et al. (2018) "Mutant KRAS-Driven Cancers Depend on PTPN11/SHP2 Phosphatase", Nature Medicine, 24 (7):13 pages.
Sarver et al. (Jan. 28, 2019) "6-Amino-3-methylpyrimidinones as Potent, Selective, and Orally Efficacious SHP2 Inhibitors", Journal of Medicinal Chemistry, 62(4);1793-1802.
Simone, Joseph V. (1996) "Oncology: Introduction", Cecil Textbook of Medicine, 20th Edition, 1996, 1:1004-1010.
Stanford et al. (May 2013) "PTPome Profile of Rheumatoid Arthritis Fibroblast-like Synoviocytes: A Novel Role for SHP-2 as a Modulator of Invasion and Survival", Arthritis & Rheumatology, 65(5):1171-1180.
Tajan et al. (2015) "SHP2 Sails from Physiology to Pathology", European Journal of Medical Genetics, 58 (10):509-525.
The Merck Manual (2013) "Acute Leukemia", Merck Manual (Online Edition), 6 Pages.
Wang et al. (May 16, 2016) "Inhibition of SHP2 Ameliorates the Pathogenesis of Systemic Lupus Erythematosus", The Journal of Clinical Investigation, 126(6):2077-2092.
Wong et al. (May 28, 2018) "Targeting wild-type KRAS-amplified gastroesophageal cancer through combined MEK and SHP2 inhibition", Nature Medicine, 24:968-977.
Zehender et al. (Aug. 14, 2018) "The tyrosine phosphatase SHP2 controls TGFβ-induced STAT3 signaling to regulate fibroblast activation and fibrosis", Nature Communications, 9(1):3259:17 pages.

(56) References Cited

OTHER PUBLICATIONS

"International Preliminary Report on Patentability received for PCT International Application No. PCT/US2019/051592", dated Apr. 1, 2021, 7 pages.
"International Preliminary Report on Patentability received for PCT International Application No. PCT/US2019/051590", dated Apr. 1, 2021, 7 pages.
Stanford et al. Protein tyrosine phosphatase expression profile of rheumatoid arthritis fibroblast-like synoviocytes: a novel role of SH2 domain-containing phosphatase 2 as a modulator of invasion and survival. Arth Rheumatol 65(5):1171-1180 (2013).

* cited by examiner

TRI-SUBSTITUTED HETEROARYL DERIVATIVES AS SRC HOMOLOGY-2 PHOSPHATASE INHIBITORS

CROSS REFERENCE TO RELATED APPLICATIONS

This application is an International Application claiming the benefit of U.S. Provisional Application No. 62/733,061 filed Sep. 18, 2018, U.S. Provisional Application No. 62/749,655 filed Oct. 23, 2018, U.S. Provisional Application No. 62/810,911 filed Feb. 26, 2019, U.S. Provisional Application No. 62/883,120 filed Aug. 6, 2019, and U.S. Provisional Application No. 62/883,121 filed Aug. 6, 2019; the entireties of which are herein incorporated by reference.

FIELD OF THE DISCLOSURE

The present disclosure provides certain tri-substituted heteroaryl derivatives that are Src Homology-2 phosphatase (SHP2) inhibitors and are therefore useful for the treatment of diseases treatable by inhibition of SHP2. Also provided are pharmaceutical compositions containing such compounds and processes for preparing such compounds.

BACKGROUND

SHP2 is a non-receptor protein phosphatase ubiquitously expressed in various tissues and cell types (see reviews: Tajan M et al., Eur J Med Genet 2016 58(10):509-25; Grossmann K S et al., Adv Cancer Res 2010 106:53-89). SHP2 is composed of two Src homology 2 (N—SH2 and C—SH2) domains in its NH2-terminus, a catalytic PTP (protein-tyrosine phosphatase) domain, and a C-terminal tail with regulatory properties. At the basal state, the intermolecular interactions between the SH2 domains and the PTP domain prevent the access of substrates to the catalytic pocket, keeping SHP2 into a closed, auto-inhibited conformation. In response to stimulation, SHP2 activating proteins bearing phosphor-tyrosine motifs bind to the SH2 domains, leading to exposure of active site and enzymatic activation of SHP2.

SHP2 plays important roles in fundamental cellular functions including proliferation, differentiation, cell cycle maintenance and motility. By dephosphorylating its associated signaling molecules, SHP2 regulates multiple intracellular signaling pathways in response to a wide range of growth factors, cytokines, and hormones. Cell signaling processes in which SHP2 participates include the RAS-MAPK (mitogen-activated protein kinase), the PI3K (phosphoinositol 3-kinase)-AKT, and the JAK-STAT pathways.

The RAS-MAPK signaling pathway is crucial for tumor formation and maintenance. Genes encoding various components of this pathway, including RTKs (receptor tyrosine kinases), SHP2, NF1, RAS, or RAF are mutated in cancers, leading to upregulation of MAPK signaling. SHP2 also plays a signal-enhancing role on this pathway, acting downstream of RTKs and upstream of RAS. RTK-driven cancer cells were demonstrated to depend on SHP2 for survival. Thus, SHP2 inhibition has been proposed as a valid treatment for RTK-driven cancers (see Prahallad, A. et al. Cell Reports 12, 1978-1985 (2015); Chen Y N, Nature 535, 148-152(2016)).

A lot of efforts have been made to develop pharmacological agents targeting various nodes along the RAS-MAPK pathway, such as RTK inhibitors, BRAF inhibitors, and MEK inhibitors for the treatment of cancer. Although these agents demonstrate good initial efficacy, resistance to these agents occurs frequently. One common mechanism of resistance involves activation of RTKs that fuel reactivation of the MAPK signaling. Since SHP2 is required downstream of multiple RTKs for signal transduction, SHP2 inhibition may provide a general strategy for preventing resistance to MAPK pathway targeted cancer drugs. Recent studies in preclinical models have shown that SHP2 inhibition overcomes resistance and offers synergistic therapeutic effects when combined with an ALK inhibitor (see Dardaei L et al. Nat Med. 24, 512-17 (2018)), MEK inhibitor (see Mainardi, S. et al. Nat. Med. https://doi.org/10.1038/s41591-018-0023-9 (2018); Ruess, D. A. et al. Nat. Med. https://doi.org/10.1038/s41591-018-0024-8 (2018); Wong, G. S. et al. Nat. Med. https://doi.org/10.1038/s41591-018-0022-x (2018); Fedele C et al. Cancer Discov pii: CD-18-0444. doi: 10.1158/2159-8290.CD-18-0444 (2018)), or BRAF inhibitor (see Prahallad, A. et al. Cell Reports 12, 1978-1985 (2015)). Especially, the combined inhibition of MEK/SHP2 has been identified to have potential to treat cancers driven by KRAS, the most frequently mutated oncogene. Despite years of efforts, inhibitors directly targeting KRAS has not yet been successfully developed for clinical use. Inhibiting MEK, the downstream effector of KRAS, only transiently suppressed MAPK signaling. The discovery of MEK/SHP2 dual inhibition makes important strides in the long-time effort to better understand and to therapeutically target KRAS-driven cancers.

Given the essential physiological functions SHP2 plays, targeting deregulation of SHP2 is expected to have broad therapeutic applications. Gain of function mutations in PTPN11, the gene that encodes SHP2, have been causally linked to several human diseases, including Noonan Syndrome, juvenile myelomonocytic leukemias, acute myeloid leukemia, myelodysplastic syndrome, and acute B lymphoblastic lymphoblastic leukemia. SHP2 functions as an oncogene, and its overexpression and/or activating mutations are reported in various solid tumors, such as neuroblastoma, breast cancer, colon cancer, lung cancer, melanoma, and hepatocellular carcinoma.

Furthermore, SHP-2 is believed to mediate inhibitory immune checkpoint signaling of multiple receptors (e.g. PD-1) by dephosphorylating CD28. To support this notion, a dominant negative SHP-2 abrogates PD-1 signaling pathways and restores function of cytotoxic CAR T cells. Therefore, SHP-2 inhibitors have potential for use in combination therapy with existing targeted and immune-oncology (IO) agents.

In addition to human tumors, increase in expression or activity of SHP2 have been implicated in the pathogenesis of autoimmune diseases such as systemic lupus erythematosus (Wang J et al. J Clin Invest. 2016 Jun. 1; 126(6):2077-92) and rheumatoid arthritis (see Stanford S. M et al. Arthritis Rheum. 2013 May; 65(5):1171-80; Maeshima K et al. JCI Insight. 2016 May 19; 1(7)). Recently, SHP2 has also been characterized as a molecular checkpoint for TGFβ-induced JAK2/STAT3 signaling, suggesting that SHP2 inhibition may offer therapeutic benefit for the treatment of fibrosis (see Zehender A et al. Nat Commun. 2018 Aug. 14; 9(1): 3259). Accordingly, SHP2 represents a highly attractive target for the development of novel therapies to treat various diseases.

SUMMARY

Provided is a compound of Formula (IA'):

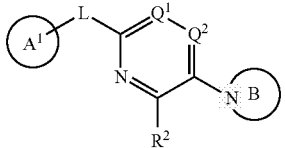

(IA')

wherein:

ring $A^1$ is a fused tricyclic heteroaryl or cycloalkyl fused bicyclic heteroaryl ring substituted with $R^a$, $R^b$, and/or $R^c$ wherein $R^a$ and $R^b$ are independently selected from hydrogen, alkyl, amino, cycloalkyl, alkyldienyl, alkenyl, halo, haloalkyl, alkoxy, haloalkoxy, hydroxy, hydroxyalkyl, alkoxyalkyl, cyano, aminoalkyl, carboxy, and alkoxycarbonyl and $R^c$ is hydrogen, alkyl, halo, hydroxy, alkoxy, optionally substituted heterocyclyl, optionally substituted aryl, optionally substituted heteroaryl, —S(O)R, S(O)$_2$R, —C(O)R, —OR', —NR'C(O)R, —NR'SO$_2$R, —OC(O)NR'R", —C(O)NR'R", —S(O)$_2$NR'R", —NR'R", or —NR'C(O)C(O)R where R is alkyl, cycloalkyl, cycloalkylalkyl, optionally substituted heterocyclyl, optionally substituted heterocyclylalkyl, optionally substituted aryl, optionally substituted aralkyl, optionally substituted heteroaryl, or optionally substituted heteroaralkyl, and R' and R" are independently hydrogen, alkyl, hydroxyalkyl, alkoxyalkyl, aminoalkyl, cycloalkylalkyl, optionally substituted heterocyclyl, optionally substituted heterocyclylalkyl, optionally substituted aryl, optionally substituted aralkyl, optionally substituted heteroaryl, or optionally substituted heteroaralkyl; or R' and R" together with the nitrogen atom to which they are attached form optionally substituted heterocyclyl; or when $R^c$ and $R^a$ are attached to the same carbon of fused heteroaryl ring, then $R^c$ and $R^a$ together with the carbon atom to which they are attached can form cycloalkylene or heterocyclylene;

$Q^1$ is N or $CR^1$ wherein $R^1$ is hydrogen or deuterium;

$Q^2$ is N or CH, or CD;

$R^2$ is alkyl, halo, hydroxy, hydroxyalkyl, —CD$_2$OH, alkylsulfoxide, alkylsulfonyl, aminosulfonyl, aminocarbonyl, carboxy, cyano, or alkoxycarbonyl;

L is bond, O, S, S(O), S(O)$_2$, or $CR^5R^6$ where $R^5$ and $R^6$ are independently hydrogen or alkyl;

and

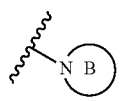

is a ring of formula (a) or (b):

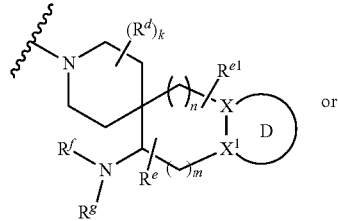

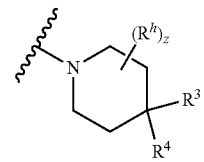

wherein:

m is 0, 1, or 2;

n is 0, 1, or 2 wherein when n is 2 then one of the CH$_2$ can be replaced with O, S, or SO$_2$; provided m+n is 1, 2, or 3;

k is 0, 1 or 2 z is 0, 1, or 2 each $R^d$ is independently hydrogen, alkyl, or halogen;

$R^e$ and $R^{e1}$ are independently hydrogen, alkyl, halogen, haloalkyl, alkoxy, haloalkoxy, hydroxy, hydroxyalkyl, cyano or oxo; or when $R^e$ and $R^{e1}$ are attached to the same carbon atom, then $R^e$ and $R^{e1}$ together with the carbon atom to which they are attached can form cycloalkylene or heterocyclylene;

$R^f$ and $R^g$ are independently hydrogen, alkyl, or haloalkyl;

each $R^h$ is independently alkyl, halo, haloalkyl, alkoxy, hydroxyalkyl, alkoxyalkyl, hydroxy, cyano, or oxo; or when one $R^h$ is connected to carbon 2 or 3 of the piperidine (b) ring and the second $R^h$ is attached to carbon 5 or 6 of the piperidine (b) ring, the nitrogen atom being position 1, then the first and second $R^h$ can combine to form alkylene chain;

ring D is phenyl or a 5 or 6 membered heteroaryl ring which, including X and $X^1$, contains one to three heteroatoms independently selected from N, O, and S and ring D can optionally be substituted with one or two groups independently selected from alkyl, halo, haloalkyl, alkoxy, haloalkoxy, hydroxy, hydroxyalkyl, cyano, amino, aminoalkyl, carboxy, cycloalkyl, heterocyclyl, heteroaryl, and acylamino;

X and $X^1$ are independently N or C; provided that only one of X and $X^1$ can be N;

$R^3$ is amino or aminoalkyl;

$R^4$ is alkyl, cycloalkylalkyl, halo, hydroxy, amino, alkoxycarbonyl, hydroxyalkyl, alkoxyalkyl, arylalkyl, heterocyclalkyl, cycloalkylalkyl, heterocyclalkyl, 5 or 6 membered heteroaryl, or 4 to 6 membered heterocyclyl wherein heteroaryl by itself or as part of heteroaralkyl and heterocyclyl by itself or as part of heterocyclylalkyl are substituted with $R^i$ and/or $R^j$ independently selected from hydrogen, alkyl, halo, haloalkyl, haloalkoxy, alkoxy, hydroxy, cyano, amino, aminoalkyl, alkylsulfoxide, and alkylsulfonyl; or $R^3$ and $R^4$ together with the carbon atom to which they are attached form a ring of formula (c):

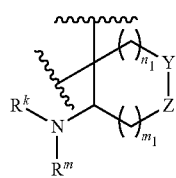

(c)

wherein:

m1 is 0, 1, or 2;

n1 is 0, 1, or 2; provided m1+n1 is 1, 2, or 3;

$R^k$ and $R^m$ are independently hydrogen, alkyl, or haloalkyl;

one of Y and Z is $CH_2$, O, S, S(O), $S(O)_2$, or NH; and the other of X and Y is $CH_2$; and wherein ring of formula (c) is substituted with $R^n$ and/or $R^o$ independently selected from hydrogen, alkyl, alkyldienyl, alkenyl, halo, haloalkyl, haloalkoxy, alkoxy, hydroxy, cyano, alkylsulfoxide, alkylsulfonyl, oxo, cycloalkyl, heterocyclyl, and heteroaryl; or when $R^n$ and $R^o$ are attached to the same carbon atom, then $R^n$ and $R^o$ together with the carbon atom to which they are attached can form cycloalkylene or heterocyclylene; or a pharmaceutically acceptable salt thereof.

In a first aspect provided is a compound of Formula (I'):

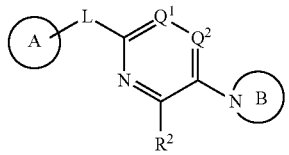

(I')

wherein:

ring A is aryl, cycloalkyl, heteroaryl, or fused heteroaryl ring, each ring substituted with $R^a$, $R^b$, and/or $R^c$ wherein $R^a$ and $R^b$ are independently selected from hydrogen, alkyl, amino, cycloalkyl, alkyldienyl, alkenyl, halo, haloalkyl, alkoxy, haloalkoxy, hydroxy, hydroxyalkyl, alkoxyalkyl, cyano, aminoalkyl, carboxy, and alkoxycarbonyl and $R^c$ is hydrogen, alkyl, halo, hydroxy, alkoxy, optionally substituted heterocyclyl, optionally substituted aryl, optionally substituted heteroaryl, —S(O)R, $S(O)_2R$, —C(O)R, —OR', —NR'C(O)R, —NR'SO₂R, —OC(O)NR'R", —C(O)NR'R", —S(O)₂NR'R", —NR'R", or —NR'C(O)C(O)R where R is alkyl, cycloalkyl, cycloalkylalkyl, optionally substituted heterocyclyl, optionally substituted heterocyclylalkyl, optionally substituted aryl, optionally substituted aralkyl, optionally substituted heteroaryl, or optionally substituted heteroaralkyl, and R' and R" are independently hydrogen, alkyl, hydroxyalkyl, alkoxyalkyl, aminoalkyl, cycloalkylalkyl, optionally substituted heterocyclyl, optionally substituted heterocyclylalkyl, optionally substituted aryl, optionally substituted aralkyl, optionally substituted heteroaryl, or optionally substituted heteroaralkyl; or R' and R" together with the nitrogen atom to which they are attached form optionally substituted heterocyclyl; or when $R^c$ and $R^a$ are attached to the same carbon of cycloalkyl or fused heteroaryl ring, then $R^c$ and $R^a$ together with the carbon atom to which they are attached can form cycloalkylene or heterocyclylene;

$Q^1$ is N or $CR^1$ wherein $R^1$ is hydrogen or deuterium;

$Q^2$ is N or CH, or CD;

$R^2$ is alkyl, halo, hydroxy, hydroxyalkyl, —$CD_2OH$, alkylsulfoxide, alkylsulfonyl, aminosulfonyl, aminocarbonyl, carboxy, cyano, or alkoxycarbonyl;

L is bond, O, S, S(O), $S(O)_2$, or $CR^5R^6$ where $R^5$ and $R^6$ are independently hydrogen or alkyl;

and

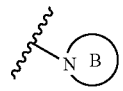

is a ring of formula (a) or (b):

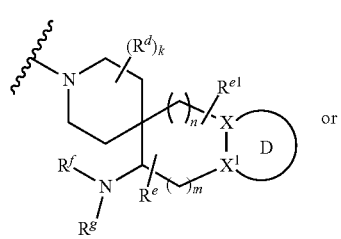

(a)

or

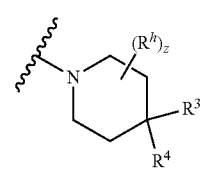

(b)

wherein:

m is 0, 1, or 2;

n is 0, 1, or 2 wherein when n is 2 then one of the $CH_2$ can be replaced with O, S, or $SO_2$; provided m+n is 1, 2, or 3;

k is 0, 1 or 2;

z is 0, 1, or 2;

each $R^d$ is independently hydrogen, alkyl, or halogen;

$R^e$ and $R^{e1}$ are independently hydrogen, alkyl, halogen, haloalkyl, alkoxy, haloalkoxy, hydroxy, hydroxyalkyl, cyano or oxo; or when $R^e$ and $R^{e1}$ are attached to the same carbon atom, then $R^e$ and $R^{e1}$ together with the carbon atom to which they are attached can form cycloalkylene or heterocyclylene;

$R^f$ and $R^g$ are independently hydrogen, alkyl, or haloalkyl;

each $R^h$ is independently alkyl, halo, haloalkyl, alkoxy, hydroxyalkyl, alkoxyalkyl, hydroxy, cyano, or oxo; or when one $R^h$ is connected to carbon 2 or 3 of the piperidine (b) ring and the second $R^h$ is attached to carbon 5 or 6 of the piperidine (b) ring, the nitrogen atom being position 1, then the first and second $R^h$ can combine to form alkylene chain;

ring D is phenyl or a 5 or 6 membered heteroaryl ring which, including X and $X^1$, contains one to three heteroatoms independently selected from N, O, and S and ring D can optionally be substituted with one or two groups independently selected from alkyl, halo, haloalkyl, alkoxy, haloalkoxy, hydroxy, hydroxyalkyl, cyano, amino, aminoalkyl, carboxy, cycloalkyl, heterocyclyl, heteroaryl, and acylamino;

X and $X^1$ are independently N or C; provided that only one of X and $X^1$ can be N;

$R^3$ is amino or aminoalkyl;

$R^4$ is alkyl, cycloalkylalkyl, halo, hydroxy, amino, alkoxycarbonyl, hydroxyalkyl, alkoxyalkyl, arylalkyl, heterocyclalkyl, cycloalkylalkyl, heterocyclalkyl, 5 or 6 membered heteroaryl, or 4 to 6 membered heterocyclyl wherein heteroaryl by itself or as part of heteroaralkyl or heterocyclyl by itself or as part of heterocyclylalkyl is substituted with $R^i$ and/or $R^j$ independently selected from hydrogen, alkyl, halo, haloalkyl, haloalkoxy, alkoxy, hydroxy, cyano, amino, aminoalkyl, alkylsulfoxide, and alkylsulfonyl; or $R^3$ and $R^4$ together with the carbon atom to which they are attached form a ring of formula (c):

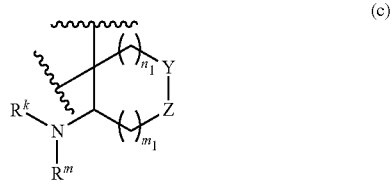

wherein:

m1 is 0, 1; or 2;

n1 is 0, 1, or 2; provided m1+n1 is 1, 2, or 3;

$R^k$ and $R^m$ are independently hydrogen, alkyl, or haloalkyl;

one of Y and Z is $CH_2$, O, S, S(O), $S(O)_2$, or NH; and the other of X and Y is $CH_2$; and wherein ring of formula (c) is substituted with $R^n$ and/or $R^o$ independently selected from hydrogen, alkyl, alkyldienyl, alkenyl, halo, haloalkyl, haloalkoxy, alkoxy, hydroxy, cyano, alkylsulfoxide, alkylsulfonyl, oxo, cycloalkyl, heterocyclyl, and heteroaryl; or when $R''$ and $R^o$ are attached to the same carbon atom, then $R''$ and $R^o$ together with the carbon atom to which they are attached can form cycloalkylene or heterocyclylene; or a pharmaceutically acceptable salt thereof.

In first embodiment of the first aspect provided is a compound of Formula (I):

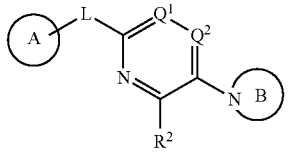

wherein:

ring A is aryl, cycloalkyl, heteroaryl, or fused heteroaryl ring, each ring substituted with $R^a$, $R^b$, and/or $R^c$ wherein $R^a$ and $R^b$ are independently selected from hydrogen, alkyl, amino, cycloalkyl, alkyldienyl, alkenyl, halo, haloalkyl, alkoxy, haloalkoxy, hydroxy, hydroxyalkyl, cyano, aminoalkyl, carboxy, and alkoxycarbonyl and $R^c$ is hydrogen, alkyl, halo, hydroxy, alkoxy, optionally substituted heterocyclyl, optionally substituted aryl, optionally substituted heteroaryl, —S(O)R, $S(O)_2R$, —C(O)R, —NR'C(O)R, —$NR'SO_2R$, —C(O)NR'R'', —$S(O)_2NR'R''$, —NR'R'', or —NR'C(O)C(O)R where R is alkyl, cycloalkyl, cycloalkylalkyl, optionally substituted heterocyclyl, optionally substituted heterocyclylalkyl, optionally substituted aryl, optionally substituted aralkyl, optionally substituted heteroaryl, or optionally substituted heteroaralkyl, and R' and R'' are independently hydrogen, alkyl, hydroxyalkyl, alkoxyalkyl, aminoalkyl, cycloalkylalkyl, optionally substituted heterocyclyl, optionally substituted heterocyclylalkyl, optionally substituted aryl, optionally substituted aralkyl, optionally substituted heteroaryl, or optionally substituted heteroaralkyl; or R' and R'' together with the nitrogen atom to which they are attached form optionally substituted heterocyclyl; or when $R^c$ and $R^a$ are attached to the same carbon of cycloalkyl or fused heteroaryl ring, then $R^c$ and $R^a$ together with the carbon atom to which they are attached can form cycloalkylene or heterocyclylene;

$Q^1$ is N or $CR^1$ wherein $R^1$ is hydrogen or deuterium;

$Q^2$ is N or CH, or CD;

$R^2$ is alkyl, halo, hydroxy, hydroxyalkyl, —$CD_2OH$, alkylsulfoxide, alkylsulfonyl, aminosulfonyl, aminocarbonyl, carboxy, cyano, or alkoxycarbonyl;

L is bond, O, S, S(O), $S(O)_2$, or $CR^5R^6$ where $R^5$ and $R^6$ are independently hydrogen or alkyl;

and

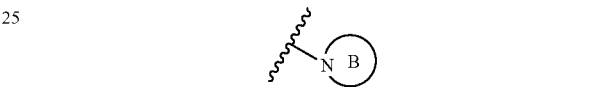

is a ring of formula (a) or (b):

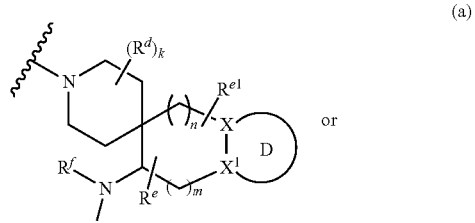

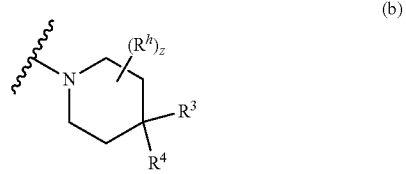

wherein:

m is 0, 1, or 2;

n is 0, 1, or 2; provided m+n is 1, 2, or 3;

k is 0, 1 or 2;

z is 0, 1, or 2;

each $R^d$ is independently hydrogen, alkyl, or halogen;

$R^e$ is hydrogen, alkyl, halogen, haloalkyl, alkoxy, haloalkoxy, hydroxy, hydroxyalkyl, cyano or oxo;

$R^f$ and $R^g$ are independently hydrogen, alkyl, or haloalkyl;

each $R^h$ is independently alkyl, halo, haloalkyl, alkoxy, hydroxyalkyl, alkoxyalkyl, hydroxy, cyano, or oxo; or when one $R^h$ is connected to carbon 2 or 3 of the piperidine (b) ring and the second $R^h$ is attached to carbon 5 or 6 of the piperidine (b) ring, the nitrogen atom being position 1, then the first and second $R^h$ can combine to form alkylene chain;

ring D is phenyl or a 5 or 6 membered heteroaryl ring which, including X and $X^1$, contains one to three heteroatoms independently selected from N, O, and S and ring D can optionally be substituted with one or two groups independently selected from alkyl, halo, haloalkyl, alkoxy, haloalkoxy, hydroxy, hydroxyalkyl, cyano, amino, aminoalkyl, carboxy, cycloalkyl, heterocyclyl, heteroaryl, and acylamino;

X and $X^1$ are independently N or C; provided that only one of X and $X^1$ can be N;

$R^3$ is amino or aminoalkyl;

$R^4$ is alkyl, cycloalkylalkyl, halo, hydroxy, amino, alkoxycarbonyl, hydroxyalkyl, alkoxyalkyl, arylalkyl, heterocyclalkyl, cycloalkylalkyl, heterocyclalkyl, 5 or 6 membered heteroaryl, or 4 to 6 membered heterocyclyl wherein heteroaryl by itself or as part of heteroaralkyl, or heterocyclyl by itself heterocyclylalkyl is substituted with $R^i$ and/or $R^j$ independently selected from hydrogen, alkyl, halo, haloalkyl, haloalkoxy, alkoxy, hydroxy, cyano, amino, aminoalkyl, alkylsulfoxide, and alkylsulfonyl; or $R^3$ and $R^4$ together with the carbon atom to which they are attached form a ring of formula (c):

(c)

wherein:
m1 is 0, 1, or 2;
n1 is 0, 1, or 2; provided m1+n1 is 1, 2, or 3;
$R^k$ and $R^m$ are independently hydrogen, alkyl, or haloalkyl;
one of Y and Z is $CH_2$, O, S, S(O), $S(O)_2$, or NH; and the other of X and Y is $CH_2$; and wherein ring of formula (c) is substituted with $R^n$ and/or $R^o$ independently selected from hydrogen, alkyl, alkyldienyl, alkenyl, halo, haloalkyl, haloalkoxy, alkoxy, hydroxy, cyano, alkylsulfoxide, alkylsulfonyl, oxo, cycloalkyl, heterocyclyl, and heteroaryl; or a pharmaceutically acceptable salt thereof.

In second embodiment of the first aspect, provided is a compound of Formula (IA):

(IA)

wherein:
ring A is aryl, cycloalkyl, heteroaryl, or fused heteroaryl ring, each ring substituted with $R^a$, $R^b$, and/or $R^c$ wherein $R^a$ and $R^b$ are independently selected from hydrogen, alkyl, halo, haloalkyl, alkoxy, haloalkoxy, hydroxy, hydroxyalkyl, cyano, aminoalkyl, carboxy, and alkoxycarbonyl and $R^c$ is hydrogen, alkyl, halo, hydroxy, alkoxy, optionally substituted aryl, optionally substituted heteroaryl, —S(O)R, $S(O)_2R$, —C(O)R, —NR'C(O)R, —NR'$SO_2$R, —C(O)NR'R", —$S(O)_2$NR'R", —NR'R", or —NR'C(O)C(O)R where R is alkyl, cycloalkyl, cycloalkylalkyl, optionally substituted heterocyclyl, optionally substituted heterocyclylalkyl, optionally substituted aryl, optionally substituted aralkyl, optionally substituted heteroaryl, or optionally substituted heteroaralkyl, and R' and R" are independently hydrogen, alkyl, hydroxyalkyl, alkoxyalkyl, aminoalkyl, cycloalkylalkyl, optionally substituted heterocyclyl, optionally substituted heterocyclylalkyl, optionally substituted aryl, optionally substituted aralkyl, optionally substituted heteroaryl, or optionally substituted heteroaralkyl; or R' and R" together with the nitrogen atom to which they are attached form optionally substituted heterocyclyl;

$Q^1$ is N or $CR^1$ wherein $R^1$ is hydrogen or deuterium;
$Q^2$ is N or CH, or CD;
$R^2$ is alkyl, halo, hydroxy, hydroxyalkyl, —$CD_2OH$, alkylsulfoxide, alkylsulfonyl, aminosulfonyl, aminocarbonyl, carboxy, cyano, or alkoxycarbonyl;
L is bond, O, S, S(O), $S(O)_2$, or $CR^5R^6$ where $R^5$ and $R^6$ are independently hydrogen or alkyl;
and is a ring of formula (a) or (b):

(a)

(b)

wherein:
m is 0, 1, or 2;
n is 0, 1, or 2; provided m+n is 1, 2, or 3;
k is 0, 1 or 2;
z is 0, 1, or 2;
each $R^d$ is independently hydrogen, alkyl, or halogen;
$R^e$ is hydrogen, alkyl, halogen, haloalkyl, alkoxy, haloalkoxy, hydroxy, hydroxyalkyl, cyano or oxo;
$R^f$ and $R^g$ are independently hydrogen, alkyl, or haloalkyl;
each $R^h$ is independently alkyl, halo, haloalkyl, alkoxy, hydroxyalkyl, alkoxyalkyl, hydroxy, cyano, or oxo; or
when one $R^h$ is connected to carbon 2 or 3 of the piperidine (b) ring and the second $R^h$ is attached to carbon 5 or 6 of the piperidine (b) ring, the nitrogen atom being position 1, then the first and second $R^h$ can combine to form alkylene chain;

ring D is phenyl or a 5 or 6 membered heteroaryl ring which, including X and $X^1$, contains one to three heteroatoms independently selected from N, O, and S and ring D can optionally be substituted with one or two groups independently selected from alkyl, halo, haloalkyl, alkoxy, haloalkoxy, hydroxy, hydroxyalkyl, cyano, amino, aminoalkyl, carboxy, cycloalkyl, heterocyclyl, heteroaryl, and acylamino;

X and $X^1$ are independently N or C; provided that only one of X and $X^1$ can be N;

$R^3$ is amino or aminoalkyl;

$R^4$ is alkyl, cycloalkylalkyl, halo, hydroxy, amino, alkoxycarbonyl, hydroxyalkyl, alkoxyalkyl, arylalkyl, heterocyclalkyl, cycloalkylalkyl, heterocyclalkyl, 5 or 6 membered heteroaryl, or 4 to 6 membered heterocyclyl wherein heteroaryl by itself or as part of heteroaralkyl or heterocyclyl by itself or as part of heterocyclylalkyl is substituted with $R^i$ and/or $R^j$ independently selected from hydrogen, alkyl, halo, haloalkyl, haloalkoxy, alkoxy, hydroxy, cyano, amino, aminoalkyl, alkylsulfoxide, and alkylsulfonyl; or $R^3$ and $R^4$ together with the carbon atom to which they are attached form a ring of formula (c):

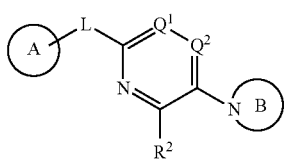

(c)

wherein:

m1 is 0, 1, or 2;

n1 is 0, 1, or 2; provided m1+n1 is 1, 2, or 3;

$R^k$ and $R^m$ are independently hydrogen, alkyl, or haloalkyl;

one of Y and Z is $CH_2$, O, S, S(O), $S(O)_2$, or NH; and the other of X and Y is $CH_2$; and wherein ring of formula (c) is substituted with $R^n$ and/or $R^o$ independently selected from hydrogen, alkyl, halo, haloalkyl, haloalkoxy, alkoxy, hydroxy, cyano, alkylsulfoxide, alkylsulfonyl, oxo, cycloalkyl, heterocyclyl, and heteroaryl; or a pharmaceutically acceptable salt thereof.

In a second aspect, provided is a compound of Formula (II):

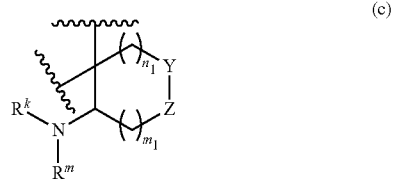

(II)

wherein:

ring A is aryl, cycloalkyl, heteroaryl, or fused heteroaryl ring, each ring substituted with $R^a$, $R^b$, and/or $R^c$ wherein $R^a$ and $R^b$ are independently selected from hydrogen, alkyl, amino, cycloalkyl, alkyldienyl, alkenyl, halo, haloalkyl, alkoxy, haloalkoxy, hydroxy, hydroxyalkyl, cyano, aminoalkyl, carboxy, and alkoxycarbonyl and $R^c$ is hydrogen, alkyl, halo, hydroxy, alkoxy, optionally substituted heterocyclyl, optionally substituted aryl, optionally substituted heteroaryl, —NHCOR, or —NR'R" where R is alkyl, cycloalkyl, optionally substituted heterocyclyl, optionally substituted aryl, optionally substituted heteroaryl, or optionally substituted heteroaralkyl, and R' and R" are independently hydrogen or alkyl; or R' and R" together with the nitrogen atom to which they are attached form optionally substituted heterocyclyl; or when $R^c$ and $R^a$ are attached to the same carbon of cycloalkyl or fused heteroaryl ring, then $R^c$ and $R^a$ together with the carbon atom to which they are attached can form cycloalkylene or heterocyclylene;

$Q^1$ is N or $CR^1$ wherein $R^1$ is hydrogen or deuterium;

$Q^2$ is N, CH, or CD;

$R^2$ is alkyl, halo, hydroxy, hydroxyalkyl, —$CD_2OH$, alkylsulfoxide, alkylsulfonyl, aminosulfonyl, aminocarbonyl, carboxy, cyano, or alkoxycarbonyl;

L is bond, O, S, SO, $SO_2$, or $CR^5R^6$ where $R^5$ and $R^6$ are independently hydrogen or alkyl;

and

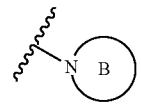

is a ring of formula (a) or (b):

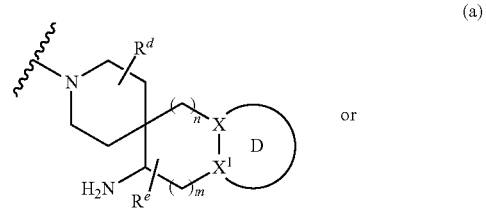

(a)

or

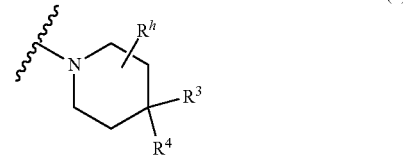

(b)

wherein:

m is 0, 1; or 2;

n is 0, 1, or 2; provided m+n is 1, 2, or 3;

$R^d$ is hydrogen or alkyl;

$R^e$ is hydrogen, alkyl, halogen, or oxo;

$R^h$ is independently alkyl, halo, haloalkyl, alkoxy, hydroxyalkyl, alkoxyalkyl, hydroxy, cyano, or oxo;

ring D is phenyl or a 5 or 6 membered heteroaryl ring which, including X and $X^1$, contains one to three heteroatoms independently selected from N, O, or S and ring D can optionally be substituted with alkyl;

X and $X^1$ are independently N or C; provided that only one of X and $X^1$ can be N;

$R^3$ is amino or aminoalkyl;

$R^4$ is alkyl, cycloalkylalkyl, halo, hydroxy, amino, alkoxycarbonyl, hydroxyalkyl, alkoxyalkyl, 5 or 6 membered heteroaryl, or 4 to 6 membered heterocyclyl wherein heteroaryl or heterocyclyl is substituted with $R^i$ and/or $R^j$ independently selected from hydrogen, alkyl, halo, haloalkyl, haloalkoxy, alkoxy, hydroxy, cyano, alkylsulfoxide, and alkylsulfonyl; or $R^3$ and $R^4$ together with the carbon atom to which they are attached form a ring of formula (c):

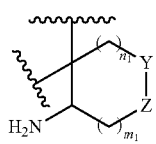

(c)

wherein:
m1 is 0, 1; or 2;
n1 is 0, 1, or 2; provided m1+n1 is 1, 2, or 3;
one of Y and Z is $CH_2$, O, S, SO, $SO_2$, or NH; and the other of X and Y is $CH_2$; and wherein ring of formula (c) is substituted with $R^n$ and/or $R^o$ independently selected from hydrogen, alkyl, alkyldienyl, alkenyl, halo, haloalkyl, haloalkoxy, alkoxy, hydroxy, cyano, alkylsulfoxide, alkylsulfonyl, and oxo; or
a pharmaceutically acceptable salt thereof.

In an embodiment of the second aspect, provided is a compound of Formula (IIA):

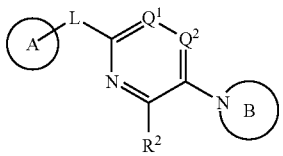

(IIA)

wherein:
ring A is aryl, cycloalkyl, heteroaryl, or fused heteroaryl ring, each ring substituted with $R^a$, $R^b$, and/or $R^c$ wherein $R^a$ and $R^b$ are independently selected from hydrogen, alkyl, halo, haloalkyl, alkoxy, haloalkoxy, hydroxy, hydroxyalkyl, cyano, aminoalkyl, carboxy, and alkoxycarbonyl and $R^c$ is hydrogen, alkyl, halo, hydroxy, alkoxy, optionally substituted heterocyclyl, optionally substituted aryl, optionally substituted heteroaryl, —NHCOR, or —NR'R'' where R is alkyl, cycloalkyl, optionally substituted heterocyclyl, optionally substituted aryl, optionally substituted heteroaryl, or optionally substituted heteroaralkyl, and R' and R'' are independently hydrogen or alkyl; or R' and R'' together with the nitrogen atom to which they are attached form optionally substituted heterocyclyl;
$Q^1$ is N or $CR^1$ wherein $R^1$ is hydrogen or deuterium;
$Q^2$ is N, CH, or CD;
$R^2$ is alkyl, halo, hydroxy, hydroxyalkyl, —$CD_2OH$, alkylsulfoxide, alkylsulfonyl, aminosulfonyl, aminocarbonyl, carboxy, cyano, or alkoxycarbonyl;
L is bond, O, S, SO, $SO_2$, or $CR^5R^6$ where $R^5$ and $R^6$ are independently hydrogen or alkyl; and

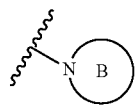

is a ring of formula (a) or (b):

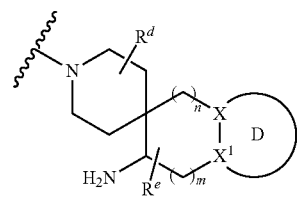

(a)

or

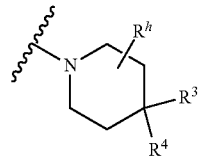

(b)

wherein:
m is 0, 1, or 2;
n is 0, 1, or 2; provided m+n is 1, 2, or 3;
$R^d$ is hydrogen or alkyl;
$R^e$ is hydrogen, alkyl, halogen, or oxo;
$R^h$ is independently alkyl, halo, haloalkyl, alkoxy, hydroxyalkyl, alkoxyalkyl, hydroxy, cyano, or oxo;
ring D is phenyl or a 5 or 6 membered heteroaryl ring which, including X and $X^1$, contains one to three heteroatoms independently selected from N, O, or S and ring D can optionally be substituted with alkyl;
X and $X^1$ are independently N or C; provided that only one of X and $X^1$ can be N;
$R^3$ is amino or aminoalkyl;
$R^4$ is alkyl, cycloalkylalkyl, halo, hydroxy, amino, alkoxycarbonyl, hydroxyalkyl, alkoxyalkyl, 5 or 6 membered heteroaryl, or 4 to 6 membered heterocyclyl wherein heteroaryl or heterocyclyl is substituted with $R^i$ and/or $R^j$ independently selected from hydrogen, alkyl, halo, haloalkyl, haloalkoxy, alkoxy, hydroxy, cyano, alkylsulfoxide, and alkylsulfonyl; or
$R^3$ and $R^4$ together with the carbon atom to which they are attached form a ring of formula of formula (c):

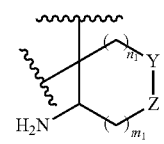

(c)

wherein:
m1 is 0, 1, or 2;
n1 is 0, 1, or 2; provided m1+n1 is 1, 2, or 3;
one of Y and Z is $CH_2$, O, S, SO, $SO_2$, or NH; and the other of X and Y is $CH_2$; and wherein ring of formula (c) is substituted with $R^n$ and/or $R^o$ independently selected from hydrogen, alkyl, halo, haloalkyl, haloalkoxy, alkoxy, hydroxy, cyano, alkylsulfoxide, alkylsulfonyl, and oxo; or
a pharmaceutically acceptable salt thereof.

In a third aspect, this disclosure is directed to a pharmaceutical composition comprising a compound of Formula (IA'), (I'), (I), (IA), (II), or (IIA) (or any of the embodiments thereof described herein), or a pharmaceutically acceptable salt thereof, and a pharmaceutically acceptable excipient.

In a fourth aspect, this disclosure is directed to a method of treating a disease treatable by inhibition of SHP2 in a patient which method comprises administering to the patient, preferably a patient in need of such treatment, a therapeutically effective amount of a compound of Formula (IA'), (I'), (I), (IA), (II), or (IIA) (or any of the embodiments thereof described herein), or comprises administering to the patient, preferably a patient in of such treatment, a pharmaceutical composition comprising a compound of Formula (IA'), (I'), (I), (IA), (II), or (IIA) (or any of the embodiments thereof described herein), and a pharmaceutically acceptable excipient. In one embodiment, the disease is cancer. In another embodiment, the disease is cancer selected from lung, stomach, liver, colon, kidney, breast, pancreatitis, juvenile myelomonocytic leukemias, neuroblastoma, melanoma, and acute myeloid leukemia. In one embodiment, the disease is selected from Noonan syndrome and Leopard syndrome.

In a fifth aspect, the disclosure is directed to a compound of Formula (IA'), (I'), (I), (IA), (II), or (IIA) (or any embodiments thereof described herein) or a pharmaceutically acceptable salt thereof for use as a medicament.

In a sixth aspect provided is the use of a compound of Formula (IA'), (I'), (I), (IA), (II), or (IIA) or a pharmaceutically acceptable salt thereof (and any embodiments thereof disclosed herein) in the manufacture of a medicament for treating a disease in a patient in need of such treatment in which the activity of SHP2 contributes to the pathology and/or symptoms of the disease.

In a seventh aspect provided is a method of inhibiting SHP2 which method comprises contacting SHP2 with a compound of Formula (IA'), (I'), (I), (IA), (II), or (IIA) (or any of the embodiments thereof described herein) or a pharmaceutically acceptable salt thereof; or contacting SHP2 with a pharmaceutical composition comprising a compound of Formula (IA'), (I'), (I), (IA), (II), or (IIA) (or any of the embodiments thereof described herein) or a pharmaceutically acceptable salt thereof, and a pharmaceutically acceptable excipient.

DETAILED DESCRIPTION

Definitions

Unless otherwise stated, the following terms used in the specification and claims are defined for the purposes of this Application and have the following meaning:

"Alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, butyl, pentyl, and the like. It will be recognized by a person skilled in the art that the term "alkyl" may include "alkylene" groups.

"Alkylene" means a linear saturated divalent hydrocarbon radical of one to six carbon atoms or a branched saturated divalent hydrocarbon radical of three to six carbon atoms unless otherwise stated e.g., methylene, ethylene, propylene, 1-methylpropylene, 2-methylpropylene, butylene, pentylene, and the like.

"Alkenyl" means a linear monovalent hydrocarbon radical of two to six carbon atoms or a branched monovalent hydrocarbon radical of three to six carbon atoms containing a double bond, e.g., propenyl, butenyl, and the like.

"Alkyldienyl" is alkenyl as defined above that is attached via the terminal divalent carbon. For example, in the compound below:

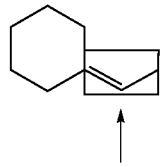

the alkyldienyl group is enclosed by the box which is indicated by the arrow.

"Alkylthio" means a —SR radical where R is alkyl as defined above, e.g., methylthio, ethylthio, and the like.

"Alkylsulfonyl" means a —SO$_2$R radical where R is alkyl as defined above, e.g., methylsulfonyl, ethylsulfonyl, and the like.

"Alkylsulfoxide" means a —SOR radical where R is alkyl as defined above, e.g., methylsulfoxide, ethylsulfoxide, and the like.

"Amino" means a —NH$_2$.

"Alkylamino" means a —NHR radical where R is alkyl as defined above, e.g., methylamino, ethylamino, propylamino, or 2-propylamino, and the like.

"Acylamino" means a —NHC(O)R radical where R is alkyl as defined above, e.g., acetylamino, propionoylamino, and the like.

"Aminoalkyl" means a linear monovalent hydrocarbon radical of one to six carbon atoms or a branched monovalent hydrocarbon radical of three to six carbons substituted with —NR'R" where R' and R" are independently hydrogen, alkyl, haloalkyl, hydroxyalkyl, alkoxyalkyl, or alkylcarbonyl, or R' and R" together with the nitrogen atom to which they are attached form optionally substituted heterocyclyl, each as defined herein, e.g., aminomethyl, aminoethyl, methylaminomethyl, morpholinylethyl, piperazin-1-ylethyl, and the like.

"Alkoxy" means a —OR radical where R is alkyl as defined above, e.g., methoxy, ethoxy, propoxy, or 2-propoxy, n-, iso-, or tert-butoxy, and the like.

"Alkoxyalkyl" means a linear monovalent hydrocarbon radical of one to six carbon atoms or a branched monovalent hydrocarbon radical of three to six carbons substituted with at least one alkoxy group, such as one or two alkoxy groups, as defined above, e.g., 2-methoxyethyl, 1-, 2-, or 3-methoxypropyl, 2-ethoxyethyl, and the like.

"Alkoxycarbonyl" means a —C(O)OR radical where R is alkyl as defined above, e.g., methoxycarbonyl, ethoxycarbonyl, and the like.

"Alkylcarbonyl" means a —C(O)R radical where R is alkyl as defined herein, e.g., methylcarbonyl, ethylcarbonyl, and the like.

"Aryl" means a monovalent monocyclic or bicyclic aromatic hydrocarbon radical of 6 to 10 ring atoms e.g., phenyl or naphthyl.

"Aralkyl" means -(alkylene)-R where R is aryl as defined above e.g., benzyl or phenethyl.

"Cycloalkyl" means a monocyclic saturated monovalent hydrocarbon radical of three to ten carbon atoms optionally substituted with one or two substituents independently selected from alkyl, halo, alkoxy, hydroxy, and cyano, unless stated otherwise. Examples include, but are not limited to, cyclopropyl, cyclobutyl, cyclopentyl, or cyclohexyl, and the like.

"Cycloalkylalkyl" means a -(alkylene)-R radical where R is cycloalkyl as defined above, e.g., cyclopropylmethyl, cyclohexylmethyl, and the like.

"Cycloalkylene" means a monocyclicsaturated bivalent hydrocarbon radical of three to six carbon atoms optionally substituted with one or two substituents independently selected from alkyl, halo, alkoxy, hydroxy, and cyano, each as defined herein. Examples include, but are not limited to, cyclopropylene, cyclobutylene, cyclopentylene, or cyclohexylene, and the like.

"Cycloalkyl fused bicyclic heteroaryl" means a bicyclic heteroaryl, as defined herein below, containing 9 or 10 rings atoms that is fused to a 5 or 6-membered cycloalkyl ring, as defined above, and which is attached to L through the 5- or 6-membered heteroaryl ring portion of the bicyclic heteroaryl ring e.g., 6,7,8,9-tetrahydro-5H-pyrido[3,2-b]indol-3-yl, and the like.

"Carboxy" means —C(O)OH.

"Dialkylamino" means a —NRR' radical where R and R' are alkyl as defined above, e.g., dimethylamino, methylethylamino, and the like.

"Aminosulfonyl" means a —SO$_2$NRR' radical where R and R' are independently hydrogen, alkyl, haloalkyl, hydroxyalkyl, or alkoxyalkyl, each as defined herein, e.g., aminosulfonyl, methylaminosulfonyl, dimethylaminosulfonyl, and the like.

"Aminocarbonyl" means a —SO$_2$NRR' radical where R and R' are independently hydrogen, alkyl, haloalkyl, hydroxyalkyl, or alkoxyalkyl, each as defined herein, e.g., aminocarbonyl, methylaminocarbonyl, dimethylaminocarbonyl, ethylmethylaminocarbonyl, and the like.

"Fused heteroaryl" means a bicyclic or tricyclic ring wherein a heteroaryl ring is fused to a heterocyclyl ring, each ring as defined herein. Examples include, but are not limited to, 6a,7,8,9-tetrahydro-6H-pyrido[3,2-b]pyrrolo[1,2-d][1,4]oxazine, 5,6,6a,7,8,9-hexahydropyrrolo[1,2-a][1,8]naphthyridine, 7,8-dihydro-6H-pyrrolo[2',1':2,3]imidazo[4,5-b]pyridine, 6'H,8'H-spiro[oxetane-3,7'-pyrrolo[2',1':2,3]imidazo[4,5-b]pyridine], 5,6,8,9-tetrahydropyrano[4',3':4,5]pyrrolo[2,3-b]pyridine, 5,7,8,9-tetrahydropyrano[3',4':4,5]-pyrrolo[2,3-b]pyridine, 1H-pyrrolo[2,3-b]pyridine, 1H-pyrrolo[3,2-b]pyridine, 5,6,7,9-tetrahydropyrano[3',4':4,5]pyrrolo[3,2-b]pyridine, 6a,7,8,9-tetrahydro-6H-pyrido[3,2-b]pyrrolo[1,2-d][1,4]oxazine, (S)-6a,7,8,9-tetrahydro-6H-pyrido[3,2-b]pyrrolo[1,2-d][1,4]oxazine, and (R)-6a,7,8,9-tetrahydro-6H-pyrido[3,2-b]pyrrolo[1,2-d][1,4]oxazine.

"Halo" means fluoro, chloro, bromo, or iodo, preferably fluoro or chloro.

"Haloalkyl" means alkyl radical as defined above, which is substituted with one or more halogen atoms, e.g., one to five halogen atoms, such as fluorine or chlorine, including those substituted with different halogens, e.g., —CH$_2$Cl, —CF$_3$, —CHF$_2$, —CH$_2$CF$_3$, —CF$_2$CF$_3$, —CF(CH$_3$)$_2$, and the like. When the alkyl is substituted with only fluoro, it can be referred to in this Application as fluoroalkyl.

"Haloalkoxy" means a —OR radical where R is haloalkyl as defined above e.g., —OCF$_3$, —OCHF$_2$, and the like. When R is haloalkyl where the alkyl is substituted with only fluoro, it is referred to in this Application as fluoroalkoxy.

"Hydroxyalkyl" means a linear monovalent hydrocarbon radical of one to six carbon atoms or a branched monovalent hydrocarbon radical of three to six carbons substituted with one or two hydroxy groups, provided that if two hydroxy groups are present they are not both on the same carbon atom. Representative examples include, but are not limited to, hydroxymethyl, 2-hydroxy-ethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl, preferably 2-hydroxyethyl, 2,3-dihydroxypropyl, and 1-(hydroxymethyl)-2-hydroxyethyl.

"Heterocyclyl" means a saturated or unsaturated monovalent monocyclic or bicyclic ring of 4 to 10 ring atoms in which one, two, or three ring atoms are heteroatom selected from N, O, and S(O)$_n$, where n is an integer from 0 to 2, the remaining ring atoms being C. Additionally, one or two ring carbon atoms in the heterocyclyl ring can optionally be replaced by a —CO— group. More specifically the term heterocyclyl includes, but is not limited to, pyrrolidinyl, piperidinyl, homopiperidinyl, 2-oxopyrrolidinyl, 2-oxopiperidinyl, morpholinyl, piperazinyl, tetrahydro-pyranyl, thiomorpholinyl, 6,7,8,9-tetrahydro-4H-pyrido[1,2-a]pyrimidin-4-one, 6,7-dihydropyrimido[2,1-c][1,4]oxazin-4(9H)-one, and the like. When the heterocyclyl ring is unsaturated it can contain one or two ring double bonds provided that the ring is not aromatic.

"Heterocyclylene" means a saturated or unsaturated bivalent monocyclic or bicyclic ring of 4 to 6 ring atoms in which one, two, or three ring atoms are heteroatom selected from N, O, and S(O)$_n$, where n is an integer from 0 to 2, the remaining ring atoms being C. Heterocyclylene can be optionally substituted with one or two substituents independently selected from alkyl, halo, haloalkyl, haloalkoxy, cyano, or hydroxy, each as defined herein.

"Heteroaryl" means a monovalent monocyclic or bicyclic aromatic radical of 5 to 10 ring atoms, unless otherwise stated, where one or more, (in one embodiment, one, two, or three), ring atoms are heteroatom selected from N, O, and S, the remaining ring atoms being carbon. Representative examples include, but are not limited to, pyrrolyl, thienyl, thiazolyl, imidazolyl, furanyl, indolyl, isoindolyl, oxazolyl, isoxazolyl, benzothiazolyl, benzoxazolyl, quinolinyl, isoquinolinyl, pyridinyl, pyrimidinyl, pyrazinyl, pyridazinyl, triazolyl, tetrazolyl, and the like. As defined herein, the terms "heteroaryl" and "aryl" are mutually exclusive. When the heteroaryl ring contains 5- or 6 ring atoms it is also referred to herein as 5- or 6-membered heteroaryl. When the heteroaryl ring is a bicyclic aromatic radical which contains 9- or 10 ring atoms, it is also referred to herein as bicyclic heteroaryl.

"Heteroaralkyl" means -(alkylene)-R where R is heteroaryl as defined above e.g., benzyl or phenethyl.

The term "oxo," as used herein, alone or in combination, refers to =(O).

When needed, any definition herein may be used in combination with any other definition to describe a composite structural group. By convention, the trailing element of any such definition is that which attaches to the parent moiety. For example, the composite group alkoxyalkyl means that an alkoxy group attached to the parent molecule through an alkyl group.

The present disclosure also includes protected derivatives of compounds of Formula (IA'), (I'), (I), (IA), (II), or (IIA). For example, when compounds of Formula (IA'), (I'), (I), (IA), (II), or (IIA) contain groups such as hydroxy, carboxy, thiol or any group containing a nitrogen atom(s), these groups can be protected with a suitable protecting groups. A comprehensive list of suitable protective groups can be found in T. W. Greene, Protective Groups in Organic Synthesis, 5$^{th}$ Ed., John Wiley & Sons, Inc. (2014), the disclosure of which is incorporated herein by reference in its entirety. The protected derivatives of compounds of Formula (IA'), (I'), (I), (IA), (II), or (IIA) can be prepared by methods well known in the art.

The present disclosure also includes polymorphic forms and deuterated forms of the compound of Formula (IA'), (I'), (I), (IA), (II), or (IIA) and/or a pharmaceutically acceptable salt thereof.

The term "prodrug" refers to a compound that is made more active in vivo. Certain compounds disclosed herein may also exist as prodrugs, as described in Hydrolysis in Drug and Prodrug Metabolism. Chemistry, Biochemistry, and Enzymology (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the active compound. Prodrugs are often useful because, in some situations, they may be easier to administer than the compound, or parent drug. They may, for instance, be bioavailable by oral administration whereas the parent drug is not. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

A "pharmaceutically acceptable salt" of a compound means a salt that is pharmaceutically acceptable and that possesses the desired pharmacological activity of the parent compound. Such salts include:

acid addition salts, formed with inorganic acids such as hydrochloric acid, hydrobromic acid, sulfuric acid, nitric acid, phosphoric acid, and the like; or formed with organic acids such as formic acid, acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference in its entirety.

The compounds of Formula (IA'), (I'), (I), (IA), (II), and (IIA) may have asymmetric centers. Compounds of Formula (IA'), (I'), (I), (IA), (II), and (IIA) containing an asymmetrically substituted atom may be isolated in optically active or racemic forms. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. All chiral, diastereomeric, all mixtures of chiral or diasteromeric forms, and racemic forms are within the scope of this disclosure, unless the specific stereochemistry or isomeric form is specifically indicated. It will also be understood by a person of ordinary skill in the art that when a compound is denoted as (R) stereoisomer, it may contain the corresponding (S) stereoisomer as an impurity and vice versa.

Certain compounds of Formula (IA'), (I'), (I), (IA), (II), and (IIA) can exist as tautomers and/or geometric isomers. All possible tautomers and cis and trans isomers, as individual forms and mixtures thereof are within the scope of this disclosure. Additionally, as used herein the term alkyl includes all the possible isomeric forms of said alkyl group albeit only a few examples are set forth. Furthermore, when the cyclic groups such as aryl, heteroaryl, heterocyclyl are substituted, they include all the positional isomers albeit only a few examples are set forth. Furthermore, all hydrates of a compound of Formula (IA'), (I'), (I), (IA), (II), and (IIA) are within the scope of this disclosure.

The compounds of Formula (IA'), (I'), (I), (IA), (II), and (IIA) may also contain unnatural amounts of isotopes at one or more of the atoms that constitute such compounds. Unnatural amounts of an isotope may be defined as ranging from the amount found in nature to an amount 100% of the atom in question. that differ only in the presence of one or more isotopically enriched atoms. Exemplary isotopes that can be incorporated into compounds of the present invention, for example a compound of Formula (I) (and any embodiments thereof disclosed herein including specific compounds) include isotopes of hydrogen, carbon, nitrogen, oxygen, phosphorus, sulfur, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$, and $^{125}I$ respectively. Isotopically-labeled compounds (e.g., those labeled with $^{3}H$ and $^{14}C$) can be useful in compound or substrate tissue distribution assays. Tritiated (i.e., $^{3}H$) and carbon-14 (i.e., $^{14}C$) isotopes can be useful for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements). In some embodiments, in compounds disclosed herein, including in Table 1 below one or more hydrogen atoms are replaced by $^{2}H$ or $^{3}H$, or one or more carbon atoms are replaced by $^{13}C$- or $^{14}C$-enriched carbon. Positron emitting isotopes such as $^{15}O$, $^{13}N$, $^{11}C$, and $^{15}F$ are useful for positron emission tomography (PET) studies to examine substrate receptor occupancy. Isotopically labeled compounds can generally be prepared by following procedures analogous to those disclosed in the Schemes or in the Examples herein, by substituting an isotopically labeled reagent for a non-isotopically labeled reagent.

"Optionally substituted aryl" means aryl that is optionally substituted with one, two, or three substituents independently selected from alkyl, hydroxyl, cycloalkyl, carboxy, alkoxycarbonyl, hydroxy, alkoxy, alkylthio, alkylsulfonyl, amino, alkylamino, dialkylamino, halo, haloalkyl, haloalkoxy, and cyano.

"Optionally substituted aralkyl" means -(alkylene)-R where R is optionally substituted aryl as defined above.

"Optionally substituted heteroaryl" means heteroaryl as defined above that is optionally substituted with one, two, or three substituents independently selected from alkyl, alkylthio, alkylsulfonyl, hydroxyl, cycloalkyl, carboxy, alkoxycarbonyl, hydroxy, alkoxy, halo, haloalkyl, haloalkoxy, amino, alkylamino, dialkylamino, and cyano.

"Optionally substituted heteroaralkyl" means -(alkylene)-R where R is optionally substituted heteroaryl as defined above.

"Optionally substituted heterocyclyl" means heterocyclyl as defined above that is optionally substituted with one, two, or three substituents independently selected from alkyl, alkylthio, alkylsulfonyl, hydroxyl, cycloalkyl, carboxy, alkoxycarbonyl, hydroxy, hydroxyalkyl, alkoxy, alkoxyalkyl, aminoalkyl, halo, haloalkyl, haloalkoxy, and cyano.

"Optionally substituted heterocyclylalkyl" means -(alkylene)-R where R is optionally substituted heterocyclyl as defined above.

A "pharmaceutically acceptable carrier or excipient" means a carrier or an excipient that is useful in preparing a pharmaceutical composition that is generally safe, non-toxic and neither biologically nor otherwise undesirable, and includes a carrier or an excipient that is acceptable for veterinary use as well as human pharmaceutical use. "A pharmaceutically acceptable carrier/excipient" as used in the specification and claims includes both one and more than one such excipient.

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass 10%, preferably +5%, the recited value and the range is included.

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a disease or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

The term "patient" is generally synonymous with the term "subject" and includes all mammals including humans. Examples of patients include humans, livestock such as cows, goats, sheep, pigs, and rabbits, and companion animals such as dogs, cats, rabbits, and horses. Preferably, the patient is a human. "Treating" or "treatment" of a disease includes:

(1) preventing the disease, i.e. causing the clinical symptoms of the disease not to develop in a mammal that may be exposed to or predisposed to the disease but does not yet experience or display symptoms of the disease;

(2) inhibiting the disease, i.e., arresting or reducing the development of the disease or its clinical symptoms; or (3) relieving the disease, i.e., causing regression of the disease or its clinical symptoms.

A "therapeutically effective amount" means the amount of a compound of Formula (IA'), (I'), (I), (IA), (II), or (IIA) and/or a pharmaceutically acceptable salt thereof that, when administered to a patient for treating a disease, is sufficient to affect such treatment for the disease. The "therapeutically effective amount" will vary depending on the compound, the disease and its severity and the age, weight, etc., of the mammal to be treated.

The terms "inhibiting" and "reducing," or any variation of these terms in relation of SHP2, includes any measurable decrease or complete inhibition to achieve a desired result. For example, there may be a decrease of about, at most about, or at least about 5%, 10%, 15%, 20%, 25%, 30%, 35%, 40%, 45%, 50%, 55%, 60%, 65%, 70%, 75%, 80%, 85%, 90%, 95%, 99%, or more, or any range derivable therein, reduction of SHP2 activity compared to normal.

Representative compounds of Formula (I) are disclosed in Table (I) below

TABLE 1

| Compound number | structure | name |
| --- | --- | --- |
| 1 | 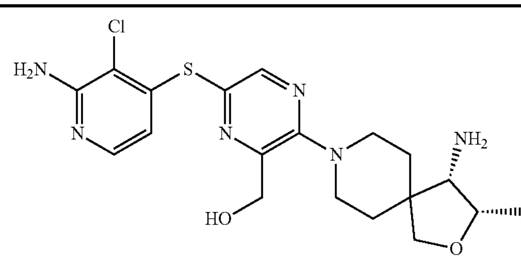 | (6-((2-amino-3-chloropyridin-4-yl)thio)-3-((3S,4S)-4-amino-3-methyl-2-oxa-8-azaspiro[4.5]decan-8-yl)pyrazin-2-yl)methanol |
| 2 | 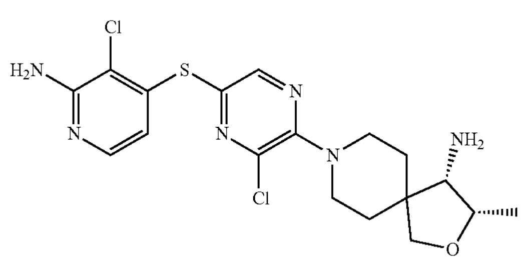 [SMILES: C[C@@H]1OCC2(CCN(c3ncc(Sc4ccnc(N)c4Cl)nc3Cl)CC2)[C@@H]1N] | (3S,4S)-8-(5-((2-amino-3-chloropyridin-4-yl)thio)-3-chloropyrazin-2-yl)-3-methyl-2-oxa-8-azaspiro[4.5]decan-4-amine |

TABLE 1-continued

| Compound number | structure | name |
|---|---|---|
| 3 | 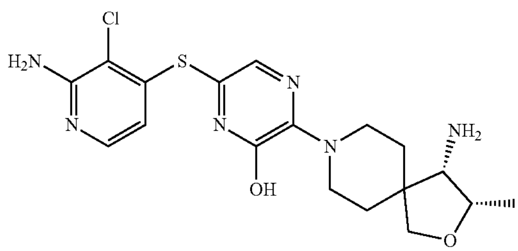 [SMILES: C[C@@H]1OCC2(CCN(c3ncc(Sc4ccnc(N)c4Cl)nc3O)CC2)[C@@H]1N] | 6-((2-amino-3-chloropyridin-4-yl)thio)-3-((3S,4S)-4-amino-3-methyl-2-oxa-8-azaspiro[4.5]decan-8-yl)pyrazin-2-ol |
| 4 | 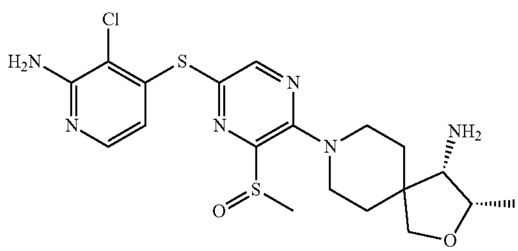 [SMILES: C[C@@H]1OCC2(CCN(c3ncc(Sc4ccnc(N)c4Cl)nc3S(C)=O)CC2)[C@@H]1N] | (3S,4S)-8-(5-((2-amino-3-chloropyridin-4-yl)thio)-3-(methylsulfinyl)pyrazin-2-yl)-3-methyl-2-oxa-8-azaspiro[4.5]decan-4-amine |
| 5 | 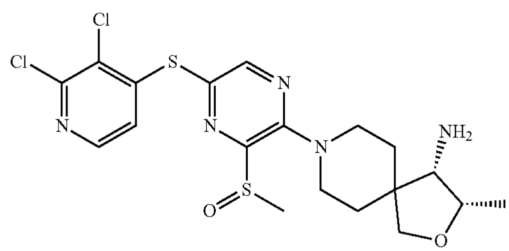 [SMILES: C[C@@H]1OCC2(CCN(c3ncc(Sc4ccnc(Cl)c4Cl)nc3S(C)=O)CC2)[C@@H]1N] | (3S,4S)-8-(5-((2,3-dichloropyridin-4-yl)thio)-3-(methylsulfinyl)pyrazin-2-yl)-3-methyl-2-oxa-8-azaspiro[4.5]decan-4-amine |
| 6 | 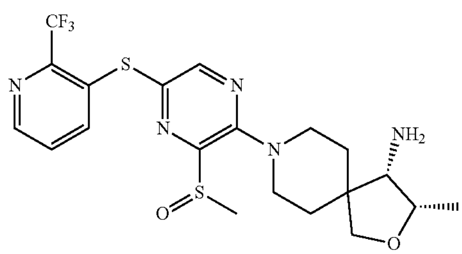 [SMILES: C[C@@H]1OCC2(CCN(c3ncc(Sc4cccnc4C(F)(F)F)nc3S(C)=O)CC2)[C@@H]1N] | (3S,4S)-3-methyl-8-(3-(methylsulfinyl)-5-(2-(trifluoromethyl)pyridin-3-yl)thio)pyrazin-2-yl)-2-oxa-8-azaspiro[4.5]decan-4-amine |
| 7 | 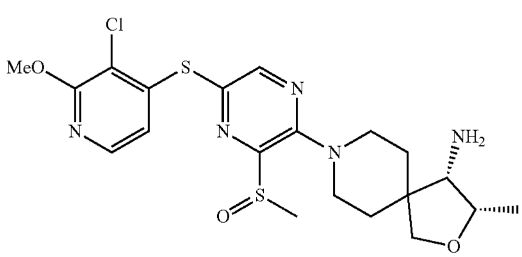 [SMILES: COc1nccc(Sc2cnc(N3CCC4(CC3)CO[C@@H](C)[C@H]4N)c(S(C)=O)n2)c1Cl] | (3S,4S)-8-(5-((3-chloro-2-methoxypyridin-4-yl)thio)-3-(methylsulfinyl)pyrazin-2-yl)-3-methyl-2-oxa-8-azaspiro[4.5]decan-4-amine |
| 8 | 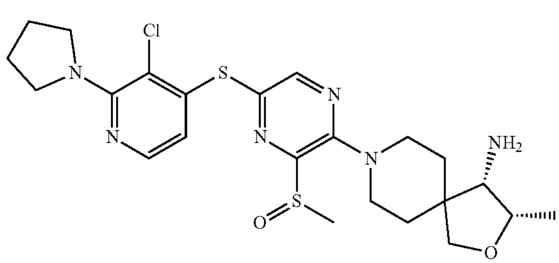 [SMILES: C[C@@H]1OCC2(CCN(c3ncc(Sc4ccnc(N5CCCC5)c4Cl)nc3S(C)=O)CC2)[C@@H]1N] | (3S,4S)-8-(5-((3-chloro-2-(pyrrolidin-1-yl)pyridin-4-yl)thio)-3-(methylsulfinyl)pyrazin-2-yl)-3-methyl-2-oxa-8-azaspiro[4.5]decan-4-amine |

TABLE 1-continued

| Compound number | structure | name |
|---|---|---|
| 9 | 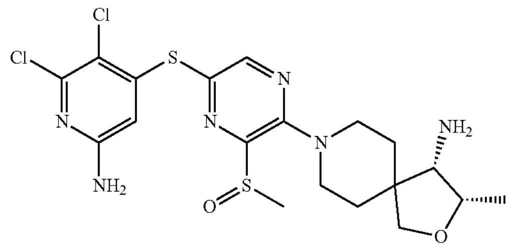 [SMILES: C[C@@H]1OCC2(CCN(c3ncc(Sc4cc(N)nc(Cl)c4Cl)nc3S(C)=O)CC2)[C@@H]1N] | (3S,4S)-8-(5-(((6-amino-2,3-dichloropyridin-4-yl)thio)-3-(methylsulfinyl)pyrazin-2-yl)-3-methyl-2-oxa-8-azaspiro[4.5]decan-4-amine |
| 10 | 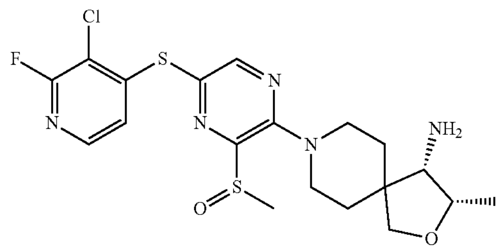 [SMILES: C[C@@H]1OCC2(CCN(c3ncc(Sc4ccnc(F)c4Cl)nc3S(C)=O)CC2)[C@@H]1N] | (3S,4S)-8-(5-(((3-chloro-2-fluoropyridin-4-yl)thio)-3-(methylsulfinyl)pyrazin-2-yl)-3-methyl-2-oxa-8-azaspiro[4.5]decan-4-amine |
| 11 | 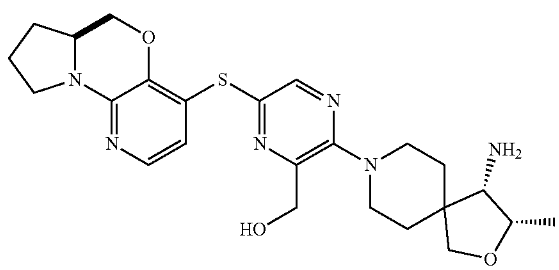 | (3-((3S,4S)-4-amino-3-methyl-2-oxa-8-azaspiro[4.5]decan-8-yl)-6-(((S)-6a,7,8,9-tetrahydro-6H-pyrido[3,2-b]pyrrolo[1,2-d][1,4]oxazin-4-yl)thio)pyrazin-2-yl)methanol |
| 12 | 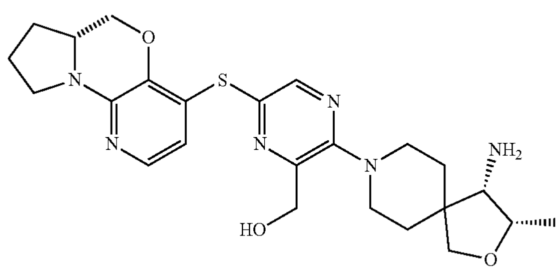 | (3-((3S,4S)-4-amino-3-methyl-2-oxa-8-azaspiro[4.5]decan-8-yl)-6-(((R)-6a,7,8,9-tetrahydro-6H-pyrido[3,2-b]pyrrolo[1,2-d][1,4]oxazin-4-yl)thio)pyrazin-2-yl)methanol |
| 13 | 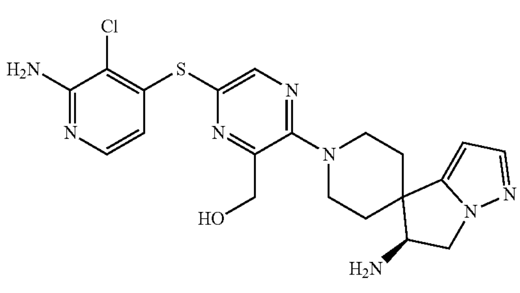 [SMILES: Nc1nccc(Sc2cnc(N3CCC4(CC3)c3ccnn3C[C@H]4N)c(CO)n2)c1Cl] | (S)-(6-((2-amino-3-chloropyridin-4-yl)thio)-3-(5'-amino-5',6'-dihydrospiro[piperidine-4,4'-pyrrolo[1,2-b]pyrazol]-1-yl)pyrazin-2-yl)methanol |

TABLE 1-continued

| Compound number | structure | name |
|---|---|---|
| 14 | 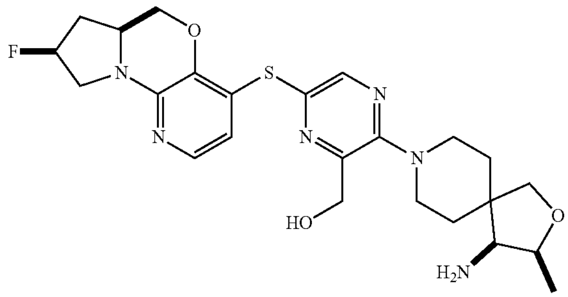 | (3-((3S,4S)-4-amino-3-methyl-2-oxa-8-azaspiro[4.5]decan-8-yl)-6-(((6aS,8S)-8-fluoro-6a,7,8,9-tetrahydro-6H-pyrido[3,2-b]pyrrolo[1,2-d][1,4]oxazin-4-yl)thio)pyrazin-2-yl)methanol |
| 15 | 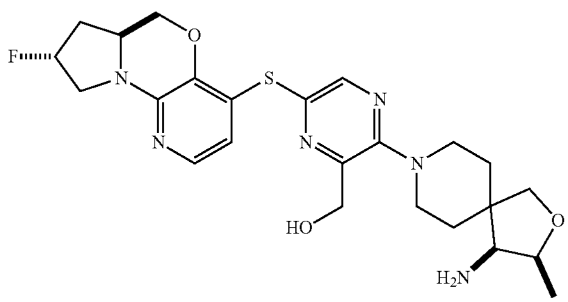 | (3-((3S,4S)-4-amino-3-methyl-2-oxa-8-azaspiro[4.5]decan-8-yl)-6-((((6aS,8R)-8-fluoro-6a,7,8,9-tetrahydro-6H-pyrido[3,2-b]pyrrolo[1,2-d][1,4]oxazin-4-yl)thio)pyrazin-2-yl)methanol |
| 16 | 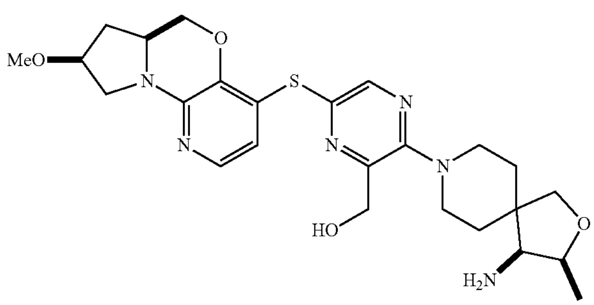 | (3-((3S,4S)-4-amino-3-methyl-2-oxa-8-azaspiro[4.5]decan-8-yl)-6-((((6aS,8S)-8-methoxy-6a,7,8,9-tetrahydro-6H-pyrido[3,2-b]pyrrolo[1,2-d][1,4]oxazin-4-yl)thio)pyrazin-2-yl)methanol |
| 17 | 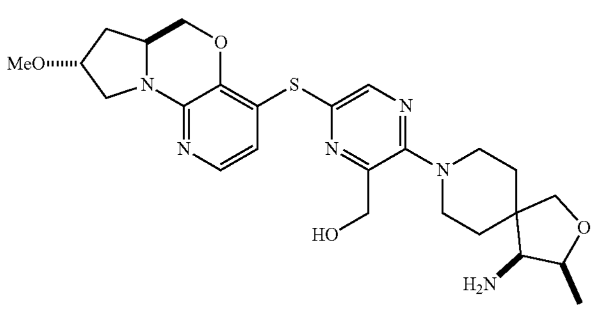 | (3-((3S,4S)-4-amino-3-methyl-2-oxa-8-azaspiro[4.5]decan-8-yl)-6-((((6aS,8R)-8-methoxy-6a,7,8,9-tetrahydro-6H-pyrido[3,2-b]pyrrolo[1,2-d][1,4]oxazin-4-yl)thio)pyrazin-2-yl)methanol |
| 18 | 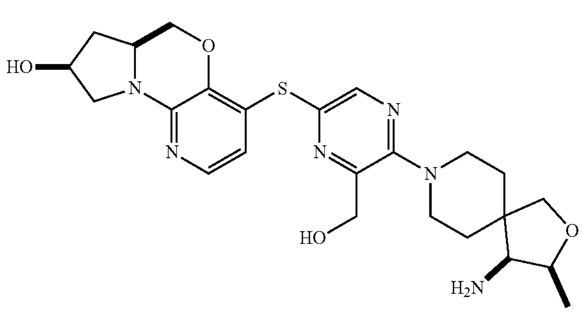 | (6aS,8S)-4-((5-((3S,4S)-4-amino-3-methyl-2-oxa-8-azaspiro[4.5]decan-8-yl)-6-(hydroxymethyl)pyrazin-2-yl)thio)-6a,7,8,9-tetrahydro-6H-pyrido[3,2-b]pyrrolo[1,2-d][1,4]oxazin-8-ol |

TABLE 1-continued

| Compound number | structure | name |
|---|---|---|
| 19 | 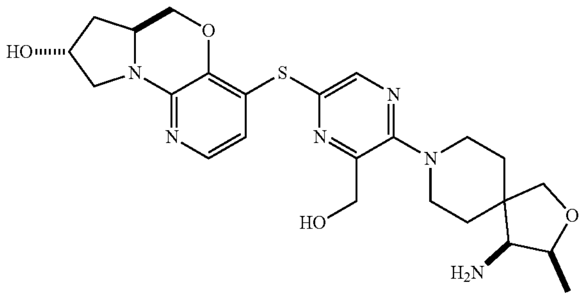 | (6aS,8R)-4-((5-((3S,4S)-4-amino-3-methyl-2-oxa-8-azaspiro[4.5]decan-8-yl)-6-(hydroxymethyl)pyrazin-2-yl)thio)-6a,7,8,9-tetrahydro-6H-pyrido[3,2-b]pyrrolo[1,2-d][1,4]oxazin-8-ol |
| 20 | 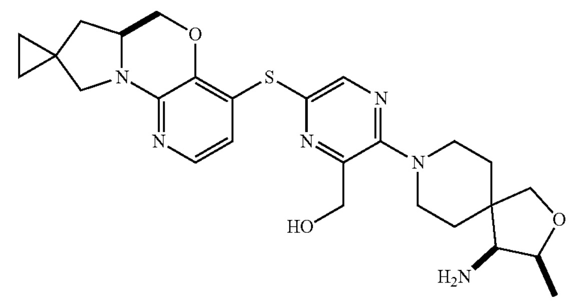 | (3-((3S,4S)-4-amino-3-methyl-2-oxa-8-azaspiro[4.5]decan-8-yl)-6-(((S)-6a',7'-dihydro-6'H,9'H-spiro[cyclopropane-1,8'-pyrido[3,2-b]pyrrolo[1,2-d][1,4]oxazin]-4'-yl)thio)pyrazin-2-yl)methanol |
| 21, | 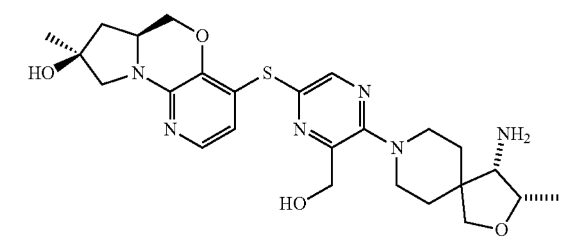 | of (6aS,8S)-4-((5-((3S,4S)-4-amino-3-methyl-2-oxa-8-azaspiro[4.5]decan-8-yl)-6-(hydroxymethyl)pyrazin-2-yl)thio)-8-methyl-6a,7,8,9-tetrahydro-6H-pyrido[3,2-b]pyrrolo[1,2-d][1,4]oxazin-8-ol |
| 22 | 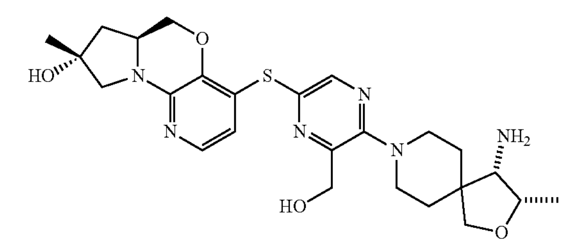 | (6aS,8R)-4-((5-((3S,4S)-4-amino-3-methyl-2-oxa-8-azaspiro[4.5]decan-8-yl)-6-(hydroxymethyl)pyrazin-2-yl)thio)-8-methyl-6a,7,8,9-tetrahydro-6H-pyrido[3,2-b]pyrrolo[1,2-d][1,4]oxazin-8-ol |
| 23, | 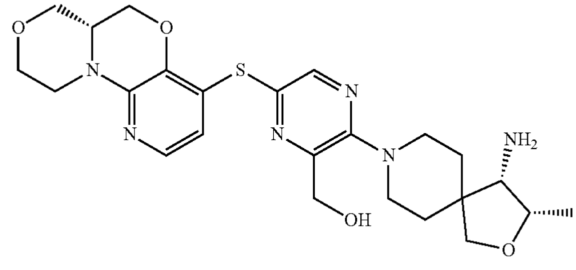 [SMILES: C[C@@H]1OCC2(CCN(c3ncc(Sc4ccnc5c4OC[C@H]4COCCN54)nc3CO)CC2)[C@@H]1N] | of (3-((3S,4S)-4-amino-3-methyl-2-oxa-8-azaspiro[4.5]decan-8-yl)-6-(((R)-6a,7,9,10-tetrahydro-6H-[1,4]oxazino[4,3-d]pyrido[3,2-b][1,4]oxazin-4-yl)thio)pyrazin-2-yl)methanol |

TABLE 1-continued

| Compound number | structure | name |
|---|---|---|
| 24 | 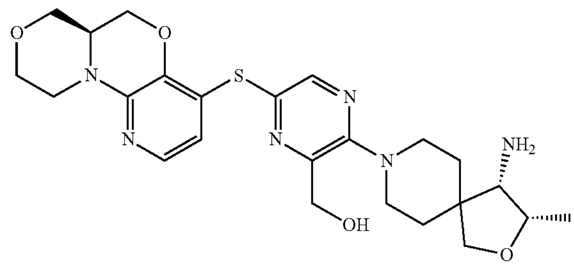 [SMILES: C[C@@H]1OCC2(CCN(c3ncc(Sc4ccnc5c4OC[C@@H]4COCCN54)nc3CO)CC2)[C@@H]1N] | (3-((3S,4S)-4-amino-3-methyl-2-oxa-8-azaspiro[4.5]decan-8-yl)-6-(((S)-6a,7,9,10-tetrahydro-6H-[1,4]oxazino[4,3-d]pyrido[3,2-b][1,4]oxazin-4-yl)thio)pyrazin-2-yl)methanol |
| 25 | 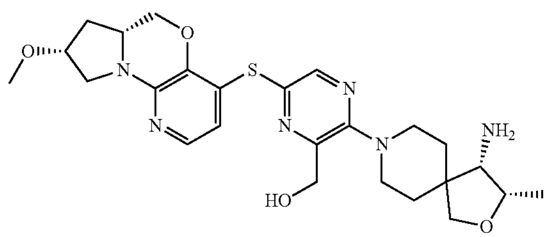 | (3-((3S,4S)-4-amino-3-methyl-2-oxa-8-azaspiro[4.5]decan-8-yl)-6-(((6aR,8R)-8-methoxy-6a,7,8,9-tetrahydro-6H-pyrido[3,2-b]pyrrolo[1,2-d][1,4]oxazin-4-yl)thio)pyrazin-2-yl)methanol |
| 26 | 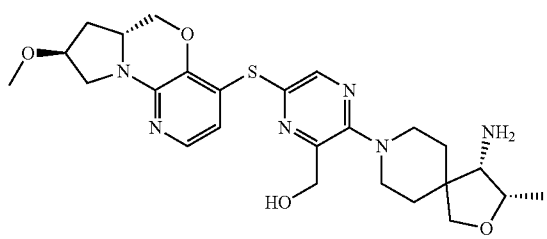 | [3-[(3S,4S)-4-amino-3-methyl-2-oxa-8-azaspiro[4.5]decan-8-yl]-6-[[(4S,6R)-4-methoxy-8-oxa-2,13-diazatricyclo[7.4.0.0^[2,6]]trideca-1(13),9,11-trien-10-yl]sulfanyl]pyrazin-2-yl]methanol |
| 27 | 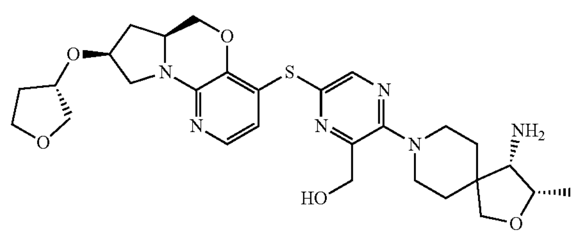 [SMILES: C[C@@H]1OCC2(CCN(c3ncc(Sc4ccnc5c4OC[C@@H]4C[C@H](O[C@H]6CCOC6)CN54)nc3CO)CC2)[C@@H]1N] | (3-((3S,4S)-4-amino-3-methyl-2-oxa-8-azaspiro[4.5]decan-8-yl)-6-(((6aS,8S)-8-(((S)-tetrahydrofuran-3-yl)oxy)-6a,7,8,9-tetrahydro-6H-pyrido[3,2-b]pyrrolo[1,2-d][1,4]oxazin-4-yl)thio)pyrazin-2-yl)methanol |
| 28 | 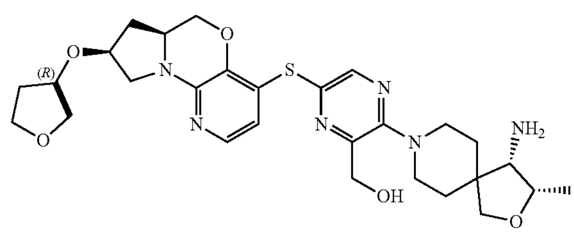 | (3-((3S,4S)-4-amino-3-methyl-2-oxa-8-azaspiro[4.5]decan-8-yl)-6-(((6aS,8S)-8-(((R)-tetrahydrofuran-3-yl)oxy)-6a,7,8,9-tetrahydro-6H-pyrido[3,2-b]pyrrolo[1,2-d][1,4]oxazin-4-yl)thio)pyrazin-2-yl)methanol |
| 29 | 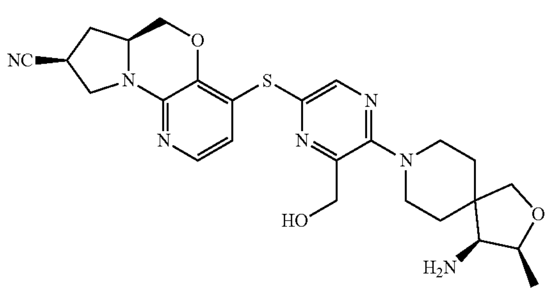 [SMILES: C[C@@H]1OCC2(CCN(c3ncc(Sc4ccnc5c4OC[C@@H]4C[C@H](C#N)CN54)nc3CO)CC2)[C@@H]1N] | (6aS,8S)-4-((5-((3S,4S)-4-amino-3-methyl-2-oxa-8-azaspiro[4.5]decan-8-yl)-6-(hydroxymethyl)pyrazin-2-yl)thio)-6a,7,8,9-tetrahydro-6H-pyrido[3,2-b]pyrrolo[1,2-d][1,4]oxazine-8-carbonitrile |

TABLE 1-continued

| Compound number | structure | name |
|---|---|---|
| 30 | 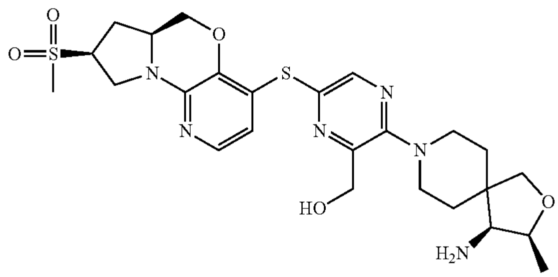 [SMILES: C[C@@H]1OCC2(CCN(c3ncc(Sc4ccnc5c4OC[C@@H]4C[C@H](S(C)(=O)=O)CN54)nc3CO)CC2)[C@@H]1N] | (3-((3S,4S)-4-amino-3-methyl-2-oxa-8-azaspiro[4.5]decan-8-yl)-6-((((6aS,8S)-8-(methylsulfonyl)-6a,7,8,9-tetrahydro-6H-pyrido[3,2-b]pyrrolo[1,2-d][1,4]oxazin-4-yl)thio)pyrazin-2-yl)methanol |
| 31 | 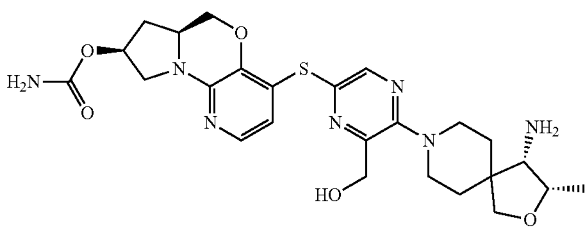 [SMILES: C[C@@H]1OCC2(CCN(c3ncc(Sc4ccnc5c4OC[C@@H]4C[C@H](OC(N)=O)CN54)nc3CO)CC2)[C@@H]1N] | (6aS,8S)-4-((5-((3S,4S)-4-amino-3-methyl-2-oxa-8-azaspiro[4.5]decan-8-yl)-6-(hydroxymethyl)pyrazin-2-yl)thio)-6a,7,8,9-tetrahydro-6H-pyrido[3,2-b]pyrrolo[1,2-d][1,4]oxazin-8-ylcarbamate |
| 32 | 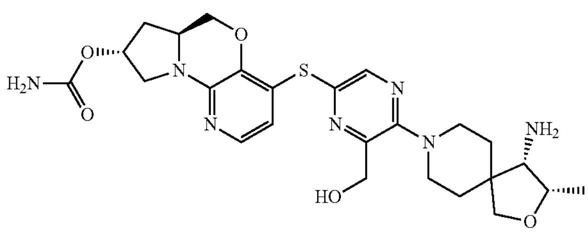 [SMILES: C[C@@H]1OCC2(CCN(c3ncc(Sc4ccnc5c4OC[C@@H]4C[C@@H](OC(N)=O)CN54)nc3CO)CC2)[C@@H]1N] | (6aS,8R)-4-((5-((3S,4S)-4-amino-3-methyl-2-oxa-8-azaspiro[4.5]decan-8-yl)-6-(hydroxymethyl)pyrazin-2-yl)thio)-6a,7,8,9-tetrahydro-6H-pyrido[3,2-b]pyrrolo[1,2-d][1,4]oxazin-8-yl carbamate |
| 33 | 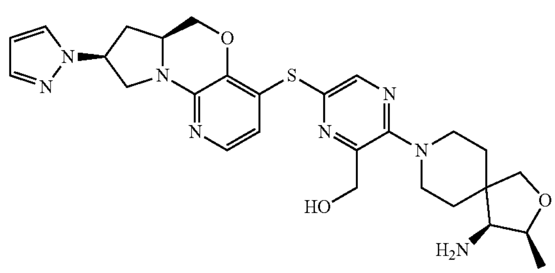 [SMILES: C[C@@H]1OCC2(CCN(c3ncc(Sc4ccnc5c4OC[C@@H]4C[C@H](n6cccn6)CN54)nc3CO)CC2)[C@@H]1N] | (6-((((6aS,8S)-8-(1H-pyrazol-1-yl)-6a,7,8,9-tetrahydro-6H-pyrido[3,2-b]-pyrrolo[1,2-d][1,4]oxazin-4-yl)thio)-3-((3S,4S)-4-amino-3-methyl-2-oxa-8-azaspiro[4.5]decan-8-yl)pyrazin-2-yl)methanol |
| 34 | 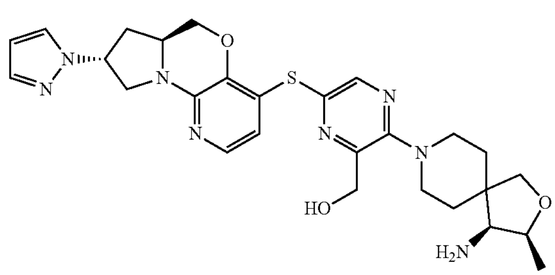 [SMILES: C[C@@H]1OCC2(CCN(c3ncc(Sc4ccnc5c4OC[C@@H]4C[C@@H](n6cccn6)CN54)nc3CO)CC2)[C@@H]1N] | (6-((((6aS,8R)-8-(1H-pyrazol-1-yl)-6a,7,8,9-tetrahydro-6H-pyrido[3,2-b]-pyrrolo[1,2-d][1,4]oxazin-4-yl)thio)-3-((3S,4S)-4-amino-3-methyl-2-oxa-8-azaspiro[4.5]decan-8-yl)pyrazin-2-yl)methanol |
| 35 | 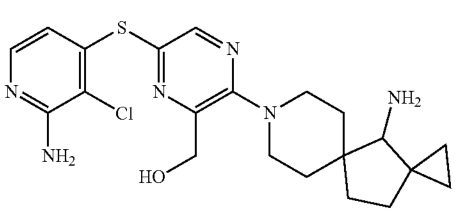 [SMILES: Nc1nccc(Sc2cnc(N3CCC4(CC3)CCC3(CC3)C4N)c(CO)n2)c1Cl] | (6-((2-amino-3-chloropyridin-4-yl)thio)-3-(4-amino-8-azadispiro-[2.1.55.23]dodecan-8-yl)pyrazin-2-yl)methanol |

TABLE 1-continued

| Compound number | structure | name |
|---|---|---|
| 36 | 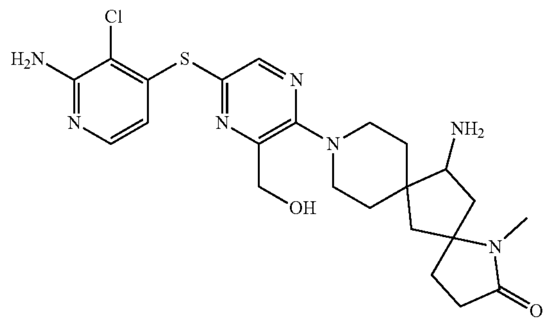 [SMILES: CN1C(=O)CCC12CC(N)C1(CCN(c3ncc(Sc4ccnc(N)c4Cl)nc3CO)CC1)C2] | 13-amino-10-(5-((2-amino-3-chloropyridin-4-yl)thio)-3-(hydroxymethyl)-pyrazin-2-yl)-1-methyl-1,10-diazadispiro[4.1.57.25]tetradecan-2-one |
| 37 | 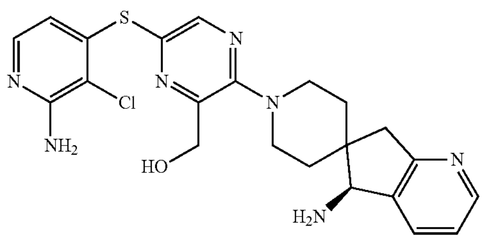 [SMILES: Nc1nccc(Sc2cnc(N3CCC4(CC3)Cc3ncccc3[C@H]4N)c(CO)n2)c1Cl] | (S)-(6-((2-amino-3-chloropyridin-4-yl)thio)-3-(5-amino-5,7-dihydrospiro-[cyclopenta[b]pyridine-6,4'-piperidin]-1'-yl)pyrazin-2-yl)methanol |
| 38 | 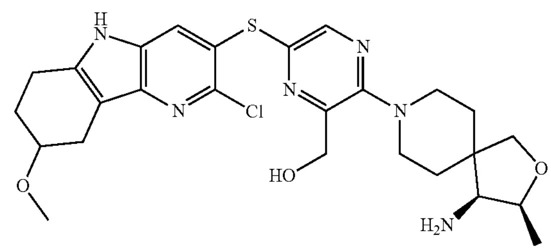 [SMILES: COC1CCc2[nH]c3cc(Sc4cnc(N5CCC6(CC5)CO[C@@H](C)[C@H]6N)c(CO)n4)c(Cl)nc3c2C1] | of (3-((3S,4S)-4-amino-3-methyl-2-oxa-8-azaspiro[4.5]decan-8-yl)-6-((2-chloro-8-methoxy-6,7,8,9-tetrahydro-5H-pyrido[3,2-b]indol-3-yl)thio)pyrazin-2-yl)-methanol |
| 39 | 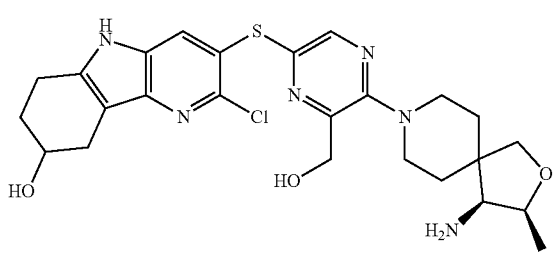 | 3-((5-((3S,4S)-4-amino-3-methyl-2-oxa-8-azaspiro[4.5]decan-8-yl)-6-(hydroxymethyl)pyrazin-2-yl)thio)-2-chloro-6,7,8,9-tetrahydro-5H-pyrido[3,2-b]indol-8-ol formate |
| 40 | 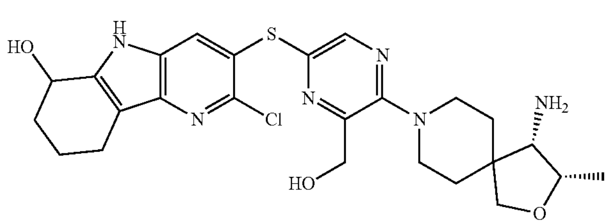 [SMILES: C[C@@H]1OCC2(CCN(c3ncc(Sc4cc5[nH]c6c(c5nc4Cl)CCCC6O)nc3CO)CC2)[C@@H]1N] | 3-((5-((3S,4S)-4-amino-3-methyl-2-oxa-8-azaspiro[4.5]decan-8-yl)-6-(hydroxymethyl) pyrazin-2-yl)thio)-2-chloro-6,7,8,9-tetrahydro-5H-pyrido[3,2-b]indol-6-ol |

Additional compounds of Formula (I) contemplated are provided in Table 2 below.
TABLE 2
| | |
|---|---|
| 1 | 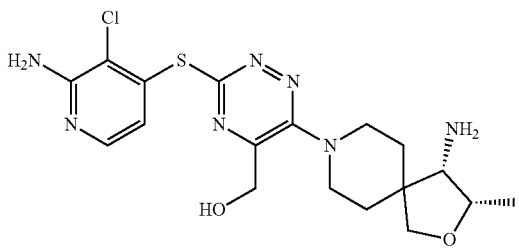 |
| 2 | 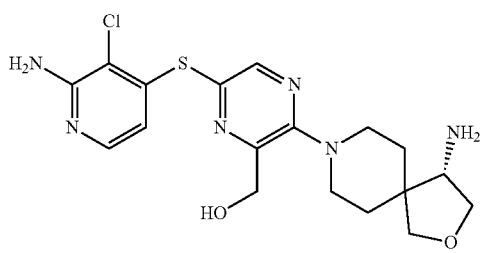 [SMILES: Nc1nccc(Sc2cnc(N3CCC4(CC3)COC[C@H]4N)c(CO)n2)c1Cl] |
| 3 | 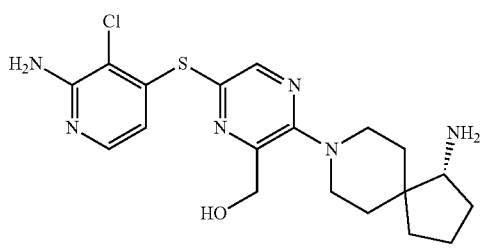 [SMILES: Nc1nccc(Sc2cnc(N3CCC4(CCC[C@H]4N)CC3)c(CO)n2)c1Cl] |
| 4 | 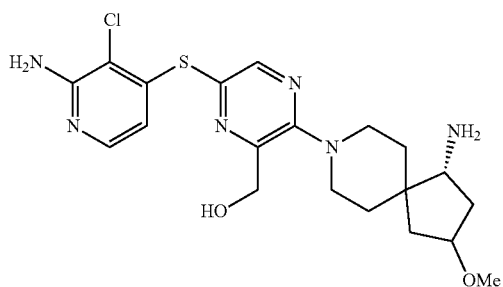 [SMILES: COC1C[C@@H](N)C2(CCN(c3ncc(Sc4ccnc(N)c4Cl)nc3CO)CC2)C1] |
| 5 | 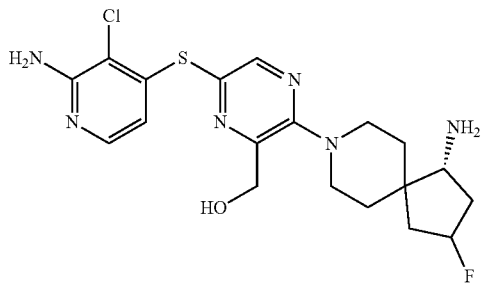 [SMILES: Nc1nccc(Sc2cnc(N3CCC4(CC3)CC(F)C[C@H]4N)c(CO)n2)c1Cl] |
| 6 | 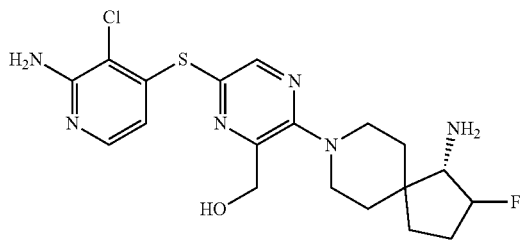 [SMILES: Nc1nccc(Sc2cnc(N3CCC4(CCC(F)[C@H]4N)CC3)c(CO)n2)c1Cl] |

TABLE 2-continued
| 7 | 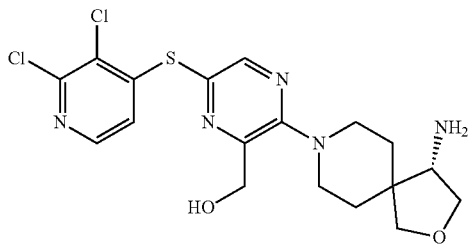 [SMILES: N[C@@H]1COCC12CCN(c1ncc(Sc3ccnc(Cl)c3Cl)nc1CO)CC2] |
| --- | --- |
| 8 | 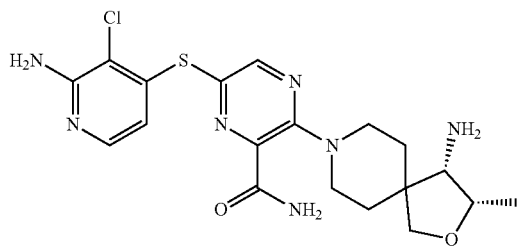 [SMILES: C[C@@H]1OCC2(CCN(c3ncc(Sc4ccnc(N)c4Cl)nc3C(N)=O)CC2)[C@@H]1N] |
| 17 | 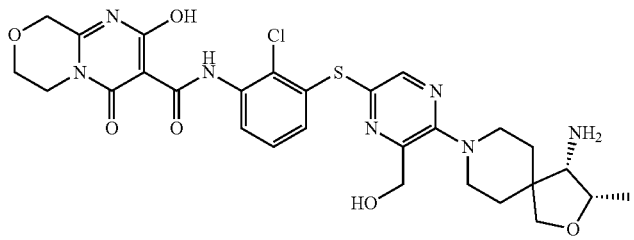 [SMILES: C[C@@H]1OCC2(CCN(c3ncc(Sc4cccc(NC(=O)c5c(O)nc6n(c5=O)CCOC6)c4Cl)nc3CO)CC2)[C@@H]1N] |
| 9 | 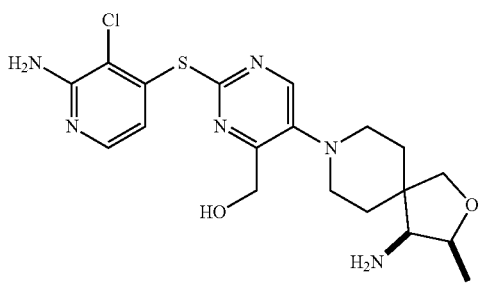 [SMILES: C[C@@H]1OCC2(CCN(c3cnc(Sc4ccnc(N)c4Cl)nc3CO)CC2)[C@@H]1N] |
| 10 | 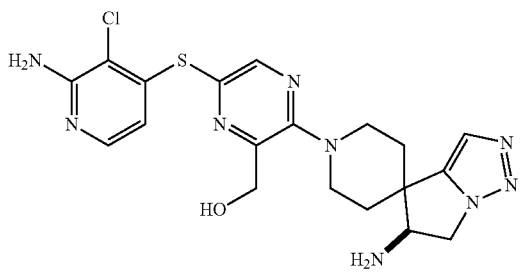 [SMILES: Nc1nccc(Sc2cnc(N3CCC4(CC3)c3cnnn3C[C@H]4N)c(CO)n2)c1Cl] |
| 11 | 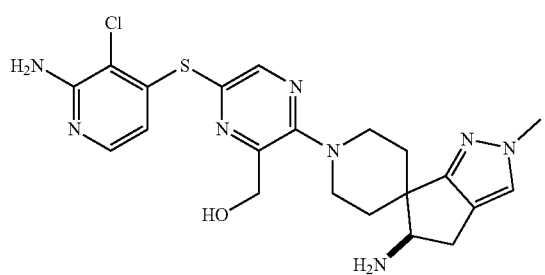 [SMILES: Cn1cc2c(n1)C1(CCN(c3ncc(Sc4ccnc(N)c4Cl)nc3CO)CC1)[C@H](N)C2] |

TABLE 2-continued
| | |
|---|---|
| 12 | 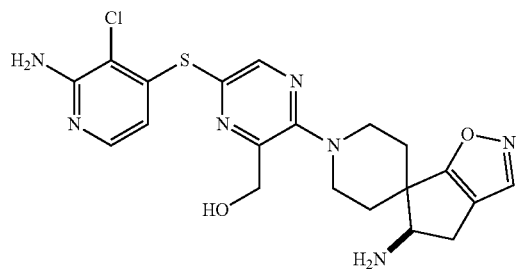 [SMILES: Nc1nccc(Sc2cnc(N3CCC4(CC3)c3oncc3C[C@H]4N)c(CO)n2)c1Cl] |
| 13 | 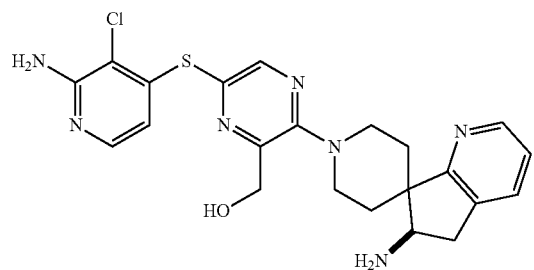 [SMILES: Nc1nccc(Sc2cnc(N3CCC4(CC3)c3ncccc3C[C@H]4N)c(CO)n2)c1Cl] |
| 14 | 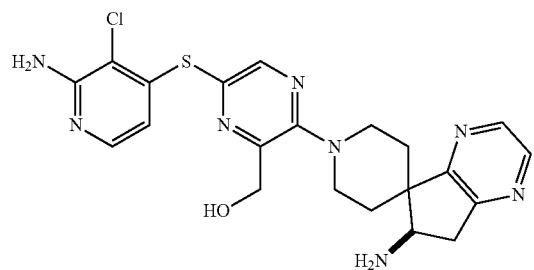 [SMILES: Nc1nccc(Sc2cnc(N3CCC4(CC3)c3nccnc3C[C@H]4N)c(CO)n2)c1Cl] |
| 15 | 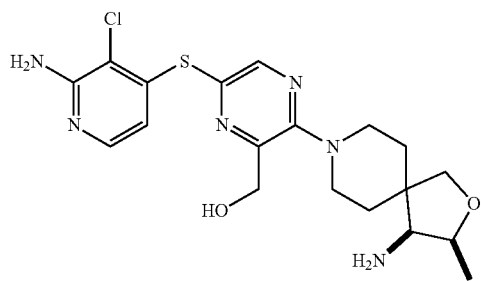 |
| 16 | 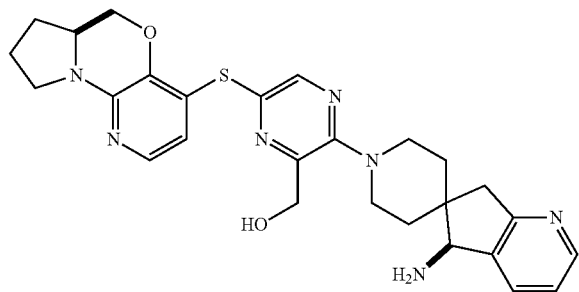 |

TABLE 2-continued
| | |
|---|---|
| 33 | 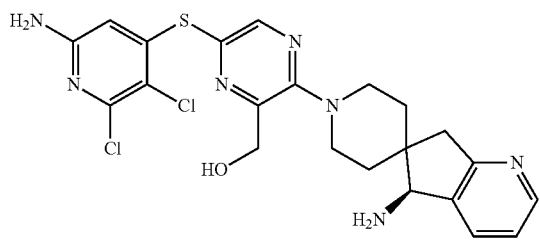 [SMILES: Nc1cc(Sc2cnc(N3CCC4(CC3)Cc3ncccc3[C@H]4N)c(CO)n2)c(Cl)c(Cl)n1] |
| 34 | 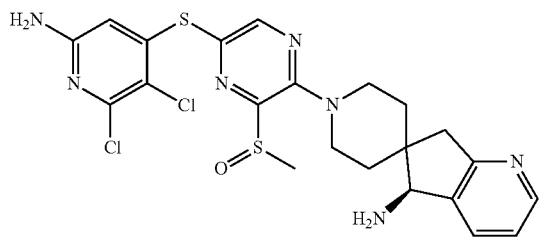 [SMILES: CS(=O)c1nc(Sc2cc(N)nc(Cl)c2Cl)cnc1N1CCC2(CC1)Cc1ncccc1[C@H]2N] |
| 35 | 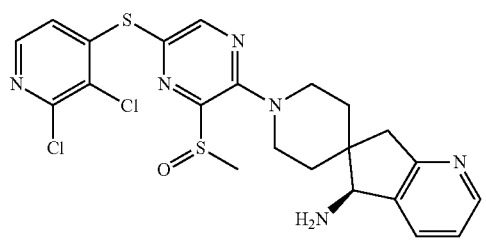 [SMILES: CS(=O)c1nc(Sc2ccnc(Cl)c2Cl)cnc1N1CCC2(CC1)Cc1ncccc1[C@H]2N] |
| 36 | 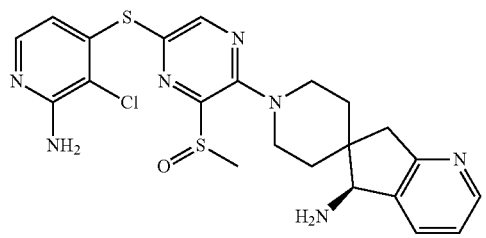 [SMILES: CS(=O)c1nc(Sc2ccnc(N)c2Cl)cnc1N1CCC2(CC1)Cc1ncccc1[C@H]2N] |
| 37 | 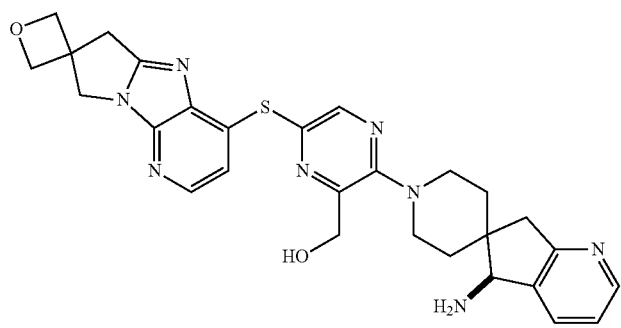 [SMILES: N[C@@H]1c2cccnc2CC12CCN(c1ncc(Sc3ccnc4c3nc3n4CC4(COC4)C3)nc1CO)CC2] |
| 38 | 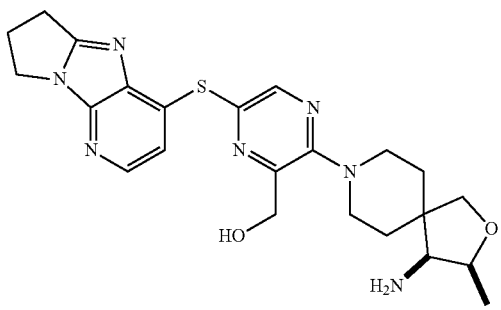 [SMILES: C[C@@H]1OCC2(CCN(c3ncc(Sc4ccnc5c4nc4n5CCC4)nc3CO)CC2)[C@@H]1N] |

TABLE 2-continued
| 17 | 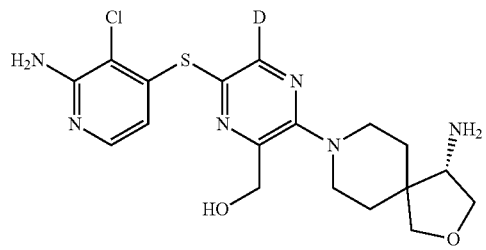 [SMILES: [2H]c1nc(N2CCC3(CC2)COC[C@H]3N)c(CO)nc1Sc1ccnc(N)c1Cl] |
| --- | --- |
| 18 | 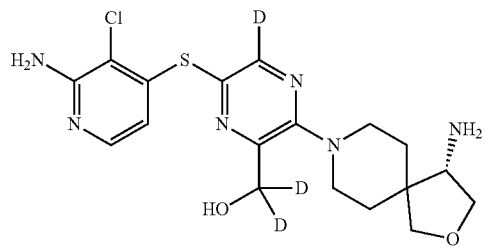 [SMILES: [2H]c1nc(N2CCC3(CC2)COC[C@H]3N)c(C([2H])([2H])O)nc1Sc1ccnc(N)c1Cl] |
| 19 | 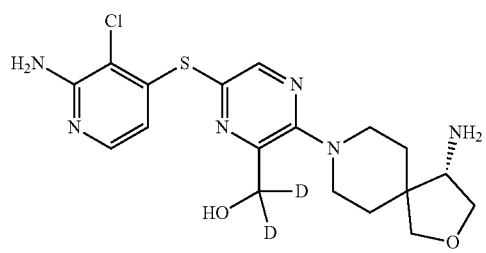 [SMILES: [2H]C([2H])(O)c1nc(Sc2ccnc(N)c2Cl)cnc1N1CCC2(CC1)COC[C@H]2N] |
| 20 | 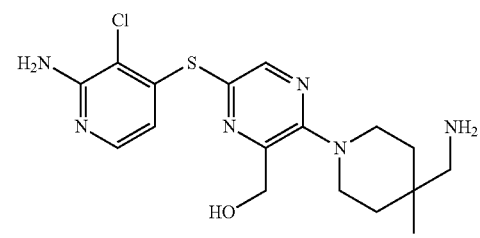 [SMILES: CC1(CN)CCN(c2ncc(Sc3ccnc(N)c3Cl)nc2CO)CC1] |
| 21 | 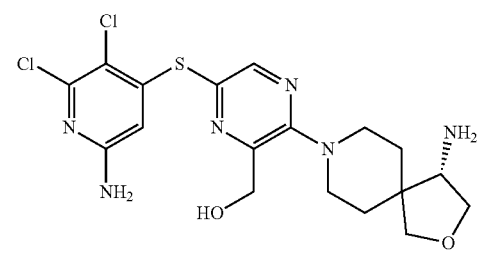 [SMILES: Nc1cc(Sc2cnc(N3CCC4(CC3)COC[C@H]4N)c(CO)n2)c(Cl)c(Cl)n1] |
| 22 | 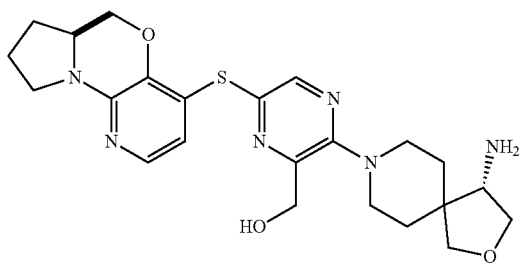 |

TABLE 2-continued
| 23 | 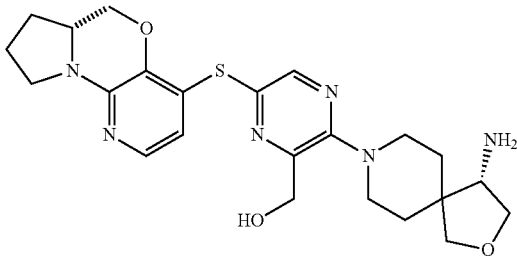 |
| --- | --- |
| 24 | 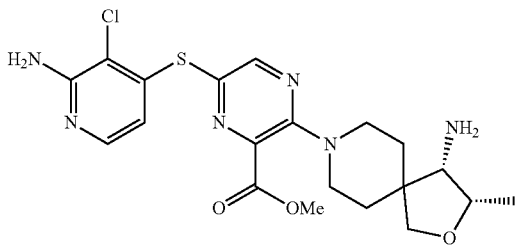 [SMILES: COC(=O)c1nc(Sc2ccnc(N)c2Cl)cnc1N1CCC2(CC1)CO[C@@H](C)[C@H]2N] |
| 25 | 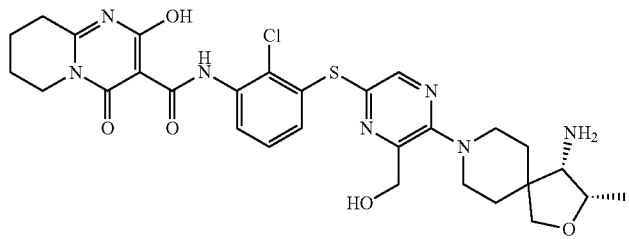 [SMILES: C[C@@H]1OCC2(CCN(c3ncc(Sc4cccc(NC(=O)c5c(O)nc6n(c5=O)CCCC6)c4Cl)nc3CO)CC2)[C@@H]1N] |
| 26 | 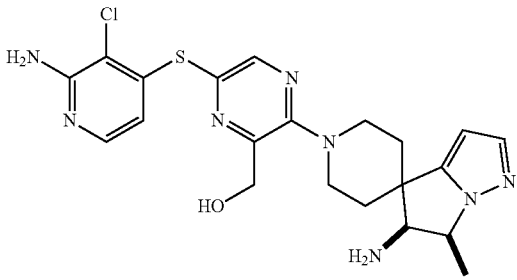 [SMILES: C[C@H]1[C@@H](N)C2(CCN(c3ncc(Sc4ccnc(N)c4Cl)nc3CO)CC2)c2ccnn21] |
| 27 | 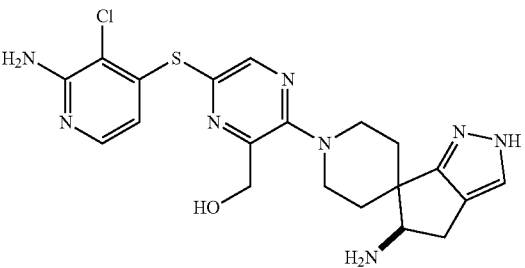 [SMILES: Nc1nccc(Sc2cnc(N3CCC4(CC3)c3n[nH]cc3C[C@H]4N)c(CO)n2)c1Cl] |
| 28 | 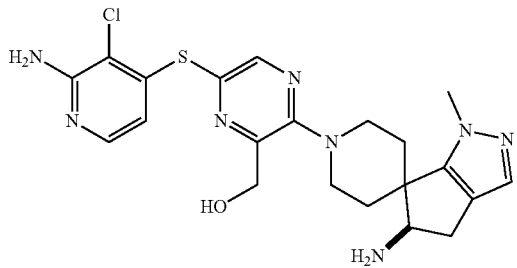 [SMILES: Cn1ncc2c1C1(CCN(c3ncc(Sc4ccnc(N)c4Cl)nc3CO)CC1)[C@H](N)C2] |

TABLE 2-continued
| 29 | 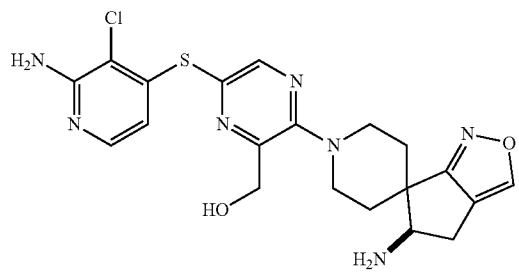 [SMILES: Nc1nccc(Sc2cnc(N3CCC4(CC3)c3nocc3C[C@H]4N)c(CO)n2)c1Cl] |
| --- | --- |
| 30 | 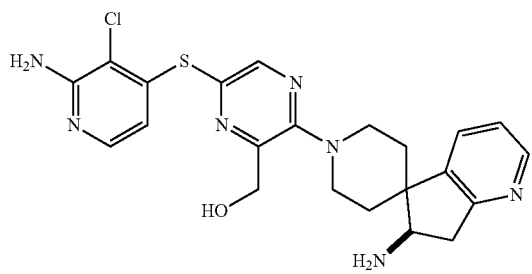 [SMILES: Nc1nccc(Sc2cnc(N3CCC4(CC3)c3cccnc3C[C@H]4N)c(CO)n2)c1Cl] |
| 31 | 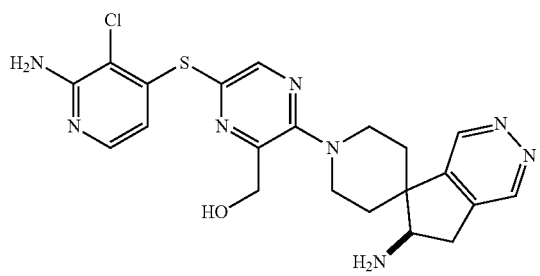 [SMILES: Nc1nccc(Sc2cnc(N3CCC4(CC3)c3cnncc3C[C@H]4N)c(CO)n2)c1Cl] |
| 32 | 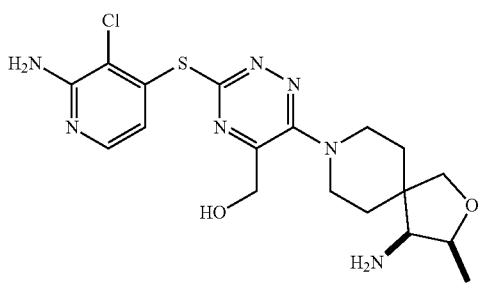 |
| 39 | 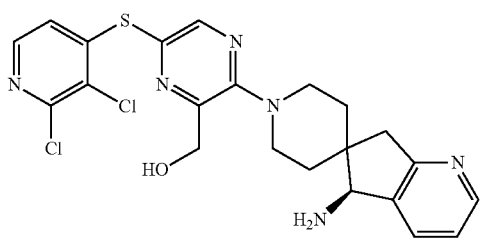 [SMILES: N[C@@H]1c2cccnc2CC12CCN(c1ncc(Sc3ccnc(Cl)c3Cl)nc1CO)CC2] |

TABLE 2-continued
| 40 | 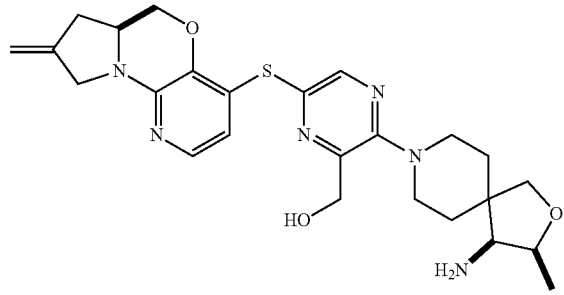 |
| --- | --- |
| 41 | 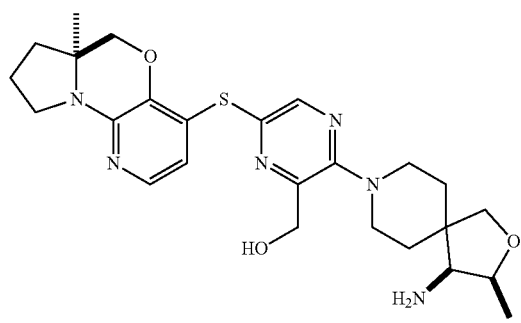 |
| 42 | 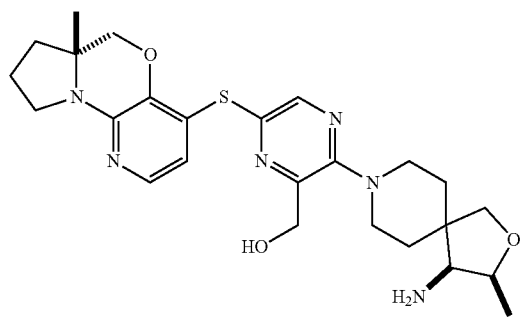 |
| 43 | 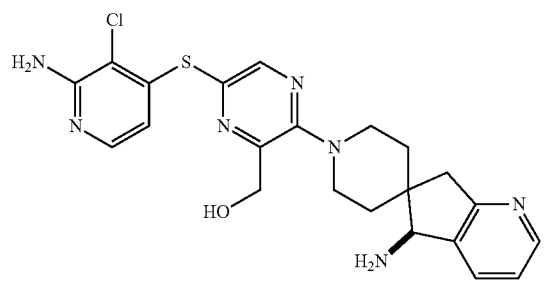 [SMILES: Nc1nccc(Sc2cnc(N3CCC4(CC3)Cc3ncccc3[C@H]4N)c(CO)n2)c1Cl] |
| 44 | 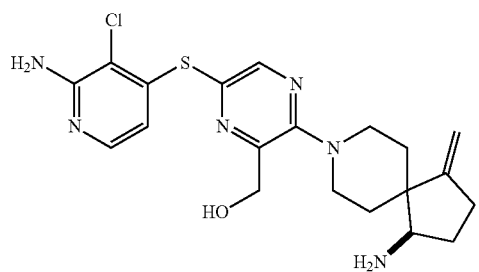 [SMILES: C=C1CC[C@@H](N)C12CCN(c1ncc(Sc3ccnc(N)c3Cl)nc1CO)CC2] |

TABLE 2-continued
| | |
|---|---|
| 45 | 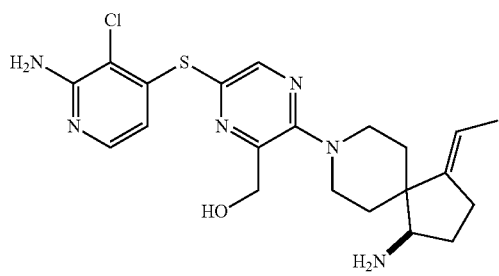 [SMILES: C/C=C1\CC[C@@H](N)C12CCN(c1ncc(Sc3ccnc(N)c3Cl)nc1CO)CC2] |
| 46 | 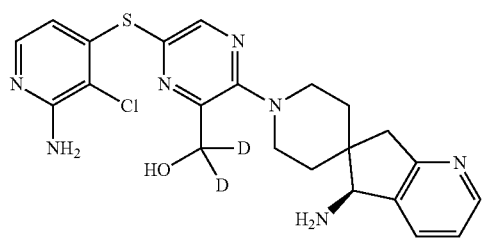 [SMILES: [2H]C([2H])(O)c1nc(Sc2ccnc(N)c2Cl)cnc1N1CCC2(CC1)Cc1ncccc1[C@H]2N] |
| 47 | 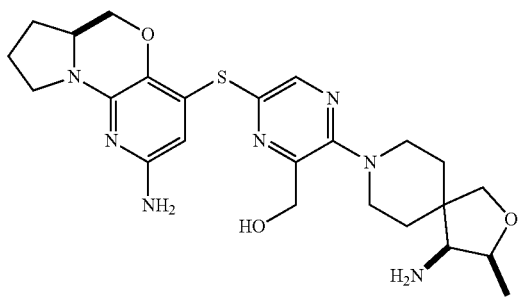 |
| 48 | 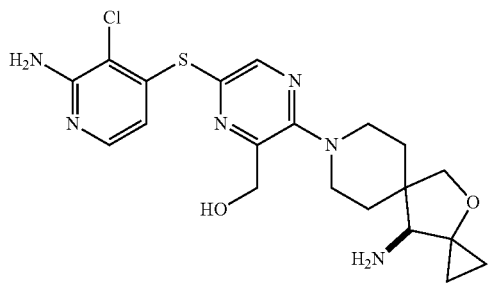 [SMILES: Nc1nccc(Sc2cnc(N3CCC4(CC3)COC3(CC3)[C@H]4N)c(CO)n2)c1Cl] |
| 49 | 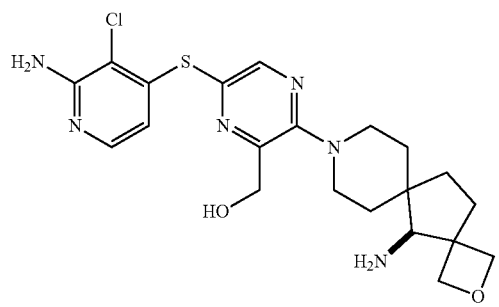 [SMILES: Nc1nccc(Sc2cnc(N3CCC4(CC3)CCC3(COC3)[C@H]4N)c(CO)n2)c1Cl] |

TABLE 2-continued
50 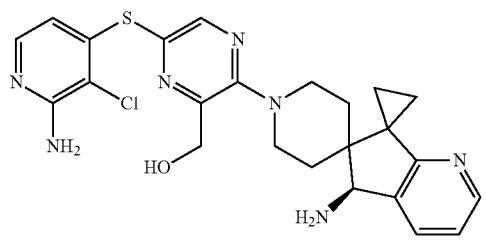 [SMILES: Nc1nccc(Sc2cnc(N3CCC4(CC3)[C@H](N)c3cccnc3C43CC3)c(CO)n2)c1Cl]
51 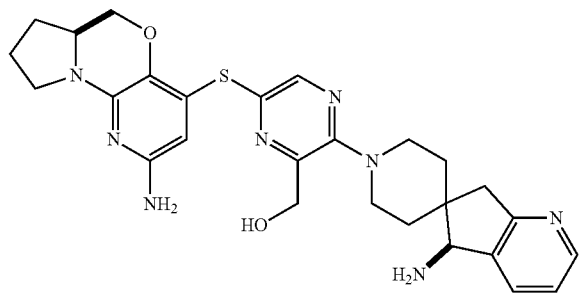
52 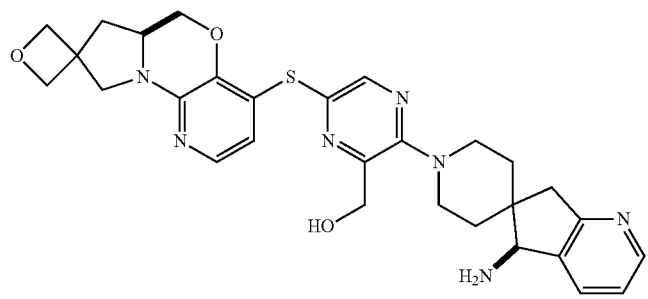
53 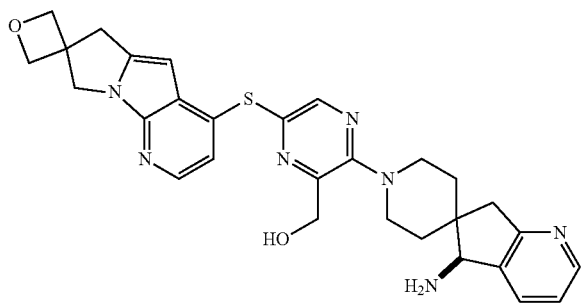 [SMILES: N[C@@H]1c2cccnc2CC12CCN(c1ncc(Sc3ccnc4c3cc3n4CC4(COC4)C3)nc1CO)CC2]
54 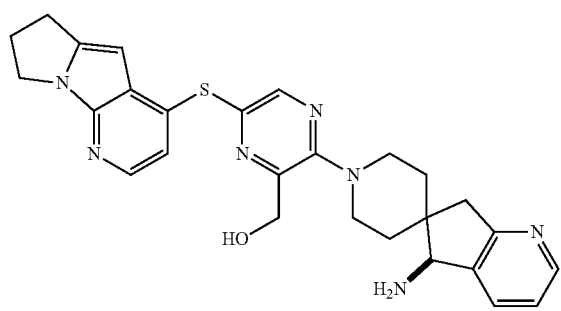 [SMILES: N[C@@H]1c2cccnc2CC12CCN(c1ncc(Sc3ccnc4c3cc3n4CCC3)nc1CO)CC2]

TABLE 2-continued
| 55 | 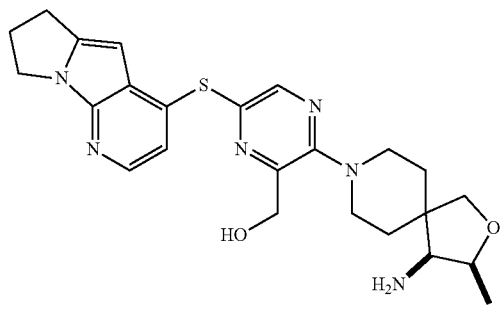 [SMILES: C[C@@H]1OCC2(CCN(c3ncc(Sc4ccnc5c4cc4n5CCC4)nc3CO)CC2)[C@@H]1N] |
| --- | --- |
| 56 | 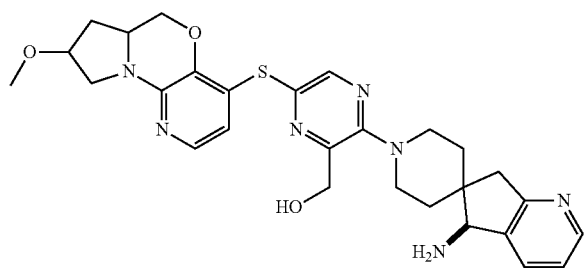 [SMILES: COC1CC2COc3c(Sc4cnc(N5CCC6(CC5)Cc5ncccc5[C@H]6N)c(CO)n4)ccnc3N2C1] |
| 57 | 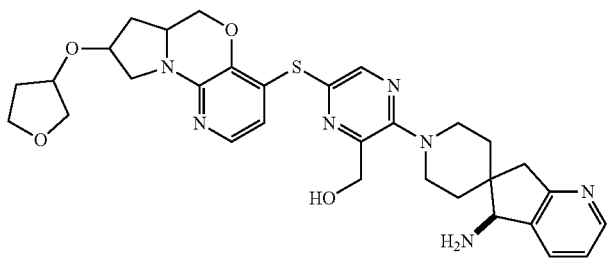 [SMILES: N[C@@H]1c2cccnc2CC12CCN(c1ncc(Sc3ccnc4c3OCC3CC(OC5CCOC5)CN43)nc1CO)CC2] |
| 58 | 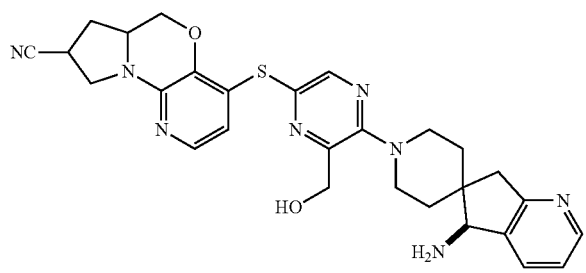 [SMILES: N#CC1CC2COc3c(Sc4cnc(N5CCC6(CC5)Cc5ncccc5[C@H]6N)c(CO)n4)ccnc3N2C1] |
| 59 | 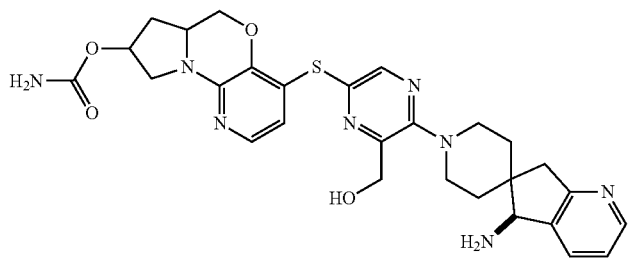 [SMILES: NC(=O)OC1CC2COc3c(Sc4cnc(N5CCC6(CC5)Cc5ncccc5[C@H]6N)c(CO)n4)ccnc3N2C1] |
| 60 | 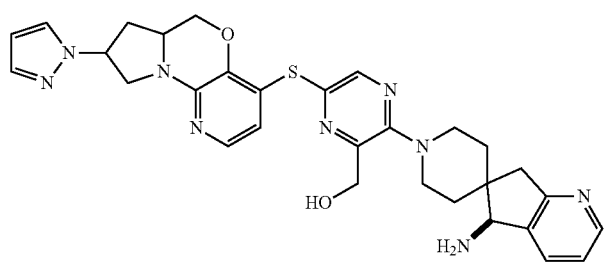 [SMILES: N[C@@H]1c2cccnc2CC12CCN(c1ncc(Sc3ccnc4c3OCC3CC(n5cccn5)CN43)nc1CO)CC2] |

TABLE 2-continued
| | |
|---|---|
| 61 | 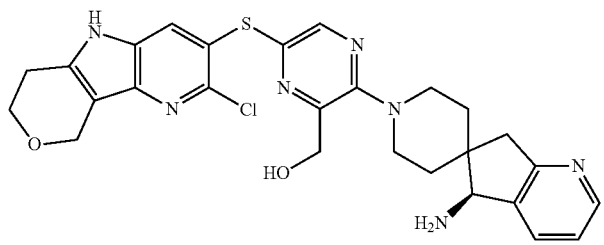 [SMILES: N[C@@H]1c2cccnc2CC12CCN(c1ncc(Sc3cc4[nH]c5c(c4nc3Cl)COCC5)nc1CO)CC2] |
| 62 | 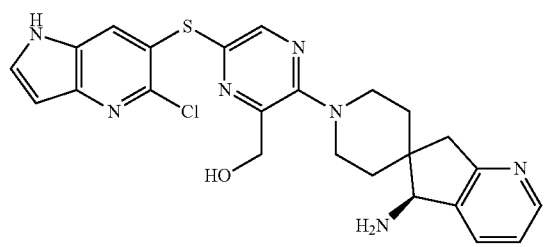 [SMILES: N[C@@H]1c2cccnc2CC12CCN(c1ncc(Sc3cc4[nH]ccc4nc3Cl)nc1CO)CC2] |
| 63 | 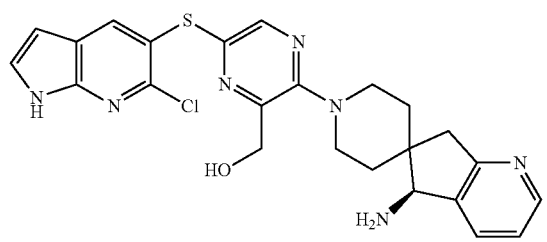 [SMILES: N[C@@H]1c2cccnc2CC12CCN(c1ncc(Sc3cc4cc[nH]c4nc3Cl)nc1CO)CC2] |
| 64 | 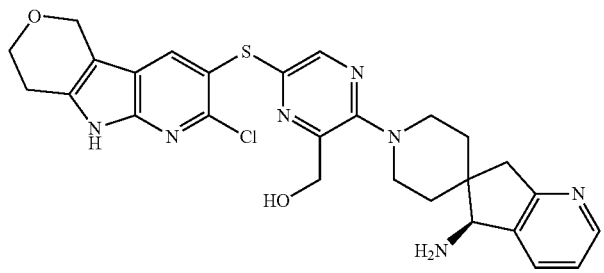 [SMILES: N[C@@H]1c2cccnc2CC12CCN(c1ncc(Sc3cc4c5c([nH]c4nc3Cl)CCOC5)nc1CO)CC2] |
| 65 | 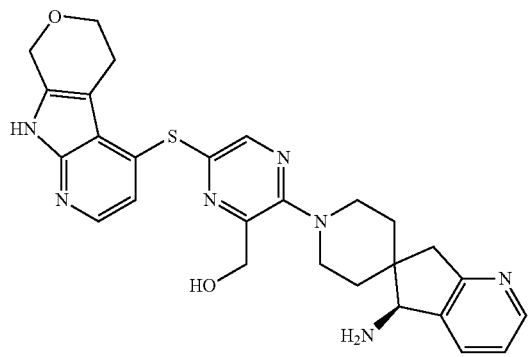 [SMILES: N[C@@H]1c2cccnc2CC12CCN(c1ncc(Sc3ccnc4[nH]c5c(c34)CCOC5)nc1CO)CC2] |

EMBODIMENTS

In further embodiments 1A', and 1A to 27 below, the present disclosure includes:

1A'. In embodiment 1A' provided is a compound of Formula (I'A) or a pharmaceutically acceptable salt thereof, where ring $A^1$, L, $Q^1$, $Q^2$, $R^3$ and

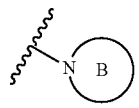

are as described in the Summary above.

In a first subembodiment of embodiment 1A', ring $A^1$ is a cycloalkyl fused bicyclic heteroaryl. In a second subembodiment of embodiment 1A', ring $A^1$ is a cycloalkyl fused bicyclic heteroaryl wherein the bicyclic heteroaryl ring is fused to five-membered cycloalkyl. In a third subembodiment of 1A', $A^1$ is a cycloalkyl fused bicyclic heteroaryl wherein the bicyclic heteroaryl ring is fused to six-membered cycloalkyl. In a fourth subembodiment of embodiment 1A' and first and second subembodiments contained therein, ring $A^1$ is attached to L through the 5- or 6-membered portion of the bicyclic heteroaryl ring in cycloalkyl fused bicyclic heteroaryl wherein said 5- or 6-membered portion of the bicyclic heteroaryl ring is not fused to said cycloalkyl. In a fifth subembodiment of embodiment 1A', ring $A^1$ is ring A as defined in any one of first to fourth subembodiments of embodiment 1A below.

1A. In embodiment 1A provided is a compound of Formula (I') or a pharmaceutically acceptable salt thereof, where ring A, L, $Q^1$, $Q^2$, $R^3$ and

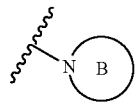

are as described in the Summary above.

In a first subembodiment of embodiment 1A, ring A is a fused tricyclic heteroaryl ring. In a second subembodiment of embodiment 1A, ring A is a fused tricyclic heteroaryl ring wherein the fused tricyclic heteroaryl ring comprises a 5- or 6-membered heteroaryl ring fused to a bicyclic heterocyclyl ring. In a third subembodiment of embodiment 1A, ring A is a fused tricyclic heteroaryl ring wherein the fused tricyclic heteroaryl ring comprises a 5- or 6-membered heteroaryl ring fused to a bicyclic heterocyclyl ring and ring A is attached to L through the 5- or 6-membered heteroaryl ring portion of the fused tricyclic heteroaryl ring. In a fourth subembodiment of embodiment 1A, ring A is a fused tricyclic heteroaryl ring wherein the fused tricyclic heteroaryl ring comprises a 9- or 10-membered bicyclic heteroaryl ring fused to a 5- or 6-membered monocyclic heterocyclyl ring and ring A is attached to L through the 9- or 10-membered bicyclic heteroaryl ring portion of the fused tricyclic heteroaryl ring.

1. In embodiment 1, provided is a compound of Formula (I), (IA), (II), or (IIA); or a pharmaceutically acceptable salt thereof, where ring A, L, $Q^1$, $Q^2$, $R^3$ and

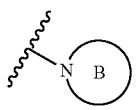

are as described in the Summary above. In a first sub-embodiment of embodiment 1, the compound or pharmaceutically acceptable salt thereof has Formula (I). In a second sub-embodiment of embodiment 1, the compound or pharmaceutically acceptable salt thereof has Formula (IA). In a third sub-embodiment of embodiment 1, the compound or pharmaceutically acceptable salt thereof has Formula (II). In a fourth sub-embodiment of embodiment 1, the compound or pharmaceutically acceptable salt thereof has Formula (IIA).

In a subembodiment of embodiment of 1, ring A is a fused tricyclic heteroaryl ring. In a second subembodiment of embodiment 1, ring A is a fused tricyclic heteroaryl ring wherein the fused tricyclic heteroaryl ring comprises a 5- or 6-membered heteroaryl ring fused to a bicyclic heterocyclyl ring. In a third subembodiment of embodiment 1, ring A is a fused tricyclic heteroaryl ring wherein the fused tricyclic heteroaryl ring comprises a 5- or 6-membered heteroaryl ring fused to a bicyclic heterocyclyl ring and ring A is attached to L through the 5- or 6-membered heteroaryl ring portion of the fused tricyclic heteroaryl ring.

2. In embodiment 2, the compound of any one of embodiments IA', 1A and 1 and sub-embodiments contained within embodiment IA', 1A and 1, or a pharmaceutically acceptable salt thereof has the structure of formula (III):

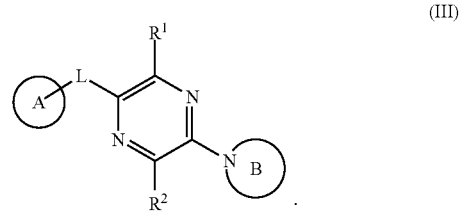

3. In embodiment 3, the compound of any one of embodiments IA', 1A and 1 and sub-embodiments contained within embodiment IA', 1A and 1, or a pharmaceutically acceptable salt thereof has the structure of formula (IV):

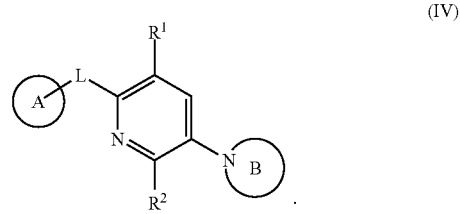

4. In embodiment 4, the compound of any one of embodiments IA', 1A and 1 and sub-embodiments contained within embodiments IA', 1A and 1, or a pharmaceutically acceptable salt thereof has the structure of formula (V) or (VI):

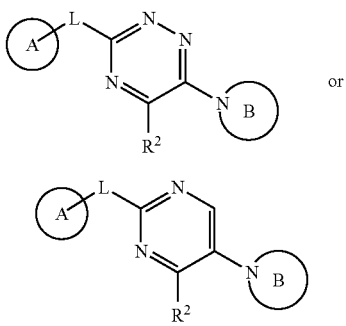

(V)

or (VI)

In one sub-embodiment of embodiment 4, the compound or a pharmaceutically acceptable salt thereof has structure (V). In another sub-embodiment of embodiment 4, the compound or a pharmaceutically acceptable salt thereof has structure (VI).

5. In embodiment 5, the compound of any one of embodiments IA', 1A, 1, 2, and 3 and sub-embodiments contained therein, or a pharmaceutically acceptable salt thereof is wherein $R^1$ is hydrogen.

6. In embodiment 6, the compound of any one of embodiments IA', 1A, 1, 2, and 3 and sub-embodiment contained therein, or a pharmaceutically acceptable salt thereof is wherein $R^1$ is deuterium.

7. In embodiment 7, the compound of any one of embodiments IA', 1A, 1, 2, 3, 4, 5 and 6 and sub-embodiments contained therein, or a pharmaceutically acceptable salt thereof is wherein L is S.

8. In embodiment 8, the compound of any one of embodiments IA', 1A, 1, 2, 3, 4, 5 and 6 and sub-embodiments contained therein, or a pharmaceutically acceptable salt thereof is wherein L is S(O) or $S(O)_2$.

9. In embodiment 9, the compound of any one of embodiments IA', 1A, 1, 2, 3, 4, 5 and 6 and sub-embodiments contained therein, or a pharmaceutically acceptable salt thereof is wherein L is bond.

10. In embodiment 7, the compound of any one of embodiments IA', 1A, 1, 2, 3, 4, 5 and 6 and sub-embodiments contained therein, or a pharmaceutically acceptable salt thereof is wherein L is $CR^5R^6$ where $R^5$ and $R^6$ are independently hydrogen or alkyl. In one sub-embodiment, of embodiment 10, L is $CH_2$. In another sub-embodiment of embodiment 10, L is $C(CH_3)_2$.

11. In embodiment 11, the compound of any one of embodiments IA', 1A, 1, 2, 3, 4, 5, 6, 7, 8, 9, and 10 and sub-embodiments contained therein, or a pharmaceutically acceptable salt thereof is wherein $R^2$ is hydroxyalkyl. In a first sub-embodiment of embodiment 11, $R^2$ is hydroxymethyl.

12. In embodiment 12, the compound of any one of embodiments IA', 1A, 1, 2, 3, 4, 5, 6, 7, 8, 9, and 10 and sub-embodiments contained therein, or a pharmaceutically acceptable salt thereof is wherein $R^2$ is alkylsulfonyl. In a first sub-embodiment of embodiment 12, $R^2$ is methylsulfonyl or ethylsulfonyl.

13. In embodiment 13, the compound of any one of embodiments IA', 1A, 1, 2, 3, 4, 5, 6, 7, 8, 9, and 10 and sub-embodiments contained therein, or a pharmaceutically acceptable salt thereof is wherein $R^2$ is alkylsulfoxide. In a first sub-embodiment of embodiment 13, $R^2$ is methylsulfoxide, ethylsulfoxide, or isopropylsulfoxide. In a second sub-embodiment of embodiment 13, $R^2$ is methylsulfoxide.

14. In embodiment 14, the compound of any one of embodiments IA', 1A, 1, 2, 3, 4, 5, 6, 7, 8, 9, and 10 and sub-embodiments contained therein, or a pharmaceutically acceptable salt thereof is wherein $R^2$ is —$CD_2OH$.

15. In embodiment 15, the compound of any one of embodiments IA', 1A, 1, 2, 3, 4, 5, 6, 7, 8, 9, and 10 and sub-embodiments contained therein, or a pharmaceutically acceptable salt thereof is wherein $R^2$ is alkoxycarbonyl, aminosulfonyl or aminocarbonyl. In a first sub-embodiment of embodiment 15, $R^2$ is —$S(O)_2NH2$. In a second sub-embodiment of embodiment 15, $R^2$ is —$CONH_2$. In a third sub-embodiment of embodiment 15, $R^2$ is —$C(O)CH_3$.

16. In embodiment 16, the compound of any one of embodiments IA', 1A, 1, 2, 3, 4, 5, 6, 7, 8, 9, and 10 and sub-embodiments contained therein, or a pharmaceutically acceptable salt thereof is wherein $R^2$ is hydroxy.

17. In embodiment 17, the compound of any one of embodiments IA', 1A, 1, 2, 3, 4, 5, 6, 7, 8, 9, and 10 and sub-embodiments contained therein, or a pharmaceutically acceptable salt thereof is wherein $R^2$ is halo. In a sub-embodiment of embodiment 17, $R^2$ is chloro.

18. In embodiment 18, the compound of any one of embodiments IA', 1A, 2, 3, 4, 5, 6, 7, 8, 9, 10, 11, 12, 13, 14, 15, 16, and 17 and sub-embodiments contained therein, or a pharmaceutically acceptable salt thereof is wherein:

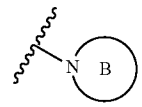

is a ring of formula (a) or (b):

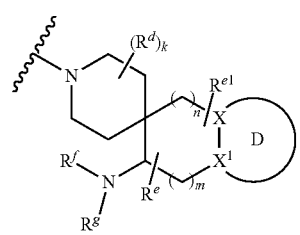

(a)

wherein:
m is 0, 1, or 2;
n is 0, 1, or 2 wherein when n is 2 then one of the $CH_2$ can be replaced with O, S, or $SO_2$; provided m+n is 1, 2, or 3;
k is 0, 1 or 2
z is 0, 1, or 2
each $R^d$ is independently hydrogen, alkyl, or halogen;
$R^e$ and $R^{e1}$ are independently hydrogen, alkyl, halogen, haloalkyl, alkoxy, haloalkoxy, hydroxy, hydroxyalkyl, cyano or oxo; or
when $R^e$ and $R^{e1}$ are attached to the same carbon atom, then $R^e$ and $R^{e1}$ together with the carbon atom to which they are attached can form cycloalkylene or heterocyclylene.

In a first embodiment of embodiment 18,

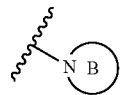

is a ring of formula (a):
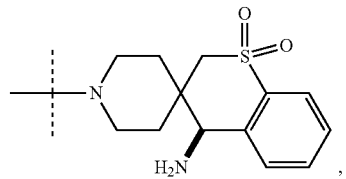
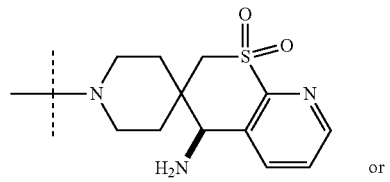
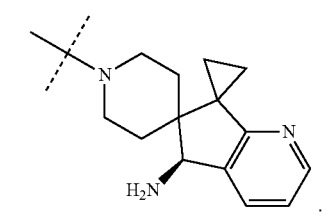
19. In embodiment 19, the compound of any one of embodiments IA', 1A, 1, 2, 3, 4, 5, 6, 7, 8, 9, 10, 11, 12, 13, 14, 15, 16, and 17 and sub-embodiments contained therein, or a pharmaceutically acceptable salt thereof is wherein:
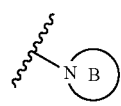
is a ring formula (a):
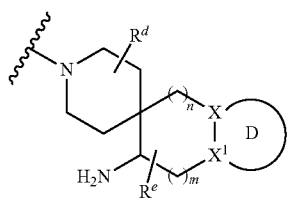
(a)
In a first sub-embodiment of embodiment 19,
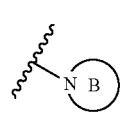
is:
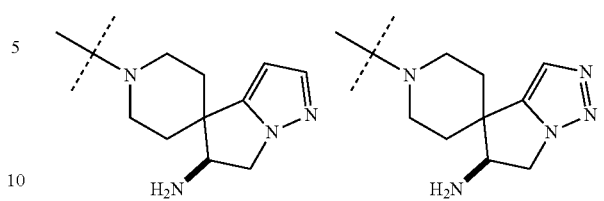
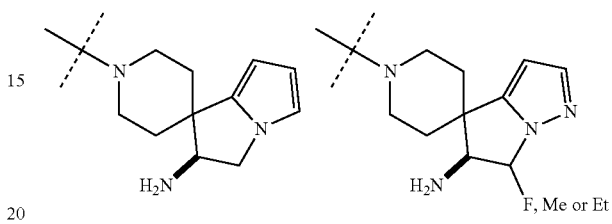
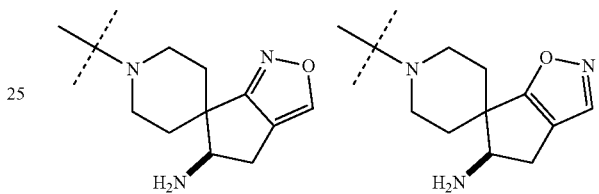
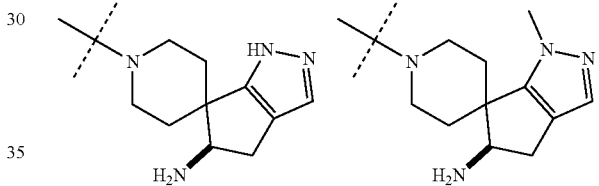
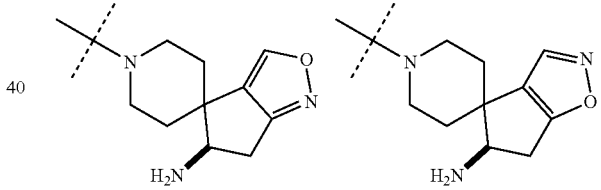
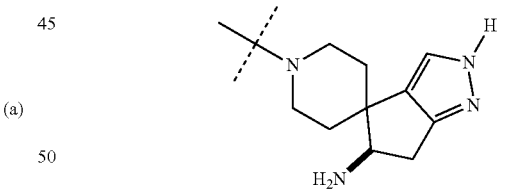
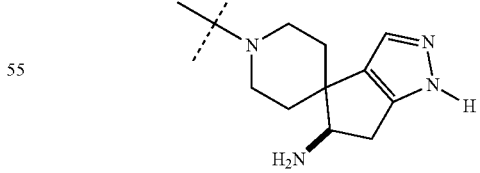
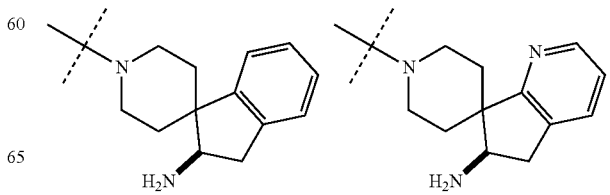

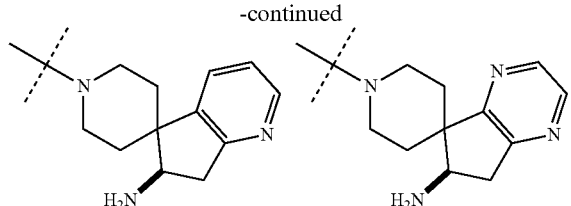
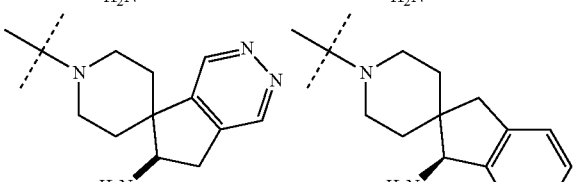
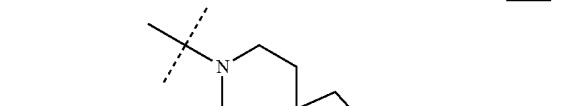
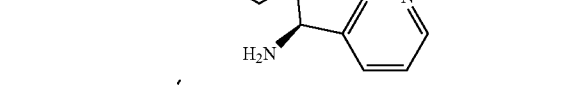
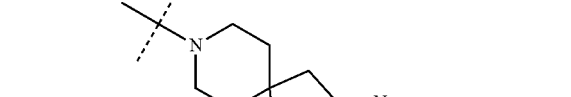
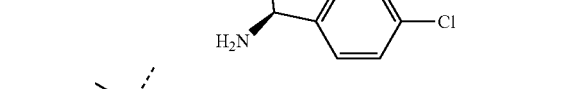
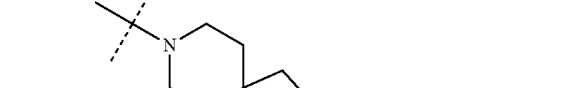
In a second sub-embodiment of embodiment 19,
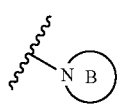
is:
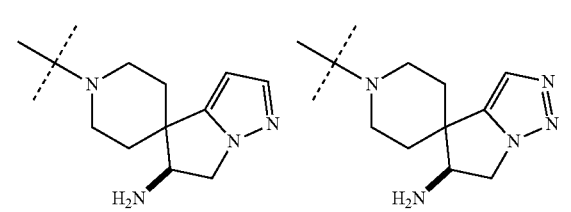
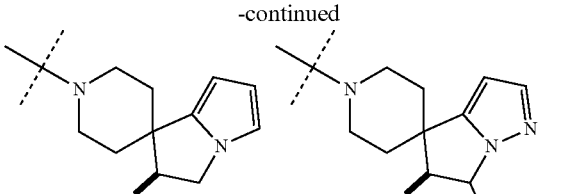
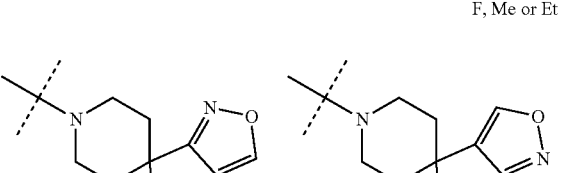
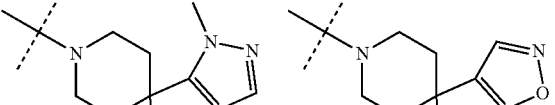
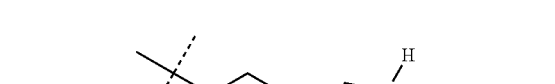
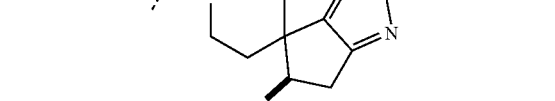
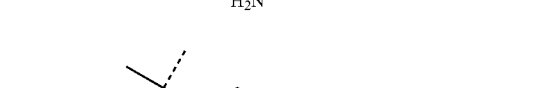
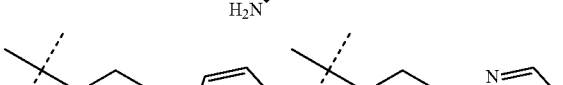
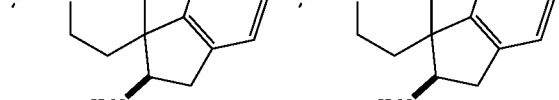
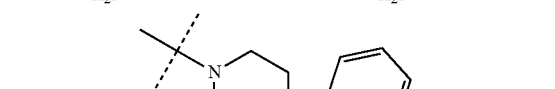
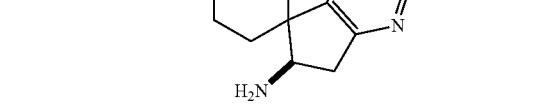

-continued

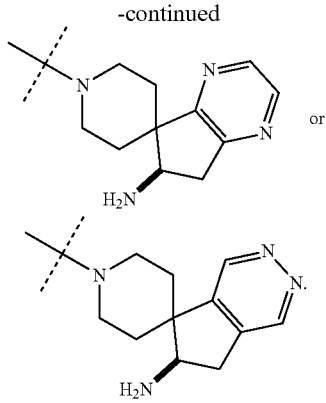

In a third sub-embodiment of embodiment 19,

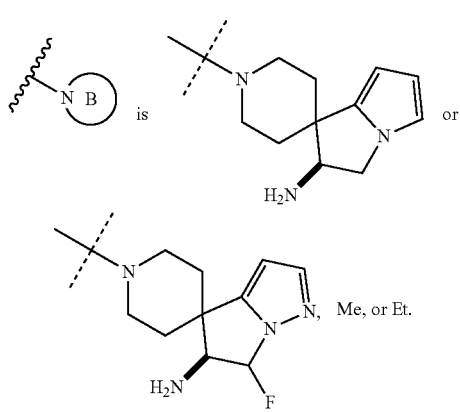

20. In embodiment 20, the compound of any one of embodiments IA', 1A, 1, 2, 3, 4, 5, 6, 7, 8, 9, 10, 11, 12, 13, 14, 15, 16, and 17 and sub-embodiments contained therein, or a pharmaceutically acceptable salt thereof is wherein

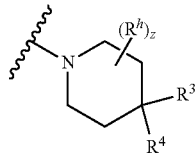

is:

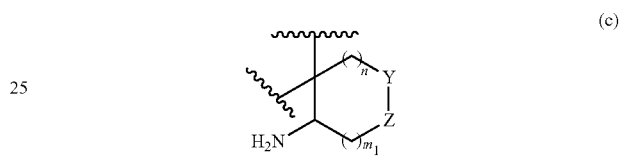

preferably where z is 1, and
where $R^3$ is amino or aminoalkyl; and
$R^4$ is alkyl, cycloalkylalkyl, halo, hydroxy, amino, alkoxycarbonyl, hydroxyalkyl, alkoxyalkyl, 5 or 6 membered heteroaryl, or 4 to 6 membered heterocyclyl wherein heteroaryl or heterocyclyl is substituted with $R^i$ and/or $R^j$ independently selected from hydrogen, alkyl, halo, haloalkyl, haloalkoxy, alkoxy, hydroxy, cyano, alkylsulfoxide, or alkylsulfonyl. In a sub-embodiment of embodiment 20, z is 0, $R^3$ is aminomethyl, and $R^4$ is methyl.

21. In embodiment 21, the compound of any one of embodiments IA', 1A, 2, 3, 4, 5, 6, 7, 8, 9, 10, 11, 12, 13, 14, 15, 16, and 17 and sub-embodiments contained therein, or a pharmaceutically acceptable salt thereof is wherein

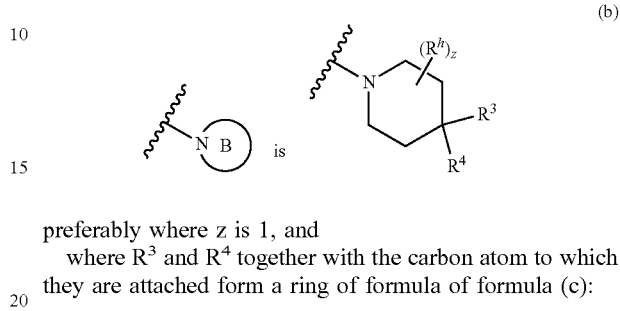

preferably where z is 1, and
where $R^3$ and $R^4$ together with the carbon atom to which they are attached form a ring of formula of formula (c):

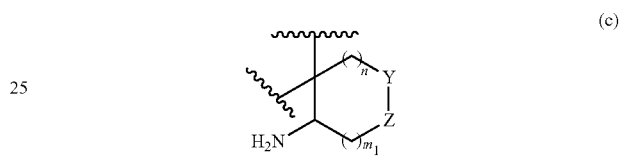

wherein:
m1 is 0, 1, or 2;
n1 is 0, 1, or 2; provided m1+n1 is 1, 2, or 3;
$R^k$ and $R^m$ are independently hydrogen, alkyl, or haloalkyl;
one of Y and Z is CH$_2$, O, S, S(O), S(O)$_2$, or NH; and the other of X and Y is CH$_2$; and wherein ring of formula (c) is substituted with $R^n$ and/or $R^o$ independently selected from hydrogen, alkyl, alkyldienyl, alkenyl, halo, haloalkyl, haloalkoxy, alkoxy, hydroxy, cyano, alkylsulfoxide, alkylsulfonyl, oxo, cycloalkyl, heterocyclyl, and heteroaryl; or
when $R^n$ and $R^o$ are attached to the same carbon atom, then $R^n$ and $R^o$ together with the carbon atom to which they are attached can form cycloalkylene or heterocyclylene;
In a first subembodiment of embodiment 21,

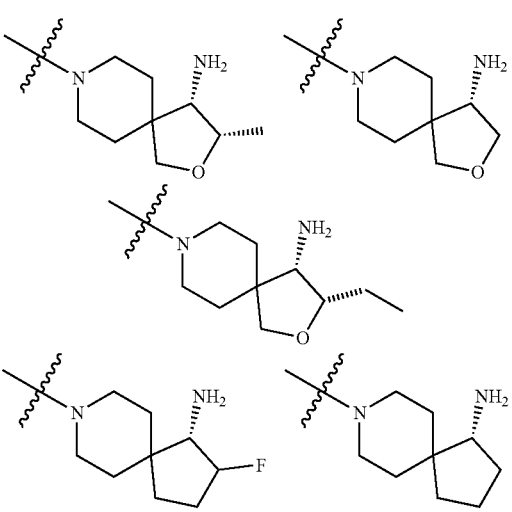

-continued

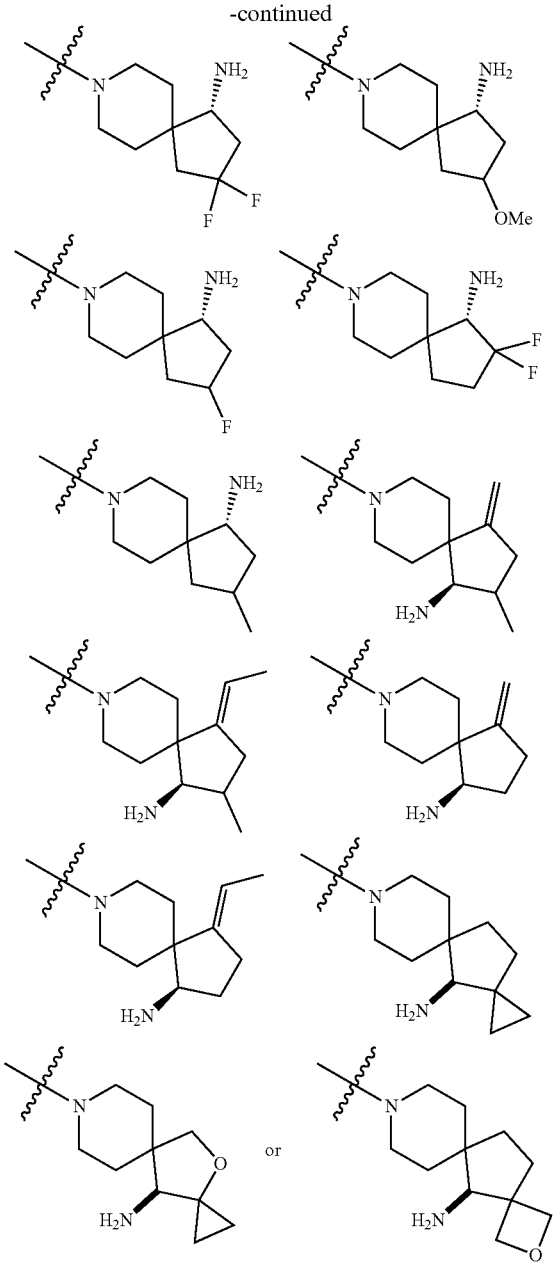

22. In embodiment 22, the compound of any one of embodiments IA', IA, 1, 2, 3, 4, 5, 6, 7, 8, 9, 10, 11, 12, 13, 14, 15, 16, and 17 and sub-embodiments contained therein, or a pharmaceutically acceptable salt thereof is wherein

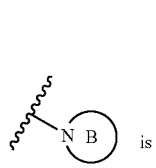 is 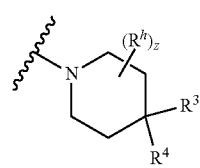

preferably where z is 1, and where $R^3$ and $R^4$ together with the carbon atom to which they are attached form a ring of formula (c):

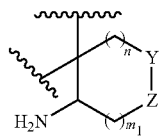

(c)

wherein:

m1 is 0, 1, or 2;

n1 is 0, 1, or 2; provided m1+n1 is 1, 2, or 3;

$R^k$ and $R^m$ are independently hydrogen, alkyl, or haloalkyl;

one of Y and Z is $CH_2$, O, S, S(O), $S(O)_2$, or NH; and the other of X and Y is $CH_2$; and wherein ring of formula (c) is substituted with $R^n$ and/or $R^o$ independently selected from hydrogen, alkyl, alkyldienyl, alkenyl, halo, haloalkyl, haloalkoxy, alkoxy, hydroxy, cyano, alkylsulfoxide, alkylsulfonyl, oxo, cycloalkyl, heterocyclyl, and heteroaryl.

In a first sub-embodiment of embodiment 22,

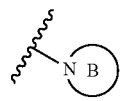

is:

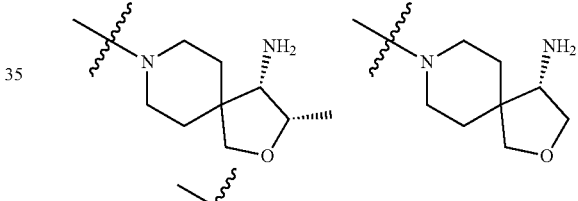

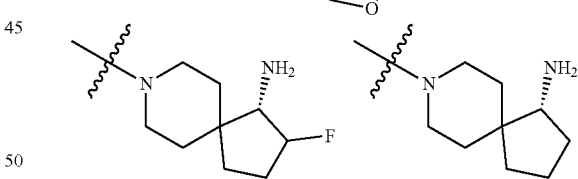

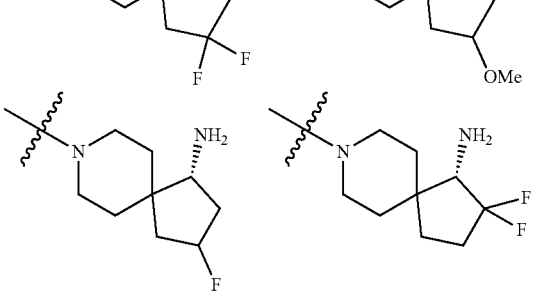

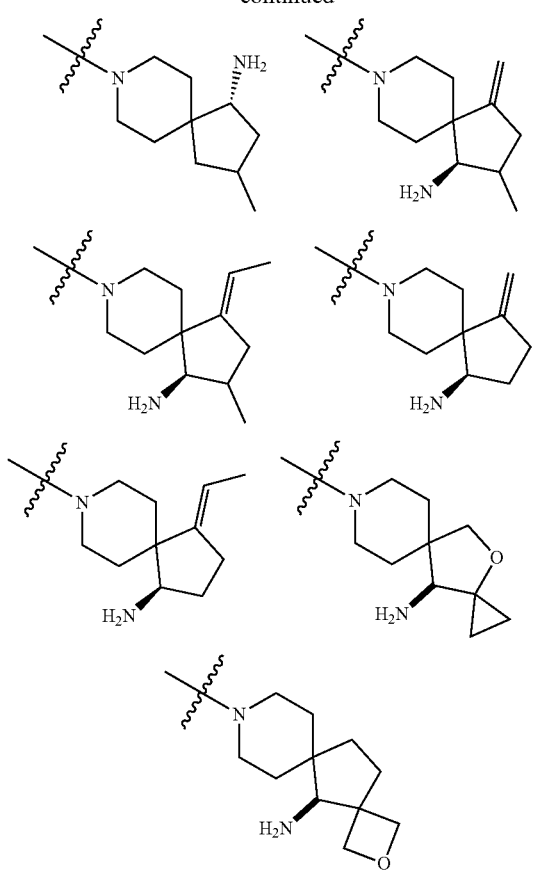
In a second subembodiment of embodiment 22,
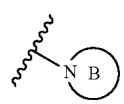
is:
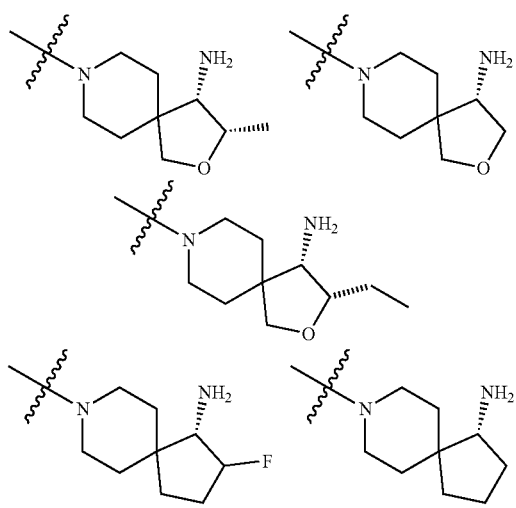
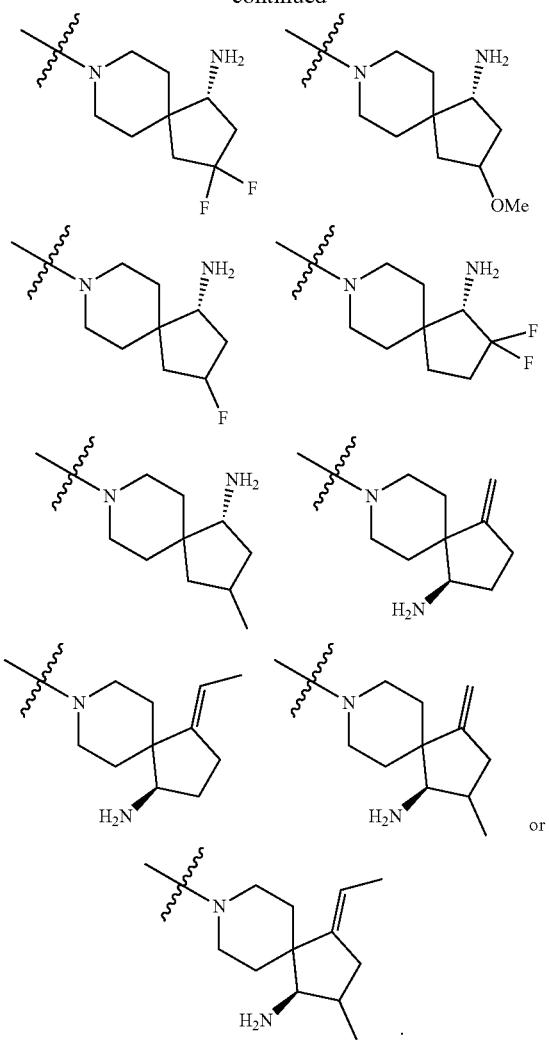
In a third sub-embodiment of embodiment 22,
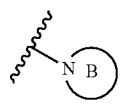
is:
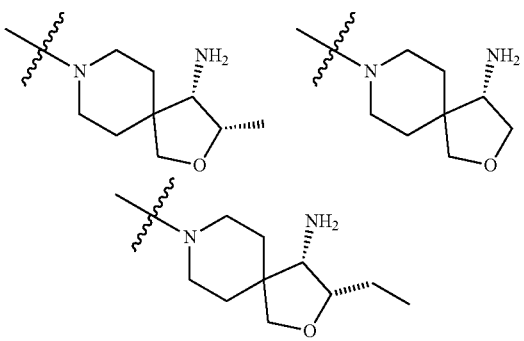

-continued

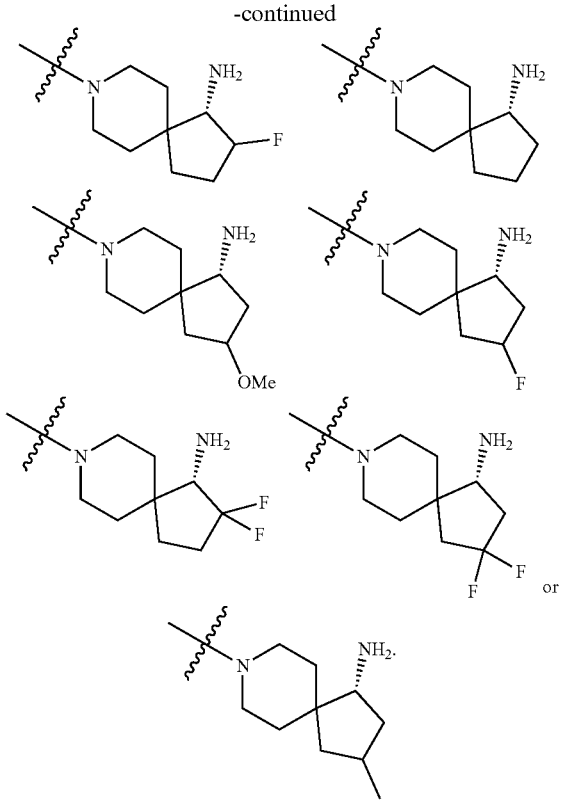

In a fourth sub-embodiment of embodiment 22,

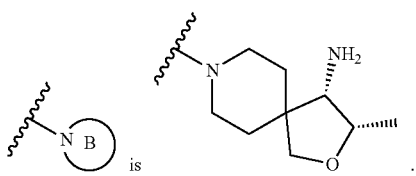

is

23. In embodiment 23, the compound of any one of embodiments 1A, 1, 2, 3, 4, 5, 6, 7, 8, 9, 10, 11, 12, 13, 14, 15, 16, 17, 18, 19, and 20 and sub-embodiments contained therein, or a pharmaceutically acceptable salt thereof is wherein ring A is heteroaryl substituted with $R^a$, $R^b$, and/or $R^c$ as defined therein.

In a first subembodiment of embodiment 23, $R^a$ and $R^b$ are independently selected from hydrogen, alkyl, amino, cycloalkyl, alkyldienyl, alkenyl, halo, haloalkyl, alkoxy, haloalkoxy, hydroxy, hydroxyalkyl, cyano, aminoalkyl, carboxy, and alkoxycarbonyl and $R^c$ is hydrogen, alkyl, halo, hydroxy, alkoxy, optionally substituted heterocyclyl, optionally substituted aryl, optionally substituted heteroaryl, —S(O)R, S(O)$_2$R, —C(O)R, —NR'C(O)R, —NR'SO$_2$R, —C(O)NR'R", —S(O)$_2$NR'R", —NR'R", or —NR'C(O)C(O)R where R is alkyl, cycloalkyl, cycloalkylalkyl, optionally substituted heterocyclyl, optionally substituted heterocyclylalkyl, optionally substituted aryl, optionally substituted aralkyl, optionally substituted heteroaryl, or optionally substituted heteroaralkyl, and R' and R" are independently hydrogen, alkyl, hydroxyalkyl, alkoxyalkyl, aminoalkyl, cycloalkyl, optionally substituted heterocyclyl, optionally substituted heterocyclylalkyl, optionally substituted aryl, optionally substituted aralkyl, optionally substituted heteroaryl, or optionally substituted heteroaralkyl; or R' and R" together with the nitrogen atom to which they are attached form optionally substituted heterocyclyl.

In a first sub-embodiment of embodiment 23 and first subembodiment therein, ring A is a five or six membered heteroaryl (preferably, thienyl, pyrazolyl, pyridinyl, pyrimidinyl, pyridazinyl, or pyrazinyl) substituted with $R^a$, $R^b$, and/or $R^c$.

In a second sub-embodiment of embodiment 23 and first subembodiment therein, ring A is a five or six membered heteroaryl (preferably, thienyl, pyrazolyl, pyridinyl, pyrimidinyl, pyridazinyl, or pyrazinyl) substituted with $R^a$ and $R^b$ independently selected from hydrogen, alkyl, amino, cycloalkyl, alkyldienyl, alkenyl, halo, haloalkyl, alkoxy, haloalkoxy, hydroxy, and cyano and $R^c$ is hydrogen, alkyl, halo, hydroxy, alkoxy, optionally substituted heterocyclyl, optionally substituted heteroaryl, —NHCOR, or —NR'R" where R is alkyl or optionally substituted heterocyclyl and R' and R" are independently hydrogen, alkyl, hydroxyalkyl, alkoxyalkyl, aminoalkyl, or optionally substituted heterocyclyl.

In a third sub-embodiment of embodiment 23 and first subembodiment therein, ring A is a five or six membered heteroaryl (preferably, thienyl, pyrazolyl, pyridinyl, pyrimidinyl, pyridazinyl, or pyrazinyl) substituted with $R^a$ and $R^b$ independently selected from hydrogen, alkyl, halo, haloalkyl, alkoxy, haloalkoxy, hydroxy, and cyano and $R^c$ is hydrogen, alkyl, halo, hydroxy, alkoxy, optionally substituted heterocyclyl, optionally substituted heteroaryl, —NHCOR, or —NR'R" where R is alkyl or optionally substituted heterocyclyl and R' and R" are independently hydrogen, alkyl, hydroxyalkyl, alkoxyalkyl, aminoalkyl, or optionally substituted heterocyclyl.

In a fourth sub-embodiment of embodiment 23 and first subembodiment therein, ring A is a five or six membered heteroaryl (preferably, thienyl, pyrazolyl, pyridinyl, pyrimidinyl, pyridazinyl, or pyrazinyl) substituted with $R^a$ and $R^b$ independently selected from hydrogen, methyl, ethyl, methoxy, ethoxy, chloro, fluoro, amino, difluoromethyl, trifluoromethyl, difluoromethoxy, trifluoromethoxy, and cyano, and $R^c$ is hydrogen, amino, pyrrolidin-1-yl, piperidin-1-yl,

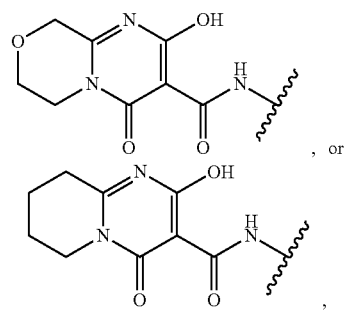

preferably ring A is a five or six membered heteroaryl (preferably, thienyl, pyrazolyl, pyridinyl, pyrimidinyl, pyridazinyl, or pyrazinyl) substituted with $R^a$ and $R^b$ independently selected from hydrogen, methyl, ethyl, methoxy, ethoxy, chloro, fluoro, difluoromethyl, trifluoromethyl, difluoromethoxy, trifluoromethoxy, and cyano, and $R^c$ is hydrogen, amino, pyrrolidin-1-yl, piperidin-1-yl,

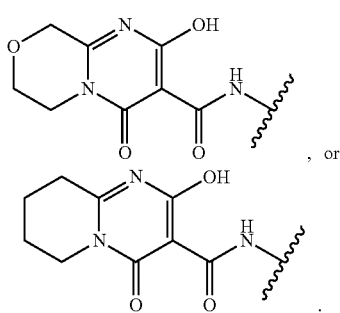

, or

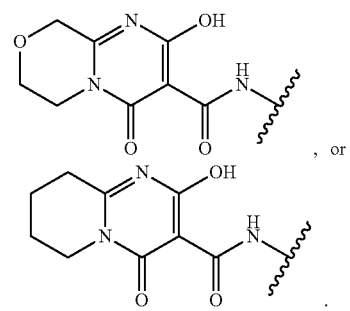

In a fifth sub-embodiment of embodiment 23, ring A is 5-chloro-1H-pyrrolo[2,3-e]pyridin-6-yl, 6-chloro-1H-pyrrolo[3,2-e]pyridin-5-yl, 5-chloro-3H-imidazo[4,5-e]pyridin-6-yl, 2-amino-3-chloropyridin-4-yl, 2-trifluoromethylpyridin-4-yl, 2,3-dichloropyridin-4-yl, 2-amino-5,6-dichloropyridin-4-yl, 3-chloro-2-methoxypyridin-4-yl, 3-chloro-2-methylpyridin-4-yl, 3-chloro-2-pyrrolidin-1-ylpyridin-4-yl, 2-fluoro-3-chloropyridin-4-yl, 3-chloro-2-dimethylaminopyridin-4-yl, 2-amino-3-trifluoromethylpyridin-4-yl, or, 2-trifluoromethylpyridin-3-yl. In a sixth sub-embodiment of embodiment 21, ring A is 2-amino-3-chloropyridin-4-yl, 2-trifluoromethylpyridin-4-yl, 2,3-dichloropyridin-4-yl, 3-chloro-2-methoxypyridin-4-yl, 3-chloro-2-pyrrolidin-1-ylpyridin-4-yl, or 2-fluoro-3-chloropyridin-4-yl.

In a sixth sub-embodiment of embodiment 23 and first subembodiment therein, ring A is 2-amino-3-chloropyridin-4-yl, 2-trifluoromethylpyridin-4-yl, 2,3-dichloropyridin-4-yl, 2-amino-5,6-dichloropyridin-4-yl, 3-chloro-2-methoxypyridin-4-yl, 3-chloro-2-methylpyridin-4-yl, 3-chloro-2-pyrrolidin-1-ylpyridin-4-yl, 2-fluoro-3-chloropyridin-4-yl, 3-chloro-2-dimethylamino-pyridin-4-yl, 2-amino-3-trifluoromethylpyridin-4-yl, or 2-trifluoromethylpyridin-3-yl.

In a seventh sub-embodiment of embodiment 23 and first subembodiment therein, ring A is 2-amino-3-chloropyridin-4-yl, 2-trifluoromethylpyridin-4-yl, 2,3-dichloropyridin-4-yl, 3-chloro-2-methoxypyridin-4-yl, 3-chloro-2-pyrrolidin-1-ylpyridin-4-yl, or 2-fluoro-3-chloropyridin-4-yl.

24. In embodiment 24, the compound of any one of embodiments IA, 1, 2, 3, 4, 5, 6, 7, 8, 9, 10, 11, 12, 13, 14, 15, 16, 17, 18, 19, and 20 and sub-embodiments contained therein, or a pharmaceutically acceptable salt thereof is wherein ring A is aryl substituted with $R^a$, $R^b$, and/or $R^c$. In a first sub-embodiment of embodiment 24, ring A is phenyl substituted with $R^a$, $R^b$, and/or $R^c$. In a second sub-embodiment of embodiment 24, ring A is phenyl substituted with $R^a$ and $R^b$ are independently selected from hydrogen, alkyl, amino, cycloalkyl, alkenyl, halo, haloalkyl, alkoxy, haloalkoxy, hydroxy, and cyano and $R^c$ is hydrogen, alkyl, halo, hydroxy, alkoxy, optionally substituted heterocyclyl, optionally substituted heteroaryl, —NHCOR, or —NR'R" where R is alkyl or optionally substituted heterocyclyl and R' and R" are independently hydrogen, alkyl, hydroxyalkyl, alkoxyalkyl, aminoalkyl, and optionally substituted heterocyclyl. In a third sub-embodiment of embodiment 24, ring A is phenyl substituted with $R^a$ and $R^b$ are independently selected from hydrogen, alkyl, halo, haloalkyl, alkoxy, haloalkoxy, hydroxy, and cyano and $R^c$ is hydrogen, alkyl, halo, hydroxy, alkoxy, optionally substituted heterocyclyl, optionally substituted heteroaryl, —NHCOR, or —NR'R" where R is alkyl or optionally substituted heterocyclyl and R' and R" are independently hydrogen, alkyl, hydroxyalkyl, alkoxyalkyl, aminoalkyl, and optionally substituted heterocyclyl. In a fourth sub-embodiment of embodiment 24, ring A is phenyl substituted with $R^a$ and $R^b$ independently selected from hydrogen, methyl, ethyl, methoxy, ethoxy, chloro, fluoro, difluoromethyl, trifluoromethyl, difluoromethoxy, trifluoromethoxy, and cyano, and $R^c$ is hydrogen, amino, pyrrolidin-1-yl, piperidin-1-yl,

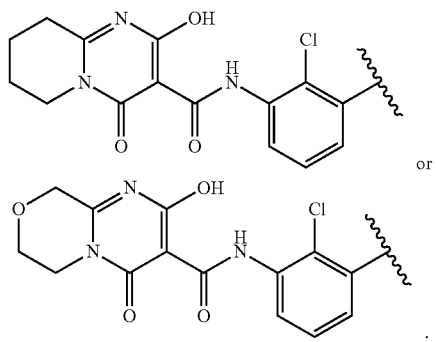

In a fifth sub-embodiment of embodiment 24, ring A is 2,3-dichlorophenyl, 2-amino-2-chlorophenyl, 25. In embodiment 25, the compound of any one of embodiments IA', 1A, 1, 2, 3, 4, 5, 6, 7, 8, 9, 10, 11, 12, 13, 14, 15, 16, 17, 18, 19, 20, 21, and 22, and sub-embodiments contained therein, or a pharmaceutically acceptable salt thereof is wherein ring A is fused heteroaryl substituted with $R^a$, $R^b$, and/or $R^c$ as defined therein, preferably the fused heteroaryl is a fused tricyclic heteroaryl. In a subembodiment of embodiment 25, ring A is a fused tricyclic heteroaryl ring wherein the fused tricyclic heteroaryl ring comprises a 5- or 6-membered heteroaryl ring fused to a bicyclic heterocyclyl. In another subembodiment of embodiment 25, ring A is a fused tricyclic heteroaryl ring wherein the fused tricyclic heteroaryl ring comprises a 5- or 6-membered heteroaryl ring fused to a bicyclic heterocyclyl and ring A is attached to L through the 5- or 6-membered heteroaryl ring portion of the fused tricyclic heteroaryl ring.

In a first subembodiment of embodiment 25 and subembodiments contained therein, $R^a$ and $R^b$ are independently selected from hydrogen, alkyl, amino, cycloalkyl, alkyldienyl, alkenyl, halo, haloalkyl, alkoxy, haloalkoxy, hydroxy, hydroxyalkyl, cyano, aminoalkyl, carboxy, and alkoxycarbonyl and $R^c$ is hydrogen, alkyl, halo, hydroxy, alkoxy, optionally substituted heterocyclyl, optionally substituted aryl, optionally substituted heteroaryl, —S(O)R, S(O)$_2$R, —C(O)R, —NR'C(O)R, —NR'SO$_2$R, —C(O)NR'R", —S(O)$_2$NR'R", —NR'R", or —NR'C(O)C(O)R where R is alkyl, cycloalkyl, cycloalkylalkyl, optionally substituted heterocyclyl, optionally substituted heterocyclylalkyl, optionally substituted aryl, optionally substituted aralkyl, optionally substituted heteroaryl, or optionally substituted heteroaralkyl, and R' and R" are independently hydrogen, alkyl, hydroxyalkyl, alkoxyalkyl, aminoalkyl, cycloalkylalkyl, optionally substituted heterocyclyl, optionally substituted heterocyclylalkyl, optionally substituted aryl, optionally substituted aralkyl, optionally substituted heteroaryl, or optionally substituted heteroaralkyl; or R' and R" together with the nitrogen atom to which they are attached form optionally substituted heterocyclyl; or when $R^c$ and $R^a$ are attached to the same carbon of fused heteroaryl ring, then $R^c$ and $R^a$ together with the carbon atom to which they are attached can form cycloalkylene or heterocyclylene.

In a second sub-embodiment of embodiment 25, subembodiments within embodiment 25, and first subembodiment contained therein, $R^a$ and $R^b$ are independently selected from hydrogen, alkyl, amino, cycloalkyl, alkyldienyl, alkenyl, halo, haloalkyl, alkoxy, haloalkoxy, hydroxy, and cyano and $R^c$ is hydrogen or —NR'R" where R' and R" are independently hydrogen, alkyl, hydroxyalkyl, alkoxyalkyl, aminoalkyl, or optionally substituted heterocyclyl.

In a third sub-embodiment of embodiment 25, subembodiments within embodiment 25, and first subembodiment therein, $R^a$ and $R^b$ are independently selected from hydrogen, alkyl, halo, haloalkyl, alkoxy, haloalkoxy, hydroxy, and cyano and $R^c$ is hydrogen or —NR'R" where R' and R" are independently hydrogen, alkyl, hydroxyalkyl, alkoxyalkyl, aminoalkyl, or optionally substituted heterocyclyl.

In a fourth sub-embodiment of embodiment 25, subembodiments within embodiment 25, and first subembodiment therein, $R^a$ and $R^b$ are independently selected from hydrogen, alkyl, halo, haloalkyl, alkoxy, haloalkoxy, hydroxy, and cyano and $R^c$ is hydrogen or —NR'R" where R' and R" are independently hydrogen, alkyl, hydroxyalkyl, alkoxyalkyl, aminoalkyl, or optionally substituted heterocyclyl.

In a fifth sub-embodiment of embodiment 25, subembodiments within embodiment 25, and first subembodiment therein, $R^a$ and $R^b$ are independently selected from hydrogen, methyl, ethyl, methoxy, ethoxy, chloro, fluoro, difluoromethyl, trifluoromethyl, difluoromethoxy, trifluoromethoxy, hydroxy, and cyano, and $R^c$ is hydrogen.

In a sixth sub-embodiment of embodiment 25, subembodiments within embodiment 25, and first subembodiment therein, ring A is

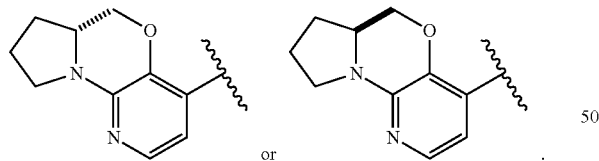

In a seventh sub-embodiment of embodiment 25, subembodiments within embodiment 25 and first subembodiment therein, ring A has the structure (d):

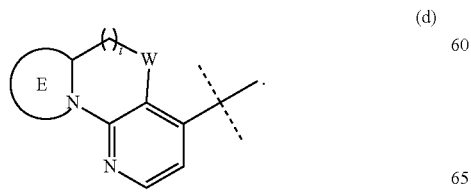

(d)

where:

t is 0, 1 or 2;

ring E is 4 to 7 membered heterocyclyl containing 1 or 2 heteroatoms independently selected from O, N, S, and $SO_2$ where the remaining atoms are carbon; and W is O, $CH_2$, or N; substituted with $R^a$, $R^b$, and/or $R^c$ wherein $R^a$ and $R^b$ are independently selected from hydrogen, amino, alkyl, alkyldienyl, alkenyl, halo, haloalkyl, alkoxy, haloalkoxy, hydroxy, hydroxyalkyl, cyano, aminoalkyl, carboxy, and alkoxycarbonyl and $R^c$ is hydrogen, alkyl, halo, hydroxy, or alkoxy; or when $R^a$ and $R^c$ are attached to the same carbon atom, $R^a$ and $R^c$ together with the carbon atom to which they are attached can form cycloalkylene or heterocyclylene.

In a first embodiment, of the seventh sub-embodiment, ring A is

In a second embodiment, of the fifth sub-embodiment, ring A is:

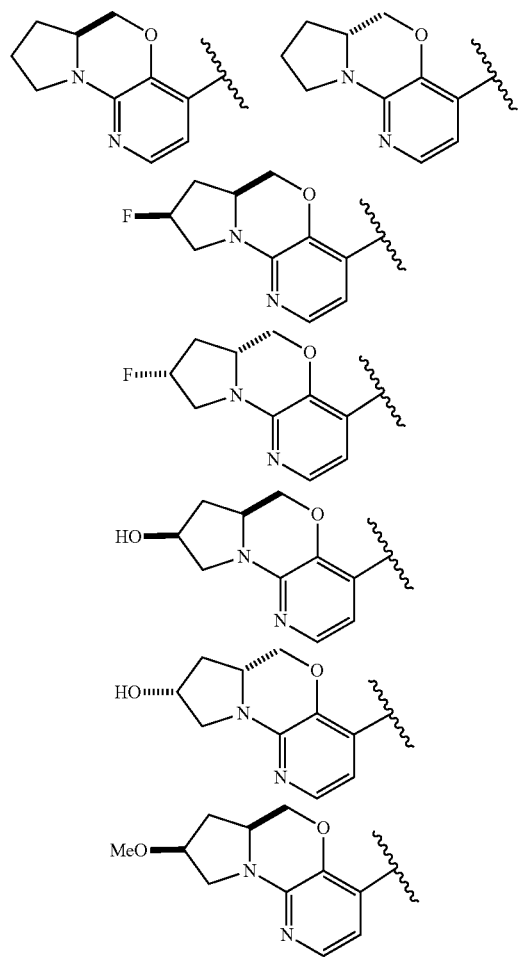

-continued
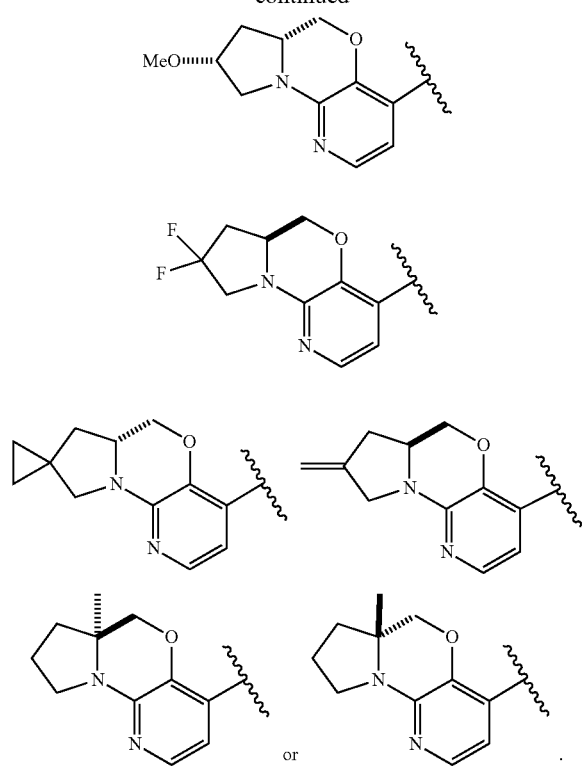
In a second embodiment of the seventh sub-embodiment, ring A is:
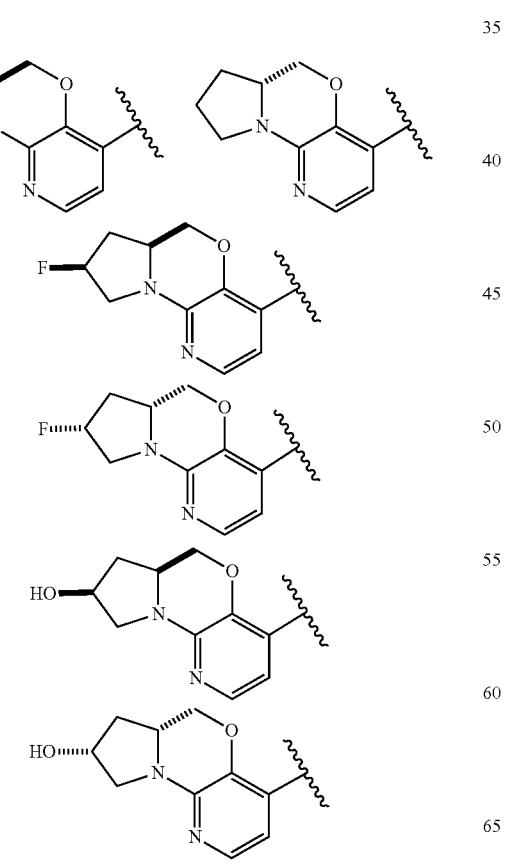
-continued
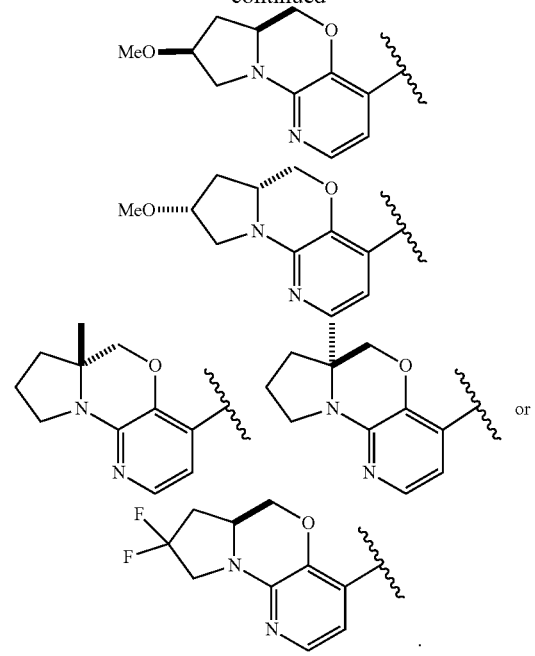
In an eighth subembodiment of embodiment 25, ring A is:
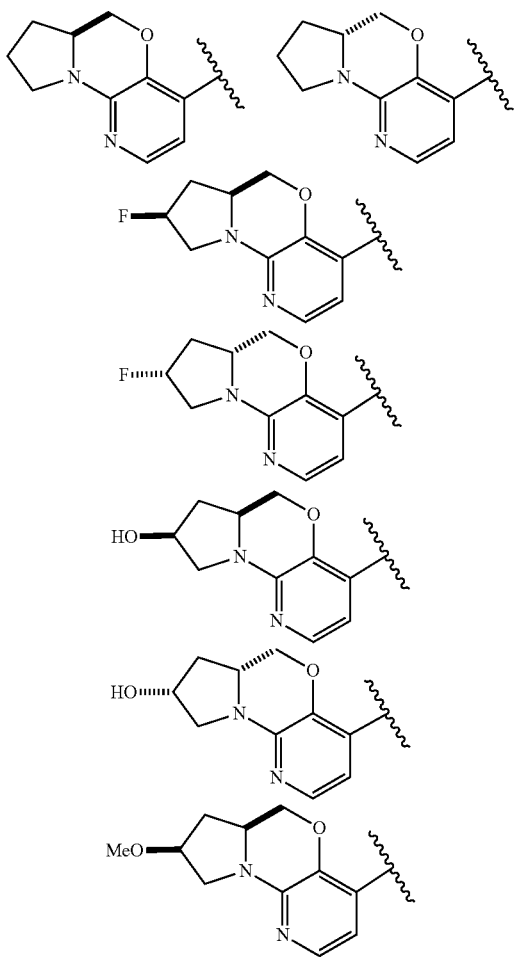

83

-continued

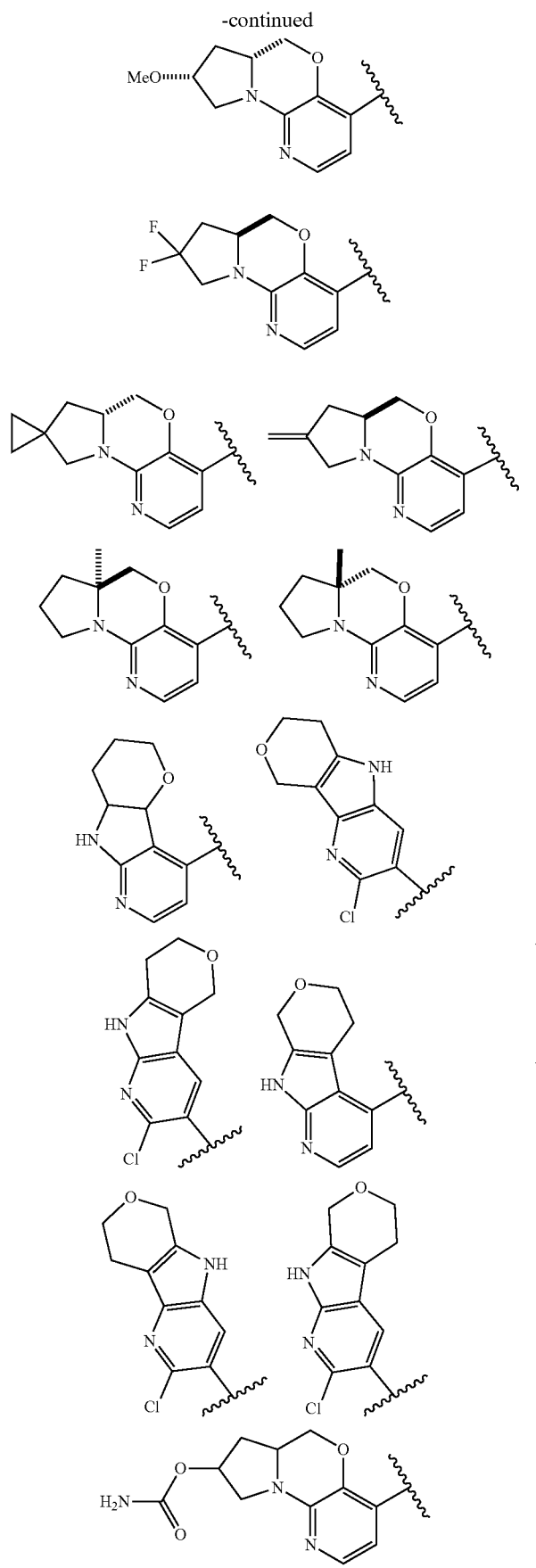

84

-continued

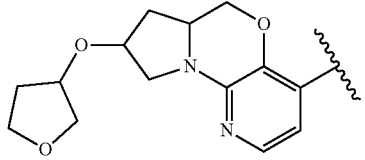
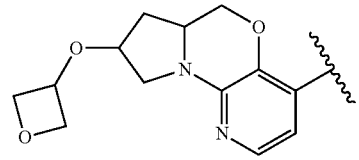
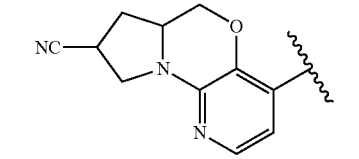
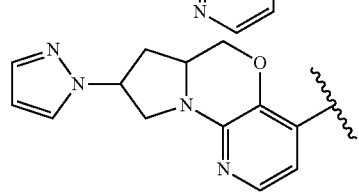
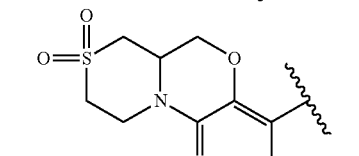
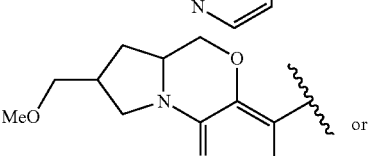
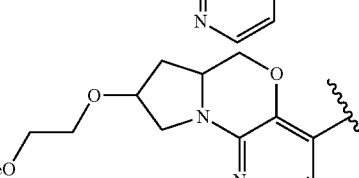 or
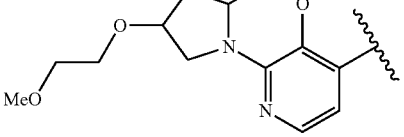

26. In embodiment 26, the compound of any one of embodiments 1A', 2, 3, 4, 5, 6, 7, 8, 9, 10, 11, 12, 13, 14, 15, 16, 17, 18, 19, 20, 21 and 22, and sub-embodiments contained therein, or a pharmaceutically acceptable salt thereof, is wherein $R^a$ and $R^b$ are independently selected from hydrogen, alkyl, amino, cycloalkyl, alkyldienyl, alkenyl, halo, haloalkyl, alkoxy, haloalkoxy, hydroxy, hydroxyalkyl, cyano, aminoalkyl, carboxy, and alkoxycarbonyl and $R^c$ is hydrogen, alkyl, halo, hydroxy, alkoxy, optionally substituted heterocyclyl, optionally substituted aryl, optionally substituted heteroaryl, —S(O)R, S(O)$_2$R, —C(O)R, —OR', —NR'C(O)R, —NR'SO$_2$R, —C(O)NR'R", —S(O)$_2$NR'R", —NR'R", or —NR'C(O)C(O)R where R is alkyl, cycloalkyl, cycloalkylalkyl, optionally substituted heterocyclyl, optionally substituted heterocyclylalkyl, optionally substituted aryl, optionally substituted aralkyl, optionally substituted heteroaryl, or optionally substituted heteroaralkyl, and R' and R" are independently hydrogen, alkyl, hydroxyalkyl, alkoxyalkyl, aminoalkyl, cycloalkylalkyl, optionally substituted heterocyclyl, optionally substituted heterocyclylalkyl, optionally substituted aryl, optionally substituted aralkyl, optionally substituted heteroaryl, or optionally substituted heteroaralkyl; or R' and R" together with the nitrogen atom to which they are attached form optionally substituted heterocyclyl; or when $R^c$ and $R^a$ are attached to the same carbon of ring $A^1$, then $R^c$ and $R^a$ together with the carbon atom to which they are attached can form cycloalkylene or heterocyclylene.

In a second sub-embodiment of embodiment 26, $R^a$ and $R^b$ are independently selected from hydrogen, alkyl, amino, cycloalkyl, halo, haloalkyl, alkoxy, haloalkoxy, hydroxy, hydroxyalkyl, alkoxyalkyl, aminoalkyl, and cyano and $R^c$ is hydrogen, OR' or —NR'R" where R' and R" are independently hydrogen, alkyl, hydroxyalkyl, alkoxyalkyl, aminoalkyl, or optionally substituted heterocyclyl.

In a third sub-embodiment of embodiment 26, $R^a$ is hydrogen, $R^b$ is hydrogen, hydroxy, hydroxyalkyl, or alkoxyalkyl, and $R^c$ is hydrogen or —OR' where R' is hydrogen, alkyl, hydroxyalkyl, alkoxyalkyl, aminoalkyl, or optionally substituted heterocyclyl.

In a fourth sub-embodiment of embodiment 26, $R^a$ is hydrogen, $R^b$ is hydrogen, methyl, chloro, methoxy, hydroxy, hydroxymethyl, methoxymethyl, ethoxymethyl, and $R^c$ is hydrogen, hydroxyethyloxy, or methoxyethyloxy.

In a fifth sub-embodiment of embodiment 26, ring $A^1$ is

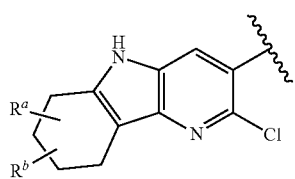

wherein $R^a$ and $R^b$ are as defined in embodiment 26 and first to fourth subembodiments therein.

27. In embodiment 27, the compound of any one of embodiments 1A', 2, 3, 4, 5, 6, 7, 8, 9, 10, 11, 12, 13, 14, 15, 16, 17, 18, 19, 20, 21 and 22, and sub-embodiments contained therein, or a pharmaceutically acceptable salt thereof is wherein ring $A^1$ is:

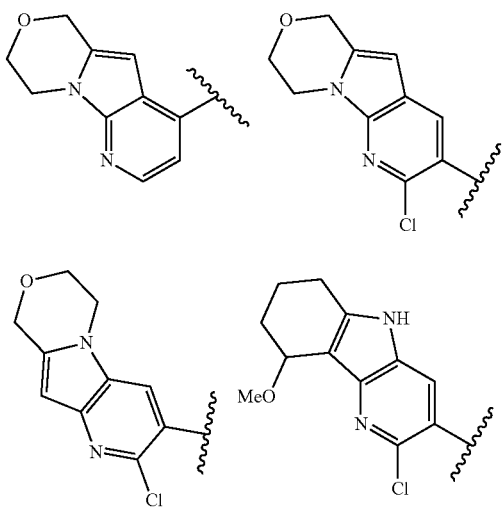

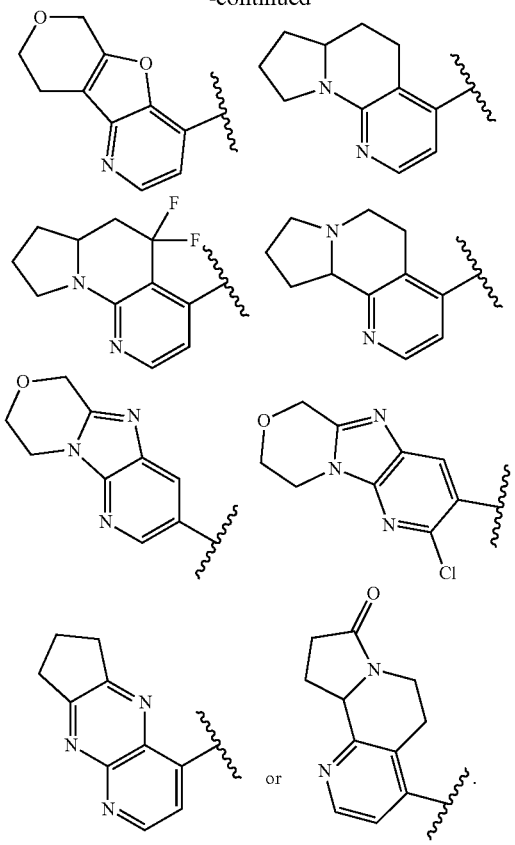

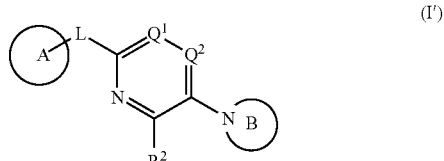

It is understood that the embodiments set forth above include all combination of embodiments and subembodiments listed therein. For example, the ring A listed in seventh sub-embodiment of embodiment 23, can independently be combined with one or more of the embodiments 1-22, 24, and 25 and/or subembodiments contained therein. Additional embodiments of the disclosure include:

A1. A compound of Formula (I'):

$$(I')$$

wherein:
ring A is aryl, cycloalkyl, heteroaryl, or fused heteroaryl ring, each ring substituted with $R^a$, $R^b$, and/or $R^c$ wherein $R^a$ and $R^b$ are independently selected from hydrogen, alkyl, amino, cycloalkyl, alkyldienyl, alkenyl, halo, haloalkyl, alkoxy, haloalkoxy, hydroxy, hydroxyalkyl, alkoxyalkyl, cyano, aminoalkyl, carboxy, and alkoxycarbonyl and $R^c$ is hydrogen, alkyl, halo, hydroxy, alkoxy, optionally substituted heterocyclyl, optionally substituted aryl, optionally substituted heteroaryl, —S(O)R, S(O)$_2$R, —C(O)R, —OR', —NR'C(O)R, —NR'SO$_2$R, —OC(O)NR'R", —C(O)NR'R", —S(O)$_2$NR'R", —NR'R", or —NR'C(O)C(O)R where R is alkyl, cycloalkyl, cycloalkylalkyl, optionally substituted heterocyclyl, optionally substituted heterocyclylalkyl, optionally substituted aryl, optionally substituted aralkyl, optionally substituted heteroaryl, or optionally substituted heteroaralkyl, and R' and R" are independently hydrogen, alkyl, hydroxyalkyl, alkoxyalkyl, aminoalkyl, cycloalkylalkyl, optionally substituted heterocyclyl, optionally substituted heterocyclylalkyl, optionally substituted aryl, optionally substituted aralkyl, optionally substituted heteroaryl, or optionally substituted heteroaralkyl; or R' and R" together with the nitrogen atom to which they are attached form optionally substituted heterocyclyl; or when $R^c$ and $R^a$ are attached to the same carbon of cycloalkyl or fused heteroaryl ring, then $R^c$ and $R^a$ together with the carbon atom to which they are attached can form cycloalkylene or heterocyclylene;

$Q^1$ is N or $CR^1$ wherein $R^1$ is hydrogen or deuterium;

$Q^2$ is N or CH, or CD;

$R^2$ is alkyl, halo, hydroxy, hydroxyalkyl, —$CD_2OH$, alkylsulfoxide, alkylsulfonyl, aminosulfonyl, aminocarbonyl, carboxy, cyano, or alkoxycarbonyl;

L is bond, O, S, S(O), $S(O)_2$, or $CR^5R^6$ where $R^5$ and $R^6$ are independently hydrogen or alkyl; and

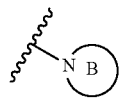

is a ring of formula (a) or (b):

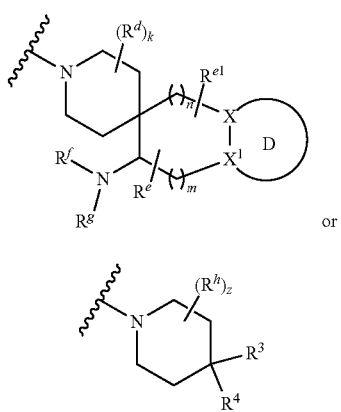

wherein:

m is 0, 1, or 2;

n is 0, 1, or 2 wherein when n is 2 then one of the $CH_2$ can be replaced with O, S, or $SO_2$; provided m+n is 1, 2, or 3;

k is 0, 1 or 2;

z is 0, 1, or 2;

each $R^d$ is independently hydrogen, alkyl, or halogen;

$R^e$ and $R^{e1}$ are independently hydrogen, alkyl, halogen, haloalkyl, alkoxy, haloalkoxy, hydroxy, hydroxyalkyl, cyano or oxo; or when $R^e$ and $R^{e1}$ are attached to the same carbon atom, then $R^e$ and $R^{e1}$ together with the carbon atom to which they are attached can form cycloalkylene or heterocyclylene;

$R^f$ and $R^g$ are independently hydrogen, alkyl, or haloalkyl;

each $R^h$ is independently alkyl, halo, haloalkyl, alkoxy, hydroxyalkyl, alkoxyalkyl, hydroxy, cyano, or oxo; or when one $R^h$ is connected to carbon 2 or 3 of the piperidine (b) ring and the second $R^h$ is attached to carbon 5 or 6 of the piperidine (b) ring, the nitrogen atom being position 1, then the first and second $R^h$ can combine to form alkylene chain;

ring D is phenyl or a 5 or 6 membered heteroaryl ring which, including X and $X^1$, contains one to three heteroatoms independently selected from N, O, and S and ring D can optionally be substituted with one or two groups independently selected from alkyl, halo, haloalkyl, alkoxy, haloalkoxy, hydroxy, hydroxyalkyl, cyano, amino, aminoalkyl, carboxy, cycloalkyl, heterocyclyl, heteroaryl, and acylamino;

X and $X^1$ are independently N or C; provided that only one of X and $X^1$ can be N;

$R^3$ is amino or aminoalkyl;

$R^4$ is alkyl, cycloalkylalkyl, halo, hydroxy, amino, alkoxycarbonyl, hydroxyalkyl, alkoxyalkyl, arylalkyl, heterocyclalkyl, cycloalkylalkyl, heterocyclalkyl, 5 or 6 membered heteroaryl, or 4 to 6 membered heterocyclyl wherein heteroaryl by itself or as part of heteroaralkyl and heterocyclyl by itself or as part of heterocyclylalkyl are substituted with $R^i$ and/or $R^j$ independently selected from hydrogen, alkyl, halo, haloalkyl, haloalkoxy, alkoxy, hydroxy, cyano, amino, aminoalkyl, alkylsulfoxide, or alkylsulfonyl; or $R^3$ and $R^4$ together with the carbon atom to which they are attached form a ring of formula (c):

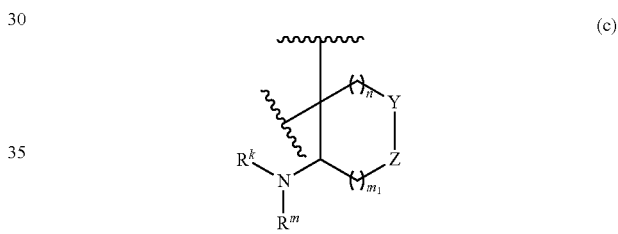

wherein:

m1 is 0, 1, or 2;

n1 is 0, 1, or 2; provided m1+n1 is 1, 2, or 3;

$R^k$ and $R^m$ are independently hydrogen, alkyl, or haloalkyl;

one of Y and Z is $CH_2$, O, S, S(O), $S(O)_2$, or NH; and the other of X and Y is $CH_2$; and wherein ring of formula (c) is substituted with $R^n$ and/or $R^o$ independently selected from hydrogen, alkyl, alkyldienyl, alkenyl, halo, haloalkyl, haloalkoxy, alkoxy, hydroxy, cyano, alkylsulfoxide, alkylsulfonyl, oxo, cycloalkyl, heterocyclyl, and heteroaryl; or when R" and $R^o$ are attached to the same carbon atom, then R" and $R^o$ together with the carbon atom to which they are attached can form cycloalkylene or heterocyclylene; or a pharmaceutically acceptable salt thereof.

A2. The compound of embodiment A1, wherein:

ring A is aryl, cycloalkyl, heteroaryl, or fused heteroaryl ring, each ring substituted with $R^a$, $R^b$, and/or $R^c$ wherein $R^a$ and $R^b$ are independently selected from hydrogen, alkyl, amino, cycloalkyl, alkyldienyl, alkenyl, halo, haloalkyl, alkoxy, haloalkoxy, hydroxy, hydroxyalkyl, cyano, aminoalkyl, carboxy, and alkoxycarbonyl and $R^c$ is hydrogen, alkyl, halo, hydroxy, alkoxy, optionally substituted heterocyclyl, optionally substituted aryl, optionally substituted heteroaryl, —S(O)R,   $S(O)_2R$,   —C(O)R,   —NR'C(O)R, —$NR'SO_2R$, —C(O)NR'R", —$S(O)_2NR'R"$, —NR'R", or —NR'C(O)C(O)R where R is alkyl, cycloalkyl, cycloalkylalkyl, optionally substituted heterocyclyl, optionally substituted heterocyclylalkyl, optionally substituted aryl, optionally substituted aralkyl, optionally substituted heteroaryl, or optionally substituted heteroaralkyl, and R' and R" are independently hydrogen, alkyl, hydroxyalkyl, alkoxyalkyl, aminoalkyl, cycloalkylalkyl, optionally substituted heterocyclyl, optionally substituted heterocyclylalkyl, optionally substituted aryl, optionally substituted aralkyl, optionally substituted heteroaryl, or optionally substituted heteroaralkyl; or R' and R" together with the nitrogen atom to which they are attached form optionally substituted heterocyclyl; or when $R^c$ and $R^a$ are attached to the same carbon of cycloalkyl or fused heteroaryl ring, then $R^c$ and $R^a$ together with the carbon atom to which they are attached can form cycloalkylene or heterocyclylene; and

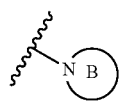

is a ring of formula (a) or (b):

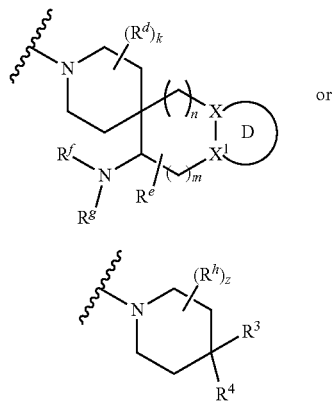

wherein:
m is 0, 1, or 2;
n is 0, 1, or 2; provided m+n is 1, 2, or 3;
k is 0, 1 or 2;
z is 0, 1, or 2;
each $R^d$ is independently hydrogen, alkyl, or halogen;
$R^e$ is hydrogen, alkyl, halogen, haloalkyl, alkoxy, haloalkoxy, hydroxy, hydroxyalkyl, cyano or oxo;
$R^f$ and $R^g$ are independently hydrogen, alkyl, or haloalkyl;
each $R^h$ is independently alkyl, halo, haloalkyl, alkoxy, hydroxyalkyl, alkoxyalkyl, hydroxy, cyano, or oxo; or
when one $R^h$ is connected to carbon 2 or 3 of the piperidine (b) ring and the second $R^h$ is attached to carbon 5 or 6 of the piperidine (b) ring, the nitrogen atom being position 1, then the first and second $R^h$ can combine to form alkylene chain; ring D is phenyl or a 5 or 6 membered heteroaryl ring which, including X and $X^1$, contains one to three heteroatoms independently selected from N, O, and S and ring D can optionally be substituted with one or two groups independently selected from alkyl, halo, haloalkyl, alkoxy, haloalkoxy, hydroxy, hydroxyalkyl, cyano, amino, aminoalkyl, carboxy, cycloalkyl, heterocyclyl, heteroaryl, and acylamino;

X and $X^1$ are independently N or C; provided that only one of X and $X^1$ can be N;

$R^3$ is amino or aminoalkyl;

$R^4$ is alkyl, cycloalkylalkyl, halo, hydroxy, amino, alkoxycarbonyl, hydroxyalkyl, alkoxyalkyl, arylalkyl, heterocyclalkyl, cycloalkylalkyl, heterocyclalkyl, 5 or 6 membered heteroaryl, or 4 to 6 membered heterocyclyl wherein heteroaryl by itself or as part of heteroaralkyl and heterocyclyl by itself or as part of heterocyclylalkyl are substituted with $R^i$ and/or $R^j$ independently selected from hydrogen, alkyl, halo, haloalkyl, haloalkoxy, alkoxy, hydroxy, cyano, amino, aminoalkyl, alkylsulfoxide, and alkylsulfonyl; or $R^3$ and $R^4$ together with the carbon atom to which they are attached form a ring of formula (c):

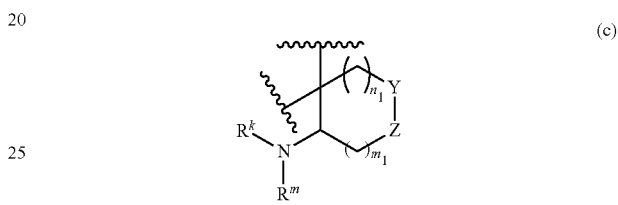

wherein:
m1 is 0, 1; or 2;
n1 is 0, 1, or 2; provided m1+n1 is 1, 2, or 3;
$R^k$ and $R^m$ are independently hydrogen, alkyl, or haloalkyl;
one of Y and Z is $CH_2$, O, S, S(O), $S(O)_2$, or NH; and the other of X and Y is $CH_2$; and wherein ring of formula (c) is substituted with R" and/or $R^o$ independently selected from hydrogen, alkyl, alkyldienyl, alkenyl, halo, haloalkyl, haloalkoxy, alkoxy, hydroxy, cyano, alkylsulfoxide, alkylsulfonyl, oxo, cycloalkyl, heterocyclyl, and heteroaryl; or a pharmaceutically acceptable salt thereof.

A3. The compound of embodiment A1 having formula (IA):

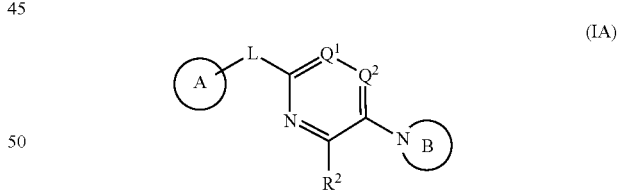

wherein:
ring A is aryl, cycloalkyl, heteroaryl, or fused heteroaryl ring, each ring substituted with $R^a$, $R^b$, and/or $R^c$ wherein $R^a$ and $R^b$ are independently selected from hydrogen, alkyl, halo, haloalkyl, alkoxy, haloalkoxy, hydroxy, hydroxyalkyl, cyano, aminoalkyl, carboxy, and alkoxycarbonyl and $R^c$ is hydrogen, alkyl, halo, hydroxy, alkoxy, optionally substituted heterocyclyl, optionally substituted aryl, optionally substituted heteroaryl, —SOR, $SO_2R$, —COR, —NR'C(O)R, —NR'S(O)$_2$R, —C(O)NR'R", —S(O)$_2$NR'R", —NR'R", or —NR'C(O)C(O)R, where R is alkyl, cycloalkyl, cycloalkylalkyl, optionally substituted heterocyclyl, optionally substituted heterocyclylalkyl, optionally substituted aryl, optionally substituted aralkyl, optionally substituted heteroaryl, or optionally substituted heteroaralkyl, and R' and R" are independently hydrogen, alkyl, hydroxyalkyl, alkoxyalkyl, aminoalkyl, cycloalkylalkyl, optionally substituted heterocyclyl, optionally substituted heterocyclylalkyl, optionally substituted aryl, optionally substituted aralkyl, optionally substituted heteroaryl, or optionally substituted heteroaralkyl; or R' and R" together with the nitrogen atom to which they are attached form optionally substituted heterocyclyl; and

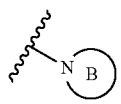

is a ring of formula (a) or (b):

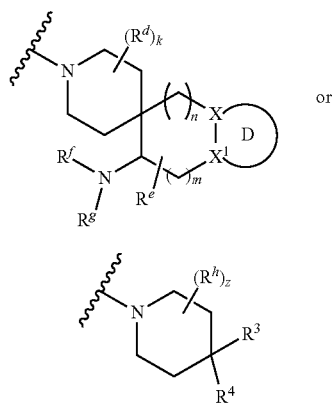

wherein:
m is 0, 1; or 2;
n is 0, 1, or 2; provided m+n is 1, 2, or 3;
k is 0, 1 or 2;
z is 0, 1, or 2;
each $R^d$ is independently hydrogen, alkyl, or halogen;
$R^e$ is hydrogen, alkyl, halogen, haloalkyl, alkoxy, haloalkoxy, hydroxy, hydroxyalkyl, cyano or oxo;
$R^f$ and $R^g$ are independently hydrogen, alkyl, or haloalkyl;
each $R^h$ is independently alkyl, halo, haloalkyl, alkoxy, hydroxyalkyl, alkoxyalkyl, hydroxy, cyano, or oxo; or
when one $R^h$ is connected to carbon 2 or 3 of the piperidine (b) ring and the second $R^h$ is attached to carbon 5 or 6 of the piperidine (b) ring, the nitrogen atom being position 1, then the first and second $R^h$ can combine to form alkylene chain; ring D is phenyl or a 5 or 6 membered heteroaryl ring which, including X and $X^1$, contains one to three heteroatoms independently selected from N, O, and S and ring D can optionally be substituted with one or two groups independently selected from alkyl, halo, haloalkyl, alkoxy, haloalkoxy, hydroxy, hydroxyalkyl, cyano, amino, aminoalkyl, carboxy, cycloalkyl, heterocyclyl, heteroaryl, and acylamino;
X and $X^1$ are independently N or C; provided that only one of X and $X^1$ can be N;
$R^3$ is amino or aminoalkyl;
$R^4$ is alkyl, cycloalkylalkyl, halo, hydroxy, amino, alkoxycarbonyl, hydroxyalkyl, alkoxyalkyl, arylalkyl, heterocyclalkyl, cycloalkylalkyl, heterocyclalkyl, 5 or 6 membered heteroaryl, or 4 to 6 membered heterocyclyl wherein heteroaryl by itself or as part of heteroaralkyl and heterocyclyl by itself or as part of heterocyclylalkyl are substituted with $R^i$ and/or $R^j$ independently selected from hydrogen, alkyl, halo, haloalkyl, haloalkoxy, alkoxy, hydroxy, cyano, amino, aminoalkyl, alkylsulfoxide, and alkylsulfonyl; or
$R^3$ and $R^4$ together with the carbon atom to which they are attached form a ring of formula (c):

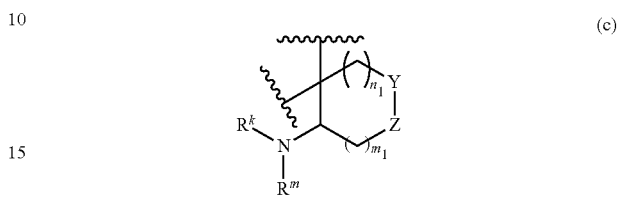

wherein:
m1 is 0, 1, or 2;
n1 is 0, 1, or 2; provided m1+n1 is 1, 2, or 3;
$R^k$ and $R^m$ are independently hydrogen, alkyl, or haloalkyl;
one of Y and Z is $CH_2$, O, S, S(O), $S(O)_2$, or NH; and the other of X and Y is $CH_2$; and wherein ring of formula (c) is substituted with $R^n$ and/or $R^o$ independently selected from hydrogen, alkyl, halo, haloalkyl, haloalkoxy, alkoxy, hydroxy, cyano, alkylsulfoxide, alkylsulfonyl, oxo, cycloalkyl, heterocyclyl, and heteroaryl; or
a pharmaceutically acceptable salt thereof.

A4. The compound of embodiment A1 or a pharmaceutically acceptable salt thereof wherein:
ring A is aryl, cycloalkyl, heteroaryl, or fused heteroaryl ring, each ring substituted with $R^a$, $R^b$, and/or $R^c$ wherein $R^a$ and $R^b$ are independently selected from hydrogen, alkyl, amino, cycloalkyl, alkyldienyl, alkenyl, halo, haloalkyl, alkoxy, haloalkoxy, hydroxy, hydroxyalkyl, cyano, aminoalkyl, carboxy, and alkoxycarbonyl and $R^c$ is hydrogen, alkyl, halo, hydroxy, alkoxy, optionally substituted heterocyclyl, optionally substituted aryl, optionally substituted heteroaryl, —NHC(O)R, or —NR'R" where R is alkyl, cycloalkyl, optionally substituted heterocyclyl, optionally substituted aryl, optionally substituted heteroaryl, or optionally substituted heteroaralkyl, and R' and R" are independently hydrogen or alkyl; or R' and R" together with the nitrogen atom to which they are attached form optionally substituted heterocyclyl;

is a ring of formula (a) or (b):

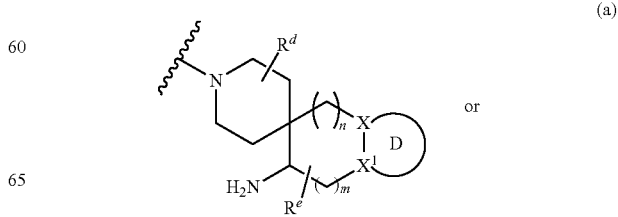

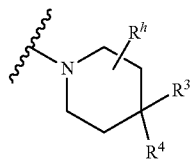

wherein:
R$^d$ is hydrogen or alkyl;
R$^e$ is hydrogen, alkyl, halogen, or oxo;
ring D is phenyl or a 5 or 6 membered heteroaryl ring which, including X and X$^1$, contains one to three heteroatoms independently selected from N, O, or S and ring D can optionally be substituted with one or two groups independently selected from alkyl;
R$^3$ is amino or aminoalkyl;
R$^4$ is alkyl, cycloalkylalkyl, halo, hydroxy, amino, alkoxycarbonyl, hydroxyalkyl, alkoxyalkyl, 5 or 6 membered heteroaryl, or 4 to 6 membered heterocyclyl wherein heteroaryl or heterocyclyl is substituted with R$^i$ and/or R$^j$ independently selected from hydrogen, alkyl, halo, haloalkyl, haloalkoxy, alkoxy, hydroxy, cyano, alkylsulfoxide, and alkylsulfonyl; or
R$^3$ and R$^4$ together with the carbon atom to which they are attached form a ring of formula (c):

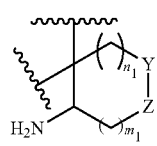

wherein:
one of Y and Z is CH$_2$, O, S, S(O), S(O)$_2$, or NH; and the other of X and Y is CH$_2$; and wherein ring of formula (c) is substituted with R$^n$ and/or R$^o$ independently selected from hydrogen, alkyl, alkyldienyl, alkenyl, halo, haloalkyl, haloalkoxy, alkoxy, hydroxy, cyano, alkylsulfoxide, alkylsulfonyl, and oxo.

A5. The compound of embodiment A3 or a pharmaceutically acceptable salt thereof wherein:
ring A is aryl, cycloalkyl, heteroaryl, or fused heteroaryl ring, each ring substituted with R$^a$, R$^b$, and/or R$^c$ wherein R$^a$ and R$^b$ are independently selected from hydrogen, alkyl, halo, haloalkyl, alkoxy, haloalkoxy, hydroxy, hydroxyalkyl, cyano, aminoalkyl, carboxy, and alkoxycarbonyl and R$^c$ is hydrogen, alkyl, halo, hydroxy, alkoxy, optionally substituted heteroaryl, optionally substituted aryl, optionally substituted heteroaryl, —NHC(O)R, or —NR'R" where R is alkyl, cycloalkyl, optionally substituted heterocyclyl, optionally substituted aryl, optionally substituted heteroaryl, or optionally substituted heteroaralkyl; and R' and R" are independently hydrogen or alkyl; or R' and R" together with the nitrogen atom to which they are attached form optionally substituted heterocyclyl;

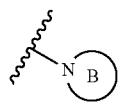

is a ring of formula (a) or (b):

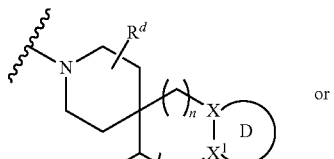

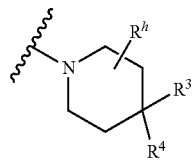

wherein:
R$^d$ is hydrogen or alkyl;
R$^e$ is hydrogen, alkyl, halogen, or oxo;
ring D is phenyl or a 5 or 6 membered heteroaryl ring which, including X and X$^1$, contains one to three heteroatoms independently selected from N, O, or S and ring D can optionally be substituted with one or two groups independently selected from alkyl;
R$^3$ is amino or aminoalkyl;
R$^4$ is alkyl, cycloalkylalkyl, halo, hydroxy, amino, alkoxycarbonyl, hydroxyalkyl, alkoxyalkyl, 5 or 6 membered heteroaryl, or 4 to 6 membered heterocyclyl wherein heteroaryl or heterocyclyl is substituted with R$^i$ and/or R$^j$ independently selected from hydrogen, alkyl, halo, haloalkyl, haloalkoxy, alkoxy, hydroxy, cyano, alkylsulfoxide, and alkylsulfonyl; or
R$^3$ and R$^4$ together with the carbon atom to which they are attached form a ring of formula (c):

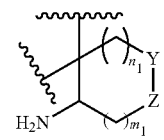

wherein:
one of Y and Z is CH$_2$, O, S, S(O), S(O)$_2$, or NH; and the other of X and Y is CH$_2$; and wherein ring of formula (c) is substituted with R$^n$ and/or R$^o$ independently selected from hydrogen, alkyl, halo, haloalkyl, haloalkoxy, alkoxy, hydroxy, cyano, alkylsulfoxide, alkylsulfonyl, and oxo.

A6. The compound of any one of embodiments A1, A2, A3, A4 and A5 or a pharmaceutically acceptable salt thereof having the structure of formula (III):

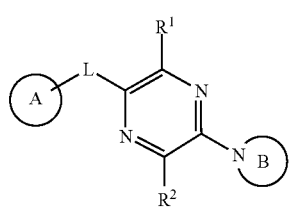

A7. The compound of any one of embodiments A1, A2, A3, A4 and A5 or a pharmaceutically acceptable salt thereof having the structure of formula (IV):

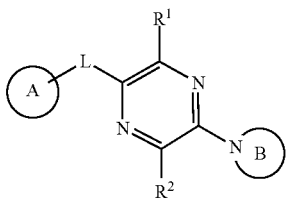

(IV)

A8. The compound of any one of embodiments A1, A2, A3, A4 and A5 or a pharmaceutically acceptable salt thereof having the structure of formula (V):

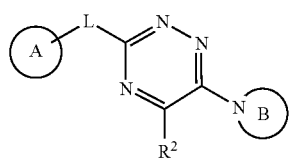

(V)

A9. The compound of any one of embodiments A1, A2, A3, A4 and A5 or a pharmaceutically acceptable salt thereof having the structure of formula (VI):

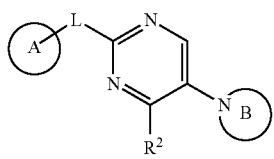

(VI)

A10. The compound of any one of embodiments A1 to A7, or a pharmaceutically acceptable salt wherein $R^1$ is hydrogen.

A11. The compound of any one of embodiments A1 to A7 or a pharmaceutically acceptable salt wherein $R^1$ is deuterium.

A12. The compound of any one of embodiments A1 to A11 or a pharmaceutically acceptable salt wherein L is S.

A13. The compound of any one of embodiments A1 to A11 or a pharmaceutically acceptable salt wherein L is S(O) or $S(O)_2$.

A14. The compound of any one of embodiments A1 to A13 or a pharmaceutically acceptable salt thereof wherein $R^2$ is hydroxyalkyl.

A15. The compound of any one of embodiments A1 to A13 or a pharmaceutically acceptable salt thereof wherein $R^2$ is hydroxymethyl.

A16. The compound of any one of embodiments A1 to A13 or a pharmaceutically acceptable salt thereof wherein $R^2$ is alkylsulfonyl.

A17. The compound of any one of embodiments A1 to A13 or a pharmaceutically acceptable salt thereof wherein $R^2$ is methylsulfonyl or ethylsulfonyl.

A18. The compound of any one of embodiments A1 to A13 or a pharmaceutically acceptable salt thereof wherein $R^2$ is alkylsulfoxide.

A19. The compound of any one of embodiments A1 to A13 or a pharmaceutically acceptable salt thereof wherein $R^2$ is methylsulfoxide.

A20. The compound of any one of embodiments A1 to A13 or a pharmaceutically acceptable salt thereof wherein $R^2$ is —$CD_2OH$.

A21. The compound of any one of embodiments A1 to A13 or a pharmaceutically acceptable salt thereof wherein $R^2$ is alkoxycarbonyl, aminosulfonyl or aminocarbonyl.

A22. The compound of any one of embodiments A1 to A13 or a pharmaceutically acceptable salt thereof wherein $R^2$ is hydroxy.

A23. The compound of any one of embodiments A1 to 13 or a pharmaceutically acceptable salt thereof wherein $R^2$ is halo.

A24. The compound of any one of embodiments A2 to A23 or a pharmaceutically acceptable salt thereof wherein

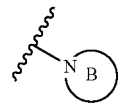

is a ring of formula (a):

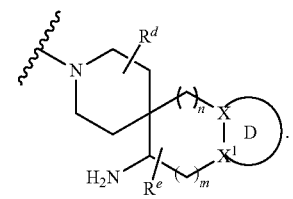

(a)

A25. The compound of any one of embodiments A1, and A6 to A23 or a pharmaceutically acceptable salt thereof wherein

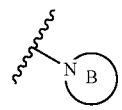

is a ring of formula (a).

A26. The compound of any one of embodiments A1 to A23 or a pharmaceutically acceptable salt thereof wherein

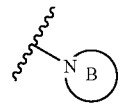

is:
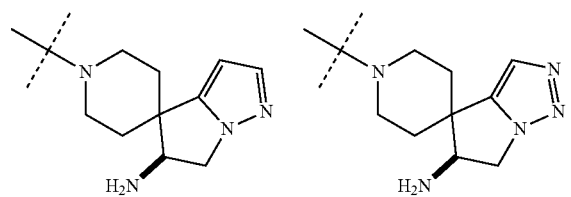
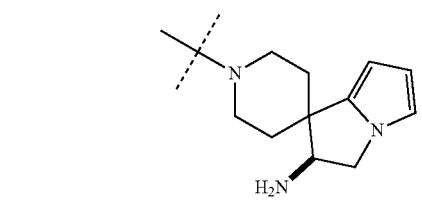
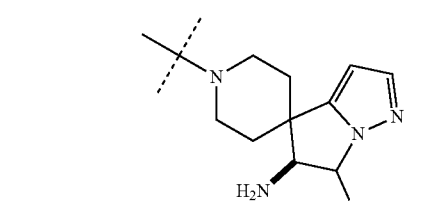
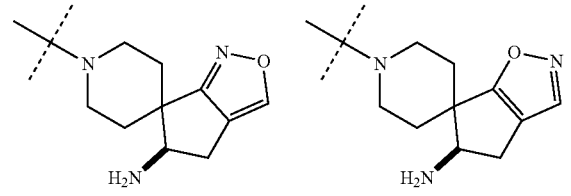
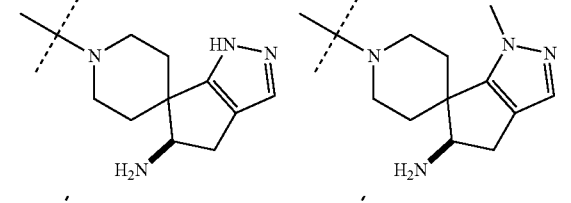
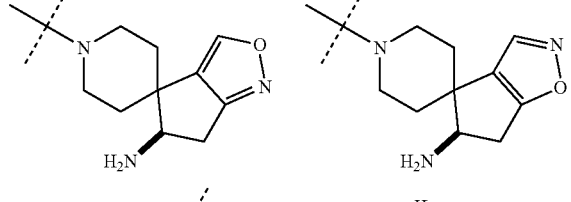
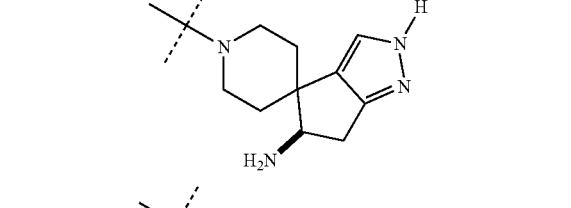
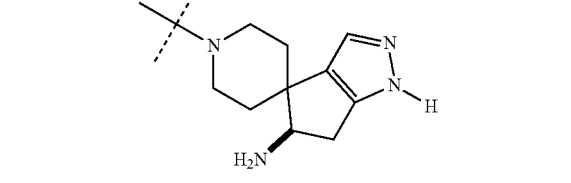
-continued
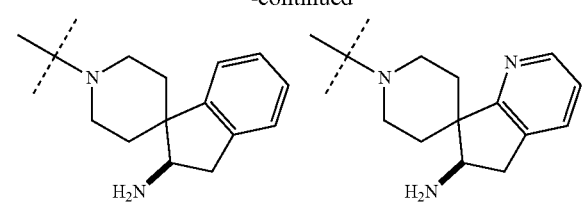
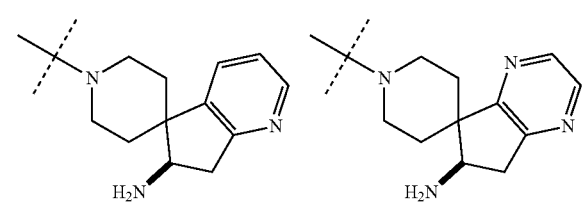
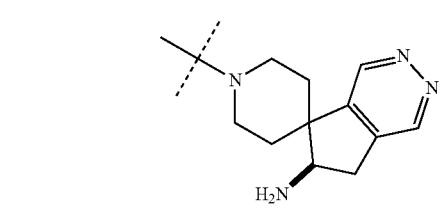
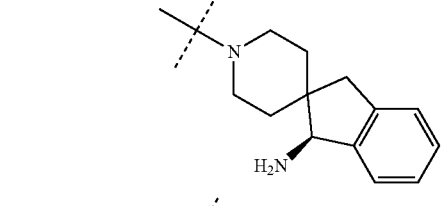
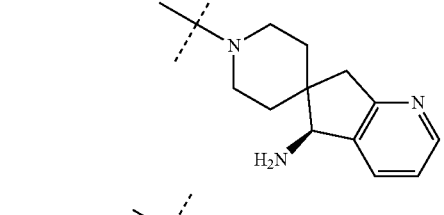
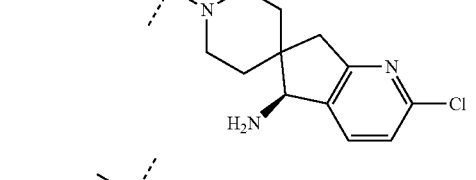
or
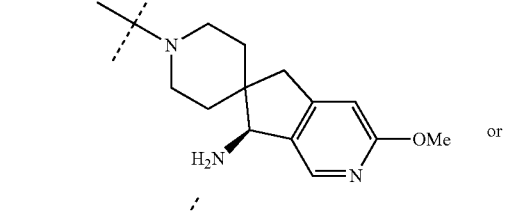
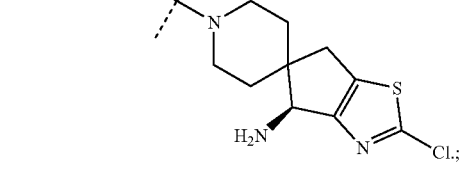

preferably

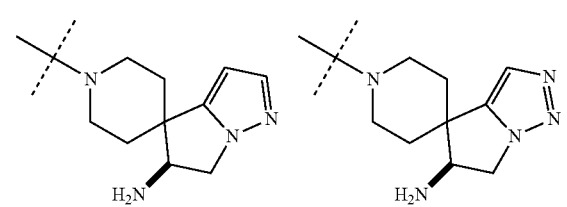
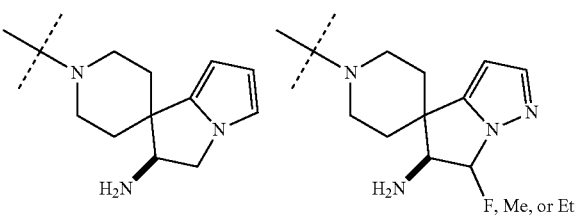
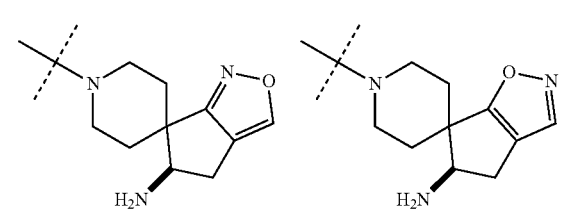
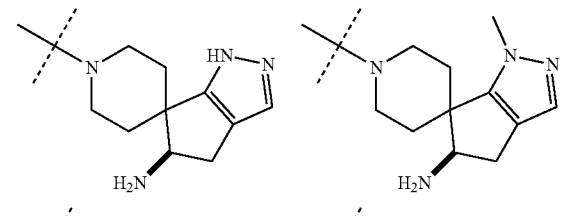
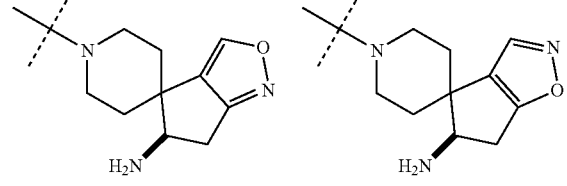
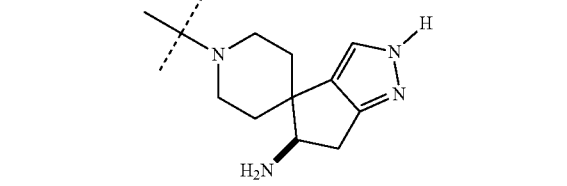
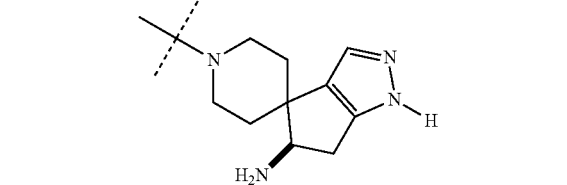
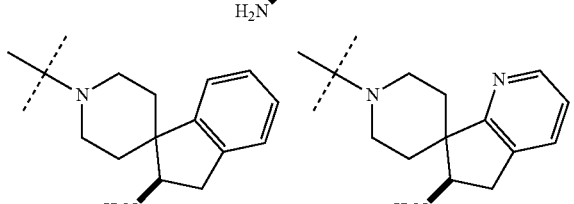

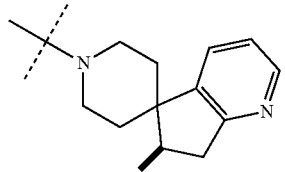
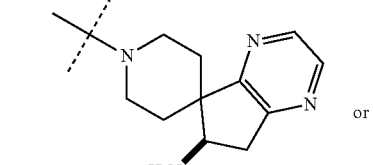
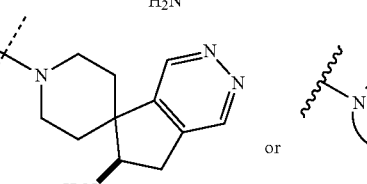
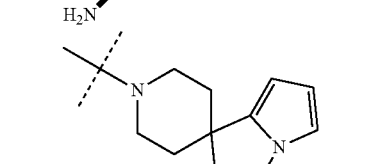
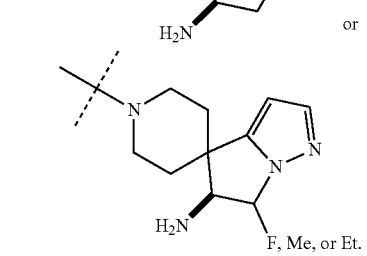

A27. The compound of any one of embodiments A2 to A23 or a pharmaceutically acceptable salt thereof wherein

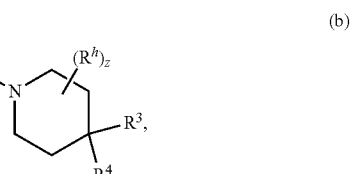

is:

(b)

preferably where z is 1, and
where $R^3$ is amino or aminoalkyl; and
$R^4$ is alkyl, cycloalkylalkyl, halo, hydroxy, amino, alkoxycarbonyl, hydroxyalkyl, alkoxyalkyl, 5 or 6 membered heteroaryl, or 4 to 6 membered heterocyclyl wherein heteroaryl or heterocyclyl is substituted with $R^i$ and/or $R^j$ independently selected from hydrogen, alkyl, halo, haloalkyl, haloalkoxy, alkoxy, hydroxy, cyano, alkylsulfoxide, or alkylsulfonyl.

A28. The compound of any one of embodiments A1 and A6 to A23 or a pharmaceutically acceptable salt thereof wherein

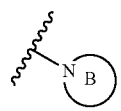

is:

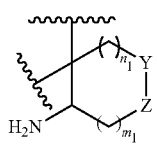

(c)

wherein:

m1 is 0, 1; or 2;

n1 is 0, 1, or 2; provided m1+n1 is 1, 2, or 3;

$R^k$ and $R^m$ are independently hydrogen, alkyl, or haloalkyl;

one of Y and Z is $CH_2$, O, S, S(O), $S(O)_2$, or NH; and the other of X and Y is $CH_2$; and wherein ring of formula (c) is substituted with R" and/or R° independently selected from hydrogen, alkyl, alkyldienyl, alkenyl, halo, haloalkyl, haloalkoxy, alkoxy, hydroxy, cyano, alkylsulfoxide, alkylsulfonyl, oxo, cycloalkyl, heterocyclyl, and heteroaryl; or when R" and R° are attached to the same carbon atom, then R" and R° together with the carbon atom to which they are attached can form cycloalkylene or heterocyclylene;

preferably,

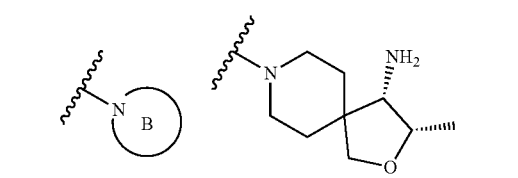

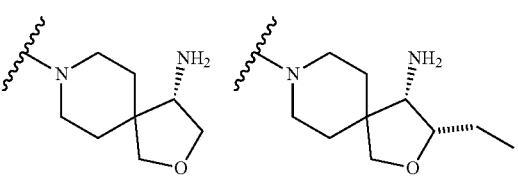

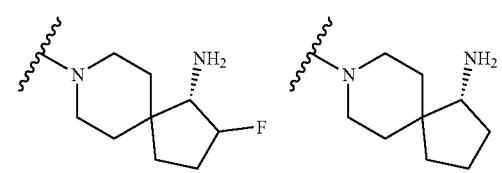

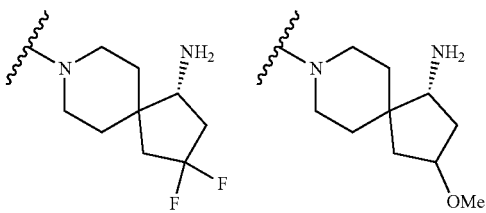

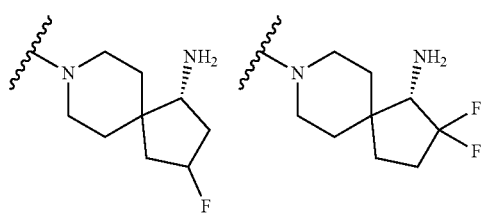

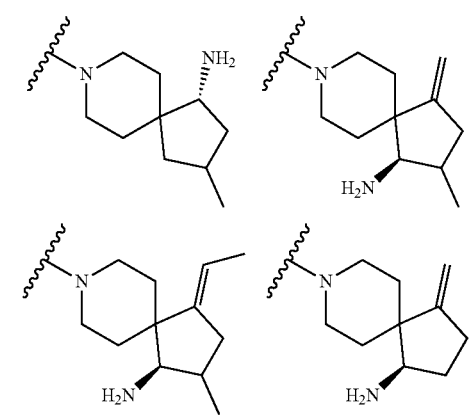

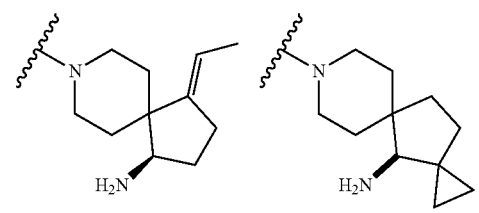

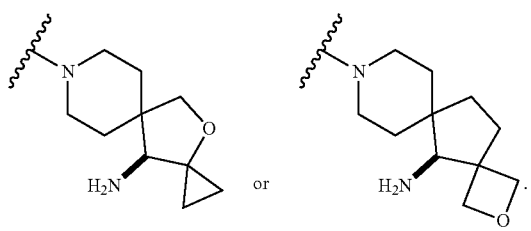

A29. The compound of embodiment A27 or a pharmaceutically acceptable salt thereof wherein z is 0, $R^3$ is aminomethyl, and $R^4$ is methyl.

A30. The compound of any one of embodiments A1 to A23 or a pharmaceutically acceptable salt thereof wherein

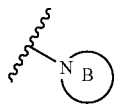

is:
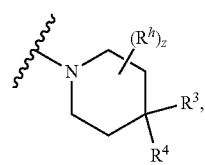
(b)
preferably where z is 1, and
where R³ and R⁴ together with the carbon atom to which they are attached form a ring of formula (c):
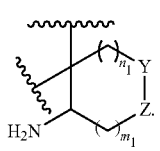
(c)
A31. The compound of embodiment A30 or a pharmaceutically acceptable salt thereof wherein
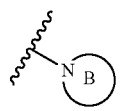
is:
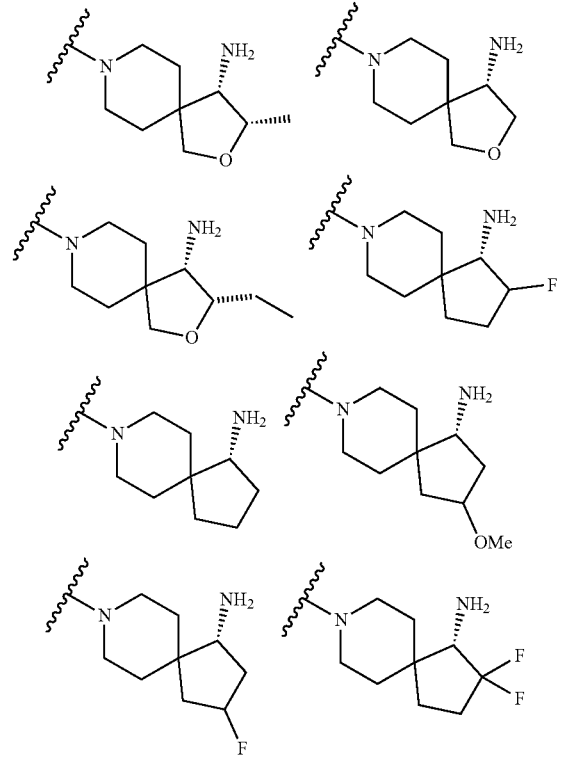
-continued
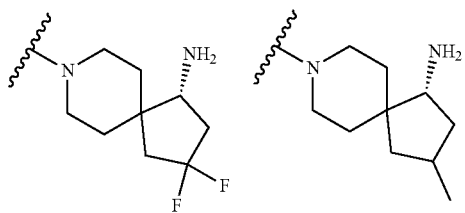
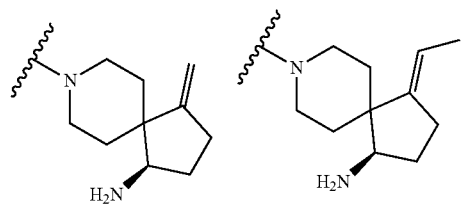
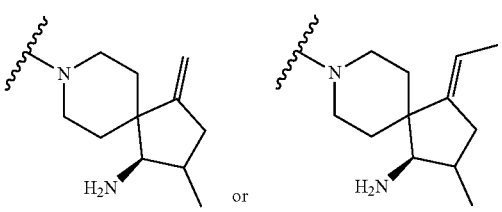
preferably,
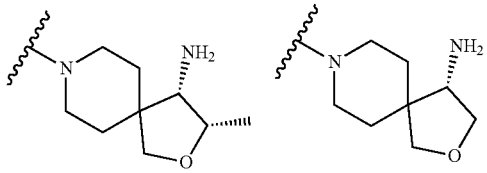
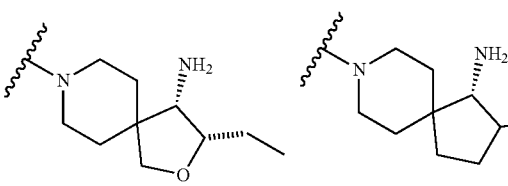
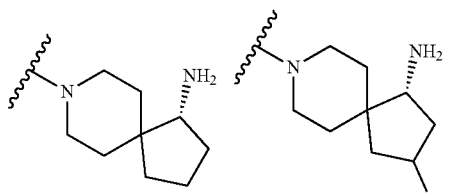
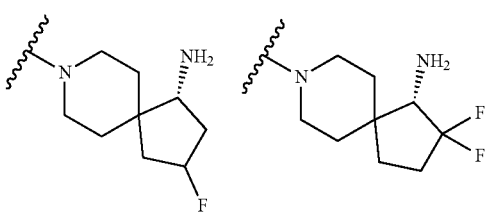

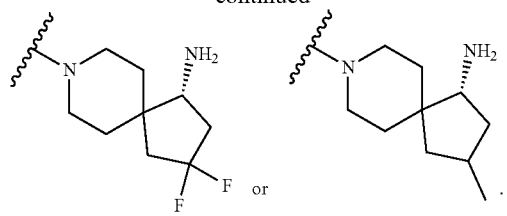

or more preferably

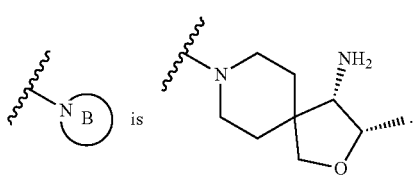

A32. The compound of any one of embodiments A1 to 31 or a pharmaceutically acceptable salt thereof wherein ring A is heteroaryl substituted with $R^a$, $R^b$, and/or $R^c$.

A33. The compound of embodiment A32 or a pharmaceutically acceptable salt thereof wherein ring A is a five or six membered heteroaryl (preferably, thienyl, pyrazolyl, pyridinyl, pyrimidinyl, pyridazinyl, or pyrazinyl) substituted with $R^a$, $R^b$, and/or $R^c$.

A34. The compound of embodiment A32 or a pharmaceutically acceptable salt thereof wherein ring A is a five or six membered heteroaryl (preferably, thienyl, pyrazolyl, pyridinyl, pyrimidinyl, pyridazinyl, or pyrazinyl) substituted with $R^a$ and $R^b$ independently selected from hydrogen, alkyl, amino, cycloalkyl, alkyldienyl, alkenyl, halo, haloalkyl, alkoxy, haloalkoxy, hydroxy, or cyano and $R^c$ is hydrogen, alkyl, halo, hydroxy, alkoxy, optionally substituted heterocyclyl, optionally substituted heteroaryl, —NHCOR, or —NR'R" where R is alkyl or optionally substituted heterocyclyl and R' and R" are independently hydrogen, alkyl, hydroxyalkyl, alkoxyalkyl, aminoalkyl, or optionally substituted heterocyclyl, preferably ring A is a five or six membered heteroaryl (preferably, thienyl, pyrazolyl, pyridinyl, pyrimidinyl, pyridazinyl, or pyrazinyl) substituted with $R^a$ and $R^b$ independently selected from hydrogen, alkyl, halo, haloalkyl, alkoxy, haloalkoxy, hydroxy, or cyano and $R^c$ is hydrogen, alkyl, halo, hydroxy, alkoxy, optionally substituted heterocyclyl, optionally substituted heteroaryl, —NHCOR, or —NR'R" where R is alkyl or optionally substituted heterocyclyl and R' and R" are independently hydrogen, alkyl, hydroxyalkyl, alkoxyalkyl, aminoalkyl, or optionally substituted heterocyclyl.

A35. The compound of embodiment A32 or a pharmaceutically acceptable salt thereof wherein ring A is a five or six membered heteroaryl (preferably, thienyl, pyrazolyl, pyridinyl, pyrimidinyl, pyridazinyl, or pyrazinyl) substituted with $R^a$ and $R^b$ independently selected from hydrogen, amino, methyl, ethyl, methoxy, ethoxy, chloro, fluoro, difluoromethyl, trifluoromethyl, difluoromethoxy, trifluoromethoxy, or cyano, and $R^c$ is hydrogen, amino, pyrrolidin-1-yl, piperidin-1-yl,

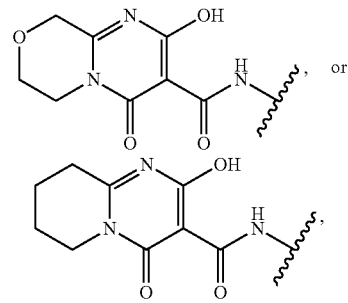

preferably ring A is 2-amino-3-chloropyridin-4-yl, 2-trifluoromethylpyridin-4-yl, 2,3-dichloropyridin-4-yl, 3-chloro-2-methoxypyridin-4-yl, 3-chloro-2-pyrrolidin-1-ylpyridin-4-yl, or 2-fluoro-3-chloropyridin-4-yl.

A36. The compound of any one of embodiments A1 to A31 or a pharmaceutically acceptable salt thereof wherein ring A is phenyl substituted with $R^a$, $R^b$, and/or $R^c$.

A37. The compound of embodiment A36 or a pharmaceutically acceptable salt thereof ring A is phenyl substituted with $R^a$ and $R^b$ are independently selected from hydrogen, alkyl, amino, cycloalkyl, alkenyl, halo, haloalkyl, alkoxy, haloalkoxy, hydroxy, or cyano and $R^c$ is hydrogen, alkyl, halo, hydroxy, alkoxy, optionally substituted heterocyclyl, optionally substituted heteroaryl, —NHC(O)R, or —NR'R" where R is alkyl or optionally substituted heterocyclyl and R' and R" are independently hydrogen, alkyl, hydroxyalkyl, alkoxyalkyl, aminoalkyl, or optionally substituted heterocyclyl; preferably, ring A is 2,3-dichlorophenyl, 2-amino-2-chlorophenyl,

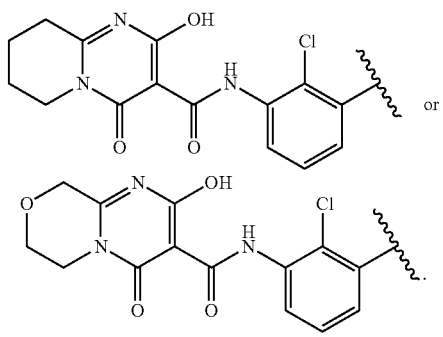

A38. The compound of any one of embodiments A1 to A31 or a pharmaceutically acceptable salt thereof wherein ring A is fused heteroaryl substituted with $R^a$, $R^b$, and/or $R^c$ wherein $R^a$ and $R^b$ are independently selected from hydrogen, alkyl, amino, cycloalkyl, alkyldienyl, alkenyl, halo, haloalkyl, alkoxy, haloalkoxy, hydroxy, or cyano and $R^c$ is hydrogen or —NR'R" where R' and R" are independently hydrogen, alkyl, hydroxyalkyl, alkoxyalkyl, aminoalkyl, or optionally substituted heterocyclyl, preferably $R^a$ and $R^b$ are independently selected from hydrogen, methyl, ethyl, methoxy, ethoxy, chloro, fluoro, difluoromethyl, trifluoromethyl, difluoromethoxy, trifluoromethoxy, hydroxy, or cyano, and $R^c$ is hydrogen.

A39. The compound of any one of embodiments A1 to A31 or a pharmaceutically acceptable salt thereof wherein ring A is fused heteroaryl of formula (d)

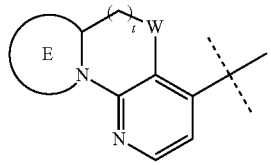

(d)

where:

t is 0, 1 or 2;

ring E is 4 to 7 membered heterocycle containing 1 or 2 heteroatoms independently selected from O, N, S, and SO$_2$ and the remaining atoms are carbon; and W is O, CH$_2$, or N; substituted with R$^a$, R$^b$, and/or R$^c$ wherein R$^a$ and R$^b$ are independently selected from hydrogen, amino, alkyl, alkyldienyl, alkenyl, halo, haloalkyl, alkoxy, haloalkoxy, hydroxy, hydroxyalkyl, cyano, aminoalkyl, carboxy, and alkoxycarbonyl and R$^c$ is hydrogen, alkyl, halo, hydroxy, or alkoxy; or when R$^a$ and R$^c$ are attached to the same carbon atom, R$^a$ and R$^c$ together with the carbon atom to which they are attached can form cycloalkylene or heterocyclylene. Preferably, ring A is:

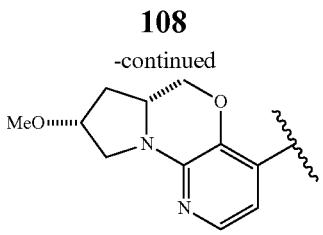

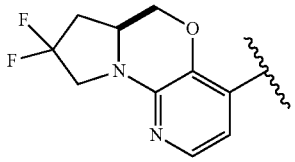

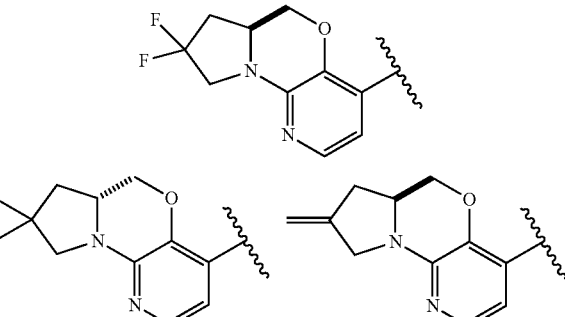

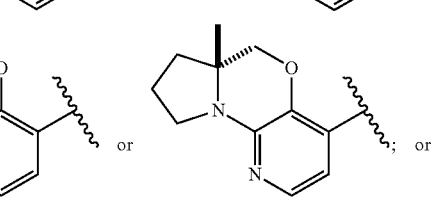

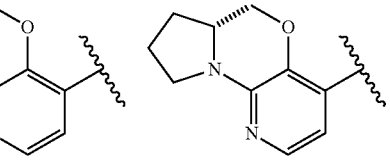

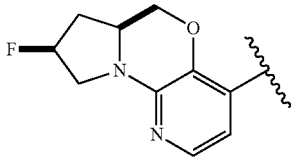

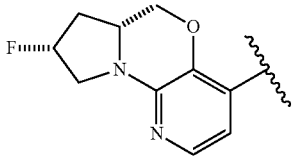

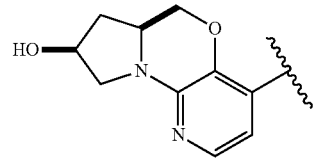

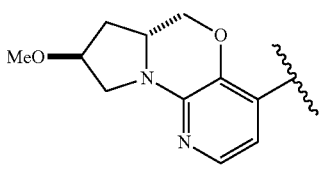

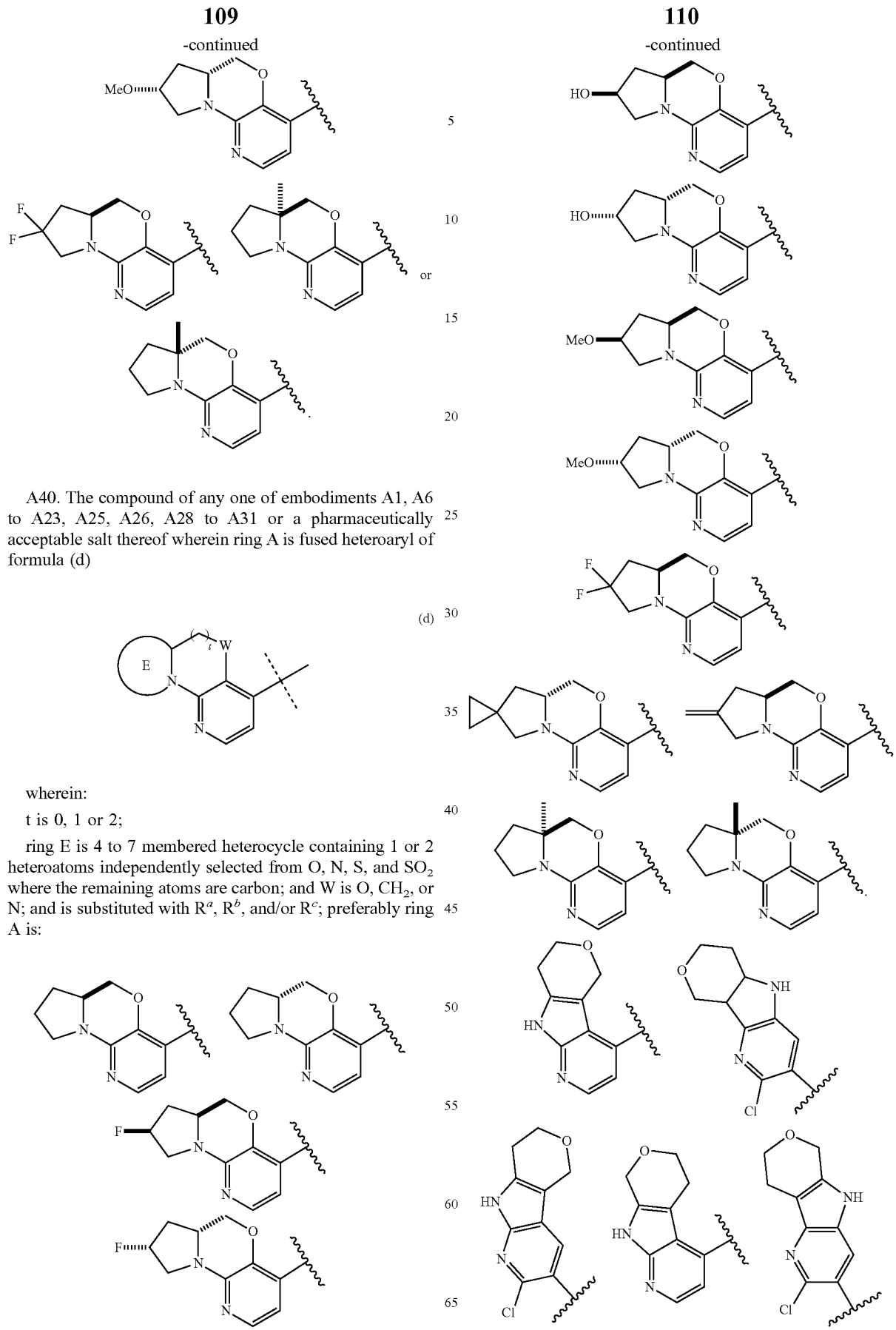

A40. The compound of any one of embodiments A1, A6 to A23, A25, A26, A28 to A31 or a pharmaceutically acceptable salt thereof wherein ring A is fused heteroaryl of formula (d)

(d)

wherein:

t is 0, 1 or 2;

ring E is 4 to 7 membered heterocycle containing 1 or 2 heteroatoms independently selected from O, N, S, and SO₂ where the remaining atoms are carbon; and W is O, CH₂, or N; and is substituted with R$^a$, R$^b$, and/or R$^c$; preferably ring A is:

-continued

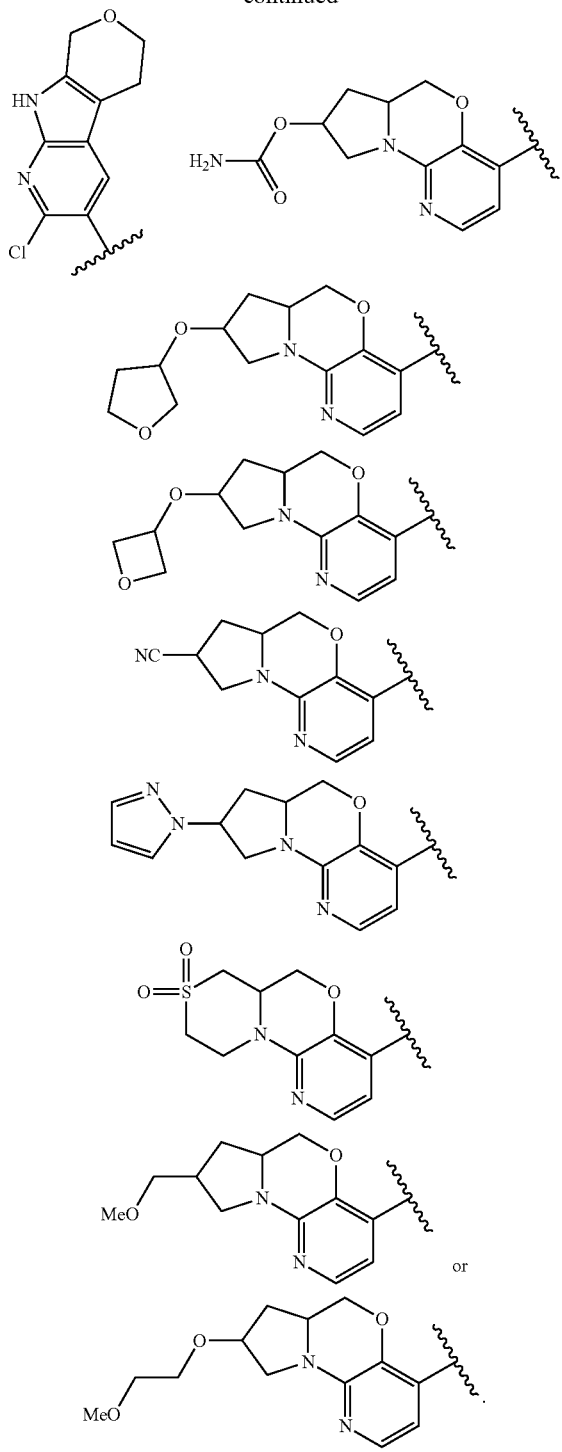

A41. A pharmaceutical composition comprising a compound of any one of embodiments A1 to A40 and a pharmaceutically acceptable excipient.

A42. A method of treating a disease treatable by inhibition of SHP2 in a patient which method comprises administering to the patient, preferably a patient in need of such treatment, a therapeutically effective amount of a compound of any one of claims A1 to A40 or which method comprises administering to the patient, preferably a patient in need of such treatment, a pharmaceutical composition comprising a compound of any one of claims A1 to A40 and a pharmaceutically acceptable excipient.

A43. The method of embodiment A42 wherein the disease is cancer.

A44. The method of embodiment A43 wherein the cancer is selected from lung, stomach, liver, colon, kidney, breast, pancreatitis, juvenile myelomonocytic leukemias, neuroblastoma, melanoma, and acute myeloid leukemia.

A45. The method of embodiment A42 wherein the disease is selected from Noonan syndrome and Leopard syndrome.

General Synthetic Scheme

Compounds of this disclosure can be made by the methods depicted in the reaction schemes shown below.

The starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4th Edition) and Larock's Comprehensive Organic Transformations (VCH Publishers Inc., 1989). These schemes are merely illustrative of some methods by which the compounds of this disclosure can be synthesized, and various modifications to these schemes can be made and will be suggested to one skilled in the art reading this disclosure. The starting materials and the intermediates, and the final products of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure over a temperature range from about −78° C. to about 150° C., such as from about 0° C. to about 125° C. and further such as at about room (or ambient) temperature, e.g., about 20° C.

Compound of formula (I) where L is a bond or S, $Q^2$ is N, and A, B are defined as in the Summary can be prepared the method illustrated and described in Scheme 1 below.

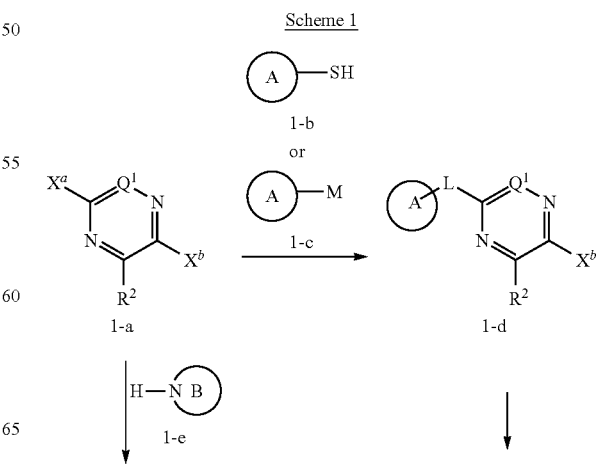

Scheme 1

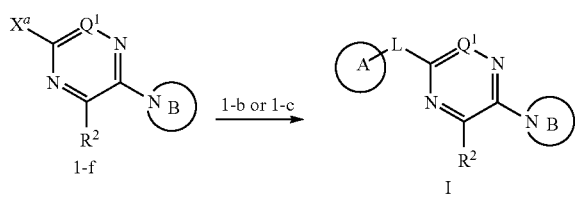

A compound of formula 1-a, in which, $X^a$ and $X^b$ are halogen such as fluoride, chloride, bromide or iodide and $Q^1$ and $R^2$ are as defined in summary, can be coupled with thiol 1-b or an organometallic reagent 1-c where ring A is as defined in the Summary, in the presence of a palladium or cupper catalyst to provide a compound of formula 1-d. Organometallic reagents include but not limit to Grignard reagent, organoboronic acid, organoboronic ester, organo zinc, organostannane or organosilicon reagent. Compounds of formula 1-a, 1-b, and 1-c are commercially available or they can be prepared by method well known in the art. For example 2-amino-3-chloropyridine-4-thiol, 2-amino-3-chloropyridine-4-thiol, 3-chloro-2-fluoropyridine-4-thiol, 3-chloro-2-methoxypyridine-4-thiol, (2,3-dichlorophenyl) boronic acid are commercially available.

Compounds of formula 1-b where ring A is a ring of formula

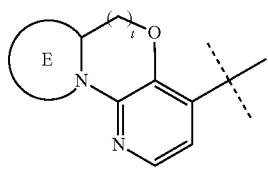

where t is 0, 1 or 2 and ring E is 4 to 7 membered heterocycle containing 1 or 2 heteroatoms independently selected from O, N, S, and $SO_2$ where the remaining atoms are carbon; and is optionally substituted with $R^a$, $R^b$, and/or R as defined in the Summary can be synthesized as illustrated and described below.

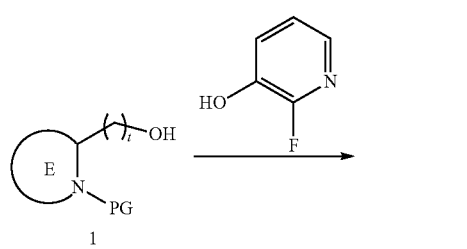

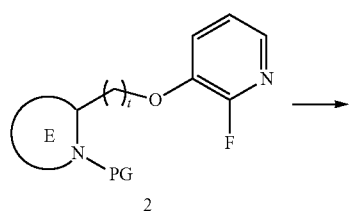

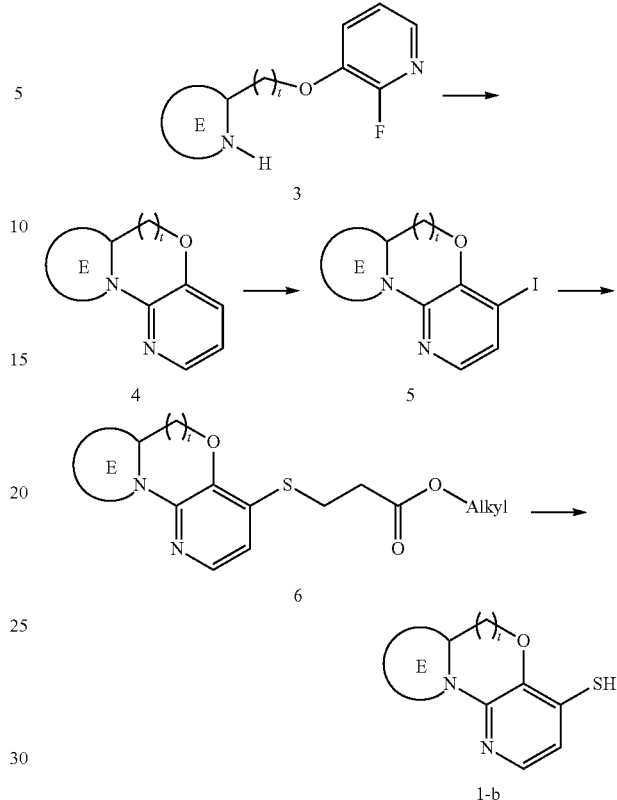

Coupling reaction between 2-fluoropyridin-3-ol and an alcohol of formula 1 where PG is an amino protecting group such as Boc, under Mitsunobu condition, for example, using diethyl azodicarboxylate and triphenyl phosphine provides a compound of formula 2. Compounds of formula 1 are commercially available or they can be prepared by methods well known in the art. For example, tert-butyl (S)-2-(hydroxymethyl)pyrrolidine-1-carboxylate, tert-butyl (R)-2-(hydroxymethyl)pyrrolidine-1-carboxylate, tert-butyl (2S,4S)-4-fluoro-2-(hydroxymethyl)-pyrrolidine-1-carboxylate, tert-butyl (2S,4R)-4-fluoro-2-(hydroxymethyl)pyrrolidine-1-carboxylate, tert-butyl (S)-4,4-difluoro-2-(hydroxymethyl)pyrrolidine-1-carboxylate, tert-butyl (2S,4R)-2-(hydroxymethyl)-4-methoxypyrrolidine-1-carboxylate, tert-butyl (2S,4S)-2-(hydroxymethyl)-4-methoxypyrrolidine-1-carboxylate, tert-butyl (S)-6-(hydroxymethyl)-5-azaspiro[2.4]heptane-5-carboxylate, tert-butyl (R)-3-(hydroxymethyl)morpholine-4-carboxylate, tert-butyl (S)-3-(hydroxymethyl)morpholine-4-carboxylate, tert-butyl (R)-2-(hydroxymethyl)azetidine-1-carboxylate, tert-butyl (S)-2-(hydroxymethyl)azetidine-1-carboxylate are commercially available.

Removal of the amino protecting group provides a compound of formula 3. For example, Boc group can be cleaved under acidic condition such HCl in dioxane. Cyclization of compound 3 with a base such as $K_2CO_3$ provides a compound of formula 4. Lithiation of compound 4 using alkyl lithium such n-BuLi, followed by trapping with iodine provides a compound of formula 5. Compound of formula 5 can be converted to thioether of formula 6 under reaction conditions that contain Pd catalyst and suitable ligand. An example of Pd catalyst and ligand combination is $Pd_2(dba)_3$ and xantphos. Treatment of compound 6 with a base such as $K_2CO_3$ provides compound with formula 1-a.

The resulting intermediate 1-d can be coupled with an amine 1-e where

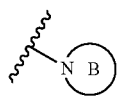

is as defined in the Summary. Alternatively, the order of coupling between 1-a with 1-b or 1-c and amine 1-e can be reversed as shown in scheme 1.

Compounds of Formula (I) can be converted to other compounds of Formula (I). Some illustrative examples are provided below.

Method i.

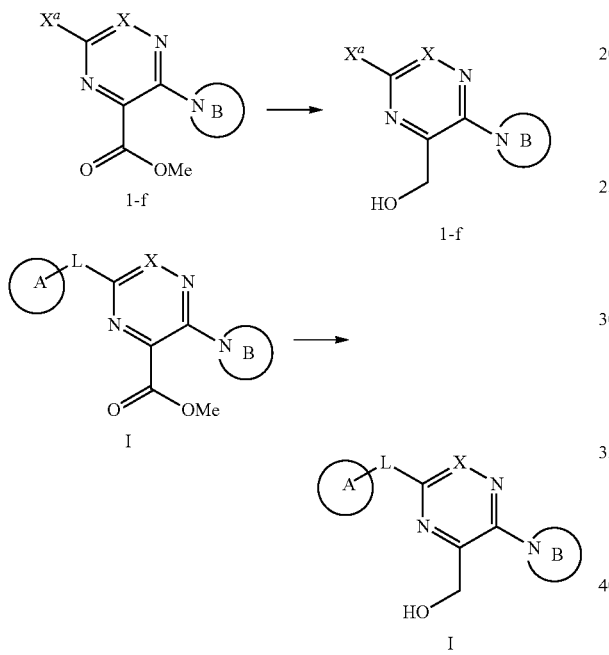

A compound of Formula (1-f or I) where $R^2$ is COOMe can be converted to a compound of Formula (1-f or I) where $R^2$ is CH$_2$OH by treating with a suitable reducing agent such as DIBAL, lithium borohydride, sodium borohydride under conditions well known in the art.

Method ii.

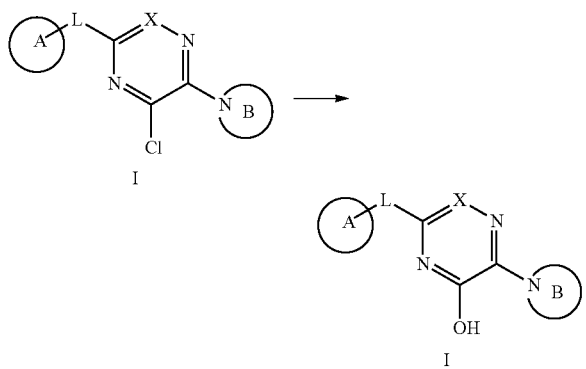

A compound of Formula (I) where $R^2$ is halogen such as chloride can be converted to a compound of formula (I) where $R^2$ is hydroxyl group under acidic condition such HCl aq. solution or basic condition such as sodium hydroxide aq solution, which is well known in the art.

Method iii.

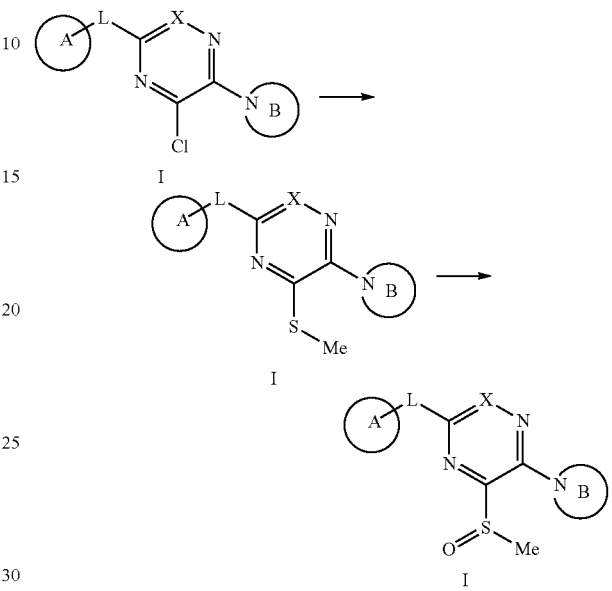

A compound of Formula (I) where $R^2$ is halogen such as chloride can be converted to a compound of formula (I) where $R^2$ is alkylthio such methyl thioether in the presence of metal alkylthiolate such as sodium methylthiolate. Furthermore, the sulfide can be oxidized with oxidation reagent such as oxone to provide another compound of formula (I) where $R^2$ is alkyl sulfoxide.

Utility

The Src Homology-2 phosphatase (SHP2) is a protein tyrosine phosphatase encoded by the PTPN11 gene that contributes to multiple cellular functions including proliferation, differentiation, cell cycle maintenance and migration. SHP2 is involved in signaling through the Ras-mitogen-activated protein kinase, the JAK-STAT or the phosphoinositol 3-kinase-AKT pathways. SHP2 mediates activation of Erk1 and Erk2 (Erk1/2, Erk) MAP kinases by receptor tyrosine kinases such as ErbB1, ErbB2 and c-Met.

SHP2 has two N-terminal Src homology 2 domains (N—SH2 and C—SH2), a catalytic domain (PTP), and a C-terminal tail. The two SH2 domains control the subcellular localization and functional regulation of SHP2. The molecule exists in an inactive conformation, inhibiting its own activity via a binding network involving residues from both the N—SH2 and PTP domains. In response to growth factor stimulation, SHP2 binds to specific tyrosine-phosphorylated sites on docking proteins such as Gab1 and Gab2 via its SH2 domains. This induces a conformational change that results in SHP2 activation.

Mutations in PTPN11 have been identified in several human diseases, such as Noonan Syndrome, Leopard Syndrome, juvenile myelomonocytic leukemias, neuroblastoma, melanoma, acute myeloid leukemia and cancers of the breast, lung and colon. SHP2 is an important downstream signaling molecule for a variety of receptor tyrosine kinases, including the receptors of platelet-derived growth factor (PDGF-R), fibroblast growth factor (FGF-R) and epidermal growth factor (EGF-R). SHP2 is also an important downstream signaling molecule for the activation of the mitogen activated protein (MAP) kinase pathway which can lead to cell transformation, a prerequisite for the development of cancer. Knock-down of SHP2 significantly inhibited cell growth of lung cancer cell lines with SHP2 mutation or EML4/ALK translocations as well as EGFR amplified breast cancers and esophageal cancers. SHP2 is also activated downstream of oncogenes in gastric carcinoma, anaplastic large-cell lymphoma and glioblastoma.

Noonan Syndrome (NS) and Leopard Syndrome (LS): PTPN11 mutations cause LS (multiple lentigenes, electrocardiographic conduction abnormalities, ocular hypertelorism, pulmonic stenosis, abnormal genitalia, retardation of growth, sensorineural deafness) and NS (congenital anomalies including cardiac defects, craniofacial abnormalities and short stature). Both disorders are part of a family of autosomal dominant syndromes caused by germline mutations in components of the RAS/RAF/MEK/ERK mitogen activating protein kinase pathway, required for normal cell growth and differentiation. Aberrant regulation of this pathway has profound effects, particularly on cardiac development, resulting in various abnormalities, including valvuloseptal defects and/or hypertrophic cardiomyopathy (HCM). Perturbations of the MAPK signaling pathway have been established as central to these disorders and several candidate genes along this pathway have been identified in humans, including mutations in KRAS, NRAS, SOS1, RAF1, BRAF, MEK1, MEK2, SHOC2, and CBL. The gene most commonly mutated in NS and LS is PTPN1 1. Germline mutations in PTPN1 1 (SHP2) are found in ~50% of the cases with NS and nearly all patients with LS that shares certain features with NS. For NS, Y62D and Y63C substitutions in the protein are largely invariant and are among the most common mutations. Both these mutations affect the catalytically inactive conformation of SHP2 without perturbing the binding of the phosphatase to its phosphorylated signaling partners.

Juvenile Myelomonocytic Leukemias (JMML):—Somatic mutations in PTPN1 1(SHP2) occur in about 35% of the patients with JMML, a childhood myeloproliferative disorder (MPD). These gain-of-function mutations are typically point mutations in the N—SH2 domain or in the phosphatase domain, which prevent self-inhibition between the catalytic domain and the N— SH2 domain, resulting in SHP2 activity.

Acute Myeloid Leukemia: PTPN1 1 mutations have been identified in: ~10% of pediatric acute leukemias, such as myelodysplastic syndrome (MDS); ~7% of B cell acute lymphoblastic leukemia (B-ALL); and ~4% of acute myeloid leukemia (AML).

NS and leukemia mutations cause changes in amino acids located at the interface formed by the N—SH2 and PTP domains in the self-inhibited SHP2 conformation, disrupting the inhibitory intramolecular interaction, leading to hyperactivity of the catalytic domain.

SHP2 acts as a positive regulator in receptor tyrosine kinase (RTK) signaling. Cancers containing RTK alterations (EGFR amp, Her2 amp, FGFR amp, Met 31"15, translocated/activated RTK, i.e. ALK, BCR/ABL) include Esophageal, Breast, Lung, Colon, Gastric, Glioma, Head and Neck cancers.

Esophageal cancer (or oesophageal cancer) is a malignancy of the esophagus. There are various subtypes, primarily squamous cell cancer (<50%) and adenocarcinoma. There is a high rate of RTK expression in esophageal adenocarcinoma and squamous cell cancer. A SHP2 inhibitor of the invention can, therefore, be employed for innovative treatment strategies.

Breast cancer is a major type of cancer and a leading cause of death in women, where patients develop resistance to current drugs. There are four major subtypes of breast cancers including luminal A, luminal B, Her2 like, and triple negative/Basal-like. Triple negative breast cancer (TNBC) is an aggressive breast cancer lacking specific targeted therapy. Epidermal growth factor receptor I (EGFR) has emerged as a promising target in TNBC. Inhibition of Her2 as well as EGFR via SHP2 may be a promising therapy in breast cancer.

Lung Cancer—NSCLC is currently a major cause of cancer-related mortality, accounting for about 85% of lung cancers (predominantly adenocarcinomas and squamous cell carcinomas). Although cytotoxic chemotherapy remains an important part of treatment, targeted therapies based on genetic alterations such as EGFR and ALK in the tumor are more likely to benefit from a targeted therapy.

Colon Cancer—Approximately 30% to 50% of colorectal tumors are known to have a mutated (abnormal) KRAS, and BRAF mutations occur in 10 to 15% of colorectal cancers. For a subset of patients whose colorectal tumors have been demonstrated to over express EGFR, these patients exhibit a favorable clinical response to anti-EGFR therapy.

Gastric Cancer is one of the most prevalent cancer types. Aberrant expression of tyrosine kinases, as reflected by the aberrant tyrosine phosphorylation in gastric cancer cells, is known in the art. Three receptor-tyrosine kinases, c-met (HGF receptor), FGF receptor 2, and erbB2/neu are frequently amplified in gastric carcinomas. Thus, subversion of different signal pathways may contribute to the progression of different types of gastric cancers.

Neuroblastoma is a pediatric tumor of the developing sympathetic nervous system, accounting for about 8% of childhood cancers. Genomic alterations of the anaplastic lymphoma kinase (ALK) gene have been postulated to contribute to neuroblastoma pathogenesis.

Squamous-cell carcinoma of the head and neck (SCCHN). High levels of EGFR expression are correlated with poor prognosis and resistance to radiation therapy in a variety of cancers, mostly in squamous-cell carcinoma of the head and neck (SCCHN). Blocking of the EGFR signaling results in inhibition of the stimulation of the receptor, cell proliferation, and reduced invasiveness and metastases. The EGFR is, therefore, a prime target for new anticancer therapy in SCCHN.

The present invention relates to compounds capable of inhibiting the activity of SHP2. The invention further provides a process for the preparation of compounds of the invention and pharmaceutical preparations comprising such compounds. Another aspect of the present invention relates to a method of treating SHP2-mediated disorders comprising the step of administering to a patient in need thereof a therapeutically effective amount of a compound of formula I as defined in the Summary.

In certain embodiments, the present invention relates to the aforementioned method, wherein said SHP2-mediated disorders are cancers selected from, but not limited to: JMML; AML; MDS; B-ALL; neuroblastoma; esophageal; breast cancer; lung cancer; colon cancer; Gastric cancer, Head and Neck cancer.

The compounds of the present invention may also be useful in the treatment of other diseases or conditions related to the aberrant activity of SHP2. Thus, as a further aspect, the invention relates to a method of treatment of a disorder selected from: NS; LS; JMML; AML; MDS; B-ALL; neuroblastoma; esophageal; breast cancer; lung cancer; colon cancer; gastric cancer; head and neck cancer.

A SHP2 inhibitor of the present invention may be usefully combined with another pharmacologically active compound, or with two or more other pharmacologically active compounds, particularly in the treatment of cancer. For example, a compound of the current invention or a pharmaceutically acceptable salt thereof, as defined above, may be administered simultaneously, sequentially or separately in combination with one or more agents selected from chemotherapy agents, for example, mitotic inhibitors such as a taxane, a *vinca* alkaloid, paclitaxel, docetaxel, vincristine, vinblastine, vinorelbine or vinflunine, and other anticancer agents, e.g. cisplatin, 5-fluorouracil or 5-fluoro-2-4(1H,3H)-pyrimidinedione (5FU), flutamide or gemcitabine. Such combinations may offer significant advantages, including synergistic activity, in therapy.

In certain embodiments, the present invention relates to the aforementioned method, wherein said compound is administered parenterally.

In certain embodiments, the present invention relates to the aforementioned method, wherein said compound is administered intramuscularly, intravenously, subcutaneously, orally, pulmonary, intrathecally, topically or intranasally.

In certain embodiments, the present invention relates to the aforementioned method, wherein said compound is administered systemically.

In certain embodiments, the present invention relates to the aforementioned method, wherein said patient is a mammal.

In certain embodiments, the present invention relates to the aforementioned method, wherein said patient is a primate.

In certain embodiments, the present invention relates to the aforementioned method, wherein said patient is a human.

In another aspect, the present invention relates to a method of treating an SHP2-mediated disorder, comprising the step of: administering to a patient in need thereof a therapeutically effective amount of a chemotherapeutic agent in combination with a therapeutically effective amount of a compound of formula I as defined in the Summary.

In addition to human cancer, inhibition of SHP2 also has the therapeutic potential for treatment of systemic lupus erythematosus, rheumatoid arthritis and fibrosis.

Testing

The SHP2 inhibitory activity of the compounds of Formula (IA'), (I'), (I), (IA), (II), or (IIA) can be tested using the in vitro assay described in Biological Examples 1 below.

Pharmaceutical Compositions

In general, the compounds of Formula (IA'), (I'), (I), (IA), (II), or (IIA) will be administered in a therapeutically effective amount by any of the accepted modes of administration for agents that serve similar utilities. Therapeutically effective amounts of compounds of Formula (IA'), (I'), (I), (IA), (II), or (IIA) may range from about 0.01 to about 500 mg per kg patient body weight per day, which can be administered in single or multiple doses. A suitable dosage level may be from about 0.1 to about 250 mg/kg per day; about 0.5 to about 100 mg/kg per day. A suitable dosage level may be about 0.01 to about 250 mg/kg per day, about 0.05 to about 100 mg/kg per day, or about 0.1 to about 50 mg/kg per day. Within this range the dosage can be about 0.05 to about 0.5, about 0.5 to about 5 or about 5 to about 50 mg/kg per day. For oral administration, the compositions can be provided in the form of tablets containing about 1.0 to about 1000 milligrams of the active ingredient, particularly about 1, 5, 10, 15, 20, 25, 50, 75, 100, 150, 200, 250, 300, 400, 500, 600, 750, 800, 900, and 1000 milligrams of the active ingredient. The actual amount of the compound of Formula (IA'), (I'), (I), (IA), (II), or (IIA), i.e., the active ingredient, will depend upon numerous factors such as the severity of the disease to be treated, the age and relative health of the patient, the potency of the compound being utilized, the route and form of administration, and other factors.

In general, compounds of Formula (IA'), (I'), (I), (IA), (II), or (IIA) will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen, which can be adjusted according to the degree of affliction. Compositions can take the form of tablets, pills, capsules, semisolids, powders, sustained release formulations, solutions, suspensions, elixirs, aerosols, or any other appropriate compositions.

The choice of formulation depends on various factors such as the mode of drug administration (e.g., for oral administration, formulations in the form of tablets, pills or capsules, including enteric coated or delayed release tablets, pills or capsules are preferred) and the bioavailability of the drug substance.

The compositions are comprised of in general, a compound of Formula (IA'), (I'), (I), (IA), (II), or (IIA) in combination with at least one pharmaceutically acceptable excipient. Acceptable excipients are non-toxic, aid administration, and do not adversely affect the therapeutic benefit of the compound of Formula (IA'), (I'), (I), (IA), (II), or (IIA). Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Certain compounds of Formula (IA'), (I'), (I), (IA), (II), or (IIA) may be administered topically, that is by non-systemic administration. This includes the application of a compound of Formula (IA'), (I'), (I), (IA), (II), or (IIA) externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

For administration by inhalation, compounds may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds of Formula (IA'), (I'), (I), (IA), (II), or (IIA) may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator. Other suitable pharmaceutical excipients and their formulations are described in Remington's Pharmaceutical Sciences, edited by E. W. Martin (Mack Publishing Company, 20th ed., 2000).

The level of the compound in a formulation can vary within the full range employed by those skilled in the art. Typically, the formulation will contain, on a weight percent (wt. %) basis, from about 0.01-99.99 wt. % of a compound of Formula (IA'), (I'), (I), (IA), (II), or (IIA) based on the total formulation, with the balance being one or more suitable pharmaceutical excipients. For example, the compound is present at a level of about 1-80 wt. %.

Combinations and Combination Therapies

The compounds of Formula (IA'), (I'), (I), (IA), (II), or (IIA) may be used in combination with one or more other drugs in the treatment of diseases or conditions for which compounds of Formula (IA'), (I'), (I), (IA), (II), or (IIA) or the other drugs may have utility. Such other drug(s) may be administered, by a route and in an amount commonly used therefore, contemporaneously or sequentially with a compound of Formula (IA'), (I'), (I), (IA), (II), or (IIA). When a compound of this disclosure is used contemporaneously with one or more other drugs, a pharmaceutical composition in unit dosage form containing such other drugs and the compound of Formula (IA'), (I'), (I), (IA), (II), or (IIA) is preferred. However, the combination therapy may also include therapies in which the compound of this disclosure and one or more other drugs are administered on different overlapping schedules. It is also contemplated that when used in combination with one or more other active ingredients, the compounds of Formula (IA'), (I'), (I), (IA), (II), or (IIA) and the other active ingredients may be used in lower doses than when each is used singly.

Accordingly, the pharmaceutical compositions of Formula (IA'), (I'), (I), (IA), (II), or (IIA) also include those that contain one or more other drugs, in addition to a compound of Formula (IA'), (I'), (I), (IA), (II), or (IIA).

The above combinations include combinations of a compound of Formula (IA'), (I'), (I), (IA), (II), or (IIA) not only with one other drug, but also with two or more other active drugs. Likewise, a compound of Formula (IA'), (I'), (I), (IA), (II), or (IIA) may be used in combination with other drugs that are used in the prevention, treatment, control, amelioration, or reduction of risk of the diseases or conditions for which a compound of Formula (IA'), (I'), (I), (IA), (II), or (IIA) is useful. Such other drugs may be administered, by a route and in an amount commonly used therefore, contemporaneously or sequentially with a compound of Formula (IA'), (I'), (I), (IA), (II), or (IIA). When a compound of Formula (IA'), (I'), (I), (IA), (II), or (IIA) is used contemporaneously with one or more other drugs, a pharmaceutical composition containing such other drugs in addition to the compound of Formula (IA'), (I'), (I), (IA), (II), or (IIA) can be used. Accordingly, the pharmaceutical compositions of Formula (IA'), (I'), (I), (IA), (II), or (IIA) also include those that also contain one or more other active ingredients, in addition to a compound of this disclosure. The weight ratio of the compound of Formula (IA'), (I'), (I), (IA), (II), or (IIA) to the second active ingredient may be varied and will depend upon the effective dose of each ingredient. Generally, an effective dose of each will be used.

Where the subject in need is suffering from or at risk of suffering from cancer, the subject can be treated with a compound of Formula (IA'), (I'), (I), (IA), (II), or (IIA) in any combination with one or more other anti-cancer agents including but not limited to:

MAP kinase pathway (RAS/RAF/MEK/ERK) inhibitors including but not limited to: Vemurafanib (PLX4032), Dabrafenib, Encorafenib (LGX818), TQ-B3233, XL-518 (Cas No. 1029872-29-4, available from ACC Corp); trametinib, selumetinib (AZD6244), TQ-B3234, PD184352, PD325901, TAK-733, pimasertinib, binimetinib, refametinib, cobimetinib (GDC-0973), AZD8330, BVD-523, LTT462, Ulixertinib, AMG510, ARS853, and any RAS inhibitors disclosed in patents WO2016049565, WO2016164675, WO2016168540, WO2017015562, WO2017058728, WO2017058768, WO2017058792, WO2017058805, WO2017058807, WO2017058902, WO2017058915, WO2017070256, WO2017087528, WO2017100546, WO2017172979, WO2017201161, WO2018064510, WO2018068017, WO2018119183;

CSF1R inhibitors (PLX3397, LY3022855, etc.) and CSF1R antibodies (IMC-054, RG7155)TGF beta receptor kinase inhibitor such as LY2157299;

BTK inhibitor such as ibrutinib; BCR-ABL inhibitors: Imatinib (Gleevec®); Inilotinib hydrochloride; Nilotinib (Tasigna®); Dasatinib (BMS-345825); Bosutinib (SKI-606); Ponatinib (AP24534); Bafetinib (INNO406); Danusertib (PHA-739358), AT9283 (CAS 1133385-83-7); Saracatinib (AZD0530); and A/-[2-[(15,4R)-6-[[4-(Cyclobutylarmno)-5-(trifluoromethyl)-2-pyrimidinyl] amino]-1,2,3,4-tetrahydronaphthalen-1,4-imin-9-yl]-2-oxoethyl]-acetamide (PF-03814735, CAS 942487-16-3);

ALK inhibitors: PF-2341066 (XALKOPJ®; crizotinib); 5-chloro-N4-(2-(isopropylsulfonyl)phenyl)-N2-(2-methoxy-4-(4-(4-methylpiper azin-1-yl)piperidin-1-yl)phenyl)pyrimidine-2,4-diamine; GSK1838705 A; CH5424802; Ceritinib (ZYKADIA); TQ-B3139, TQ-B3101 PI3K inhibitors: 4-[2-(1H-Indazol-4-yl)-6-[[4-(methylsulfonyl)-piperazin-1-yl]methyl]thieno[3,2-d]pyrimidin-4-yl]mopholine (also known as GDC 0941 and described in PCT Publication Nos. WO 09/036082 and WO 09/055730), 2-methyl-2-[4-[3-methyl-2-oxo-8-(quinolin-3-yl)-2,3-dihydroimidazo[4,5-c]quinolin-1-yl]phenyl]propionitrile (also known as BEZ 235 or NVP-BEZ 235, and described in PCT Publication No. WO 06/122806);

Vascular Endothelial Growth Factor (VEGF) receptor inhibitors: Bevacizumab (sold under the trademark Avastin® by Genentech/Roche), axitinib, (N-methyl-2-[[3-[(E)-2-pyridin-2-ylethenyl]-1H-indazol-6-yl]sulfanyl]benzamide, also known as AG013736, and described in PCT Publication No. WO 01/002369), Brivanib Alaninate ((S)—((R)-1-(4-(4-Fluoro-2-methyl-1H-indol-5-yloxy)-5-methylpyrrolo[2,1-f][1,2,4]triazin-6-yloxy)propan-2-yl)$_2$-aminopropanoate, also known as BMS-582664), motesanib (N-(2, 3-dihydro-3,3-dimethyl-1H-indol-6-yl)-2-[(4-pyridinylmethyl)amino]-3-pyridinecarboxamide, and described in PCT Publication No. WO 02/066470), pasireotide (also known as SOM230, and described in PCT Publication No. WO 02/010192), sorafenib (sold under the tradename Nexavar®); AL-2846 MET inhibitor such as foretinib, carbozantinib, or crizotinib;

FLT3 inhibitors—sunitinib malate (sold under the tradename Sutent® by Pfizer); PKC412 (midostaurin); tanutinib, sorafenib, lestaurtinib, KW-2449, quizartinib (AC220) and crenolanib;

Epidermal growth factor receptor (EGFR) inhibitors: Gefitnib (sold under the tradename Iressa®), N-[4-[(3-Chloro-4-fluorophenyl)amino]-7-[[(3"S")-tetrahydro-3-furanyl]oxy]-6-quinazolinyl]-4(dimethylamino)-2-butenamide, sold under the tradename Tovok® by Boehringer Ingelheim), cetuximab (sold under the tradename Erbitux® by Bristol-Myers Squibb), panitumumab (sold under the tradename Vectibix® by Amgen);

HER2 receptor inhibitors: Trastuzumab (sold under the trademark Herceptin® by Genentech/Roche), neratinib (also known as HKI-272, (2E)-N-[4-[[3-chloro-4-[(pyridin-2-yl)methoxy]phenyl]amino]-3-cyano-7-ethoxyquinolin-6-yl]-4-(d imethylamino)but-2-enamide, and described PCT Publication No. WO 05/028443), lapatinib or lapatinib ditosylate (sold under the trademark Tykerb® by GlaxoSmithKline); Trastuzumab emtansine (in the United States, ado-trastuzumab emtansine, trade name Kadcyla) —an antibody-drug conjugate consisting of the monoclonal antibody trastuzumab (Herceptin) linked to the cytotoxic agent mertansine (DM1);

HER dimerization inhibitors: Pertuzumab (sold under the trademark Omnitarg®, by Genentech);

CD20 antibodies: Rituximab (sold under the trademarks Riuxan® and MabThera® by Genentech/Roche), tositumomab (sold under the trademarks Bexxar® by GlaxoSmithKline), ofatumumab (sold under the trademark Arzerra® by GlaxoSmithKline);

Tyrosine kinase inhibitors: Erlotinib hydrochloride (sold under the trademark Tarceva® by Genentech/Roche), Linifanib (N-[4-(3-amino-1H-indazol-4-yl)phenyl]-N'-(2-fluoro-5-methylphenyl)urea, also known as ABT 869, available from Genentech), sunitinib malate (sold under the tradename Sutent® by Pfizer), bosutinib (4-[(2,4-dichloro-5-methoxyphenyl)amino]-6-methoxy-7-[3-(4-methylpiperazin-1-yl)propoxy]quinoline-3-car bonitrile, also known as SKI-606, and described in U.S. Pat. No. 6,780,996), dasatinib (sold under the tradename Sprycel® by Bristol-Myers Squibb), armala (also known as pazopanib, sold under the tradename Votrient® by GlaxoSmithKline), imatinib and imatinib mesylate (sold under the tradenames Gilvec® and Gleevec® by Novartis);

DNA Synthesis inhibitors: Capecitabine (sold under the trademark Xeloda® by Roche), gemcitabine hydrochloride (sold under the trademark Gemzar® by Eli Lilly and Company), nelarabine ((2R3S,4R,5R)-2-(2-amino-6-methoxypurin-9-yl)-5-(hydroxymet hyl)oxolane-3,4-diol, sold under the tradenames Arranon® and Atriance® by GlaxoSmithKline);

Antineoplastic agents: oxaliplatin (sold under the tradename Eloxatin® ay Sanofi-Aventis and described in U.S. Pat. No. 4,169,846);

Human Granulocyte colony-stimulating factor (G-CSF) modulators: Filgrastim (sold under the tradename Neupogen® by Amgen);

Immunomodulators: Afutuzumab (available from Roche®), pegfilgrastim (sold under the tradename Neulasta® by Amgen), lenalidomide (also known as CC-5013, sold under the tradename Revlimid®), thalidomide (sold under the tradename Thalomid®);

CD40 inhibitors: Dacetuzumab (also known as SGN-40 or huS2C6, available from Seattle Genetics, Inc); Proapoptotic receptor agonists (PARAs): Dulanermin (also known as AMG-951, available from Amgen/Genentech);

Hedgehog antagonists: 2-chloro-N-[4-chloro-3-(2-pyridinyl)phenyl]-4-(methylsulfony 1)-benzamide (also known as GDC-0449, and described in PCT Publication No. WO 06/028958);

Phospholipase A2 inhibitors: Anagrelide (sold under the tradename Agrylin®);

BCL-2 inhibitors: 4-[4-[[2-(4-chlorophenyl)-5,5-dimethyl-1-cyclohexen-1-yl]met hyl]-1-piperazinyl]-N-[[4-[[(1R)-3-(4-morpholinyl)-1-[(phenylthio)methyl]propyl]amino]-3-[(trifluoromethyl)sulfonyl]phenyl]sulfonyl]benzamide (also known as ABT-263 and described in PCT Publication No. WO 09/155386);

MCl-1 inhibitors: MIK665, S64315, AMG 397, and AZD5991;

Aromatase inhibitors: Exemestane (sold under the trademark Aromasin® by Pfizer), letrozole (sold under the tradename Femara® by Novartis), anastrozole (sold under the tradename Arimidex®);

Topoisomerase I inhibitors: Irinotecan (sold under the trademark Camptosar® by Pfizer), topotecan hydrochloride (sold under the tradename Hycamtin® by GlaxoSmithKline);

Topoisomerase II inhibitors: etoposide (also known as VP-16 and Etoposide phosphate, sold under the tradenames Toposar®, VePesid® and Etopophos®), teniposide (also known as VM-26, sold under the tradename Vumon®);

mTOR inhibitors: Temsirolimus (sold under the tradename Torisel® by Pfizer), ridaforolimus (formally known as deferolimus, (1R,2R,4S)-4-[(2R)-2[(1R,9S,12S,15R,16E,18R,19R,21R,23S,24E,26E,28Z,30S,32S,35R)-1,18-dihydroxy-19,30-dimethoxy-15,17,21,23,29,35-hexamethyl-2,3,10,14,20-pentaoxo-11,36-dioxa-4-azatricyclo[30.3.1.0 4' 9]hexatriaconta-16,24,26,28-tetraen-12-yl]propyl]-2-methoxycyc lohexyl dimethylphosphinate, also known as AP23573 and MK8669, and described in PCT Publication No. WO 03/064383), everolimus (sold under the tradename Afinitor® by Novartis);

Proteasome inhibitor such as carfilzomib, MLN9708, delanzomib, or bortezomib

BET inhibitors such as INCB054329, OTX015, CPI-0610; LSD1 inhibitors such as GSK2979552, INCB059872; HIF-2α inhibitors such as PT2977 and PT2385;

Osteoclastic bone resorption inhibitors: 1-Hydroxy-2-imidazol-1-yl-phosphonoethyl) phosphonic acid monohydrate (sold under the tradename Zometa® by Novartis);

CD33 Antibody Drug Conjugates: Gemtuzumab ozogamicin (sold under the tradename Mylotarg® by Pfizer/Wyeth);

CD22 Antibody Drug Conjugates: Inotuzumab ozogamicin (also referred to as CMC-544 and WAY-207294, available from Hangzhou Sage Chemical Co., Ltd.);

CD20 Antibody Drug Conjugates: Ibritumomab tiuxetan (sold under the tradename Zevalin®);

Somatostain analogs: octreotide (also known as octreotide acetate, sold under the tradenames Sandostatin® and Sandostatin LAR®);

Synthetic Interleukin-11 (IL-11): oprelvekin (sold under the tradename Neumega® by Pfizer/Wyeth);

Synthetic erythropoietin: Darbepoetin alfa (sold under the tradename Aranesp® by Amgen);

Receptor Activator for Nuclear Factor κ B (RANK) inhibitors: Denosumab (sold under the tradename Prolia® by Amgen);

Thrombopoietin mimetic peptibodies: Romiplostim (sold under the tradename Nplate® by Amgen;

Cell growth stimulators: Palifermin (sold under the tradename Kepivance® by Amgen);

Anti-Insulin-like Growth Factor-1 receptor (IGF-1R) antibodies: Figitumumab (also known as CP-751,871, available from ACC Corp), robatumumab (CAS No. 934235-44-6);

Anti-CS1 antibodies: Elotuzumab (HuLuc63, CAS No. 915296-00-3);

CD52 antibodies: Alemtuzumab (sold under the tradename Campath®);

Histone deacetylase inhibitors (HDI): Voninostat (sold under the tradename Zolinza® by Merck);

Alkylating agents: Temozolomide (sold under the tradenames Temodar® and Temodal® by Schering-Plough/Merck), dactinomycin (also known as actinomycin-D and sold under the tradename Cosmegen®), melphalan (also known as L-PAM, L-sarcolysin, and phenylalanine mustard, sold under the tradename Alkeran®), altretamine (also known as hexamethylmelamine (HMM), sold under the tradename Hexalen®), carmustine (sold under the tradename BiCNU®), bendamustine (sold under the tradename Treanda®), busulfan (sold under the tradenames Busulfex® and Myleran®), carboplatin (sold under the tradename Paraplatin®), lomustine (also known as CCNU, sold under the tradename CeeNU®), cisplatin (also known as CDDP, sold under the tradenames Platinol® and Platinol®-AQ), chlorambucil (sold under the tradename Leukeran®), cyclophosphamide (sold under the tradenames Cytoxan® and Neosar®), dacarbazine (also known as DTIC, DIC and imidazole carboxamide, sold under the tradename DTIC-Dome®), altretamine (also known as hexamethylmelamine (HMM) sold under the tradename Hexalen®), ifosfamide (sold under the tradename Ifex®), procarbazine (sold under the tradename Matulane®), mechlorethamine (also known as nitrogen mustard, mustine and mechloroethamine hydrochloride, sold under the tradename Mustargen®), streptozocin (sold under the tradename Zanosar®), thiotepa (also known as thiophosphoamide, TESPA and TSPA, sold under the tradename Thioplex®; Biologic response modifiers: *bacillus* calmette-guerin (sold under the tradenames theraCys® and TICE® BCG), denileukin diftitox (sold under the tradename Ontak®);

Anti-tumor antibiotics: doxorubicin (sold under the tradenames Adriamycin® and Rubex®), bleomycin (sold under the tradename Lenoxane®), daunorubicin (also known as dauorubicin hydrochloride, daunomycin, and rubidomycin hydrochloride, sold under the tradename Cerubidine®), daunorubicin liposomal (daunorubicin citrate liposome, sold under the tradename DaunoXome®), mitoxantrone (also known as DHAD, sold under the tradename Novantrone®), epirubicin (sold under the tradename Ellence™), idarubicin (sold under the tradenames Idamycin®, Idamycin PFS®), mitomycin C (sold under the tradename Mutamycin®);

Anti-microtubule agents: Estramustine (sold under the tradename Emcyl®);

Cathepsin K inhibitors: Odanacatib (also know as MK-0822, N-(1-cyanocyclopropyl)-4-fluoro-N 2-{(1S)-2,2,2-trifluoro-1-[4'-(methylsulfonyl)biphenyl-4-yl]ethyl}-L-leucinamide, available from Lanzhou Chon Chemicals, ACC Corp., and ChemieTek, and described in PCT Publication no. WO 03/075836); Epothilone B analogs: Ixabepilone (sold under the tradename Lxempra® by Bristol-Myers Squibb);

Heat Shock Protein (HSP) inhibitors: Tanespimycin (17-allylamino-17-demethoxygeldanamycin, also known as KOS-953 and 17-AAG, available from SIGMA, and described in U.S. Pat. No. 4,261,989), NVP-HSP990, AUY922, AT13387, STA-9090, Debio 0932, KW-2478, XL888, CNF2024, and TAS-116;

TpoR agonists: Eltrombopag (sold under the tradenames Promacta® and Revolade® by GlaxoSmithKline);

Anti-mitotic agents: Docetaxel (sold under the tradename Taxotere® by Sanofi-Aventis); Adrenal steroid inhibitors: aminoglutethimide (sold under the tradename Cytadren®);

Anti-androgens: Nilutamide (sold under the tradenames Nilandron® and Anandron®), bicalutamide (sold under tradename Casodex®), flutamide (sold under the tradename Fulexin™);

Androgens: Fluoxymesterone (sold under the tradename Halotestin®);

Proteasome inhibitors: Bortezomib (sold under the tradename Velcade®);

CDK (CDK1, CDK2, CDK3, CDK5, CDK7, CDK8, or CDK9) inhibitors including but not limited to Alvocidib (pan-CDK inhibitor, also known as flovopirdol or HMR-1275, 2-(2-chlorophenyl)-5,7-dihydroxy-8-[(3S,4R)-3-hydroxy-1-methyl-4-piperidinyl]-4-chromenone, and described in U.S. Pat. No. 5,621,002);

CDK4/6 inhibitors paboclib, ribocilib, abemaciclib, and Trilaciclib; CDK9 inhibtiors AZD 4573, P276-00, AT7519M, TP-1287;

Gonadotropin-releasing hormone (GnRH) receptor agonists: Leuprolide or leuprolide acetate (sold under the tradenames Viadure® by Bayer AG, Eligard® by Sanofi-Aventis and Lupron® by Abbott Lab);

Taxane anti-neoplastic agents: Cabazitaxel (1-hydroxy-7,10-dimethoxy-9-oxo-5,20-epoxytax-1 1-ene-2a,4,13a-triyl-4-acetate-2-benzoate-13-[(2R,3S)-3-{[(tert-butoxy)carbonyl]-amino}-2-hydroxy-3-phenylpropanoate), larotaxel ((2α,3ξ,4α,5β,7α,10β,13α)-4,10-bis(acetyloxy)-13-({(2R,3S)-3-[(tert-butoxycarbonyl) amino]-2-hydroxy-3-phenylpropanoyl}oxy)-1-hydroxy-9-oxo-5,20-epoxy-7,19-cyclotax-11-en-2-yl benzoate);

5HT1a receptor agonists: Xaliproden (also known as SR57746, 1-[2-(2-naphthyl)ethyl]-4-[3-(trifluoromethyl) phenyl]-1,2,3,6-tetrahydropyridine, and described in U.S. Pat. No. 5,266,573); HPC vaccines: Cervarix® sold by GlaxoSmithKline, Gardasil® sold by Merck; Iron Chelating agents: Deferasinox (sold under the tradename Exjade® by Novartis);

Anti-metabolites: Claribine (2-chlorodeoxyadenosine, sold under the tradename Leustatin®), 5-fluorouracil (sold under the tradename Adrucil®), 6-thioguanine (sold under the tradename Purinethol®), pemetrexed (sold under the tradename Alimta®), cytarabine (also known as arabinosylcytosine (Ara-C), sold under the tradename Cytosar-U®), cytarabine liposomal (also known as Liposomal Ara-C, sold under the tradename DepoCyt™), decitabine (sold under the tradename Dacogen®), hydroxyurea (sold under the tradenames Hydrea®, Droxia™ and Mylocel™), fludarabine (sold under the tradename Fludara®), floxuridine (sold under the tradename FUDR®), cladribine (also known as 2-chlorodeoxyadenosine (2-CdA) sold under the tradename Leustatin™), methotrexate (also known as amethopterin, methotrexate sodim (MTX), sold under the tradenames Rheumatrex® and Trexall™), pentostatin (sold under the tradename Nipent®);

Bisphosphonates: Pamidronate (sold under the tradename Aredia®), zoledronic acid (sold under the tradename Zometa®); Demethylating agents: 5-azacitidine (sold under the tradename Vidaza®), decitabine (sold under the tradename Dacogen®);

Plant Alkaloids: Paclitaxel protein-bound (sold under the tradename Abraxane®), vinblastine (also known as vinblastine sulfate, vincaleukoblastine and VLB, sold under the tradenames Alkaban-AQ® and Velban®), vincristine (also known as vincristine sulfate, LCR, and VCR, sold under the tradenames Oncovin® and Vincasar Pfs®), vinorelbine (sold under the tradename Navelbine®), paclitaxel (sold under the tradenames Taxol and Onxal™);

Retinoids: Ali tretinoin (sold under the tradename Panretin®), tretinoin (all-trans retinoic acid, also known as ATRA, sold under the tradename Vesanoid®), Isotretinoin (13-cis-retinoic acid, sold under the tradenames Accutane®, Amnesteem®, Claravis®, *Clarus*®, Decutan®, Isotane®, Izotech®, Oratane®, Isotret®, and Sotret®), bexarotene (sold under the tradename Targretin®);

Glucocorticosteroids: Hydrocortisone (also known as cortisone, hydrocortisone sodium succinate, hydrocortisone sodium phosphate, and sold under the tradenames Ala-Cort®, Hydrocortisone Phosphate, Solu-Cortef®, Hydrocort Acetate® and Lanacort®), dexamethazone ((8S,9R,10S,11S,13S,14S,16R,17R)-9-fluoro-11,17-dihydroxy-17-(2-hydroxyacetyl)-10,13,16-trimethyl-6,7,8,9,10,11,12,13,14,15,16,17-dodecahydro-3H-cyclopenta[a]phenanthren-3-one), prednisolone (sold under the tradenames Delta-Cortel®, Orapred®, Pediapred® and Prelone®), prednisone (sold under the tradenames Deltasone®, Liquid Red®, Meticorten® and Orasone®), methylprednisolone (also known as 6-Methylprednisolone, Methylprednisolone Acetate, Methylprednisolone Sodium Succinate, sold under the tradenames Duralone®, Medralone®, Medrol®, M-Prednisol® and Solu-Medrol®);

Cytokines: interleukin-2 (also known as aldesleukin and IL-2, sold under the tradename Proleukin®), interleukin-11 (also known as oprevelkin, sold under the tradename Neumega®), alpha interferon alfa (also known as IFN-alpha, sold under the tradenames Intron® A, and Roferon-A®);

[00209] Estrogen receptor downregulators: Fulvestrant (sold under the tradename Faslodex®);

Anti-estrogens: tamoxifen (sold under the tradename Novaldex®); Toremifene (sold under the tradename Fareston®);

Selective estrogen receptor modulators (SERMs): Raloxifene (sold under the tradename Evista®);

Leutinizing hormone releasing hormone (LHRH) agonists: Goserelin (sold under the tradename Zoladex®); Progesterones: megestrol (also known as megestrol acetate, sold under the tradename Megace®);

Miscellaneous cytotoxic agents: Arsenic trioxide (sold under the tradename Trisenox®), asparaginase (also known as L-asparaginase, *Erwinia* L-asparaginase, sold under the tradenames Elspar® and Kidrolase®);

One or more additional immune checkpoint inhibitors can be used in combination with a compound as described herein for treatment of SHP2-associated diseases, disorders or conditions. Exemplary immune checkpoint inhibitors include inhibitors (smack molecules or biologics) against immune checkpoint molecules such as CD27, CD28, CD40, CD122, CD96, CD73, CD39, CD47, OX40, GITR, CSF1R, JAK, PI3K delta, PI3K gamma, TAM kinase, arginase, CD137 (also known as 4-1BB), ICOS, A2AR, A2BR, HIF-2α, B7-H3, B7-H4, BTLA, CTLA-4, LAG3, TIM3, VISTA, CD96, TIGIT, PD-1, PD-L1 and PD-L2. In some embodiments, the immune checkpoint molecule is a stimulatory checkpoint molecule selected from CD27, CD28, CD40, ICOS, OX40, GITR, CD137 and STING. In some embodiments, the immune checkpoint molecule is an inhibitory checkpoint molecule selected from B7-H3, B7-H4, BTLA, CTLA-4, IDO, TDO, Arginase, KIR, LAG3, PD-1, TIM3, CD96, TIGIT and VISTA. In some embodiments, the compounds provided herein can be used in combination with one or more agents selected from KIR inhibitors, TIGIT inhibitors, LAIR1 inhibitors, CD160 inhibitors, 2B4 inhibitors and TGFR beta inhibitors.

In some embodiments, the inhibitor of an immune checkpoint molecule is an inhibitor of PD-1, e.g., an anti-PD-1 monoclonal antibody. In some embodiments, the anti-PD-1 monoclonal antibody is nivolumab, pembrolizumab (also known as MK-3475), pidilizumab, SHR-1210, PDR001, or AMP-224. In some embodiments, the anti-PD-1 monoclonal antibody is nivolumab, or pembrolizumab or PDR001. In some embodiments, the anti-PDi antibody is pembrolizumab.

In some embodiments, the inhibitor of an immune checkpoint molecule is an inhibitor of PD-L1, e.g., an anti-PD-L1 monoclonal antibody. In some embodiments, the anti-PD-L1 monoclonal antibody is BMS-935559, MEDI4736, MPDL3280A (also known as RG7446), or MSB0010718C. In some embodiments, the anti-PD-L1 monoclonal antibody is MPDL3280A (atezolizumab) or MEDI4736 (durvalumab).

In some embodiments, the inhibitor of an immune checkpoint molecule is an inhibitor of CTLA-4, e.g., an anti-CTLA-4 antibody. In some embodiments, the anti-CTLA-4 antibody is ipilimumab or tremelimumab. In some embodiments, the inhibitor of an immune checkpoint molecule is an inhibitor of LAG3, e.g., an anti-LAG3 antibody. In some embodiments, the anti-LAG3 antibody is BMS-986016 or LAG525. In some embodiments, the inhibitor of an immune checkpoint molecule is an inhibitor of GITR, e.g., an anti-GITR antibody. In some embodiments, the anti-GITR antibody is TRX518 or, MK-4166, INCAGN01876 or MK-1248. In some embodiments, the inhibitor of an immune checkpoint molecule is an inhibitor of OX40, e.g., an anti-OX40 antibody or OX40L fusion protein. In some embodiments, the anti-OX40 antibody is MEDI0562 or, INCAGN01949, GSK2831781, GSK-3174998, MOXR-0916, PF-04518600 or LAG525. In some embodiments, the OX40L fusion protein is MEDI6383.

Compounds of the invention can also be used to increase or enhance an immune response, including increasing the immune response to an antigen; to improve immunization, including increasing vaccine efficacy; and to increase inflammation. In some embodiments, the compounds of the invention can be sued to enhance the immune response to vaccines including, but not limited, *Listeria* vaccines, oncolytic viarl vaccines, and cancer vaccines such as GVAX® (granulocyte-macrophage colony-stimulating factor (GM-CF) gene-transfected tumor cell vaccine). Anti-cancer vaccines include dendritic cells, synthetic peptides, DNA vaccines and recombinant viruses. Other immune-modulatory agents also include those that block immune cell migration such as antagonists to chemokine receptors, including CCR2 and CCR4; Sting agonists and Toll receptor agonists.

Other anti-cancer agents also include those that augment the immune system such as adjuvants or adoptive T cell transfer. Compounds of this application may be effective in combination with CAR (Chimeric antigen receptor) T cell treatment as a booster for T cell activation.

A compound of the invention can also be used in combination with the following adjunct therapies:

Anti-nausea drugs: NK-1 receptor antagonists: Casopitant (sold under the tradenames Rezonic® and Zunrisa® by GlaxoSmithKline); and Cytoprotective agents: Amifostine (sold under the tradename Ethyol®), leucovorin (also known as calcium leucovorin, citrovorum factor and folinic acid).

EXAMPLES

The following preparations of intermediates (References) compounds of Formula (I) are given to enable those skilled in the art to more clearly understand and to practice the present disclosure. They should not be considered as limiting the scope of the disclosure, but merely as being illustrative and representative thereof.

Reference 1

Synthesis of (5S)-5,6-dihydrospiro[piperidine-4,4-pyrrolo[1,2-b]pyrazol]-5-amine dihydrochloride

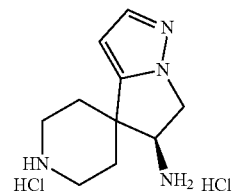 [SMILES: Cl ; N[C@@H]1Cn2nccc2C12CCNCC2 ; Cl]

Step 1: 1-[1-[(tert-butoxy)(hydroxy)methyl]-4-[hydroxy(methoxy)methyl]piperidin-4-yl]ethan-1-ol

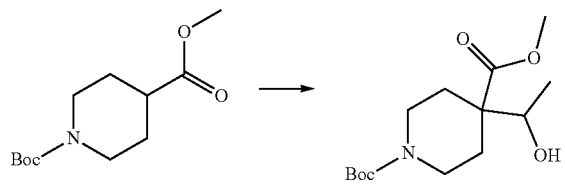 [SMILES: COC(=O)C1CCN(C(=O)OC(C)(C)C)CC1 ; COC(=O)C1(C(C)O)CCN(C(=O)OC(C)(C)C)CC1]

To a solution of [1-[(tert-butoxy)(hydroxy)methyl]piperidin-4-yl](methoxy)methanol (20 g, 80.86 mmol, 1.0 equiv) in THF (200 mL) at −78° C. was added LDA (48.52 mL, 97.03 mmol, 1.2 equiv) dropwise under nitrogen atmosphere. After stirring for 1.5 h at −78° C.~−60° C., to the above mixture was added acetaldehyde (5.34 g, 121.29 mmol, 1.5 equiv) dropwise over 5 minutes at −78° C. and the resulting mixture was stirred for additional 2 h at −78° C.~−40° C. The reaction mixture was then poured into sat. NH$_4$Cl aq. solution and extracted with EtOAc. The organic layer was washed with brine, dried over anhydrous Na$_2$SO$_4$ and concentrated. The residue was purified by silica gel column chromatography (EtOAc/PE, 0-50%) to afford 12 g (50.9% yield) of the title compound as light yellow oil.

Step 2: 1-tert-butyl 4-methyl 4-[1-(trifluoromethanesulfonyloxy)ethyl]piperidine-1,4-dicarboxylate

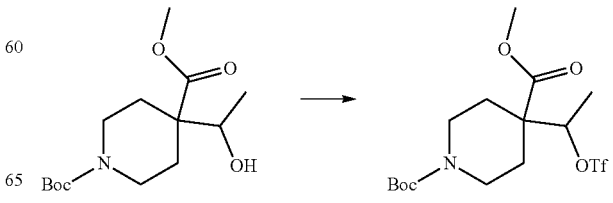

To a solution of 1-tert-butyl 4-methyl 4-(1-hydroxyethyl)piperidine-1,4-dicarboxylate (9.5 g, 33.06 mmol, 1 equiv) in DCM (100 mL) were added pyridine (10.4 g, 131.48 mmol, 4.0 equiv) and (trifluoromethane)sulfonyl trifluoromethanesulfonate (18.7 g, 66.27 mmol, 2.0 equiv) dropwise at 0° C. under nitrogen atmosphere. After stirring for 2 h at 0° C., the reaction mixture was quenched with water at 0° C. The resulting mixture was extracted with CH₂Cl₂. The organic layer was washed with brine, dried over anhydrous Na₂SO₄ and concentrated under reduced pressure to give 20 g (crude) of the title compound. This crude product was used directly in next step without further purification.

Step 3: 1-tert-butyl 4-methyl 4-ethenylpiperidine-1,4-dicarboxylate

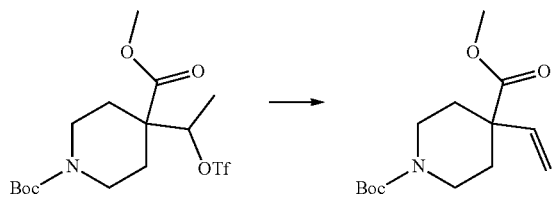 [SMILES: COC(=O)C1(C(C)OS(=O)(=O)C(F)(F)F)CCN(C(=O)OC(C)(C)C)CC1 ; C=CC1(C(=O)OC)CCN(C(=O)OC(C)(C)C)CC1]

To a stirred solution of 1-tert-butyl 4-methyl 4-[1-(trifluoromethanesulfonyloxy)-ethyl]piperidine-1,4-dicarboxylate (20 g, crude) in DCM (300 mL) was added DBU (28.50 mL, 187.18 mmol) at rt under nitrogen atmosphere. After stirring for 4 h at rt, the reaction mixture was concentrated under reduced pressure and the residue was purified by silica gel column chromatography (EtOAc/PE, 6%) to afford the title compound (4.5 g) as light yellow oil.

Step 4: 1-[(tert-butoxy)carbonyl]-4-ethenylpiperidine-4-carboxylic acid

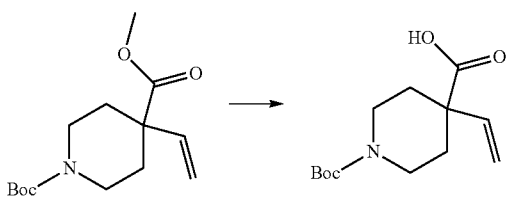 [SMILES: C=CC1(C(=O)OC)CCN(C(=O)OC(C)(C)C)CC1 ; C=CC1(C(=O)O)CCN(C(=O)OC(C)(C)C)CC1]

To a solution of 1-tert-butyl 4-methyl 4-ethenylpiperidine-1,4-dicarboxylate (4.8 g, 17.82 mmol, 1.0 equiv) in MeOH (40 mL) were added water (10 mL) and LiGH (2.35 g, 98.01 mmol, 5.5 equiv) at room temperature. After stirring for 16 h at rt, the mixture was acidified to pH=5 with 0.5 M HCl aq. solution. The reaction mixture was then extracted with CH₂Cl₂. The combined organic layers were washed with brine, dried over anhydrous Na₂SO₄ and concentrated to give the title compound (4.5 g, 98.9% yield) as a light yellow oil.

Step 5: Tert-Butyl 4-ethenyl-4-[methoxy(methyl)carbamoyl]piperidine-1-carboxylate

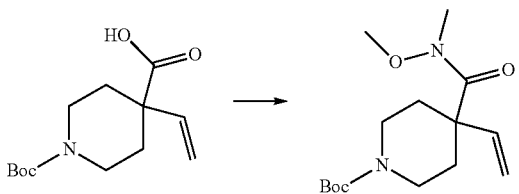 [SMILES: C=CC1(C(=O)O)CCN(C(=O)OC(C)(C)C)CC1 ; C=CC1(C(=O)N(C)OC)CCN(C(=O)OC(C)(C)C)CC1]

To a solution of 1-[(tert-butoxy)carbonyl]-4-ethenylpiperidine-4-carboxylic acid (4.5 g, 17.62 mmol, 1.0 equiv) and methoxy(methyl)amine (1.61 g, 26.43 mmol, 1.5 equiv) in DCM (70 mL) were added HATU (13.40 g, 35.25 mmol, 2.0 equiv) and Et₃N (0.12 g, 1.17 mmol, 3.0 equiv) at rt under nitrogen atmosphere. After stirring for 12 h at rt, the reaction mixture was quenched with water at room temperature and extracted with DCM. The organic layer was washed with brine, dried over anhydrous Na₂SO₄ and concentrated. The residue was purified by silica gel column chromatography (EtOAc/PE, 5%) to afford the title compound (5 g, 95% yield) as a white solid.

Step 6: Tert-Butyl 4-acetyl-4-ethenylpiperidine-1-carboxylate

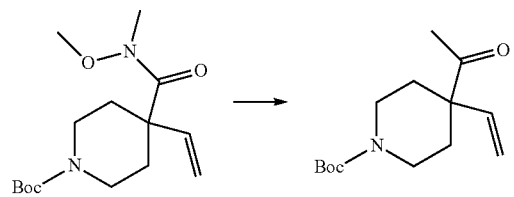 [SMILES: C=CC1(C(=O)N(C)OC)CCN(C(=O)OC(C)(C)C)CC1 ; C=CC1(C(C)=O)CCN(C(=O)OC(C)(C)C)CC1]

To a solution of tert-butyl 4-ethenyl-4-[methoxy(methyl)carbamoyl]piperidine-1-carboxylate (5 g, 16.75 mmol, 1.0 equiv) in THF (60 mL) was added CH₃MgBr (16.76 mL, 41.89 mmol, 2.50 equiv) dropwise at 0° C. under nitrogen atmosphere. After stirring for 12 h at rt, the reaction was quenched with sat. NH₄Cl aq. solution at 0° C. and the mixture was extracted with EtOAc. The organic layer was washed with brine, dried over anhydrous Na₂SO₄ and concentrated. The residue was purified by silica gel column chromatography (EtOAc/PE, 1/3) to afford the title compound (3.5 g, 82.4% yield) as light yellow oil.

Step 7: Tert-Butyl 4-[(2Z)-3-(dimethylamino)prop-2-enoyl]-4-ethenylpiperidine-1-carboxylate

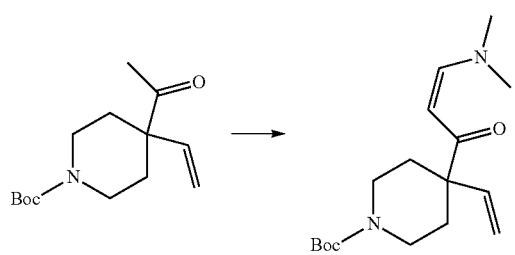 [SMILES: C=CC1(C(C)=O)CCN(C(=O)OC(C)(C)C)CC1 ; C=CC1(C(=O)/C=C\N(C)C)CCN(C(=O)OC(C)(C)C)CC1]

A solution of tert-butyl 4-acetyl-4-ethenylpiperidine-1-carboxylate (2.2 g, 1.0 equiv) in [(tert-butoxy)(dimethylamino)methyl]dimethylamine (1 mL) was stirred for 4 h at 100° C. under nitrogen atmosphere. The reaction mixture was concentrated under reduced pressure. The residue was purified by silica gel column chromatography, eluted with PE/EtOAc (1:1) to afford the title compound (1.6 g, 59.7% yield) as light yellow oil.

Step 8: Tert-Butyl 4-ethenyl-4-(1H-pyrazol-5-yl)piperidine-1-carboxylate

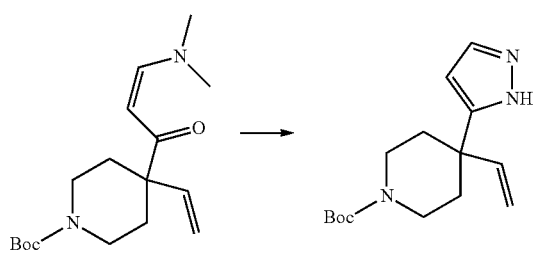 [SMILES: C=CC1(C(=O)/C=C\N(C)C)CCN(C(=O)OC(C)(C)C)CC1 ; C=CC1(c2ccn[nH]2)CCN(C(=O)OC(C)(C)C)CC1]

To a stirred solution of tert-butyl 4-[(2Z)-3-(dimethylamino)prop-2-enoyl]-4-ethenylpiperidine-1-carboxylate (2.2 g, 7.13 mmol, 1.0 equiv.) in EtOH (50 mL) was added hydrazine monohydrate (0.54 g, 10.78 mmol, 1.5 equiv) at 25° C. under nitrogen atmosphere. After stirring for 16 h at 25° C., the reaction was quenched with water and the resulting mixture was extracted with DCM. The organic layer was washed with brine, dried over anhydrous $Na_2SO_4$ and concentrated. The residue was purified by silica gel column chromatography, eluted with EtOAc/PE (30%-60%) to afford the title compound (1.6 g, 80.8% yield) as a white solid.

Step 9: Tert-Butyl 4-(oxiran-2-yl)-4-(1H-pyrazol-5-yl)piperidine-1-carboxylate

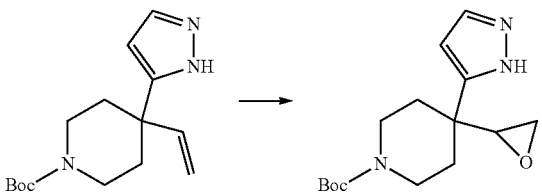 [SMILES: C=CC1(c2ccn[nH]2)CCN(C(=O)OC(C)(C)C)CC1 ; CC(C)(C)OC(=O)N1CCC(c2ccn[nH]2)(C2CO2)CC1]

To a stirred mixture of tert-butyl 4-ethenyl-4-(1H-pyrazol-5-yl)piperidine-1-carboxylate (2 g, 7.2 mmol, 1.0 equiv) and methyltrioxorhenium(VII) (179.72 mg, 0.72 mmol, 0.1 equiv) in DCM (30 mL) were added pyridine (228.14 mg, 2.88 mmol, 0.4 equiv) and $H_2O_2$ (30%) (1.23 g, 36.05 mmol, 5.0 equiv) at rt. After stirring for 16 h at rt, the reaction was quenched with water and extracted with DCM. The organic layer was washed with brine, dried over anhydrous $Na_2SO_4$ and concentrated. The residue was purified by silica gel column chromatography, eluted with EtOAc/PE (30%-60%) to afford the tittle compound (0.8 g, 37.82%) as a white solid.

Step 10: Tert-Butyl 5-hydroxy-5,6-dihydrospiro[piperidine-4,4-pyrrolo[1,2-b]pyrazole]-1-carboxylate

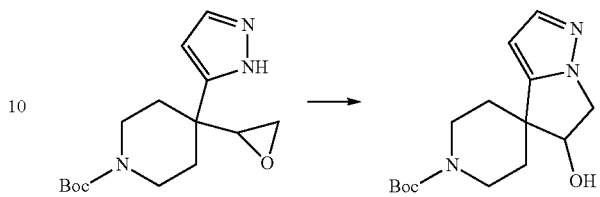

To a stirred solution of tert-butyl 4-(oxiran-2-yl)-4-(1H-pyrazol-5-yl)piperidine-1-carboxylate (0.7 g, 2.38 mmol, 1.0 equiv) in THF (10 mL) were added LiBr (0.62 g, 7.15 mmol, 3.0 equiv) and $CH_3COOH$ (0.43 g, 7.15 mmol, 3.0 equiv) at room temperature. After stirring for 16 h at rt, the reaction mixture was stirred at 45° C. for 8 h. After cooling to rt, the reaction mixture was quenched with sat. $NaHCO_3$ aq. solution and the mixture was extracted with EtOAc. The organic layer was washed with brine, dried over anhydrous $Na_2SO_4$ and concentrated. The residue was purified by silica gel column chromatography, eluted with EtOAc/PE (30%-100%) to afford the title compound (0.4 g, 57.1% yield) as a white solid.

Step 11: Tert-Butyl 5-oxo-5,6-dihydrospiro[piperidine-4,4-pyrrolo[1,2-b]pyrazole]-1-carboxylate

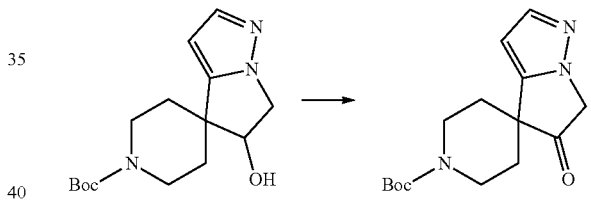

To a solution of tert-butyl 5-hydroxy-5,6-dihydrospiro[piperidine-4,4-pyrrolo[1,2-b]pyrazole]-1-carboxylate (0.4 g, 1.36 mmol, 1.0 equiv) in DCM (8 mL) was added Dess-Martin (0.87 g, 2.04 mmol, 1.5 equiv) at rt. After stirring for 4 h at room temperature, the reaction mixture was quenched with sat. $NaHCO_3$ aq. solution at room temperature and extracted with DCM. The organic layer was washed with brine, dried over anhydrous $Na_2SO_4$ and concentrated. The residue was purified by silica gel column chromatography (EtOAc/PE, 20%-60%) to afford the title compound (0.36 g, 90.62%) as a white solid.

Step 12: Tert-Butyl (S)-5-[(R)-2-methylpropane-2-sulfinyl)amino]-5,6-dihydrospiro[piperidine-4,4-pyrrolo[1,2-b]pyrazole]-1-carboxylate

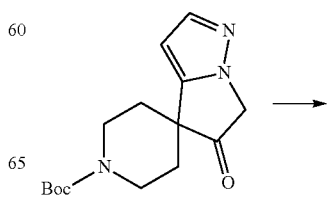

-continued

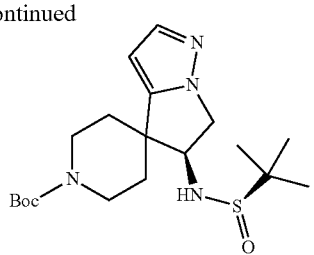

To a solution of tert-butyl 5-oxo-5,6-dihydrospiro[piperidine-4,4-pyrrolo[1,2-b]pyrazole]-1-carboxylate (0.36 g, 1.23 mmol, 1.0 equiv.) in THF (6 mL) was added (R)-2-methylpropane-2-sulfinamide (0.30 g, 2.47 mmol, 2.0 equiv.) and Ti(OEt)$_4$ (1.13 g, 4.94 mmol, 4.0 equiv.) at rt under nitrogen atmosphere. After stirred for 4 hrs at 75° C., the reaction mixture was cooled to −20° C. To the above mixture was added MeOH (1 mL) and LiBH$_4$ (40.38 mg, 1.85 mmol, 1.50 equiv) at −20° C. After stirring for additional 6 h at 0° C., the reaction mixture was quenched with sat. NH$_4$Cl aq. solution at 0° C. The mixture was then filtered and the filter cake was washed with EtOAc. The filtrate was concentrated under reduced pressure and the residue was dissolved in MeOH (3 mL). To the above mixture was added LiBH$_4$ (80.75 mg, 3.71 mmol, 3.0 equiv) at room temperature. The resulting mixture was stirred for additional 8 h at 45° C. The reaction mixture was quenched with sat. NH$_4$Cl aq. solution at 0° C. The resulting mixture was extracted with EtOAc. The organic layer was washed with brine, dried over anhydrous Na$_2$SO$_4$ and concentrated under reduced pressure. The residue was purified by silica gel column chromatography, eluted with EtOAc/PE (30%-70%) to afford the title compound (200 mg, 40.8% yield) as a white solid.

Step 13: (5S)-5,6-dihydrospiro[piperidine-4,4-pyrrolo[1,2-b]pyrazol]-5-amine dihydrochloride

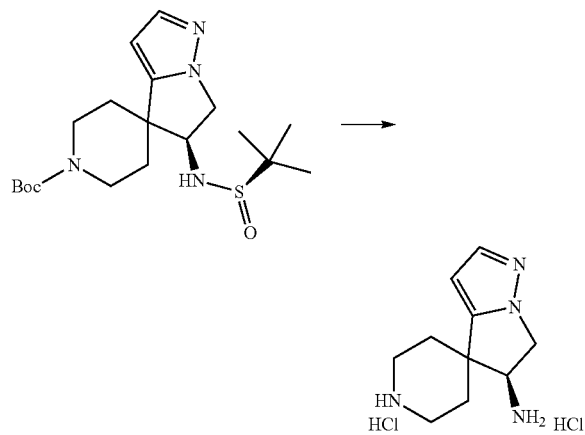

To a stirred solution of tert-butyl (S)-5-[(R)-2-methylpropane-2-sulfinyl)amino]-5,6-dihydrospiro[piperidine-4,4-pyrrolo[1,2-b]pyrazole]-1-carboxylate (100 mg, 0.252 mmol, 1.0 equiv) in 1,4-dioxane (0.5 mL) was added the solution of HCl in dioxane (4 M, 0.50 mL) dropwise at room temperature. After stirring for 30 mins at rt, the reaction mixture was concentrated under reduced pressure. To the residue was added Et$_2$O (1 mL) and the precipitate was collected by filtration to afford the title compound (60 mg) as a white solid.

Example 1

Synthesis of (6-((2-amino-3-chloropyridin-4-yl)thio)-3-((3S,4S)-4-amino-3-methyl-2-oxa-8-azaspiro[4.5]decan-8-yl)pyrazin-2-yl)methanol

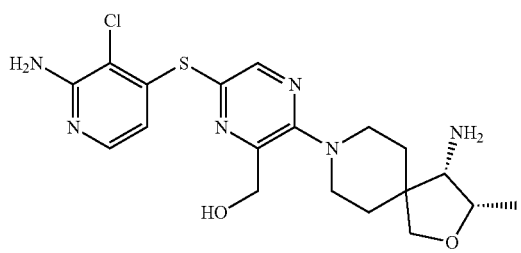

Step 1: methyl 6-bromo-3-[(3S,4S)-4-[[(tert-butoxy)carbonyl]amino]-3-methyl-2-oxa-8-azaspiro[4.5]decan-8-yl]pyrazine-2-carboxylate

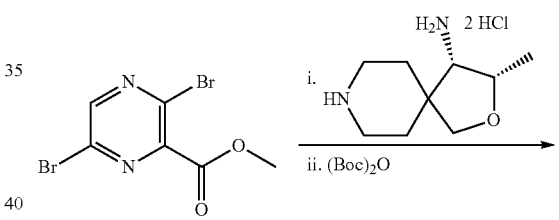

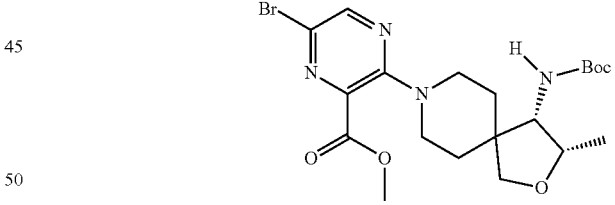

A solution of methyl 3,6-dibromopyrazine-2-carboxylate (500 mg, 1.690 mmol, 1 equiv), (3S,4S)-3-methyl-2-oxa-8-azaspiro[4.5]decan-4-amine dihydrochloride (493.05 mg, 2.028 mmol, 1.2 equiv) and DIEA (1091.88 mg, 8.448 mmol, 5.0 equiv) in DMA (10 mL) was stirred for 2 at 55° C. Di-tert-butyl dicarbonate (552.33 mg, 2.531 mmol, 1.5 equiv) was then added and the resulting mixture was stirred for 2 h at room temperature. The reaction mixture was diluted with water and extracted with EtOAc. The organic layer was washed with water and brine, dried over anhydrous Na$_2$SO$_4$ and concentrated. The residue was purified by silica gel column chromatography, eluted with PE/EtOAc=1:1 to afford the title compound (615 mg, 2 steps yield 75%) as yellow oil.

Step 2: Tert-Butyl N-[(3S,4S)-8-[5-bromo-3-(hydroxymethyl)pyrazin-2-yl]-3-methyl-2-oxa-8-azaspiro[4.5]decan-4-yl]carbamate

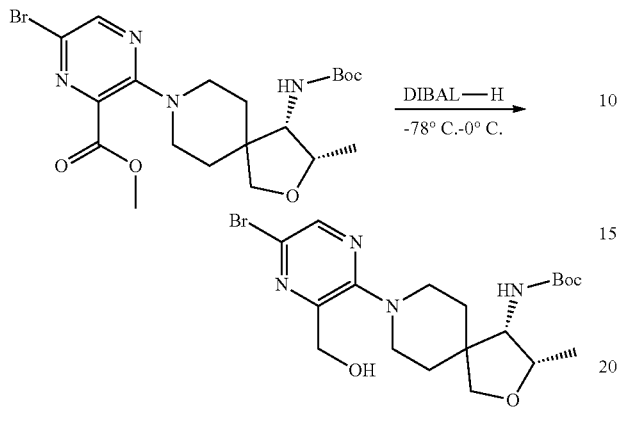

To a stirred solution of methyl 6-bromo-3-[(3S,4S)-4-[[(tert-butoxy)carbonyl]-amino]-3-methyl-2-oxa-8-azaspiro[4.5]decan-8-yl]pyrazine-2-carboxylate (150 mg, 0.309 mmol, 1 equiv) in DCM (3.75 mL) was added DIBAL-H (1.24 mL, 1.240 mmol, 4.01 equiv) dropwise at −78° C. under nitrogen atmosphere. The resulting mixture was stirred for 30 min at −78° C. under nitrogen atmosphere. The reaction was warmed to rt and then quenched by adding sat. Rochelle's salt aq. solution at −78° C. The resulting mixture was extracted with EtOAc. The organic layer was washed with brine, dried over anhydrous Na$_2$SO$_4$ and concentrated. The residue was purified by silica gel column chromatography, eluted with EtOAc/PE (0-50%) to afford the title compound (65 mg, 46%) as a yellow solid.

Step 3: Tert-Butyl N-[(3S,4S)-8-[5-[(2-amino-3-chloropyridin-4-yl)sulfanyl]-3-(hydroxy-methyl)pyrazin-2-yl]-3-methyl-2-oxa-8-azaspiro[4.5]decan-4-yl]carbamate

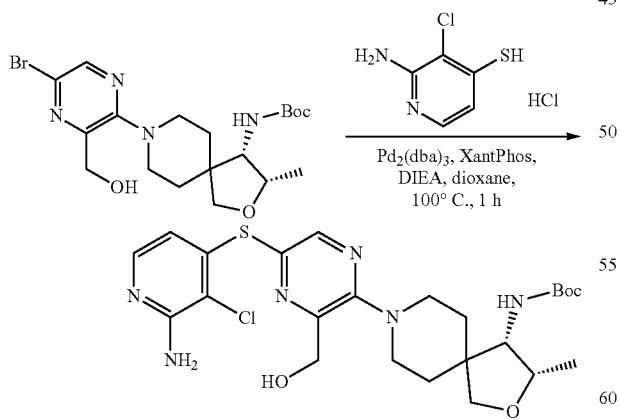

A solution of tert-butyl N-[(3S,4S)-8-[5-bromo-3-(hydroxymethyl)pyrazin-2-yl]-3-methyl-2-oxa-8-azaspiro[4.5]decan-4-yl]carbamate (46 mg, 0.101 mmol, 1 equiv), 2-amino-3-chloropyridine-4-thiol hydrochloride (39.64 mg, 0.201 mmol, 2.0 equiv), Pd$_2$(dba)$_3$ (27.63 mg, 0.030 mmol, 0.3 equiv), XantPhos (17.46 mg, 0.030 mmol, 0.3 equiv) and DIEA (64.99 mg, 0.503 mmol, 5.0 equiv) in Dioxane (1.15 mL, 13.053 mmol, 134.97 equiv) was stirred for 1 h at 100° C. under nitrogen atmosphere. The reaction mixture was concentrated under vacuum. The residue was purified by silica gel column chromatography, eluted with EtOAc/PE (0-100%) to afford the title compound (35 mg, 64.79%) as a light brown solid.

Step 4: [6-[(2-amino-3-chloropyridin-4-yl)sulfanyl]-3-[(3S,4S)-4-amino-3-methyl-2-oxa-8-azaspiro[4.5]decan-8-yl]pyrazin-2-yl]methanol formic acid

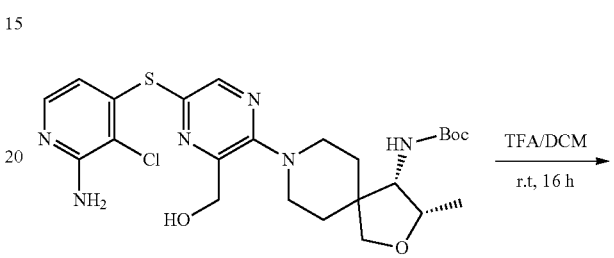

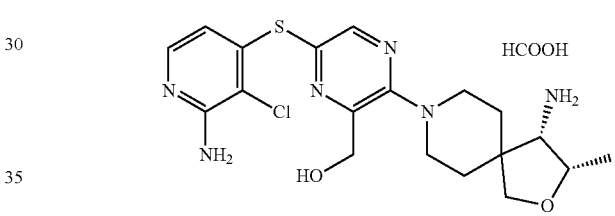

To a stirred solution of tert-butyl N-[(3S,4S)-8-[5-[(2-amino-3-chloropyridin-4-yl)sulfanyl]-3-(hydroxymethyl)pyrazin-2-yl]-3-methyl-2-oxa-8-azaspiro[4.5]decan-4-yl]carbamate (15 mg, 0.028 mmol, 1 equiv) in DCM (1.0 mL) was added TFA (0.25 mL, 3.366 mmol, 120.51 equiv) dropwise at 5° C. After stirred at rt for 16 hrs, the reaction solution was concentrated under vacuum. The residue was purified by Pre-HPLC to afford the title compound (4.0 mg, 29.6% yield) as yellow solid. MS (ES, m/z): [M+1]$^+$=437.2.

Example 2

Synthesis of (3S,4S)-8-(5-((2-amino-3-chloropyridin-4-yl)thio)-3-chloropyrazin-2-yl)-3-methyl-2-oxa-8-azaspiro[4.5]decan-4-amine

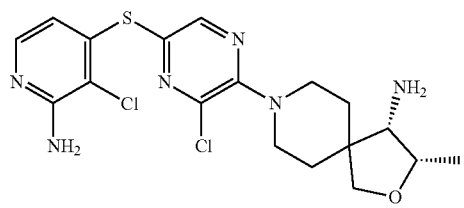 [SMILES: C[C@@H]1OCC2(CCN(c3ncc(Sc4ccnc(N)c4Cl)nc3Cl)CC2)[C@@H]1N]

Step 1: (S)—N-((3S,4S)-8-(3-chloropyrazin-2-yl)-3-methyl-2-oxa-8-azaspiro[4.5]decan-4-yl)-2-methyl-propane-2-sulfinamide

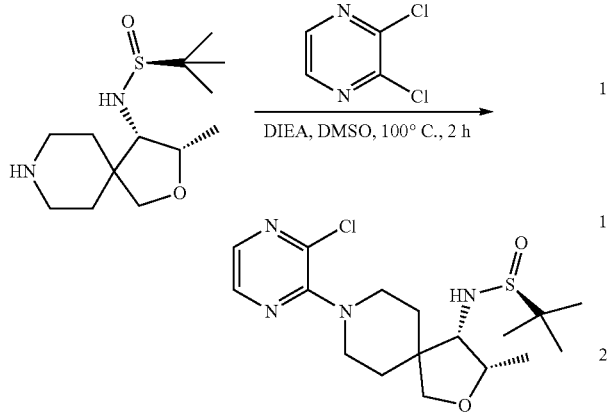

A solution (S)-2-methyl-N-[(3S,4S)-3-methyl-2-oxa-8-azaspiro[4.5]decan-4-yl]propane-2-sulfinamide (800 mg, 2.915 mmol, 1 equiv), 2,3-dichloropyrazine (651.42 mg, 4.373 mmol, 1.5 equiv) and DIEA (1130.32 mg, 8.746 mmol, 3.0 equiv) in DMSO (8 mL, 112.628 mmol, 38.63 equiv) was stirred for 2 h at 100° C. The resulting mixture was diluted with water and extracted with EtOAc. The combined organic layers were washed with water, brine, dried over anhydrous Na$_2$SO$_4$ and concentrated. The residue was purified by silica gel column chromatography, eluted with PE/EtOAc (0-100%) to afford the title compound (800 mg, 70.9% yield) as a light yellow solid.

Step 2: Tert-Butyl ((3S,4S)-8-(3-chloropyrazin-2-yl)-3-methyl-2-oxa-8-azaspiro[4.5]decan-4-yl)carbamate

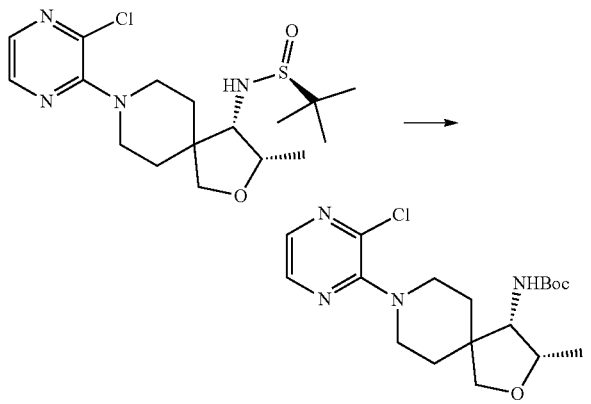

A solution of (S)—N-[(3S,4S)-8-(3-chloropyrazin-2-yl)-3-methyl-2-oxa-8-azaspiro[4.5]decan-4-yl]-2-methylpropane-2-sulfinamide (800 mg, 1 equiv) in HCl in Dioxane (8 mL) was stirred for 2 h at r.t. The resulting mixture was concentrated under vacuum. The residue was washed with Et$_2$O to get the title compound (900 mg) as yellow solid.

Step 3: Tert-Butyl ((3S,4S)-8-(3-chloropyrazin-2-yl)-3-methyl-2-oxa-8-azaspiro[4.5]decan-4-yl)-carbamate

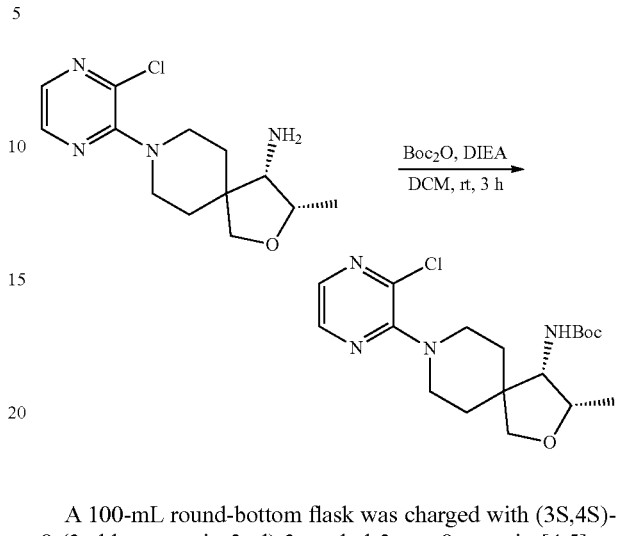

A 100-mL round-bottom flask was charged with (3S,4S)-8-(3-chloropyrazin-2-yl)-3-methyl-2-oxa-8-azaspiro[4.5]decan-4-amine hydrochloride (633 mg, 1.983 mmol, 1 equiv), Boc$_2$O (519 mg, 2.378 mmol, 1.20 equiv), DIEA (613 mg, 4.743 mmol, 2.39 equiv.) and DCM (10 mL). The resulting solution was stirred for 3 h at room temperature and then diluted with DCM and washed with water. The organic phase was dried over anhydrous sodium sulfate and then concentrated. The residue was purified by silica gel column (ethyl acetate/petroleum ether, 0-50%) to give 562 mg (74.02%) of the title product as a yellow solid.

Step 4: Tert-Butyl ((3S,4S)-8-(5-bromo-3-chloropyrazin-2-yl)-3-methyl-2-oxa-8-azaspiro[4.5]decan-4-yl)carbamate

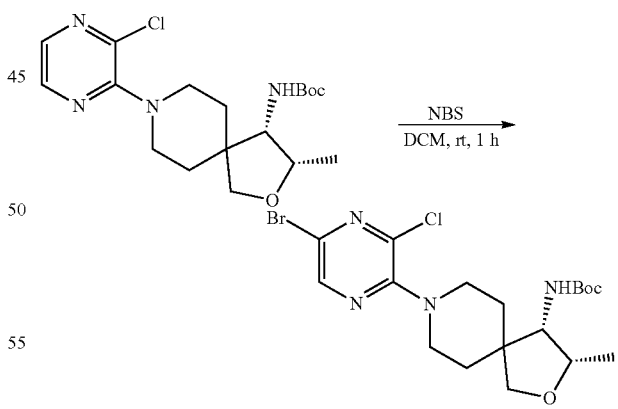

NBS (393 mg) was added to a solution of tert-butyl N-[(3S,4S)-8-(3-chloropyrazin-2-yl)-3-methyl-2-oxa-8-azaspiro[4.5]decan-4-yl]carbamate (562 mg, 1 equiv.) in DCM (10 mL) and the resulting solution was stirred for 1 hr at room temperature. The reaction mixture was then concentrated and the residue was purified by silica gel column chromatography (ethyl acetate/petroleum ether, 0-50%) to give the title compound 300 mg (44.26%) as a yellow solid.

Step 5: Tert-Butyl ((3S,4S)-8-(5-((2-amino-3-chloropyridin-4-yl)thio)-3-chloropyrazin-2-yl)-3-methyl-2-oxa-8-azaspiro[4.5]decan-4-yl)carbamate

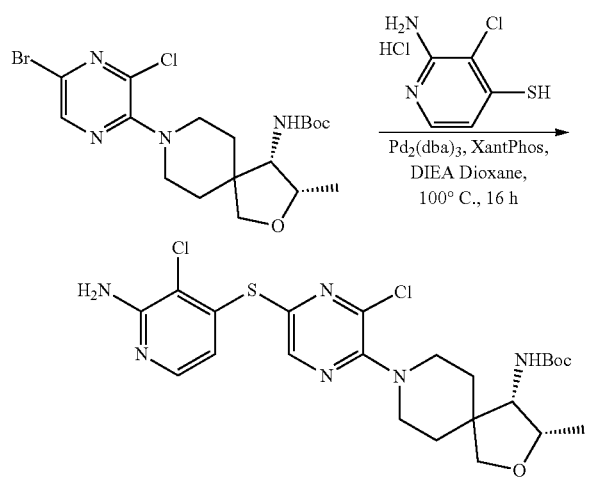

A 8-mL vial was charged with tert-butyl N-[(3S,4S)-8-(5-bromo-3-chloropyrazin-2-yl)-3-methyl-2-oxa-8-azaspiro[4.5]decan-4-yl]carbamate (50 mg, 0.108 mmol, 1 equiv), 2-amino-3-chloropyridine-4-thiol hydrochloride (42.68 mg, 0.217 mmol, 2 equiv), Pd$_2$(dba)$_3$ (9.91 mg, 0.011 mmol, 0.1 equiv), XantPhos (6.26 mg, 0.011 mmol, 0.1 equiv), DIEA (41.98 mg, 0.325 mmol, 3.0 equiv), dioxane (0.4 mL) and DMSO (0.2 mL). The resulting solution was stirred for 2 h at 100° C. The reaction mixture was then diluted with EtOAc and washed H$_2$O. The organic phase was dried over anhydrous sodium sulfate and concentrated. The residue was applied onto a silica gel column chromatography (EtOAc/petroleum ether, 0-100%) to give the title compound (17 mg, 29%) as a yellow solid.

Step 6: (3S,4S)-8-(5-((2-amino-3-chloropyridin-4-yl)thio)-3-chloropyrazin-2-yl)-3-methyl-2-oxa-8-azaspiro[4.5]decan-4-amine

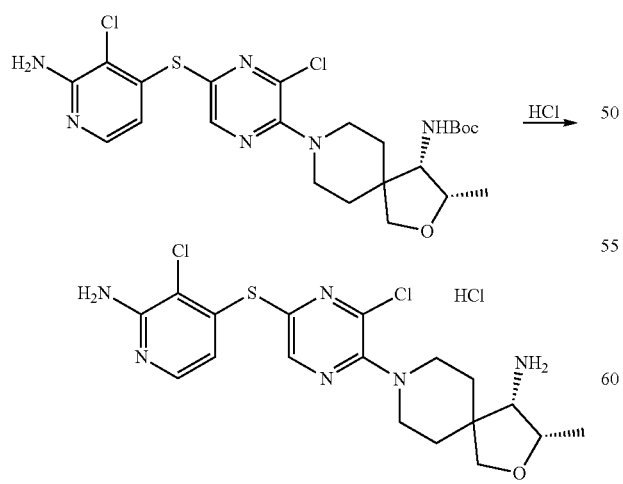

A vial was charged with tert-butyl N-[(3S,4S)-8-[5-[(2-amino-3-chloropyridin-4-yl)sulfanyl]-3-chloropyrazin-2-yl]-3-methyl-2-oxa-8-azaspiro[4.5]decan-4-yl]carbamate (17 mg, 0.031 mmol, 1 equiv) and HCl in 1,4-dioxane (0.5 mL, 2M). After stirring at rt for 1 h, the reaction solution was concentrated. The residue was purified by Prep-HPLC to give the title compound (2.1 mg, 15.15%) as a yellow solid. LCMS (m/z): [M+1]$^+$=441.1.

Example 3

Synthesis of 6-((2-amino-3-chloropyridin-4-yl)thio)-3-((3S,4S)-4-amino-3-methyl-2-oxa-8-azaspiro[4.5]decan-8-yl)pyrazin-2(1H)-one

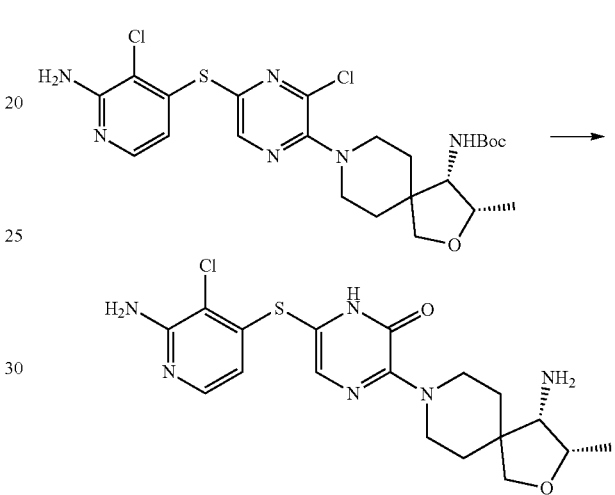

A vial was charged with tert-butyl N-[(3S,4S)-8-[5-[(2-amino-3-chloropyridin-4-yl)-sulfanyl]-3-chloropyrazin-2-yl]-3-methyl-2-oxa-8-azaspiro[4.5]decan-4-yl]carbamate (19 mg, 0.035 mmol, 1 equiv) and conc. HCl (0.2 mL, 6.582 mmol, 187.59 equiv). The resulting solution was stirred for 3 hrs at 30° C. The reaction mixture was diluted with 3 mL of H$_2$O and purified by Prep-HPLC to give the title compound (2.3 mg, 15.5% yield) as a light yellow solid. LCMS (m/z): [M+1]$^+$=423.1

Example 4

Synthesis of (3S,4S)-8-[5-[(2-amino-3-chloropyridin-4-yl)sulfanyl]-3-methanesulfinyl-pyrazin-2-yl]-3-methyl-2-oxa-8-azaspiro[4.5]decan-4-amine

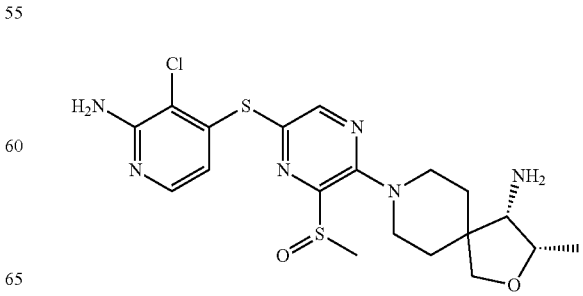

Step 1: Tert-Butyl N-[(3S,4S)-8-[5-[(2-amino-3-chloropyridin-4-yl)sulfanyl]-3-chloropyrazin-2-yl]-3-methyl-2-oxa-8-azaspiro[4.5]decan-4-yl]carbamate

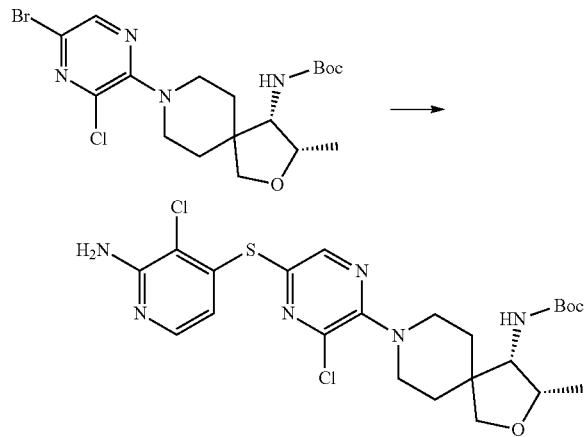

A vial was charged with tert-butyl N-[(3S,4S)-8-(5-bromo-3-chloropyrazin-2-yl)-3-methyl-2-oxa-8-azaspiro[4.5]decan-4-yl]carbamate (146 mg, 0.32 mmol, 1.0 equiv), 2-amino-3-chloropyridine-4-thiol hydrochloride (124.62 mg, 0.63 mmol, 2.0 equiv), $Pd_2(dba)_3$ (57.90 mg, 0.06 mmol, 0.20 equiv), Xantphos (36.59 mg, 0.06 mmol, 0.20 equiv), DIEA (122.58 mg, 0.95 mmol, 3.0 equiv) and Dioxane (30 mL). The resulting mixture was stirred for 3 hrs at 100° C. under a nitrogen atmosphere. After cooled at rt, the mixture was filtered and the filtrate was concentrated under reduced pressure. The residue was purified by silica gel column chromatography (PE/EA, 1/1) to afford the title compound (43 mg, 25.1% yield) as a light yellow solid.

Step 2: Tert-Butyl N-[(3S,4S)-8-[5-[(2-amino-3-chloropyridin-4-yl)sulfanyl]-3-(methyl-sulfanyl)pyrazin-2-yl]-3-methyl-2-oxa-8-azaspiro[4.5]decan-4-yl]carbamate

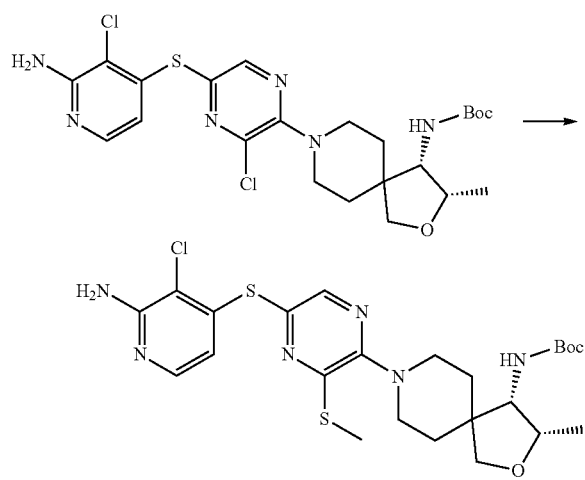

Sodium methylthiolate (8.54 mg, 0.12 mmol, 2.0 equiv) was added to a stirred solution of tert-butyl N-[(3S,4S)-8-[5-[(2-amino-3-chloropyridin-4-yl)sulfanyl]-3-chloropyrazin-2-yl]-3-methyl-2-oxa-8-azaspiro[4.5]decan-4-yl]carbamate (33 mg, 0.06 mmol, 1.00 equiv) in DMF/EtOH (0.9 mL, 1/1) at room temperature and the resulting mixture was stirred for 4 hrs at 80° C. The reaction mixture was diluted with EtOAc and washed with water and brine, dried over anhydrous $Na_2SO_4$ and concentrated. The residue was purified by silica gel column chromatography (EtOAc/PE, 0 to 50%) to afford the title compound (32 mg, 94.9% yield) as a yellow solid.

Step 3: Tert-Butyl N-[(3S,4S)-8-[5-[(2-amino-3-chloropyridin-4-yl)sulfanyl]-3-methanesulfinyl-pyrazin-2-yl]-3-methyl-2-oxa-8-azaspiro[4.5]decan-4-yl]carbamate

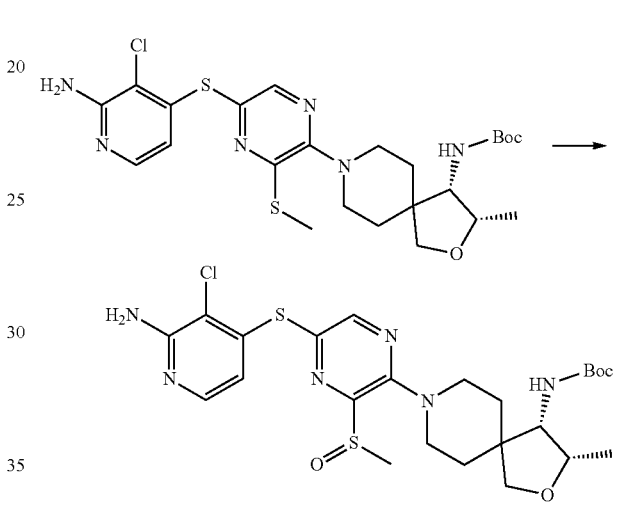

To a stirred solution of tert-butyl N-[(3S,4S)-8-[5-[(2-amino-3-chloropyridin-4-yl)sulfanyl]-3-(methylsulfanyl)pyrazin-2-yl]-3-methyl-2-oxa-8-azaspiro[4.5]decan-4-yl]carbamate (32 mg, 0.05 mmol, 1.00 equiv) in ACN (320 uL) was added oxone (36 mg, 0.05 mmol, 1.00 equiv) in $H_2O$ (32 uL) dropwise at 0~−5° C. and the resulting mixture was stirred for 30 mins at 0° C. The reaction was quenched with sat. $NaHSO_3$ aq. solution and then extracted with EtOAc. The organic layer was washed with brine, dried over anhydrous $Na_2SO_4$ and concentrated under reduced pressure. The residue was purified by silica gel column chromatography (EtOAc/PE, 0 to 50%) to afford the title compound (25 mg, 75.9% yield) as a yellow solid.

Step 4: (3S,4S)-8-[5-[(2-amino-3-chloropyridin-4-yl)sulfanyl]-3-methanesulfinylpyrazin-2-yl]-3-methyl-2-oxa-8-azaspiro[4.5]decan-4-amine

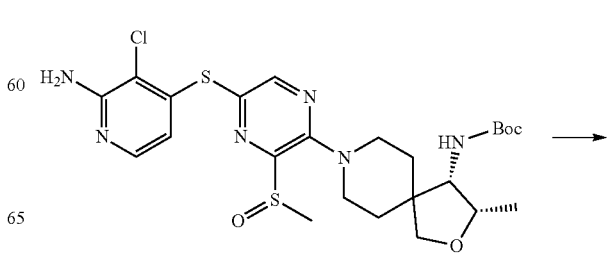

-continued

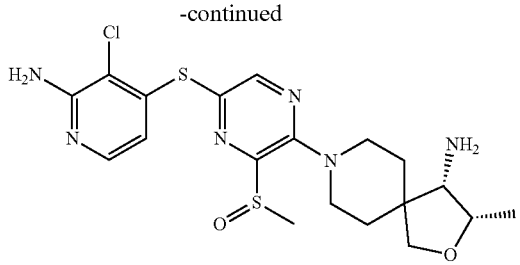

A solution of tert-butyl N-[(3S,4S)-8-[5-[(2-amino-3-chloropyridin-4-yl)sulfanyl]-3-methanesulfinylpyrazin-2-yl]-3-methyl-2-oxa-8-azaspiro[4.5]decan-4-yl]carbamate (20 mg, 0.03 mmol, 1.0 equiv) in TFA and DCM (1/10, 0.5 mL) was stirred for 2 hrs at room temperature. The reaction mixture was concentrated under vacuum and the residue was purified by Prep-HPLC to afford the title compound (6 mg, 36.4% yield) as a light yellow solid. MS (ES, m/z): [M+1]$^+$=469.0.

Example 5

Synthesis of (3S,4S)-8-(5-[5H,5aH,6H,7H,8H-pyrido[3,2-b]pyrrolizin-4-ylsulfanyl]-6-aminopyrazin-2-yl)-3-methyl-2-oxa-8-azaspiro[4.5]decan-4-amine The title compound was synthesized by the method in Example 4 using 2,3-dichloro-4-(sodiosulfanyl)pyridine instead of 2-amino-3-chloropyridine-4-thiol hydrochloride in step 1. LCMS (ES, m/z): [M+1]$^+$=488.1.

Example 6

Synthesis of (3S,4S)-8-(3-methanesulfinyl-5-[[2-(trifluoromethyl)pyridin-3-yl]sulfanyl]-pyrazin-2-yl)-3-methyl-2-oxa-8-azaspiro[4.5]decan-4-amine

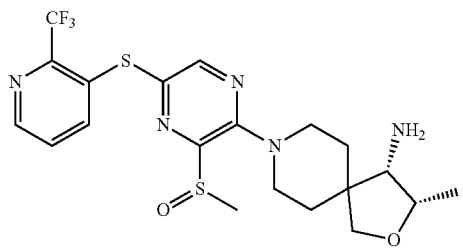 [SMILES: C[C@@H]1OCC2(CCN(c3ncc(Sc4cccnc4C(F)(F)F)nc3S(C)=O)CC2)[C@@H]1N]

The title compound was synthesized by the method in Example 4 using 2-(trifluoromethyl)-pyridine-3-thiol instead of 2-amino-3-chloropyridine-4-thiol hydrochloride in step 1. LCMS (ES, m/z): [M+1]$^+$=488.0.

Example 7

Synthesis of (3S,4S)-8-(5-((3-chloro-2-methoxypyridin-4-yl)thio)-3-(methylsulfinyl)pyrazin-2-yl)-3-methyl-2-oxa-8-azaspiro[4.5]decan-4-amine

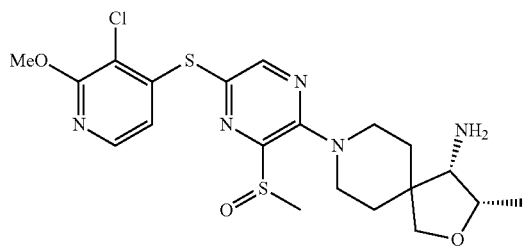 [SMILES: COc1nccc(Sc2cnc(N3CCC4(CC3)CO[C@@H](C)[C@H]4N)c(S(C)=O)n2)c1Cl]

The title compound was synthesized by the method in Example 4. LCMS (ES, m/z): [M+1]$^+$=484.2.

Example 8

Synthesis of (3S,4S)-8-(5-((3-chloro-2-(pyrrolidin-1-yl)pyridin-4-yl)thio)-3-(methylsulfinyl)-pyrazin-2-yl)-3-methyl-2-oxa-8-azaspiro[4.5]decan-4-amine

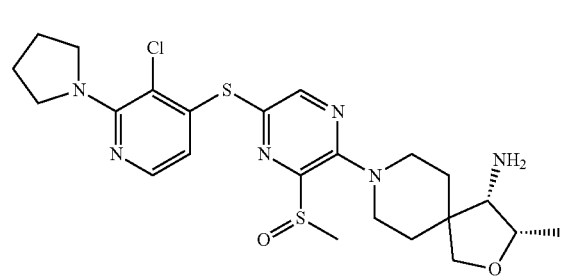 [SMILES: C[C@@H]1OCC2(CCN(c3ncc(Sc4ccnc(N5CCCC5)c4Cl)nc3S(C)=O)CC2)[C@@H]1N]

The title compound was synthesized by the method in Example 4. LCMS (ES, m/z): [M+1]$^+$=523.2.

Example 9

Synthesis of (3S,4S)-8-(5-((6-amino-2,3-dichloropyridin-4-yl)thio)-3-(methylsulfinyl)-pyrazin-2-yl)-3-methyl-2-oxa-8-azaspiro[4.5]decan-4-amine

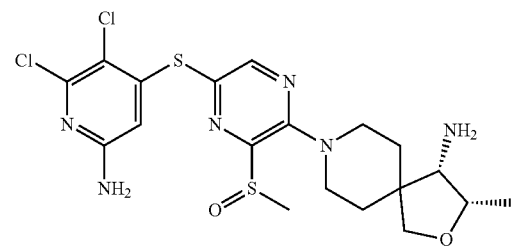 [SMILES: C[C@@H]1OCC2(CCN(c3ncc(Sc4cc(N)nc(Cl)c4Cl)nc3S(C)=O)CC2)[C@@H]1N]

The title compound was synthesized by the method in Example 4. LCMS (ES, m/z): [M+1]$^+$=503.1.

Example 10

Synthesis of (3S,4S)-8-(5-((3-chloro-2-fluoropyridin-4-yl)thio)-3-(methylsulfinyl)pyrazin-2-yl)-3-methyl-2-oxa-8-azaspiro[4.5]decan-4-amine

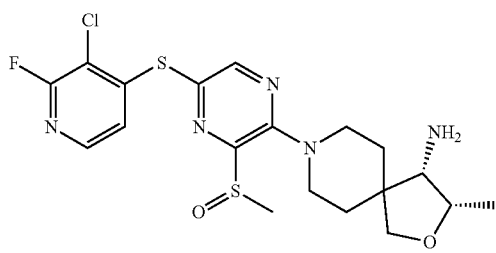 [SMILES: C[C@@H]1OCC2(CCN(c3ncc(Sc4ccnc(F)c4Cl)nc3S(C)=O)CC2)[C@@H]1N]

The title compound was synthesized by the method in Example 4. LCMS (ES, m/z): [M+1]⁺=472.2.

Example 11

Synthesis of (3-((3S,4S)-4-amino-3-methyl-2-oxa-8-azaspiro[4.5]decan-8-yl)-6-(((S)-6a,7,8,9-tetrahydro-6H-pyrido[3,2-b]pyrrolo[1,2-d][1,4]oxazin-4-yl)thio)pyrazin-2-yl)methanol

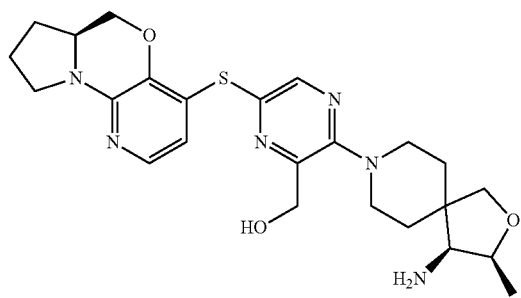 [SMILES: C[C@@H]1OCC2(CCN(c3ncc(Sc4ccnc5c4OC[C@@H]4CCCN54)nc3CO)CC2)[C@@H]1N]

Step 1: Tert-Butyl (2S)-2-[[(2-fluoropyridin-3-yl)oxy]methyl]pyrrolidine-1-carboxylate

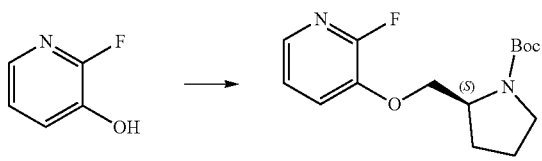

To a stirred mixture of 2-fluoropyridin-3-ol (1 g, 8.84 mmol, 1.00 equiv.) and tert-butyl (2S)-2-(hydroxymethyl)pyrrolidine-1-carboxylate (2.14 g, 10.61 mmol, 1.2 equiv.) in THF (15 mL) were added PPh₃ (3.48 g, 13.26 mmol, 1.50 equiv) and DEAD (2.31 g, 13.26 mmol, 1.5 equiv.) at room temperature under nitrogen atmosphere. After stirring for 16 h at room temperature, the reaction mixture was concentrated under reduce pressure. The residue was purified by silica gel column chromatography, eluted with PE/EtOAc (15:1) to afford the title compound (2.5 g, 95.4% yield) as a light yellow oil.

Step 2: 2-fluoro-3-[[(2S)-pyrrolidin-2-yl]methoxy]pyridine dihydrochloride

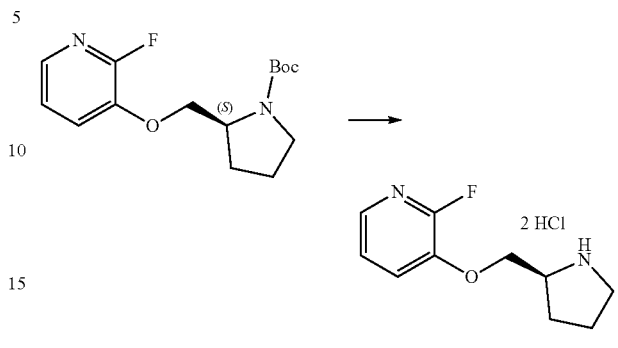

To a solution of tert-butyl (2S)-2-[[(2-fluoropyridin-3-yl)oxy]methyl]-pyrrolidine-1-carboxylate (2500 mg, 8.43 mmol, 1.00 equiv) in DCM (15 mL) was added hydrogen chloride (4 M in dioxane) (15 mL) at room temperature. After stirring at rt for 4 h, the reaction mixture was concentrated under vacuum to afford the title compound (2.20 g, 96.8% yield) as a white solid.

Step 3: (S)-6a,7,8,9-tetrahydro-6H-pyrido[3,2-b]pyrrolo[1,2-d][1,4]oxazine

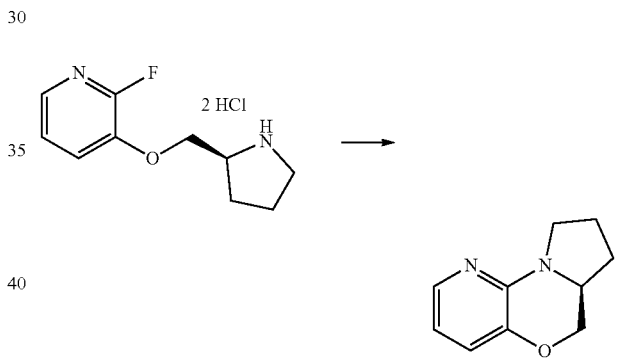

To a solution of 2-fluoro-3-[[(2S)-pyrrolidin-2-yl]methoxy]pyridine dihydrochloride (2.20 g, 8.17 mmol, 1.00 equiv) in ethanol (50 mL) was added K₂CO₃ (5.64 g, 40.87 mmol, 5.00 equiv) at room temperature and the resulting mixture was stirred for 12 h at 65° C. The mixture was then filtered and the filtrate was concentrated under reduced pressure. The residue was purified by silica gel column chromatography, eluted with PE/EtOAc (3:1) to afford the title compound (1.34 g, 93% yield) as colorless oil.

Step 4: (S)-4-iodo-6a,7,8,9-tetrahydro-6H-pyrido[3,2-b]pyrrolo[1,2-d][1,4]oxazine

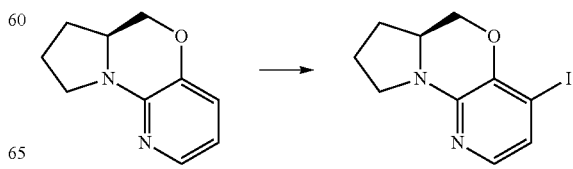

To a solution of (S)-6a,7,8,9-tetrahydro-6H-pyrido[3,2-b]pyrrolo[1,2-d][1,4]oxazine (600 mg, 3.41 mmol, 1.00 equiv) in THF (15 mL) was added dropwise n-butyllithium solution (2.5 M in hexane, 3.4 mL, 8.5 mmol, 2.50 equiv) at −78° C. under $N_2$ atmosphere. The reaction mixture was allowed to warm to 0° C. and stirred for 1.5 h. To the above mixture was added $I_2$ (950.60 mg, 3.74 mmol, 1.10 equiv) in THF (2 mL) dropwise at −78° C. The resulting mixture was allowed to warm to room temperature and stirred for 2 h at room temperature. The reaction mixture was quenched with sat. $NH_4Cl$ aq. Solution and diluted with EtOAc. The organic layer was washed with brine, dried over anhydrous $Na_2SO_4$. After filtration, the filtrate was concentrated under reduced pressure. The residue was purified by silica gel column chromatography, eluted with PE/EtOAc (3:1) to afford the title compound (700 mg, 68% yield) as a yellow solid.

Step 5: 2-ethylhexyl 3-(((S)-6a,7,8,9-tetrahydro-6H-pyrido[3,2-b]pyrrolo[1,2-d][1,4]oxazin-4-yl)thio)propanoate

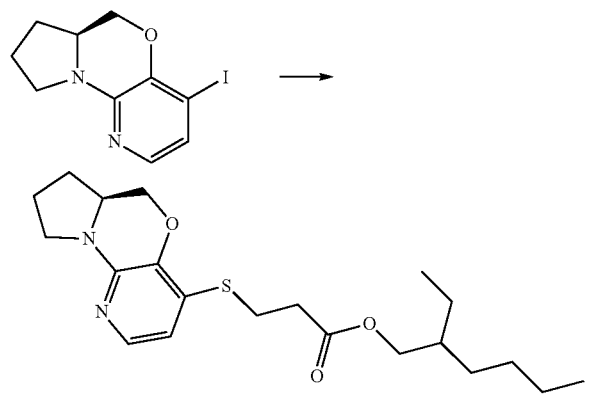

To a stirred mixture of (S)-4-iodo-6a,7,8,9-tetrahydro-6H-pyrido[3,2-b]pyrrolo[1,2-d][1,4]oxazine (150.00 mg, 0.496 mmol, 1.00 equiv), 2-ethylhexyl 3-sulfanylpropanoate (162.62 mg, 0.745 mmol, 1.50 equiv), $Pd_2(dba)_3$ (22.73 mg, 0.025 mmol, 0.05 equiv) and Xantphos (14.36 mg, 0.025 mmol, 0.05 equiv) in 1,4-dioxane (2 mL) was added DIEA (192.51 mg, 1.489 mmol, 3.00 equiv) at room temperature under nitrogen atmosphere. After stirring for 1 h at 90° C., the reaction mixture was concentrated under reduced pressure. The residue was purified by silica gel column chromatography, eluted with EtOAc/PE (0-30%) to afford the title compound (160 mg, 82% yield) as a light yellow solid.

Step 6: potassium (S)-6a,7,8,9-tetrahydro-6H-pyrido[3,2-b]pyrrolo[1,2-d][1,4]oxazine-4-thiolate

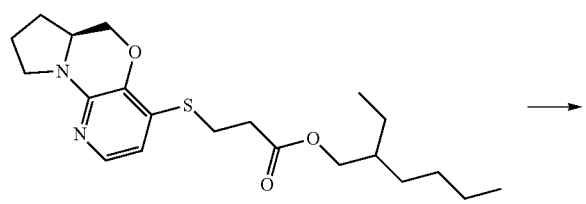

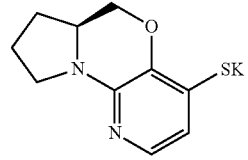

To a stirred solution of 2-ethylhexyl 3-(((S)-6a,7,8,9-tetrahydro-6H-pyrido[3,2-b]-pyrrolo[1,2-d][1,4]oxazin-4-yl)thio)propanoate (140.00 mg, 0.357 mmol, 1.0 equiv) in THF (2 mL) was added t-BuOK (0.43 mL, 0.428 mmol, 1.20 equiv) at −10° C. After stirring for 0.5 h at 0° C., the reaction mixture was diluted with PE. The precipitated solids were collected by filtration and washed with ethyl acetate to afford the title compound (75 mg, 85% yield) as a light yellow solid.

Step 7: Tert-Butyl ((3S,4S)-8-(3-(hydroxymethyl)-5-(((S)-6a,7,8,9-tetrahydro-6H-pyrido[3,2-b]pyrrolo[1,2-d][1,4]oxazin-4-yl)thio)pyrazin-2-yl)-3-methyl-2-oxa-8-azaspiro[4.5]decan-4-yl)carbamate

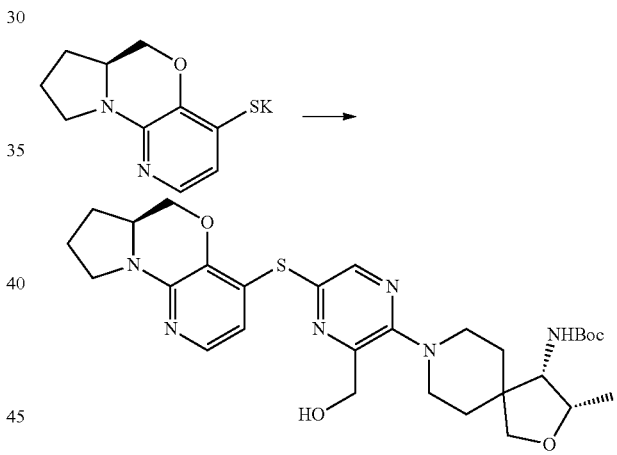

To a stirred mixture of tert-butyl N-[(3S,4S)-8-[5-bromo-3-(hydroxymethyl)pyrazin-2-yl]-3-methyl-2-oxa-8-azaspiro[4.5]decan-4-yl]carbamate (25.00 mg, 0.055 mmol, 1.00 equiv potassium (S)-6a,7,8,9-tetrahydro-6H-pyrido[3,2-b]pyrrolo[1,2-d][1,4]oxazine-4-thiolate (20.20 mg, 0.082 mmol, 1.50 equiv), $Pd_2(dba)_3$ (15.02 mg, 0.016 mmol, 0.30 equiv) and Xantphos (9.49 mg, 0.016 mmol, 0.30 equiv) in 1,4-dioxane (1 mL) was added DIEA (21.19 mg, 0.164 mmol, 3.00 equiv) at room temperature under nitrogen atmosphere. After stirring for 1.5 h at 100° C., the reaction mixture was concentrated under reduced pressure. The residue was purified by silica gel column chromatography, eluted with EtOAc/PE (50%-100%) to afford the title compound (25 mg, 78% yield) as a light yellow solid.

Step 8: (3-((3S,4S)-4-amino-3-methyl-2-oxa-8-azaspiro[4.5]decan-8-yl)-6-(((S)-6a,7,8,9-tetrahydro-6H-pyrido[3,2-b]pyrrolo[1,2-d][1,4]oxazin-4-yl)thio)pyrazin-2-yl)methanol Formate

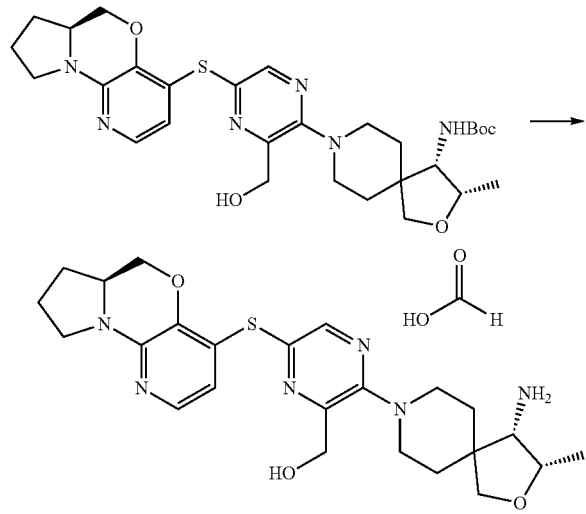

To a stirred solution of tert-butyl ((3S,4S)-8-(3-(hydroxymethyl)-5-(((S)-6a,7,8,9-tetrahydro-6H-pyrido[3,2-b]pyrrolo[1,2-d][1,4]oxazin-4-yl)thio)pyrazin-2-yl)-3-methyl-2-oxa-8-azaspiro[4.5]decan-4-yl)carbamate (20.00 mg, 0.034 mmol, 1.0 equiv) in DCM (1.5 mL) was added TFA (0.3 mL) at room temperature. After stirring for 5 h at room temperature, the reaction mixture was concentrated under reduced pressure. The crude product was purified by Prep-HPLC with to afford the title compound (7 mg, 30% yield) as a light yellow solid. MS (ES, m/z): [M+1]$^+$=485.2.

Example 12

Synthesis of (3-((3S,4S)-4-amino-3-methyl-2-oxa-8-azaspiro[4.5]decan-8-yl)-6-(((R)-6a,7,8,9-tetrahydro-6H-pyrido[3,2-b]pyrrolo[1,2-d][1,4]oxazin-4-yl)thio)pyrazin-2-yl)methanol

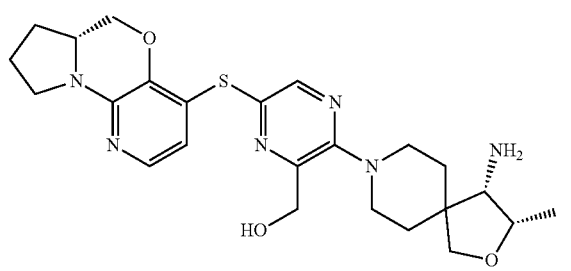 [SMILES: C[C@@H]1OCC2(CCN(c3ncc(Sc4ccnc5c4OC[C@H]4CCCN54)nc3CO)CC2)[C@@H]1N]

Compound 12 was synthesized by the method described in Example 11 using tert-butyl (2R)-2-(hydroxylmethyl)pyrrolidine-1-carboxylate instead of tert-butyl (2S)-2-(hydroxylmethyl)-pyrrolidine-1-carboxylate in step 1. MS (ES, m/z): [M+1]$^+$=485.3.

Example 13

Synthesis of [6-[(2-amino-3-chloropyridin-4-yl)sulfanyl]-3-[(5S)-5-amino-5,6-dihydrospiro-[piperidine-4,4-pyrrolo[1,2-b]pyrazol]-1-yl]pyrazin-2-yl]methanol

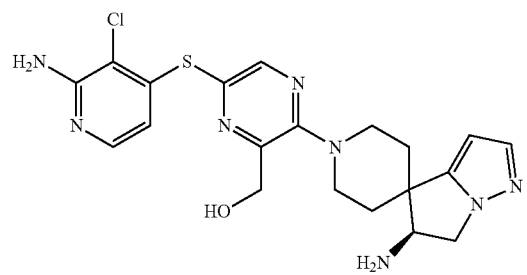 [SMILES: Nc1nccc(Sc2cnc(N3CCC4(CC3)c3ccnn3C[C@H]4N)c(CO)n2)c1Cl]

Into a 8 mL sealed tube were added (5S)-5,6-dihydrospiro[piperidine-4,4-pyrrolo[1,2-b]pyrazol]-5-amine dihydrochloride (10.50 mg, 0.040 mmol, 1.20 equiv), [6-[(2-amino-3-chloropyridin-4-yl)sulfanyl]-3-chloropyrazin-2-yl]methano 1 (10.00 mg, 0.033 mmol, 1.00 equiv), DIEA (21.32 mg, 0.165 mmol, 5.0 equiv) and DMSO (0.50 mL) at room temperature. The resulting mixture was stirred for overnight at 80° C. under nitrogen atmosphere. After cooled at rt, the mixture was purified by Prep-HPLC with the following conditions to afford the title compound (4 mg, 26% yield) as a white solid. MS (ES, m/z): [M+1]$^+$=459.1.

Example 14

Synthesis of (3-((3S,4S)-4-amino-3-methyl-2-oxa-8-azaspiro[4.5]decan-8-yl)-6-((((6aS,8S)-8-fluoro-6a,7,8,9-tetrahydro-6H-pyrido[3,2-b]pyrrolo[1,2-d][1,4]oxazin-4-yl)thio)pyrazin-2-yl)methanol

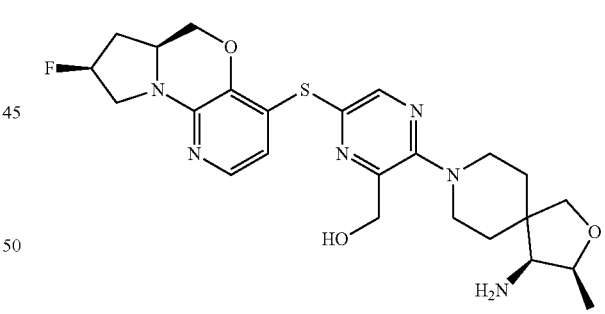

Step 1: Tert-Butyl (2S,4S)-4-fluoro-2-(hydroxymethyl)pyrrolidine-1-carboxylate

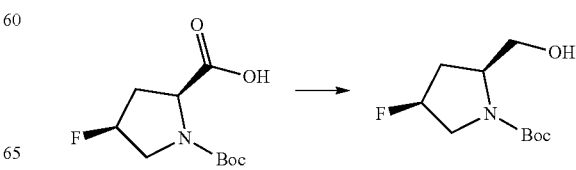

To a stirred solution of (2S,4S)-1-(tert-butoxycarbonyl)-4-fluoropyrrolidine-2-carboxylic acid (2.33 g, 9.99 mmol, 1.0 equiv) in THF (25 mL) was added BH₃-Me₂S (2.8 mL, 37.4 mmol, 3.0 equiv) dropwise at 0-5° C. under nitrogen atmosphere and the resulting mixture was stirred overnight at room temperature. The mixture was cooled at 0° C. and quenched with MeOH. The resulting mixture was concentrated under reduced pressure and the residue was purified by silica gel column chromatography, eluted with EtOAc/PE (1/1) to give the title compound (2.0 g, 91.3%).

Step 2: Tert-Butyl (2S,4S)-4-fluoro-2-[[(2-fluoro-4-iodopyridin-3-yl)oxy]methyl]pyrrolidine-1-carboxylate

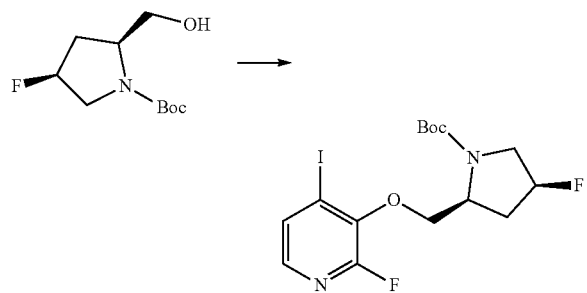

To a solution of 2-fluoro-4-iodopyridin-3-ol (436 mg, 1.82 mmol, 1.0 equiv), tert-butyl (2S,4S)-4-fluoro-2-(hydroxymethyl)pyrrolidine-1-carboxylate (400 mg, 1.82 mmol, 1.0 equiv) and PPh₃ (717 mg, 2.737 mmol, 1.5 equiv) in THF (4.00 mL) was added DEAD (476 mg, 2.737 mmol, 1.50 equiv) dropwise at 0° C. under nitrogen atmosphere. The resulting mixture was stirred overnight at room temperature under nitrogen atmosphere. The reaction mixture was quenched with water and the resulting mixture was extracted with EtOAc. The combined organic layers were washed with water and brine, dried over anhydrous Na₂SO₄ and concentrated. The residue was purified by silica gel column chromatography, eluted with EtOAc/PE (0-50%), to afford the title compound (610 mg, 75.5%).

Step 3: 2-fluoro-3-(((2S,4S)-4-fluoropyrrolidin-2-yl)methoxy)-4-iodopyridine hydrochloride

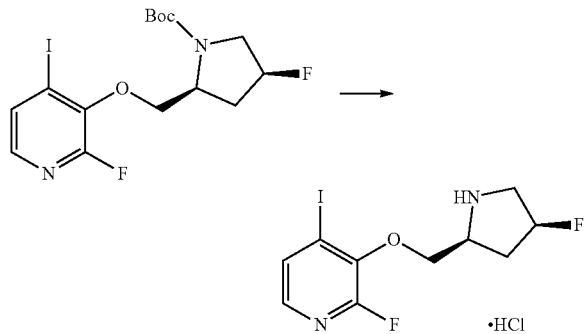

To a stirred solution of tert-butyl (2S,4S)-4-fluoro-2-[[(2-fluoro-4-iodopyridin-3-yl)oxy]methyl]pyrrolidine-1-carboxylate (560 mg, 1.272 mmol, 1.0 equiv) in 1,4-dioxane (5 mL) was added a solution of HCl in 1,4-dioxane (5 mL, 164.5 mmol, 129 equiv) dropwise at 0° C. After stirring at room temperature for 1 hour, the reaction mixture was concentrated under reduced pressure and the residue was washed with Et₂O. The solid was collected by filtration and dried under vacuum to give product as HCl salt (375 mg, 78.3%).

Step 4: (6aS,8S)-8-fluoro-4-iodo-6a,7,8,9-tetrahydro-6H-pyrido[3,2-b]pyrrolo[1,2-d][1,4]oxazine

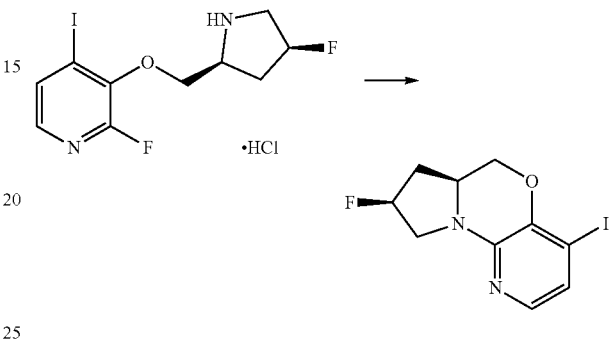

A mixture of 2-fluoro-3-(((2S,4S)-4-fluoropyrrolidin-2-yl)methoxy)-4-iodopyridine hydrochloride (370 mg, 0.983 mmol, 1.0 equiv) and K₂CO₃ (407 mg, 2.948 mmol, 3.0 equiv) in EtOH (4 mL) was stirred for 2 h at 60° C. The resulting mixture was diluted with water and extracted with EtOAc. The combined organic layers were washed with water and brine, dried over anhydrous Na₂SO₄ and concentrated. The residue was purified by silica gel column chromatography, eluted with EtOAc/PE (0-30%), to afford the title compound (245 mg, 77.9%).

Step 5: 2-ethylhexyl 3-([5-[(3S,4S)-4-[(tert-butoxycarbonyl)amino]-3-methyl-2-oxa-8-azaspiro[4.5]decan-8-yl]-6-(hydroxymethyl)pyrazin-2-yl]sulfanyl)propanoate

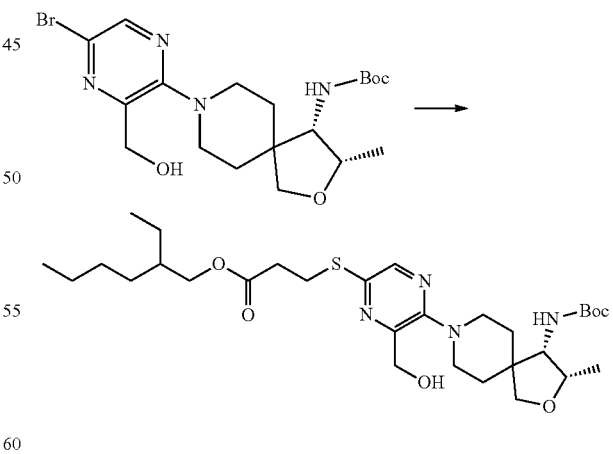

A solution of tert-butyl N-[(3S,4S)-8-[5-bromo-3-(hydroxymethyl)pyrazin-2-yl]-3-methyl-2-oxa-8-azaspiro[4.5]decan-4-yl]carbamate (580.0 mg, 1.26 mmol, 1.0 equiv), 2-ethylhexyl 3-sulfanylpropanoate (332.29 mg, 1.52 mmol, 1.2 equiv), Pd₂(dba)₃ (116.1 mg, 0.12 mmol, 0.10 equiv), XantPhos (73.38 mg, 0.127 mmol, 0.10 equiv) and DIEA (491.69 mg, 3.804 mmol, 3.00 equiv) in 1,4-dioxane (12.0 mL, 141.6 mmol, 111.7 equiv) was stirred for 1 h at 100° C. under nitrogen atmosphere. The resulting mixture was concentrated under vacuum and the residue was purified by silica gel column chromatography, eluted with EtOAc/PE (0-50%), to afford the title compound (600 mg, 79.54%).

Step 6: Tert-Butyl N-[(3S,4S)-8-[3-(hydroxymethyl)-5-(sodiosulfanyl)pyrazin-2-yl]-3-methyl-2-oxa-8-azaspiro[4.5]decan-4-yl]carbamate

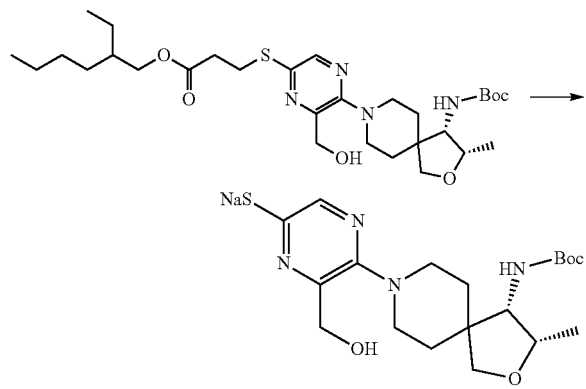

To a stirred solution of 2-ethylhexyl 3-([5-[(3S,4S)-4-[(tert-butoxycarbonyl)amino]-3-methyl-2-oxa-8-azaspiro[4.5]decan-8-yl]-6-(hydroxymethyl)pyrazin-2-yl]sulfanyl)propanoate (680.0 mg, 1.14 mmol, 1.0 equiv) in CH$_3$OH (6.80 mL) was added CH$_3$ONa (247.04 mg, 1.372 mmol, 1.20 equiv, 30% in MeOH) dropwise at 5° C. After stirring at rt for 16 h, the reaction mixture was concentrated under vacuum and the residue was triturated with Et$_2$O to afford the title compound (390 mg, crude).

Step 7: Tert-Butyl ((3S,4S)-8-(5-((((6aS,8S)-8-fluoro-6a,7,8,9-tetrahydro-6H-pyrido[3,2-b]pyrrolo[1,2-d][1,4]oxazin-4-yl)thio)-3-(hydroxymethyl)pyrazin-2-yl)-3-methyl-2-oxa-8-azaspiro[4.5]decan-4-yl)carbamate

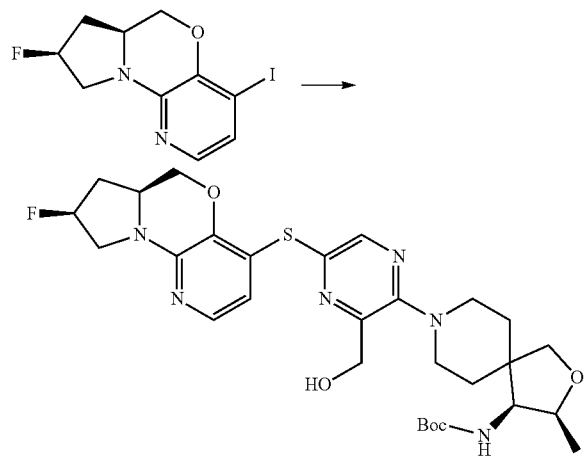

A solution of (6aS,8S)-8-fluoro-4-iodo-6a,7,8,9-tetrahydro-6H-pyrido[3,2-b]pyrrolo[1,2-d][1,4]oxazine (30.00 mg, 0.094 mmol, 1.0 equiv), tert-butyl N-[(3S,4S)-8-[3-(hydroxymethyl)-5-(sodiosulfanyl)pyrazin-2-yl]-3-methyl-2-oxa-8-azaspiro[4.5]decan-4-yl]carbamate (48.64 mg, 0.112 mmol, 1.2 equiv), Pd$_2$(dba)$_3$ (25.75 mg, 0.028 mmol, 0.30 equiv), XantPhos (16.27 mg, 0.028 mmol, 0.30 equiv) and DIEA (36.34 mg, 0.281 mmol, 3.00 equiv) in dioxane (0.90 mL, 10.215 mmol, 113.36 equiv) was stirred for 1 h at 80° C. under nitrogen atmosphere. After cooling the reaction mixture to rt, the reaction mixture was diluted with water, extracted with EtOAc. The organic layer was washed with water and brine, dried over Na$_2$SO$_4$ and concentrated. The residue was purified by silica gel column chromatography, eluted with MeOH/CH$_2$Cl$_2$ (0-10%), to afford the title compound (32 mg, 56.65%).

Step 8: (3-((S)-4-amino-2-oxa-8-azaspiro[4.5]decan-8-yl)-6-((((6aS,8S)-8-fluoro-6a,7,8,9-tetrahydro-6H-pyrido[3,2-b]pyrrolo[1,2-d][1,4]oxazin-4-yl)thio)pyrazin-2-yl)methanol

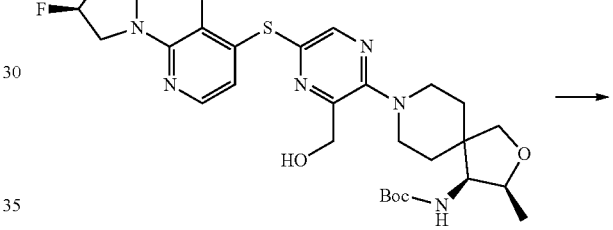

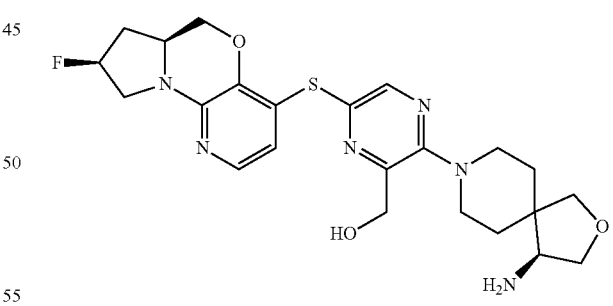

To a solution tert-butyl ((3S,4S)-8-(5-((((6aS,8S)-8-fluoro-6a,7,8,9-tetrahydro-6H-pyrido[3,2-b]pyrrolo[1,2-d][1,4]oxazin-4-yl)thio)-3-(hydroxymethyl)pyrazin-2-yl)-3-methyl-2-oxa-8-azaspiro[4.5]decan-4-yl)carbamate (26 mg, 0.043 mmol, 1.00 equiv) in DCM (1.2 mL) was added TFA (0.4 mL, 5.385 mmol, 124.84 equiv) dropwise at 5° C. After stirring at rt for 1 h, the reaction mixture was concentrated under vacuum and the residue was purified by Prep-HPLC to give the title compound (3.1 mg, 14.30%). MS (ES, m/z): [M+1]$^+$=503.2

Example 15

Synthesis of (3-((3S,4S)-4-amino-3-methyl-2-oxa-8-azaspiro[4.5]decan-8-yl)-6-(((6aS,8R)-8-fluoro-6a,7,8,9-tetrahydro-6H-pyrido[3,2-b]pyrrolo[1,2-d][1,4]oxazin-4-yl)thio)pyrazin-2-yl)methanol

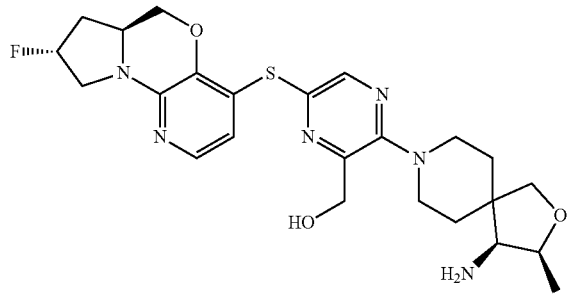 [SMILES: C[C@@H]1OCC2(CCN(c3ncc(Sc4ccnc5c4OC[C@@H]4C[C@@H](F)CN54)nc3CO)CC2)[C@@H]1N]

Compound 15 was synthesized by the method described in Example 14 using (2S,4R)-1-(tert-butoxycarbonyl)-4-fluoropyrrolidine-2-carboxylic acid in step 1. MS (ES, m/z): [M+1]$^+$=503.3.

Example 16

Synthesis of (3-((3S,4S)-4-amino-3-methyl-2-oxa-8-azaspiro[4.5]decan-8-yl)-6-(((6aS,8S)-8-methoxy-6a,7,8,9-tetrahydro-6H-pyrido[3,2-b]pyrrolo[1,2-d][1,4]oxazin-4-yl)thio)pyrazin-2-yl)methanol

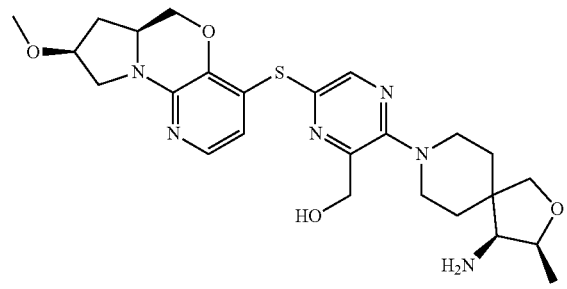 [SMILES: CO[C@H]1C[C@H]2COc3c(Sc4cnc(N5CCC6(CC5)CO[C@@H](C)[C@H]6N)c(CO)n4)ccnc3N2C1]

Step 1: 1-tert-butyl 2-methyl (2S,4S)-4-[(tert-butyldimethylsilyl)oxy]pyrrolidine-1,2-dicarboxylate

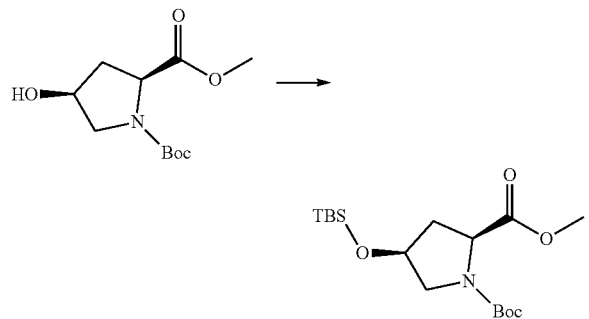

To a stirred solution of 1-tert-butyl 2-methyl (2S,4S)-4-hydroxypyrrolidine-1,2-dicarboxylate (6 g, 24.46 mmol, 1.0 equiv) and imidazole (2.5 g, 36.694 mmol, 1.50 equiv) in DCM (60 mL) was added TBS-Cl (5.53 g, 36.690 mmol, 1.50 equiv) in portions at 0-5° C. After stirring overnight at room temperature, the reaction mixture was quenched with MeOH and water and the resulting mixture was extracted with EtOAc. The combined organic layers were washed with water and brine, dried over anhydrous Na$_2$SO$_4$ and concentrated. The residue was purified by silica gel column chromatography, eluted with EtOAc/PE (0-10%), to afford the title compound (9.0 g, 97.2%).

Step 2: Tert-Butyl (2S,4S)-4-[(tert-butyldimethylsilyl)oxy]-2-(hydroxymethyl)pyrrolidine-1-carboxylate

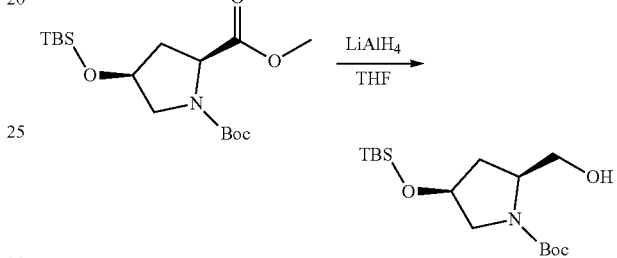

To a stirred mixture of 1-tert-butyl 2-methyl (2S,4S)-4-[(tert-butyldimethylsilyl)oxy]-pyrrolidine-1,2-dicarboxylate (3 g, 8.344 mmol, 1.0 equiv) in THF (30 mL) were added LiAlH$_4$ (475 mg, 12.516 mmol, 1.50 equiv) in portions at 0° C. under nitrogen atmosphere and the resulting mixture was stirred for 2 h at room temperature under nitrogen atmosphere. After cooling the reaction mixture at 0° C., the reaction mixture was quenched with sat. aq. Na$_2$SO$_4$ solution. The resulting mixture was filtered and the filtrate was concentrated under reduced pressure. The residue was purified by silica gel column chromatography, eluted with EtOAc/PE (0-100%), to afford the title compound (1.6 g, 57.8%).

Step 3: Tert-Butyl (2S,4S)-4-[(tert-butyldimethylsilyl)oxy]-2-[[(2-fluoro-4-iodopyridin-3-yl)oxy]methyl] pyrrolidine-1-carboxylate

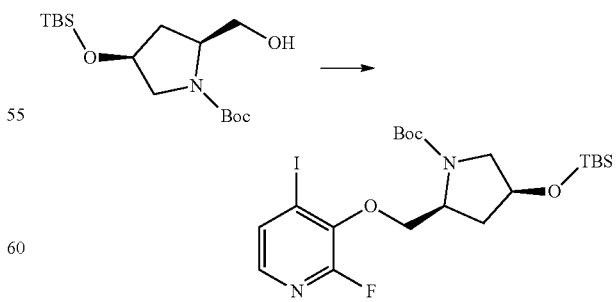

To a stirred mixture of 2-fluoro-4-iodopyridin-3-ol (400 mg, 1.674 mmol, 1.0 equiv), tert-butyl (2S,4S)-4-[(tert-butyldimethylsilyl)oxy]-2-(hydroxymethyl)pyrrolidine-1-carboxylate (555 mg, 1.674 mmol, 1.00 equiv) and PPh$_3$ (658 mg, 2.511 mmol, 1.50 equiv) in THF (4 mL) was added DEAD (437 mg, 2.511 mmol, 1.50 equiv) dropwise at 0° C. under nitrogen atmosphere. The resulting mixture was stirred for 2 h at room temperature under nitrogen atmosphere and then quenched with water at 0° C. and extracted with EtOAc. The combined organic layers were washed with water and brine, dried over anhydrous Na₂SO₄ and concentrated. The residue was purified by silica gel column chromatography, eluted with EtOAc/PE (0-30%), to afford the title compound (735 mg, 79.4%).

Step 4: (3S,5S)-5-[[(2-fluoro-4-iodopyridin-3-yl)oxy]methyl]pyrrolidin-3-ol hydrochloride

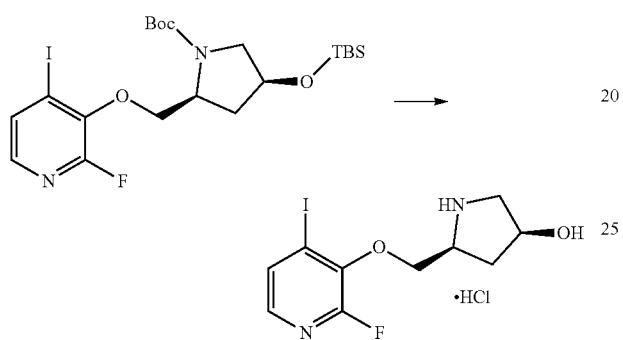

To a stirred solution of tert-butyl (2S,4S)-4-[(tert-butyldimethylsilyl)oxy]-2-[[(2-fluoro-4-iodopyridin-3-yl)oxy]methyl]pyrrolidine-1-carboxylate (750 mg, 1.357 mmol, 1.0 equiv) was added a solution of HCl in 1,4-dioxane (5 mL, 164.5 mmol, 121.2 equiv) dropwise at 0-5° C. After stirring at room temperature for 1 h, the reaction mixture was concentrated under reduced pressure and the residue was triturated with Et₂O. The precipitates were collected by filtration and dried under reduced pressure to give the title compound (400 mg, 78.67%).

Step 5: (6aS,8S)-4-iodo-6a,7,8,9-tetrahydro-6H-pyrido[3,2-b]pyrrolo[1,2-d][1,4]oxazin-8-ol

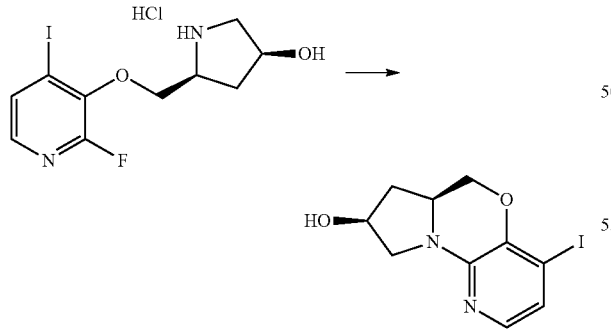

A mixture of (3S,5S)-5-[[(2-fluoro-4-iodopyridin-3-yl)oxy]methyl]pyrrolidin-3-ol hydrochloride (400 mg, 1.068 mmol, 1.00 equiv) and K₂CO₃ (443 mg, 3.204 mmol, 3.00 equiv) in EtOH (4 mL) was stirred for 2 h at 60° C. After cooling to rt, the resulting mixture was diluted with water and extracted with EtOAc. The combined organic layers were washed with water and brine, dried over anhydrous Na₂SO₄ and concentrated. The residue was purified by silica gel column chromatography, eluted with EtOAc/PE (0-40%), to afford the title compound (300 mg, 88.3%).

Step 6: (6aS,8S)-4-iodo-8-methoxy-6a,7,8,9-tetrahydro-6H-pyrido[3,2-b]pyrrolo[1,2-d][1,4]oxazine

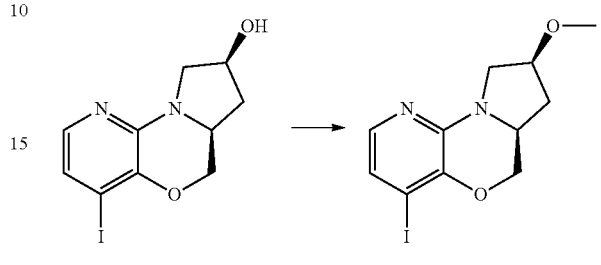

To a stirred solution of (6aS,8S)-4-iodo-6a,7,8,9-tetrahydro-6H-pyrido[3,2-b]pyrrolo[1,2-d][1,4]oxazin-8-ol (100.00 mg, 0.314 mmol, 1.0 equiv) and Ag₂O (364.23 mg, 1.572 mmol, 5.0 equiv) in DMF (1.00 mL) was added MeI (133.86 mg, 0.943 mmol, 3.00 equiv) dropwise at room temperature and the resulting mixture was stirred for 4 h at 50° C. After cooling to room temperature, the reaction mixture was filtered. The filtrate was washed with H₂O and brine, dried over anhydrous Na₂SO₄ and concentrated. The residue was purified by silica gel column chromatography, eluted with PE/EA (2/1), to afford the title compound (89 mg, 85.24%).

Step 7: Tert-Butyl ((3S,4S)-8-(3-(hydroxymethyl)-5-((((6aS,8S)-8-methoxy-6a,7,8,9-tetrahydro-6H-pyrido[3,2-b]pyrrolo[1,2-d][1,4]oxazin-4-yl)thio)pyrazin-2-yl)-3-methyl-2-oxa-8-azaspiro[4.5]decan-4-yl)carbamate

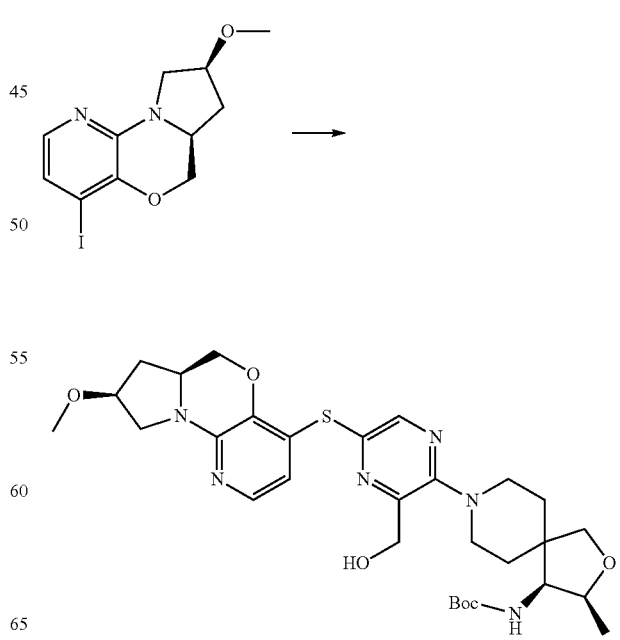

To a stirred mixture of (6aS,8S)-4-iodo-8-methoxy-6a,7,8,9-tetrahydro-6H-pyrido[3,2-b]pyrrolo[1,2-d][1,4]oxazine (30.00 mg, 0.090 mmol, 1.0 equiv) and tert-butyl N-[(3S,4S)-8-[3-(hydroxymethyl)-5-sulfanylpyrazin-2-yl]-3-methyl-2-oxa-8-azaspiro[4.5]decan-4-yl]carbamate (37.08 mg, 0.090 mmol, 1.0 equiv) in dioxane (0.30 mL) were added Pd₂(dba)₃ (24.81 mg, 0.027 mmol, 0.30 equiv), Xantphos (15.68 mg, 0.027 mmol, 0.30 equiv) and DIEA (35.02 mg, 0.271 mmol, 3.00 equiv) at room temperature under N₂ atmosphere. The resulting mixture was stirred for 1 h at 80° C. under N₂ atmosphere. After cooling to room temperature, the reaction mixture was concentrated under vacuum and the residue was purified by silica gel column chromatography, eluted with DCM/MeOH (10/1), to afford the title compound (25 mg, 45.6%).

Step 8: (3-((3S,4S)-4-amino-3-methyl-2-oxa-8-azaspiro[4.5]decan-8-yl)-6-(((6aS,8S)-8-methoxy-6a,7,8,9-tetrahydro-6H-pyrido[3,2-b]pyrrolo[1,2-d][1,4]oxazin-4-yl)thio)pyrazin-2-yl)methanol formate

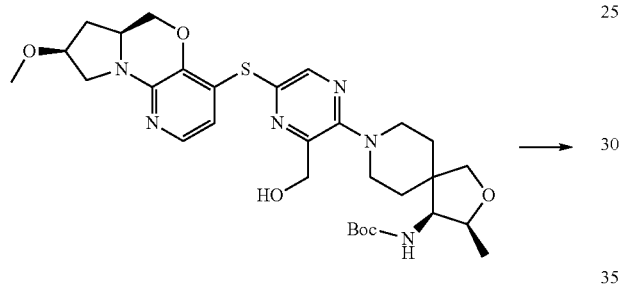

TFA (1.3 mL) was added to a solution of tert-butyl ((3S,4S)-8-(3-(hydroxymethyl)-5-(((6aS,8S)-8-methoxy-6a,7,8,9-tetrahydro-6H-pyrido[3,2-b]pyrrolo[1,2-d][1,4]oxazin-4-yl)thio)pyrazin-2-yl)-3-methyl-2-oxa-8-azaspiro[4.5]decan-4-yl)carbamate (130.0 mg, 0.21 mmol, 1.0 equiv) in DCM (3.0 mL) at room temperature. After stirring at rt for 2 h, the reaction solution was concentrated and residue was purified by Prep-HPLC to give product (19 mg, 16.08%). MS (ES, m/z): [M+1]⁺=515.3.

Example 17

Synthesis of (3-((3S,4S)-4-amino-3-methyl-2-oxa-8-azaspiro[4.5]decan-8-yl)-6-(((6aS,8R)-8-methoxy-6a,7,8,9-tetrahydro-6H-pyrido[3,2-b]pyrrolo[1,2-d][1,4]oxazin-4-yl)thio)pyrazin-2-yl)methanol

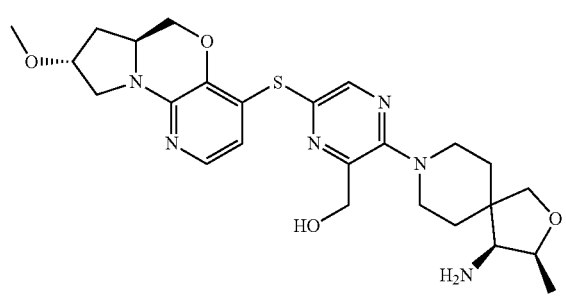 [SMILES: CO[C@@H]1C[C@H]2COc3c(Sc4cnc(N5CCC6(CC5)CO[C@@H](C)[C@H]6N)c(CO)n4)ccnc3N2C1]

Step 1: (6aS,8R)-4-iodo-8-methoxy-6a,7,8,9-tetrahydro-6H-pyrido[3,2-b]pyrrolo[1,2-d][1,4]oxazine

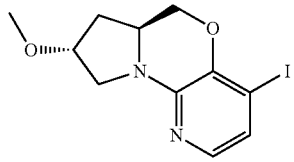 [SMILES: CO[C@@H]1C[C@H]2COc3c(I)ccnc3N2C1]

Compound (6aS,8R)-4-iodo-8-methoxy-6a,7,8,9-tetrahydro-6H-pyrido[3,2-b]pyrrolo[1,2-d][1,4]oxazine was synthesized by the method described in Example 16, Steps 1-6 using 1-(tert-butyl) 2-methyl (2S,4S)-4-hydroxypyrrolidine-1,2-dicarboxylate in Step 1.

Step 2: (3-((3S,4S)-4-amino-3-methyl-2-oxa-8-azaspiro[4.5]decan-8-yl)-6-(((6aS,8R)-8-methoxy-6a,7,8,9-tetrahydro-6H-pyrido[3,2-b]pyrrolo[1,2-d][1,4]oxazin-4-yl)thio)pyrazin-2-yl)methanol

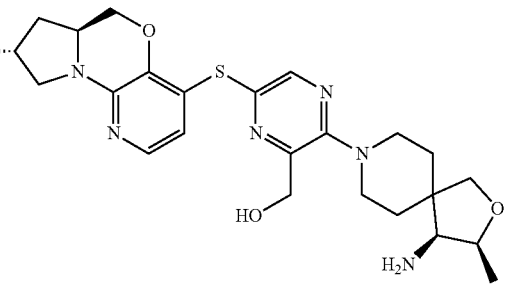

(3-((3S,4S)-4-Amino-3-methyl-2-oxa-8-azaspiro[4.5]decan-8-yl)-6-(((6aS,8R)-8-methoxy-6a,7,8,9-tetrahydro-6H-pyrido[3,2-b]pyrrolo[1,2-d][1,4]oxazin-4-yl)thio)pyrazin-2-yl)methanol was synthesized by proceeding analogously as described in Example 11, Step 5-8. MS (ES, m/z). [M+1]⁺=503.3.

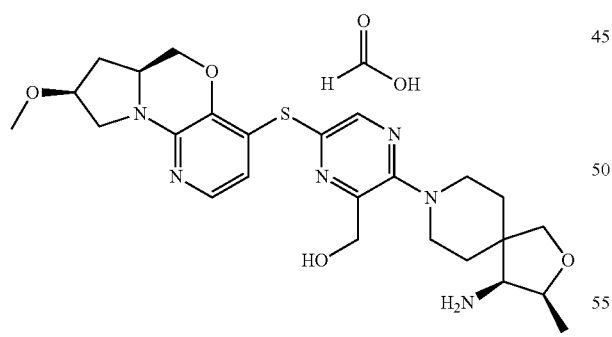

Example 18

Synthesis of (6aS,8S)-4-((5-((3S,4S)-4-amino-3-methyl-2-oxa-8-azaspiro[4.5]decan-8-yl)-6-(hydroxymethyl)pyrazin-2-yl)thio)-6a,7,8,9-tetrahydro-6H-pyrido[3,2-b]pyrrolo[1,2-d][1,4]oxazin-8-ol

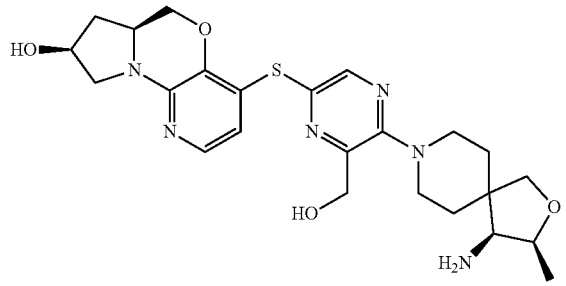

Step 1: (6aS,8S)-4-iodo-6a,7,8,9-tetrahydro-6H-pyrido[3,2-b]pyrrolo[1,2-d][1,4]oxazin-8-ol

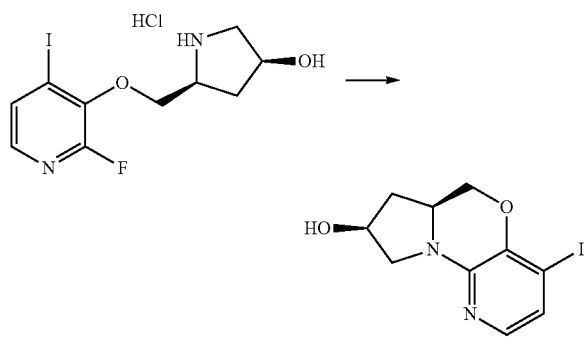

A mixture of (3S,5S)-5-[[(2-fluoro-4-iodopyridin-3-yl)oxy]methyl]pyrrolidin-3-ol hydrochloride (400 mg, 1.068 mmol, 1.0 equiv) and $K_2CO_3$ (443 mg, 3.204 mmol, 3.0 equiv) in EtOH (4 mL) was stirred for 2 h at 60° C. After cooled at rt, the resulting mixture was diluted with water and extracted with EtOAc. The combined organic layers were washed with water and brine, dried over anhydrous $Na_2SO_4$ and concentrated. The residue was purified by silica gel column chromatography, eluted with EtOAc/PE (0-40%) to afford the title compound (300 mg, 88.31%).

Step 2: Tert-Butyl ((3S,4S)-8-(5-(((6aS,8S)-8-hydroxy-6a,7,8,9-tetrahydro-6H-pyrido[3,2-b]pyrrolo[1,2-d][1,4]oxazin-4-yl)thio)-3-(hydroxymethyl)pyrazin-2-yl)-3-methyl-2-oxa-8-azaspiro[4.5]decan-4-yl)carbamate

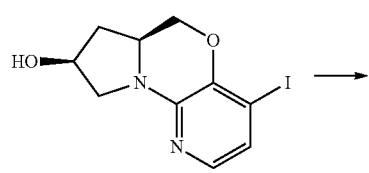

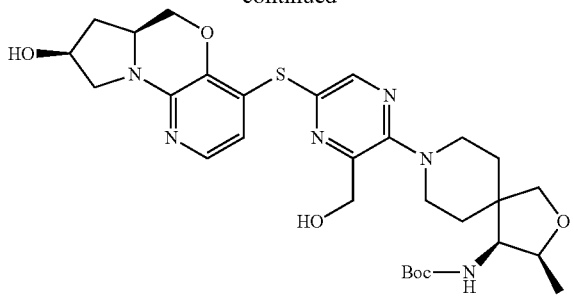

A mixture of tert-butyl N-[(3 S,4S)-8-[3-(hydroxymethyl)-5-(sodiosulfanyl)pyrazin-2-yl]-3-methyl-2-oxa-8-azaspiro[4.5]decan-4-yl]carbamate (49 mg, 0.113 mmol, 1.2 equiv), (6aS,8S)-4-iodo-6a,7,8,9-tetrahydro-6H-pyrido[3,2-b]pyrrolo[1,2-d][1,4]oxazin-8-ol (30 mg, 0.094 mmol, 1.00 equiv), $Pd_2(dba)_3$ (26 mg, 0.028 mmol, 0.30 equiv), XantPhos (16 mg, 0.028 mmol, 0.30 equiv) and DIEA (36 mg, 0.283 mmol, 3.00 equiv) in dioxane (0.3 mL) was stirred for 1 h at 100° C. under nitrogen atmosphere. After cooling to room temperature, the resulting mixture was diluted with water and extracted with EtOAc. The combined organic layers were washed with water and brine, dried over anhydrous $Na_2SO_4$ and concentrated. The residue was purified by silica gel column chromatography, eluted with EtOAc/PE (50-100%) to afford the title compound (50 mg, 65.6%).

Step 3: (6aS,8S)-4-((5-((3S,4S)-4-amino-3-methyl-2-oxa-8-azaspiro[4.5]decan-8-yl)-6-(hydroxymethyl)pyrazin-2-yl)thio)-6a,7,8,9-tetrahydro-6H-pyrido[3,2-b]pyrrolo[1,2-d][1,4]oxazin-8-ol

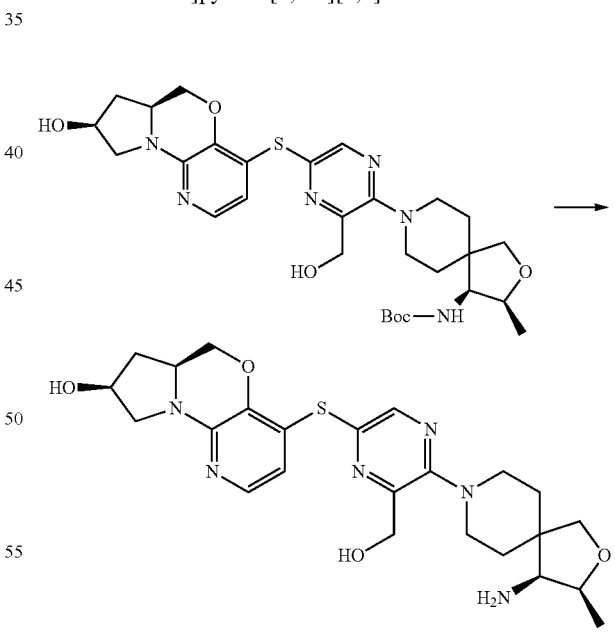

To a stirred solution of tert-butyl ((3S,4S)-8-(5-(((6aS,8S)-8-hydroxy-6a,7,8,9-tetrahydro-6H-pyrido[3,2-b]pyrrolo[1,2-d][1,4]oxazin-4-yl)thio)-3-(hydroxymethyl)pyrazin-2-yl)-3-methyl-2-oxa-8-azaspiro[4.5]decan-4-yl)carbamate (60 mg) in DCM (0.60 mL) was added TFA (0.20 mL) dropwise at 0° C. and the resulting mixture was stirred for 1 h at room temperature. The reaction mixture was then concentrated under reduced pressure and the residue was purified by Prep-HPLC to afford the title compound (18.7 mg, 60.32%). MS (ES, m/z): [M+1]⁺=501.2.

Example 19

Synthesis of (6aS,8R)-4-((5-((3S,4S)-4-amino-3-methyl-2-oxa-8-azaspiro[4.5]decan-8-yl)-6-(hydroxymethyl)pyrazin-2-yl)thio)-6a,7,8,9-tetrahydro-6H-pyrido[3,2-b]pyrrolo[1,2-d][1,4]oxazin-8-ol

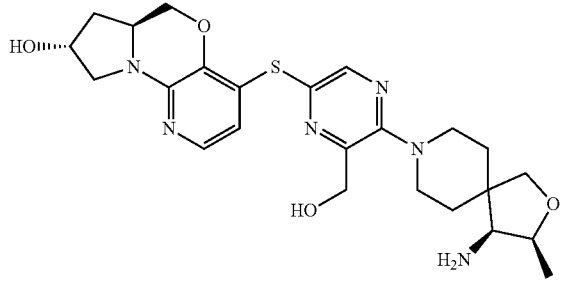 [SMILES: C[C@@H]1OCC2(CCN(c3ncc(Sc4ccnc5c4OC[C@@H]4C[C@@H](O)CN54)nc3CO)CC2)[C@@H]1N]

The title compound was synthesized by proceeding analogously as described in Example 18. MS (ES, m/z): [M+1]⁺=501.3.

Example 20

Synthesis of (3-((3S,4S)-4-amino-3-methyl-2-oxa-8-azaspiro[4.5]decan-8-yl)-6-(((S)-6a',7'-dihydro-6'H,9'H-spiro[cyclopropane-1,8'-pyrido[3,2-b]pyrrolo[1,2-d][1,4]oxazin]-4'-yl)thio)pyrazin-2-yl)methanol

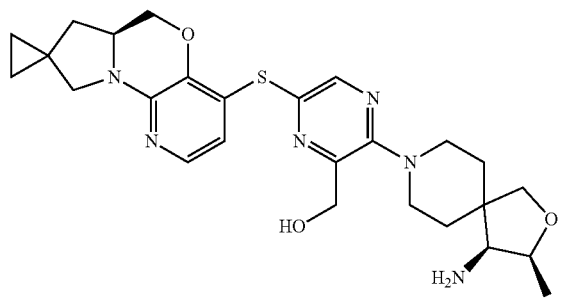 [SMILES: C[C@@H]1OCC2(CCN(c3ncc(Sc4ccnc5c4OC[C@@H]4CC6(CC6)CN54)nc3CO)CC2)[C@@H]1N]

Step 1: (S)-4'-iodo-6a',7'-dihydro-6'H,9'H-spiro[cyclopropane-1,8'-pyrido[3,2-b]pyrrolo[1,2-d][1,4]oxazine]

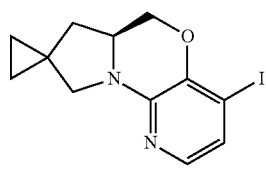 [SMILES: Ic1ccnc2c1OC[C@@H]1CC3(CC3)CN21]

Compound (S)-4'-iodo-6a',7'-dihydro-6'H,9'H-spiro[cyclopropane-1,8'-pyrido[3,2-b]pyrrolo[1,2-d][1,4]oxazine] was synthesized by proceeding analogously as described in Example 14, Steps 1-4 using 5-tert-butyl 6-methyl (6S)-5-azaspiro[2.4]heptane-5,6-dicarboxylate in Step 1.

Step 2: (3-((3S,4S)-4-amino-3-methyl-2-oxa-8-azaspiro[4.5]decan-8-yl)-6-(((S)-6a',7'-dihydro-6'H,9'H-spiro[cyclopropane-1,8'-pyrido[3,2-b]pyrrolo[1,2-d][1,4]oxazin]-4'-yl)thio)pyrazin-2-yl)methanol

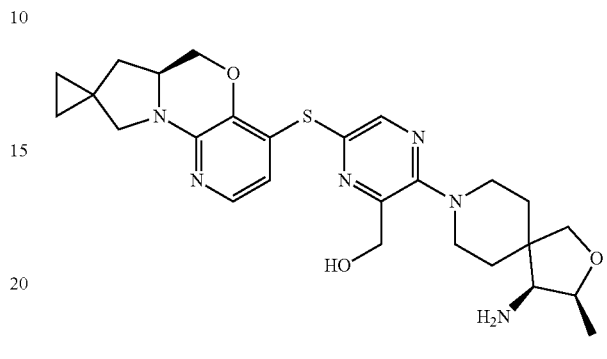

The title compound was synthesized by proceeding analogously as described in Example 11, Step 5-8. MS (ES, m/z): [M+1]⁺=511.3.

Example 21 and 22

Synthesis of (6aS,8S)-4-((5-((3S,4S)-4-amino-3-methyl-2-oxa-8-azaspiro[4.5]decan-8-yl)-6-(hydroxymethyl)pyrazin-2-yl)thio)-8-methyl-6a,7,8,9-tetrahydro-6H-pyrido[3,2-b]pyrrolo[1,2-d][1,4]oxazin-8-ol and (6aS,8R)-4-((5-((3S,4S)-4-amino-3-methyl-2-oxa-8-azaspiro[4.5]decan-8-yl)-6-(hydroxymethyl)pyrazin-2-yl)thio)-8-methyl-6a,7,8,9-tetrahydro-6H-pyrido[3,2-b]pyrrolo[1,2-d][1,4]oxazin-8-ol

21

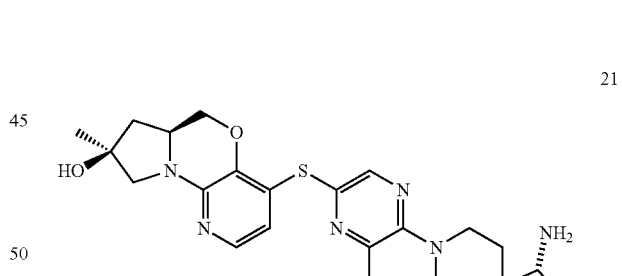

22

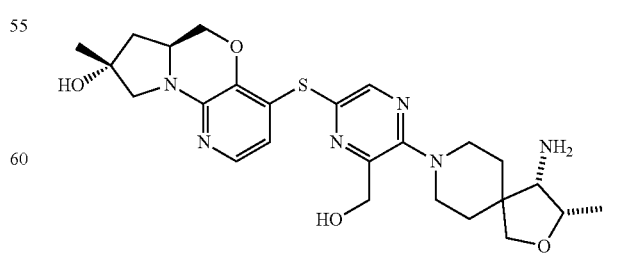

stereochemistry of the tertiary alcohol arbitrarily assigned in 21 and 22

Step 1: (S)-4-iodo-6a,7-dihydro-6H-pyrido[3,2-b]pyrrolo[1,2-d][1,4]oxazin-8(9H)-one

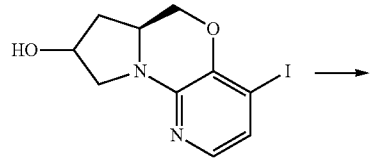

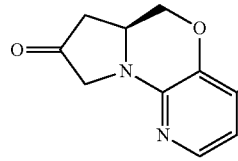

To a stirred solution of oxalyl chloride (209.47 mg, 1.650 mmol, 1.5 equiv) in DCM (1.4 mL) was added DMSO (257.89 mg, 3.301 mmol, 3.0 equiv) in DCM (0.2 mL) dropwise at −78° C. under nitrogen atmosphere and stirred at that temperature for 30 min. To the above solution was added a solution of (6aS)-4-iodo-6a,7,8,9-tetrahydro-6H-pyrido[3,2-b]pyrrolo[1,2-d][1,4]oxazin-8-ol (350.00 mg, 1.100 mmol, 1.00 equiv) in DCM (2.0 mL) at −78° C. After stirring at −78° C. for 30 min, DIEA (121.88 mg, 0.943 mmol, 6.0 equiv) was added dropwise at −78° C. The resulting mixture was stirred for additional 30 min at −78° C., and then warmed to room temperature over 30 min. After stirring at rt for 10 min, the reaction mixture was cooled rt 5° C. and then quenched by addition of sat. NH$_4$Cl aq. solution at 5° C. The resulting mixture was extracted with EtOAc and the combined organic layers were washed with brine, dried over anhydrous Na$_2$SO$_4$ and concentrated to afford the title compound (250 mg, 71.8%).

Step 2: 2-ethylhexyl 3-(((S)-8-oxo-6a,7,8,9-tetra-hydro-6H-pyrido[3,2-b]pyrrolo[1,2-d][1,4]-oxazin-4-yl)thio)propanoate

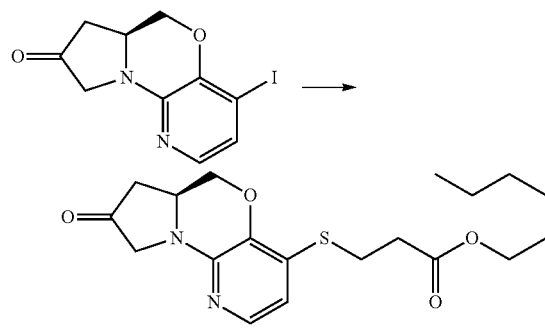

A solution of (S)-4-iodo-6a,7-dihydro-6H-pyrido[3,2-b]pyrrolo[1,2-d][1,4]oxazin-8(9H)-one (220.00 mg, 0.696 mmol, 1.00 equiv), 2-ethylhexyl 3-sulfanylpropanoate (182.37 mg, 0.835 mmol, 1.20 equiv), Pd$_2$(dba)$_3$ (63.73 mg, 0.070 mmol, 0.10 equiv), XantPhos (40.27 mg, 0.070 mmol, 0.10 equiv) and DIEA (269.85 mg, 2.088 mmol, 3.00 equiv) in dioxane (4.40 mL, 49.937 mmol, 74.62 equiv) was stirred for 1 h at 100° C. under nitrogen atmosphere. The resulting mixture was concentrated under vacuum and the residue was purified by silica gel column chromatography, eluted with EtOAc/PE (0-50%), to afford the title compound (280 mg, 98.96%).

Step 3: 2-ethylhexyl 3-(((6aS)-8-hydroxy-8-methyl-6a,7,8,9-tetrahydro-6H-pyrido[3,2-b]pyrrolo[1,2-d][1,4]oxazin-4-yl)thio)propanoate

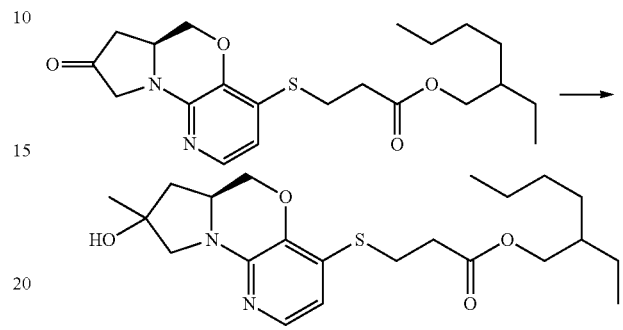

To a stirred solution of 2-ethylhexyl 3-(((S)-8-oxo-6a,7,8,9-tetrahydro-6H-pyrido[3,2-b]pyrrolo[1,2-d][1,4]oxazin-4-yl)thio)propanoate (160 mg, 0.394 mmol, 1.00 equiv) in THF (1.60 mL, 19.749 mmol, 50.18 equiv) was added bromo(methyl)magnesium (0.24 mL, 0.473 mmol, 1.20 equiv) dropwise at 5° C. under nitrogen atmosphere and the resulting mixture was stirred at 5° C. for 1 h. The reaction was quenched by addition of sat. NH$_4$Cl aq. solution at 5° C. and extracted with EtOAc. The combined organic layers were washed with brine, dried over anhydrous Na$_2$SO$_4$ and concentrated. The residue was purified by silica gel column chromatography, eluted with EtOAc/PE (0-100%), to afford the title compound (90 mg, 54.1%).

Step 4: (6aS,8S)-4-((5-((3S,4S)-4-amino-3-methyl-2-oxa-8-azaspiro[4.5]decan-8-yl)-6-(hydroxymethyl)pyrazin-2-yl)thio)-8-methyl-6a,7,8,9-tetrahydro-6H-pyrido[3,2-b]pyrrolo[1,2-d][1,4]oxazin-8-ol and (6aS,8R)-4-((5-((3S,4S)-4-amino-3-methyl-2-oxa-8-azaspiro[4.5]decan-8-yl)-6-(hydroxymethyl)pyrazin-2-yl)thio)-8-methyl-6a,7,8,9-tetrahydro-6H-pyrido[3,2-b]pyrrolo[1,2-d][1,4]oxazin-8-ol

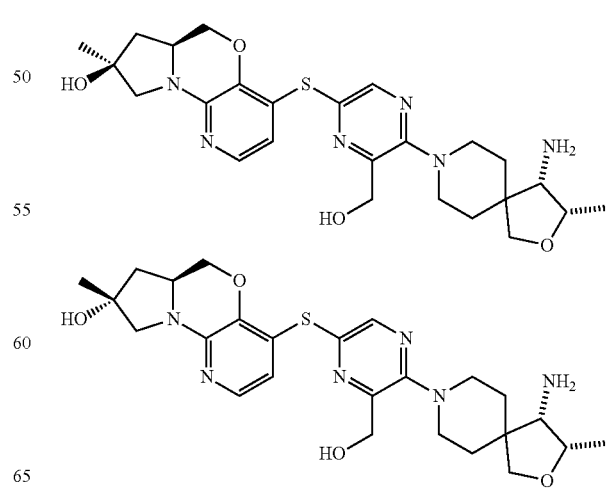

The title compounds were synthesized from 2-ethylhexyl 3-(((6aS)-8-hydroxy-8-methyl-6a,7,8,9-tetrahydro-6H-pyrido[3,2-b]pyrrolo[1,2-d][1,4]oxazin-4-yl)thio)propanoate by proceeding analogously as described in Example 11, Step 6-8. MS (ES, m/z): [M+1]⁺=515.3.

Example 23 and 24

Synthesis of (3-((3S,4S)-4-amino-3-methyl-2-oxa-8-azaspiro[4.5]decan-8-yl)-6-(((R)-6a,7,9,10-tetrahydro-6H-[1,4]oxazino[4,3-d]pyrido[3,2-b][1,4]oxazin-4-yl)thio)pyrazin-2-yl)methanol and (3-((3S,4S)-4-amino-3-methyl-2-oxa-8-azaspiro[4.5]decan-8-yl)-6-(((S)-6a,7,9,10-tetrahydro-6H-[1,4]oxazino[4,3-d]pyrido[3,2-b][1,4]oxazin-4-yl)thio)pyrazin-2-yl)methanol

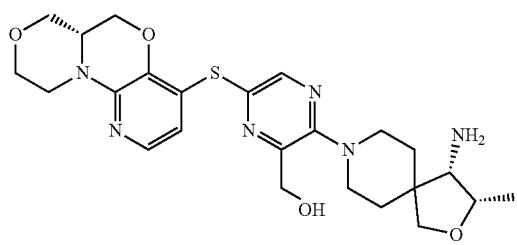

23

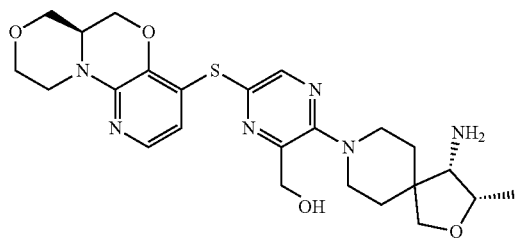

24 stereochemistry arbitrarily assigned to cpd 23 and 24

The title compounds were synthesized by proceeding analogously as described in Example 14, Steps 2-8 using tert-butyl 3-(hydroxymethyl)morpholine-4-carboxylate in Step 2. MS (ES, m/z): [M+1]⁺=501.2.

Example 25

Synthesis of (3-((3S,4S)-4-amino-3-methyl-2-oxa-8-azaspiro[4.5]decan-8-yl)-6-(((6aR,8R)-8-methoxy-6a,7,8,9-tetrahydro-6H-pyrido[3,2-b]pyrrolo[1,2-d][1,4]oxazin-4-yl)thio)pyrazin-2-yl)methanol

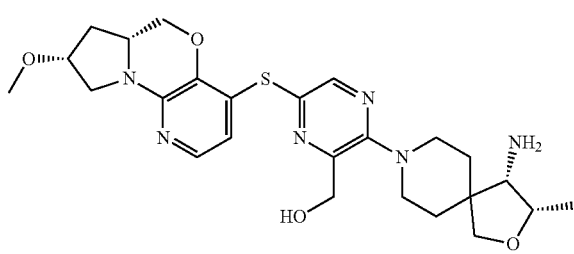

The title compound was synthesized by proceeding analogously as described in Example 14, Step 2-8 using 1-tert-butyl 2-methyl (2R,4R)-4-methoxy-pyrrolidine-1,2-dicarboxylate in Step 2. MS (ES, m/z): [M+1]⁺=515.3.

Example 26

Synthesis of [3-[(3S,4S)-4-amino-3-methyl-2-oxa-8-azaspiro[4.5]decan-8-yl]-6-[[(4S,6R)-4-methoxy-8-oxa-2,13-diazatricyclo[7.4.0.0^[2,6]]trideca-1(13),9,11-trien-10-yl]sulfanyl]pyrazin-2-yl]methanol

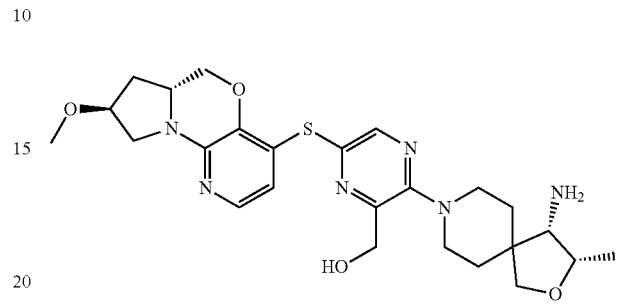

The title compound was synthesized by proceeding analogously as described in Example 33 step 2-8 using tert-butyl (2R,4S)-2-(hydroxymethyl)-4-methoxypyrrolidine-1-carboxylate in Step 2. MS (ES, m/z): [M+1]⁺=515.2.

Example 27

Synthesis of (3-((3S,4S)-4-amino-3-methyl-2-oxa-8-azaspiro[4.5]decan-8-yl)-6-(((6aS,8S)-8-(((S)-tetrahydrofuran-3-yl)oxy)-6a,7,8,9-tetrahydro-6H-pyrido[3,2-b]pyrrolo[1,2-d][1,4]oxazin-4-yl)thio)pyrazin-2-yl)methanol

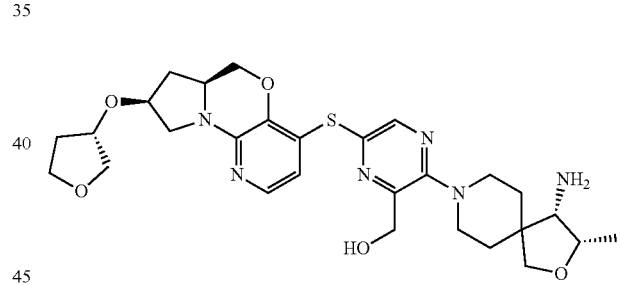

Step 1: (6aS,8S)-4-iodo-8-(((S)-tetrahydrofuran-3-yl)oxy)-6a,7,8,9-tetrahydro-6H-pyrido[3,2-b]pyrrolo[1,2-d][1,4]oxazine

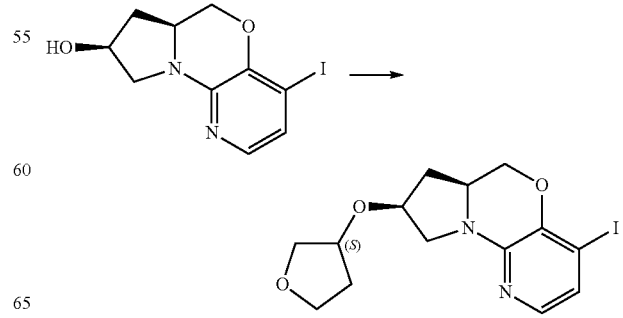

To a stirred solution of (3R)-oxolan-3-yl 4-methylbenzenesulfonate (457 mg, 1.886 mmol, 3 equiv) and (6aS,8S)-4-iodo-6a,7,8,9-tetrahydro-6H-pyrido[3,2-b]pyrrolo[1,2-d][1,4]oxazin-8-ol (200 mg, 0.629 mmol, 1.00 equiv) in DMF (2.00 mL) was added NaH (88 mg, 2.200 mmol, 3.5 equiv, 60%) in portions at 0° C. under nitrogen atmosphere and the resulting mixture was stirred overnight at room temperature under nitrogen atmosphere. After cooling at 0° C., the reaction was quenched with water and the resulting mixture was diluted with water and extracted with EtOAc. The combined organic layers were washed with water and brine, dried over anhydrous Na$_2$SO$_4$ and concentrated. The residue was purified by Prep-TLC (EtOAc 100%) to afford the title compound (70 mg, 28.68%).

Step 2: (3-((3S,4S)-4-amino-3-methyl-2-oxa-8-azaspiro[4.5]decan-8-yl)-6-((((6aS,8S)-8-(((S)-tetrahydrofuran-3-yl)oxy)-6a,7,8,9-tetrahydro-6H-pyrido[3,2-b]pyrrolo[1,2-d][1,4]oxazin-4-yl)thio)pyrazin-2-yl)methanol

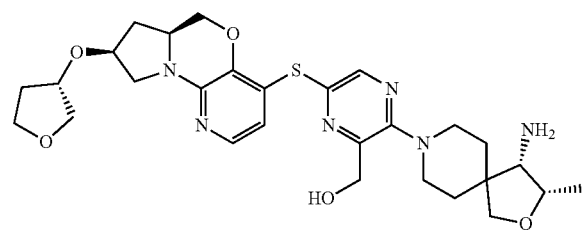 [SMILES: C[C@@H]1OCC2(CCN(c3ncc(Sc4ccnc5c4OC[C@@H]4C[C@H](O[C@H]6CCOC6)CN54)nc3CO)CC2)[C@@H]1N]

The title compound was synthesized from (6aS,8S)-4-iodo-8-(((S)-tetrahydrofuran-3-yl)oxy)-6a,7,8,9-tetrahydro-6H-pyrido[3,2-b]pyrrolo[1,2-d][1,4]oxazine by proceeding analogously as described in Example 14, Steps 7-8. MS (ES, m/z): [M+1]$^+$=571.3.

Example 28

Synthesis of (3-((3S,4S)-4-amino-3-methyl-2-oxa-8-azaspiro[4.5]decan-8-yl)-6-((((6aS,8S)-8-(((R)-tetrahydrofuran-3-yl)oxy)-6a,7,8,9-tetrahydro-6H-pyrido[3,2-b]pyrrolo[1,2-d][1,4]oxazin-4-yl)thio)pyrazin-2-yl)methanol

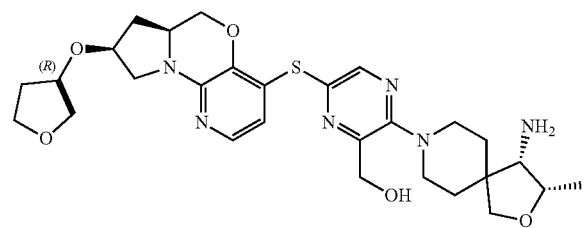

The title compound was synthesized from (3S)-oxolan-3-yl 4-methylbenzenesulfonate by proceeding analogously as described in Example 27. MS (ES, m/z): [M+1]$^+$=571.3.

Example 29

Synthesis of (6aS,8S)-4-((5-((3S,4S)-4-amino-3-methyl-2-oxa-8-azaspiro[4.5]decan-8-yl)-6-(hydroxymethyl)pyrazin-2-yl)thio)-6a,7,8,9-tetrahydro-6H-pyrido[3,2-b]pyrrolo[1,2-d][1,4]oxazine-8-carbonitrile

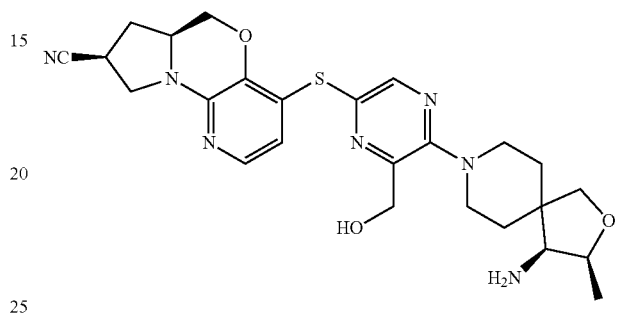

Step 1: (6aS,8R)-4-iodo-6a,7,8,9-tetrahydro-6H-pyrido[3,2-b]pyrrolo[1,2-d][1,4]oxazin-8-yl methanesulfonate

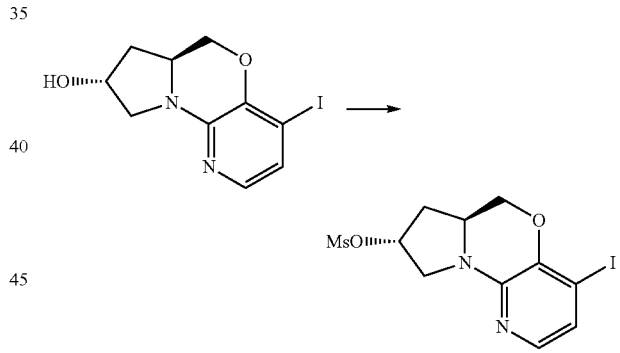

To a stirred solution of (6aS,8R)-4-iodo-6a,7,8,9-tetrahydro-6H-pyrido[3,2-b]pyrrolo[1,2-d][1,4]oxazin-8-ol (400.00 mg, 1.257 mmol, 1.00 equiv) in DCM (6.00 mL) were added TEA (190.86 mg, 1.886 mmol, 1.50 equiv) and MsCl (172.85 mg, 1.509 mmol, 1.20 equiv) at room temperature. After stirring for 16 h at room temperature, the reaction mixture was cooled at 0° C. and quenched with water. The resulting mixture was extracted with EtOAc and the combined organic layers were washed with brine, dried over anhydrous Na$_2$SO$_4$ and concentrated. The residue was purified by silica gel column chromatography, eluted with EtOAc/PE (0-50%) to afford the title compound (450 mg, 90.3%).

Step 2: (6aS,8S)-4-iodo-6a,7,8,9-tetrahydro-6H-pyrido[3,2-b]pyrrolo[1,2-d][1,4]oxazine-8-carbonitrile

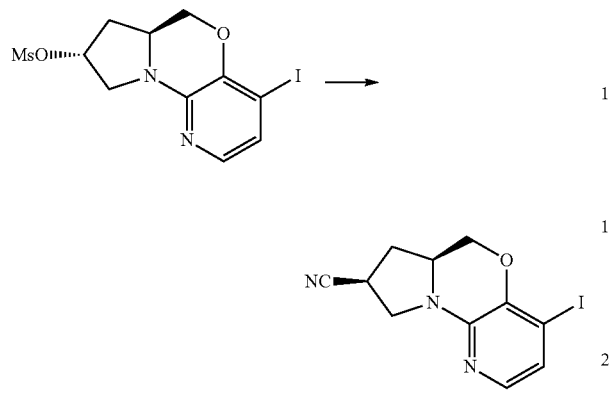

To a stirred solution of (6aS,8R)-4-iodo-6a,7,8,9-tetrahydro-6H-pyrido[3,2-b]pyrrolo[1,2-d][1,4]oxazin-8-yl methanesulfonate (300.00 mg, 0.757 mmol, 1.00 equiv) in DMF (5.00 mL) was added NaCN (55.66 mg, 1.136 mmol, 1.50 equiv) at room temperature. After stirring at 75° C. for 16 h, the reaction mixture was cooled at room temperature and quenched with water. The mixture was then extracted with EtOAc and the combined organic layers were washed with brine, dried over anhydrous Na$_2$SO$_4$ and concentrated. The residue was purified by silica gel column chromatography, eluted with EtOAc/PE (0-50%), to afford the title compound (140 mg, 56.5%).

Step 3: (6aS,8S)-4-((5-((3S,4S)-4-amino-3-methyl-2-oxa-8-azaspiro[4.5]decan-8-yl)-6-(hydroxymethyl)pyrazin-2-yl)thio)-6a,7,8,9-tetrahydro-6H-pyrido[3,2-b]pyrrolo[1,2-d][1,4]oxazine-8-carbonitrile

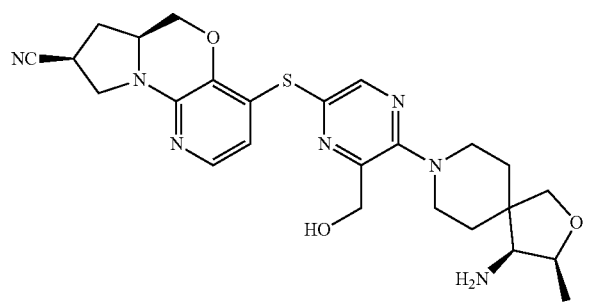 [SMILES: C[C@@H]1OCC2(CCN(c3ncc(Sc4ccnc5c4OC[C@@H]4C[C@H](C#N)CN54)nc3CO)CC2)[C@@H]1N]

The compound was synthesized from (6aS,8S)-4-iodo-6a,7,8,9-tetrahydro-6H-pyrido[3,2-b]pyrrolo[1,2-d][1,4]oxazine-8-carbonitrile by proceeding analogously as described in Example 14, Steps 7-8. [M+1]$^+$=510.2.

Example 30

Synthesis of (3-((3S,4S)-4-amino-3-methyl-2-oxa-8-azaspiro[4.5]decan-8-yl)-6-((((6aS,8S)-8-(methylsulfonyl)-6a,7,8,9-tetrahydro-6H-pyrido[3,2-b]pyrrolo[1,2-d][1,4]oxazin-4-yl)thio)pyrazin-2-yl)methanol

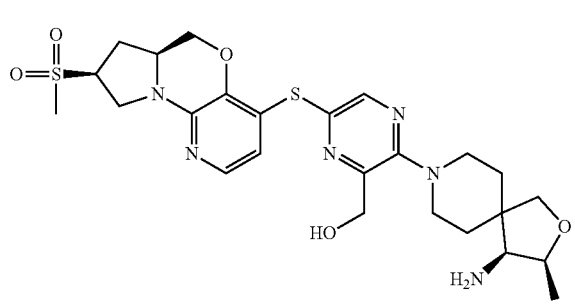 [SMILES: C[C@@H]1OCC2(CCN(c3ncc(Sc4ccnc5c4OC[C@@H]4C[C@H](S(C)(=O)=O)CN54)nc3CO)CC2)[C@@H]1N]

Step 1: 1-tert-butyl 2-methyl (2S,4R)-4-(methanesulfonyloxy)pyrrolidine-1,2-dicarboxylate

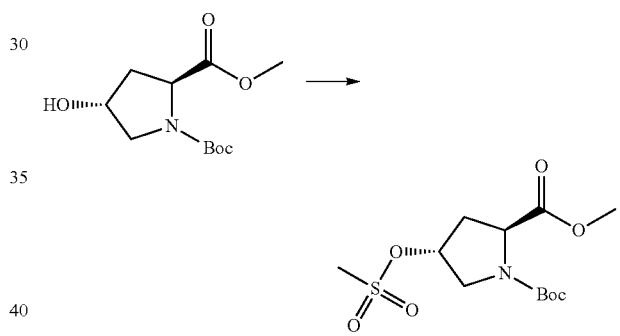

To a stirred solution of 1-tert-butyl 2-methyl (2S,4R)-4-hydroxypyrrolidine-1,2-dicarboxylate (9 g, 36.7 mmol, 1.0 equiv) and TEA (7.43 g, 73 mmol, 2.0 equiv) in DCM (100 mL) was added MsCl (5 g, 44 mmol, 1.2 equiv) dropwise at 0° C. and the resulting mixture was stirred for 1 h at 0° C. The reaction was quenched with water and extracted with DCM. The combined organic layers were washed with water and brine, dried over anhydrous Na$_2$SO$_4$ and concentrated. The residue was purified by silica gel column chromatography, eluted with EtOAc/PE (0-50%), to afford the title compound (10.5 g, 88.49%).

Step 2: 1-(tert-butyl) 2-methyl (2R,4R)-4-methoxypyrrolidine-1,2-dicarboxylate

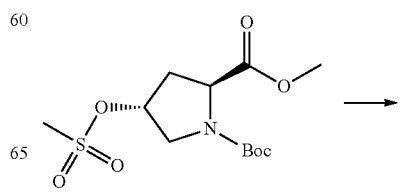

-continued

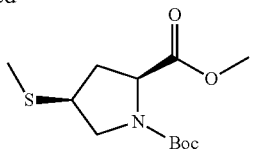

A solution of 1-tert-butyl 2-methyl (2S,4R)-4-(methanesulfonyloxy)pyrrolidine-1,2-dicarboxylate (4.30 g, 13.298 mmol, 1.00 equiv) in dry DMF (20.00 mL) was added NaSCH$_3$ (1.07 g, 15.293 mmol, 1.15 equiv) at 30° C. After stirring overnight at rt, the reaction mixture was poured into water and extracted with EtOAc. The combined organic layers were washed with water and brine, dried over Na$_2$SO$_4$ and concentrated. The residue was purified by silica gel column chromatography, eluted with PE/EA (1/1) to afford the title compound (4 g, 49.2%).

Step 3: Tert-Butyl (2S,4S)-2-(hydroxymethyl)-4-(methylthio)pyrrolidine-1-carboxylate

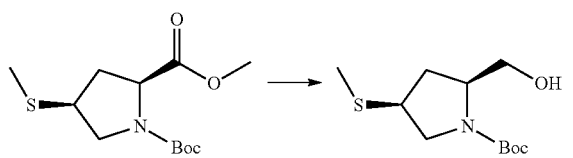

To a stirred mixture of 1-tert-butyl 2-methyl (2S,4S)-4-(methylsulfanyl)pyrrolidine-1,2-dicarboxylate (3.70 mg, 0.013 mmol, 1.0 equiv) in THF (37.0 mL) were added LiAlH$_4$ (0.76 mg, 0.020 mmol, 1.5 equiv) in portion at 0° C. After stirring at room temperature for 2 h, the reaction mixture was quenched with Na$_2$SO$_4$.10H$_2$O at room temperature. The resulting mixture was filtered and the filtrate was concentrated under reduced pressure to give the title compound (2.6 g, 78.2%).

Step 4: Tert-Butyl (2S,4S)-2-(hydroxymethyl)-4-(methylsulfonyl)pyrrolidine-1-carboxylate

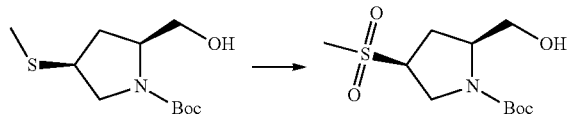 [SMILES: CS[C@H]1C[C@@H](CO)N(C(=O)OC(C)(C)C)C1 ; CC(C)(C)OC(=O)N1C[C@@H](S(C)(=O)=O)C[C@H]1CO]

To a stirred solution of tert-butyl (2S,4S)-2-(hydroxymethyl)-4-(methylsulfanyl)-pyrrolidine-1-carboxylate (3.70 g, 14.959 mmol, 1.00 equiv) in DCM (40.00 mL) at room temperature were added m-CPBA (12.91 g, 74.793 mmol, 5.00 equiv) in portions over 5 h. The resulting mixture was diluted with DCM and washed with sat. aq.NaHCO$_3$ solution and brine, dried over anhydrous Na$_2$SO$_4$ and concentrated. The residue was purified by silica gel column chromatography, eluted with DCM/MeOH (20/1), to afford the title compound (1 g, 23.9).

Step 5: (3-((3S,4S)-4-amino-3-methyl-2-oxa-8-azaspiro[4.5]decan-8-yl)-6-(((6aS,8S)-8-(methylsulfonyl)-6a,7,8,9-tetrahydro-6H-pyrido[3,2-b]pyrrolo[1,2-d][1,4]oxazin-4-yl)thio)pyrazin-2-yl)methanol

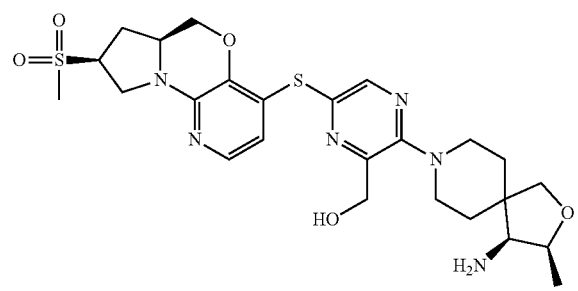 [SMILES: C[C@@H]1OCC2(CCN(c3ncc(Sc4ccnc5c4OC[C@@H]4C[C@H](S(C)(=O)=O)CN54)nc3CO)CC2)[C@@H]1N]

The title compound was synthesized tert-butyl (2S,4S)-2-(hydroxymethyl)-4-(methylsulfonyl)pyrrolidine-1-carboxylate by the method described in Example 14, Steps 2-8. MS (ES, m/z): [M+1]$^+$=563.3.

Example 31

Synthesis of (6aS,8S)-4-((5-((3S,4S)-4-amino-3-methyl-2-oxa-8-azaspiro[4.5]decan-8-yl)-6-(hydroxymethyl)pyrazin-2-yl)thio)-6a,7,8,9-tetrahydro-6H-pyrido[3,2-b]pyrrolo[1,2-d][1,4]oxazin-8-yl carbamate

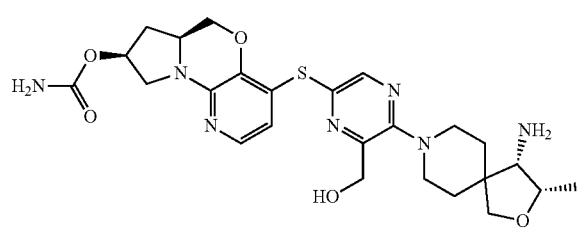 [SMILES: C[C@@H]1OCC2(CCN(c3ncc(Sc4ccnc5c4OC[C@@H]4C[C@H](OC(N)=O)CN54)nc3CO)CC2)[C@@H]1N]

Step 1: (6aS,8S)-4-iodo-6a,7,8,9-tetrahydro-6H-pyrido[3,2-b]pyrrolo[1,2-d][1,4]oxazin-8-yl carbamate

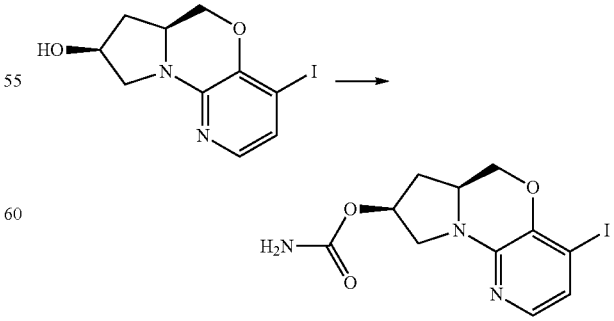

To a stirred solution of (6aS,8S)-4-iodo-6a,7,8,9-tetrahydro-6H-pyrido[3,2-b]pyrrolo[1,2-d][1,4]oxazin-8-ol (150.00 mg, 0.472 mmol, 1.0 equiv) in DCM (1.80 mL) was added trichloroethanecarbonyl isocyanate (222.08 mg, 1.179 mmol, 2.5 equiv) dropwise at 5° C. and the resulting mixture was stirred at that temperature for about 30 min. To the above solution, K$_2$CO$_3$ (129.88 mg, 0.940 mmol, 2.00 equiv) and MeOH (1.80 mL) were then added at room temperature and the resulting mixture was stirred for additional 6 h at room temperature. The mixture was diluted with water and extracted with EtOAc. The combined organic layers were washed with brine, dried over anhydrous Na$_2$SO$_4$ and concentrated. The residue was purified by silica gel column chromatography, eluted with EtOAc/PE (0-100%) to afford the title compound (100 mg, 58.9%).

Step 2: (6aS,8S)-4-((5-((3S,4S)-4-amino-3-methyl-2-oxa-8-azaspiro[4.5]decan-8-yl)-6-(hydroxymethyl) pyrazin-2-yl)thio)-6a,7,8,9-tetrahydro-6H-pyrido[3,2-b]pyrrolo[1,2-d][1,4]oxazin-8-yl carbamate

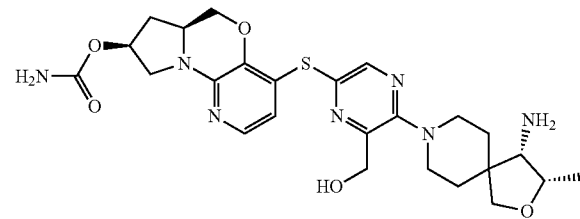 [SMILES: C[C@@H]1OCC2(CCN(c3ncc(Sc4ccnc5c4OC[C@@H]4C[C@H](OC(N)=O)CN54)nc3CO)CC2)[C@@H]1N]

The title compound was synthesized from tert-butyl (2S,4S)-2-(hydroxymethyl)-4-(methylsulfonyl)pyrrolidine-1-carboxylate by proceeding analogously as described in Example 14, Steps 7-8. MS (ES, m/z): [M+1]$^+$=544.3.

Example 32

Synthesis of (6aS,8R)-4-((5-((3S,4S)-4-amino-3-methyl-2-oxa-8-azaspiro[4.5]decan-8-yl)-6-(hydroxymethyl)pyrazin-2-yl)thio)-6a,7,8,9-tetrahydro-6H-pyrido[3,2-b]pyrrolo[1,2-d][1,4]oxazin-8-yl carbamate

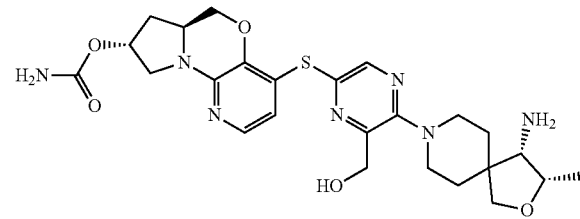 [SMILES: C[C@@H]1OCC2(CCN(c3ncc(Sc4ccnc5c4OC[C@@H]4C[C@@H](OC(N)=O)CN54)nc3CO)CC2)[C@@H]1N]

The title compound was synthesized from ((6aS,8R)-4-iodo-6a,7,8,9-tetrahydro-6H-pyrido[3,2-b]pyrrolo[1,2-d][1,4]oxazin-8-ol by as described in example 31. MS (ES, m/z): [M+1]$^+$=544.2.

Example 33

Synthesis of (6-((((6aS,8S)-8-(1H-pyrazol-1-yl)-6a,7,8,9-tetrahydro-6H-pyrido[3,2-b]-pyrrolo[1,2-d][1,4] oxazin-4-yl)thio)-3-((3S,4S)-4-amino-3-methyl-2-oxa-8-azaspiro[4.5]decan-8-yl)pyrazin-2-yl) methanol

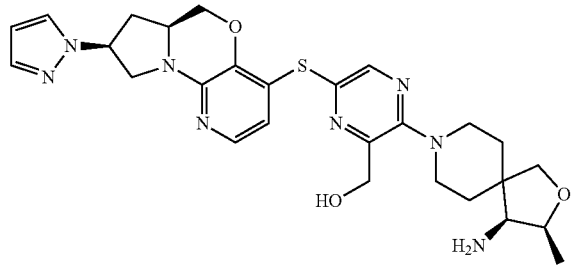 [SMILES: C[C@@H]1OCC2(CCN(c3ncc(Sc4ccnc5c4OC[C@@H]4C[C@H](n6cccn6)CN54)nc3CO)CC2)[C@@H]1N]

Step 1: (6aS,8S)-4-iodo-8-(1H-pyrazol-1-yl)-6a,7,8,9-tetrahydro-6H-pyrido[3,2-b]pyrrolo[1,2-d][1,4] oxazine

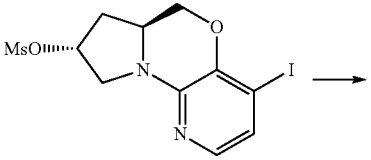

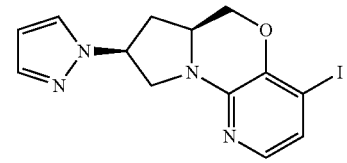

To a stirred solution of pyrazole (17.18 mg, 0.252 mmol, 1.0 equiv) in DMF (0.75 mL) was added NaH (20.19 mg, 0.505 mmol, 2.0 equiv, 60%) in portions at 5° C. and the resulting mixture was stirred at 5° C. for 1 h. To the above mixture was added (6aS,8R)-4-iodo-6a,7,8,9-tetrahydro-6H-pyrido[3,2-b]pyrrolo[1,2-d][1,4]oxazin-8-yl methanesulfonate (100.00 mg, 0.252 mmol, 1.00 equiv) at room temperature and the resulting mixture was stirred at 50° C. After cooling to 0° C., the reaction was quenched by addition of water and then extracted with EtOAc. The combined organic layers were washed with water, brine, dried over anhydrous Na$_2$SO$_4$ and concentrated. The residue was purified by silica gel column chromatography, eluted with EtOAc/PE (0-100%), to afford the title compound (60 mg, 64.5%). MS (ES, m/z): [M+1]$^+$=369.0.

Step 2: (6-((((6aS,8S)-8-(1H-pyrazol-1-yl)-6a,7,8,9-tetrahydro-6H-pyrido[3,2-b]pyrrolo[1,2-d][1,4]oxazin-4-yl)thio)-3-((3S,4S)-4-amino-3-methyl-2-oxa-8-azaspiro[4.5]decan-8-yl)pyrazin-2-yl)methanol

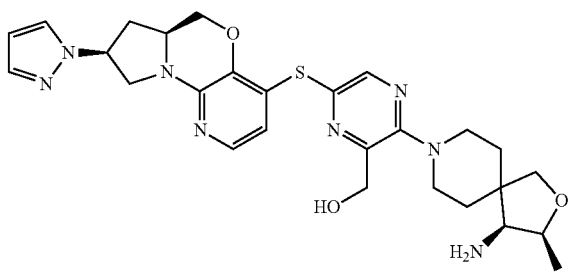 [SMILES: C[C@@H]1OCC2(CCN(c3ncc(Sc4ccnc5c4OC[C@@H]4C[C@H](n6cccn6)CN54)nc3CO)CC2)[C@@H]1N]

The title compound was synthesized from (6aS,8S)-4-iodo-8-(1H-pyrazol-1-yl)-6a,7,8,9-tetrahydro-6H-pyrido[3,2-b]pyrrolo[1,2-d][1,4]oxazine by proceeding analogously described in Example 14, Steps 7-8.

Example 34

Synthesis of (6-((((6aS,8R)-8-(1H-pyrazol-1-yl)-6a,7,8,9-tetrahydro-6H-pyrido[3,2-b]-pyrrolo[1,2-d][1,4]oxazin-4-yl)thio)-3-((3S,4S)-4-amino-3-methyl-2-oxa-8-azaspiro[4.5]decan-8-yl)pyrazin-2-yl)methanol

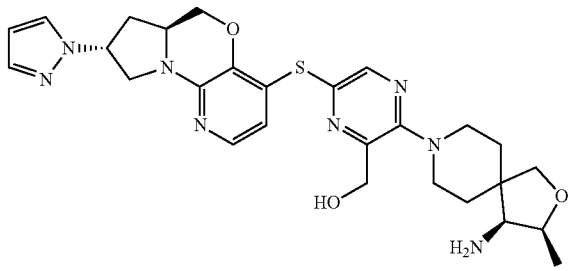 [SMILES: C[C@@H]1OCC2(CCN(c3ncc(Sc4ccnc5c4OC[C@@H]4C[C@@H](n6cccn6)CN54)nc3CO)CC2)[C@@H]1N]

The title compound was synthesized from (6aS,8S)-4-iodo-6a,7,8,9-tetrahydro-6H-pyrido[3,2-b]pyrrolo[1,2-d][1,4]oxazin-8-yl methanesulfonate by the method described in Example 14, Steps 7-8. MS (ES, m/z): [M+1]⁺=551.3.

Example 35

Synthesis of (6-((2-amino-3-chloropyridin-4-yl)thio)-3-(4-amino-8-azadispiro-[2.1.55.23]dodecan-8-yl)pyrazin-2-yl)methanol

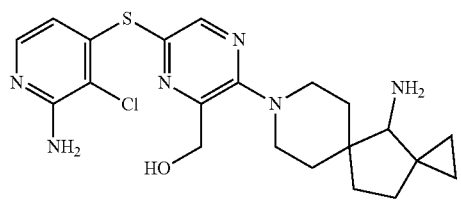 [SMILES: Nc1nccc(Sc2cnc(N3CCC4(CC3)CCC3(CC3)C4N)c(CO)n2)c1Cl]

Step 1: Tert-Butyl 4-oxo-8-azadispiro[2.1.55.23]dodecane-8-carboxylate

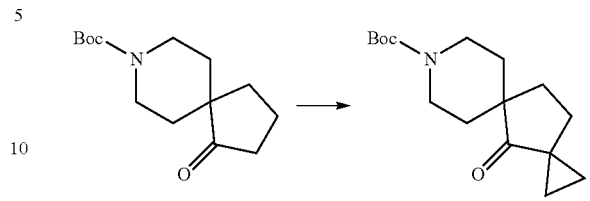

To a stirred solution of tert-butyl 1-oxo-8-azaspiro[4.5]decane-8-carboxylate (600.00 mg, 2.368 mmol, 1.0 equiv) in t-BuOH (0.50 mL, 5.262 mmol, 109.87 equiv) was added t-BuOK (531.51 mg, 4.737 mmol, 2.0 equiv) at 25° C. under nitrogen and the resulting mixture was stirred for 15 min at room temperature. To the mixture was added (2-chloroethyl)dimethyl-sulfanium iodide (598.10 mg, 2.368 mmol, 1.00 equiv) and the resulting mixture was stirred for additional 16 h at room temperature. After cooling to rt, the reaction mixture was quenched with water at 0° C. and extracted with EtOAc. The combined organic layers were washed with brine, dried over anhydrous Na₂SO₄ and concentrated. The residue was purified by silica gel column chromatography, eluted with EtOAc/PE (0-50%), to afford the title compound (350 mg, 52.9%).

Step 2: Tert-Butyl 4-amino-8-azadispiro[2.1.55.23]dodecane-8-carboxylate

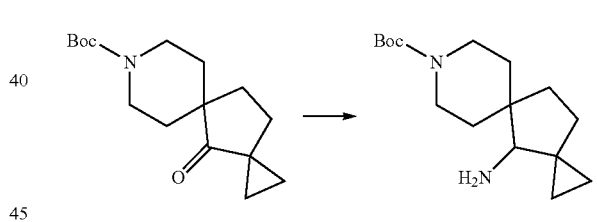

To a solution of tert-butyl 4-oxo-8-azadispiro[2.1.55.23]dodecane-8-carboxylate (200.0 mg, 0.716 mmol, 1.0 equiv) in MeOH (5 mL) was added NH₄OAc (1.10 g, 14.3 mmol, 20.0 equiv) at room temperature under nitrogen atmosphere and the resulting mixture was stirred at 65° C. for 2 h. To the mixture was added NaBH₃CN (0.90 g, 14.317 mmol, 20.00 equiv) and the resulting mixture was stirred for additional 24 h at 65° C. Another portion of NH₄OAc (1.10 g, 14.317 mmol, 20.00 equiv) and NaBH₃CN (0.90 g, 14.317 mmol, 20.00 equiv) were added at room temperature and the resulting mixture was stirred for additional 24 h at 65° C. After cooling to 0° C., the reaction mixture was quenched with water and extracted with CH₂Cl₂. The combined organic layers were washed with water, brine, dried over anhydrous Na₂SO₄ and concentrated. The residue was purified by silica gel column chromatography, eluted with MeOH/CH₂Cl₂ (0-20%) to afford the title compound (30 mg, 14.9%).

Step 3: 8-azadispiro[2.1.55.23]dodecan-4-amine

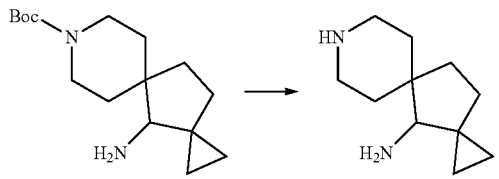 [SMILES: CC(C)(C)OC(=O)N1CCC2(CC1)CCC1(CC1)C2N ; NC1C2(CCNCC2)CCC12CC2]

To a stirred solution of tert-butyl 4-amino-8-azadispiro[2.1.55.23]dodecane-8-carboxylate (30.00 mg, 0.107 mmol, 1.0 equiv) in dioxane (0.50 mL, 5.9 mmol, 55.2 equiv) was added a HCl solution (4.0 M in dioxane, 0.50 mL, 2.0 mmol, 18.7 equiv) at room temperature. After stirring for 5 h at room temperature, the reaction mixture was concentrated under reduced pressure to afford the title compound (20 mg, 86.2%).

Step 4: (6-((2-amino-3-chloropyridin-4-yl)thio)-3-(4-amino-8-azadispiro[2.1.55.23]dodecan-8-yl)pyrazin-2-yl)methanol

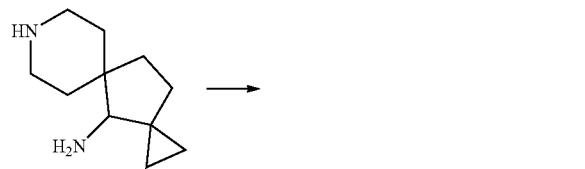

To a stirred solution of 8-azadispiro[2.1.55.23]dodecan-4-amine HCl salt (20.00 mg, 0.092 mmol, 1.0 equiv) and [6-[(2-amino-3-chloropyridin-4-yl)sulfanyl]-3-chloropyrazin-2-yl]methanol (25.18 mg, 0.083 mmol, 0.90 equiv) in ACN (0.60 mL, 11.415 mmol, 123.71 equiv) was added DIEA (59.63 mg, 0.461 mmol, 5.0 equiv) at room temperature. After stirring for 16 h at 60° C., the reaction mixture was cooled to room temperature and the crude product was purified by Prep-HPLC to afford the title compound (7.3 mg, 16.0%). [M+1]$^+$=447.1.

Example 36

Synthesis of 13-amino-10-(5-((2-amino-3-chloro-pyridin-4-yl)thio)-3-(hydroxymethyl)-pyrazin-2-yl)-1-methyl-1,10-diazadispiro[4.1.57.25]tetradecan-2-one

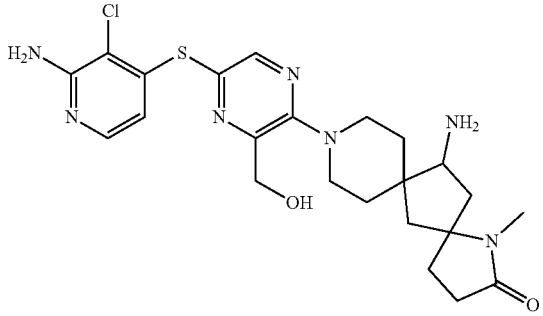 [SMILES: CN1C(=O)CCC12CC(N)C1(CCN(c3ncc(Sc4ccnc(N)c4Cl)nc3CO)CC1)C2]

Step 1: 1-benzyl 4-methyl 4-(2-methylprop-2-en-1-yl)piperidine-1,4-dicarboxylate

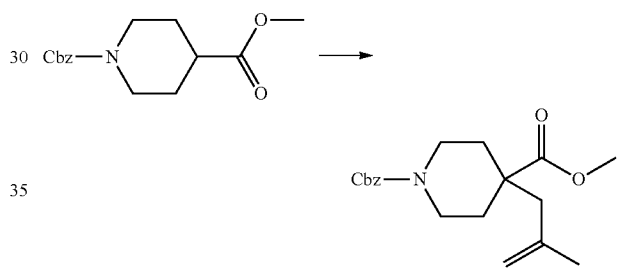

To a solution of 1-benzyl 4-methyl piperidine-1,4-dicarboxylate (2 g, 7.2 mmol, 1.0 equiv) in THF (20 mL) was added LiHMDS (1.0 M I THF, 14.4 mL, 14.4 mmol, 2.0 equiv) dropwise at −78° C. under nitrogen atmosphere and the resulting solution was stirred at −78° C. for 30 min. To the above mixture was added 3-bromo-2-methylprop-1-ene (1.4 g, 10.385 mmol, 1.44 equiv) dropwise at −78° C. and the resulting mixture was stirred for additional 1 h at this temperature. The reaction was quenched by adding sat. aq. NH$_4$Cl solution and the resulting mixture was extracted with EtOAc. The combined organic layers were washed with water and brine, dried over anhydrous Na$_2$SO$_4$ and concentrated. The residue was purified by silica gel column chromatography, eluted with EtOAc/PE (0-30%) to afford the title compound (1.6 g, 66.9%).

Step 2: 1-[(benzyloxy)carbonyl]-4-(2-methylprop-2-en-1-yl)piperidine-4-carboxylic acid

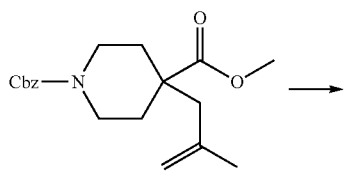

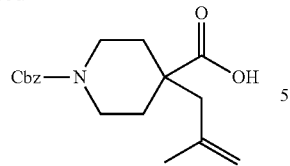

A mixture of 1-benzyl 4-methyl 4-(2-methylprop-2-en-1-yl)piperidine-1,4-dicarboxylate (5 g, 15.087 mmol, 1.00 equiv) and LiOH.H₂O (3.17 g, 75.435 mmol, 5.00 equiv) in THF (30 mL), MeOH (36 mL) and H₂O (30 mL) was stirred overnight at 60° C. The reaction mixture was then concentrated under vacuum. The residue was diluted with water and extracted with Et₂O. The aqueous layer was acidified to pH 3 by adding 1.0 M HCl aq. solution and then extracted with EtOAc. The combined organic layers were washed with water and brine, dried over anhydrous Na₂SO₄ and concentrated give the title compound (2.9 g, 60.5%).

Step 3: benzyl 3-methyl-1-oxo-8-azaspiro[4.5]dec-2-ene-8-carboxylate

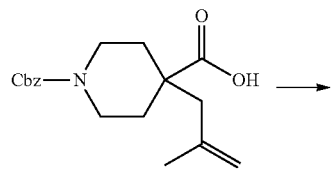

To a solution of 1-[(benzyloxy)carbonyl]-4-(2-methylprop-2-en-1-yl)piperidine-4-carboxylic acid (2.9 g, 9.14 mmol, 1.0 equiv) and DMF (0.10 mL) in DCM (30 mL) was added oxalic dichloride (1.28 g, 10.051 mmol, 1.10 equiv) dropwise at 0° C. After stirring at rt for 30 min, the resulting mixture was concentrated under reduced pressure. To the residue was added DCM (30 mL) and silver triflate (2.61 g, 10.05 mmol, 1.1 equiv). The resulting mixture was stirred for additional 1 h at this temperature and then quenched by adding Et₃N (1.02 g, 10.0 mmol, 1.1 equiv). The resulting mixture was diluted with water and extracted with EtOAc. The combined organic layers were washed with water and brine, dried over anhydrous Na₂SO₄ and concentrated. The residue was purified by silica gel column chromatography, eluted with EtOAc/PE (0-50%), to afford the title compound (1.8 g, 65.8%).

Step 4: benzyl 3-(3-methoxy-3-oxopropyl)-1-oxo-8-azaspiro[4.5]dec-2-ene-8-carboxylate

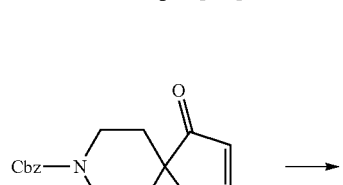

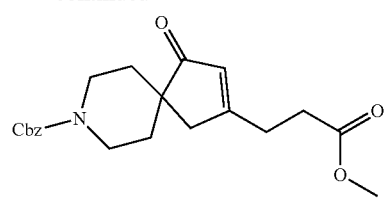

To a stirred solution of benzyl 3-methyl-1-oxo-8-azaspiro[4.5]dec-2-ene-8-carboxylate (2 g, 6.68 mmol, 1.0 equiv) in THF (20 mL) was added LiHMDS (13.36 mL, 13.3 mmol, 2.0 equiv) dropwise at −78° C. under nitrogen atmosphere and the resulting mixture was stirred for 30 min at this temperature. To the above mixture was added a solution of methyl 2-bromoacetate (2 g, 13.36 mmol, 2.0 equiv) in THF (0.3 mL) dropwise at −78° C. and the resulting mixture was stirred for additional 2 h at room temperature. The reaction was quenched by adding sat. aq. NH₄Cl solution and then extracted with EtOAc. The combined organic layers were washed with water and brine, dried over anhydrous Na₂SO₄ and concentrated. The residue was purified by silica gel column chromatography, eluted with EtOAc/PE (0-50%). The product was further purified by Prep-HPLC to afford the title compound (300 mg, 12.0%).

Step 5: benzyl 1-methyl-2,13-dioxo-1,10-diazadispiro[4.1.57.25]tetradecane-10-carboxylate

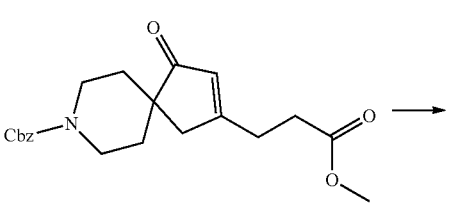

To a stirred solution of CH₃NH₂ in THF (2.0 M, 1.35 mL, 2.69 mmol, 2.0 equiv) and Tin (II) triflate (56.50 mg, 0.135 mmol, 0.10 equiv) in CH₃CN (5.00 mL) was added a solution of AlCl₃ in toluene (2.0 M, 1.38 mL, 2.75 mmol, 2.05 equiv) dropwise at 0° C. under nitrogen atmosphere and the resulting mixture was stirred for 1 h at room temperature under nitrogen atmosphere. To the above mixture was added a solution of benzyl 3-(3-methoxy-3-oxopropyl)-1-oxo-8-azaspiro[4.5]dec-2-ene-8-carboxylate (500.0 mg, 1.34 mmol, 1.0 equiv) in CH₃CN (2.5 mL) dropwise at room temperature and the resulting mixture was stirred for additional 40 h at room temperature. The reaction was quenched by adding aq. HCl solution (1.0 M) and the mixture was extracted with EtOAc. The combined organic layers were washed with water and brine, dried over anhydrous Na₂SO₄ and concentrated. The residue was purified by Prep-HPLC to afford the title compound (200 mg, 40.1%).

Step 6: benzyl 13-amino-1-methyl-2-oxo-1,10-diaz-adispiro[4.1.57.25]tetradecane-10-carboxylate

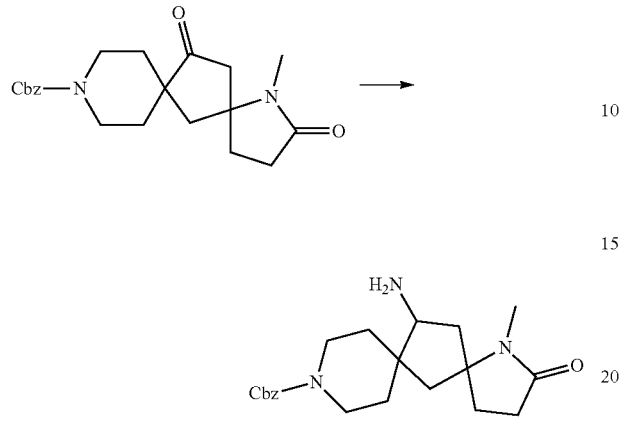

To a stirred solution of benzyl 1-methyl-2,13-dioxo-1,10-diazadispiro[4.1.57.25]-tetradecane-10-carboxylate (160 mg, 0.43 mmol, 1.0 equiv) and NH$_4$OAc (332.9 mg, 4.32 mmol, 10.0 equiv) in MeOH (2.00 mL) was added NaBH$_3$CN (54.2 mg, 0.86 mmol, 2.0 equiv) in portions at 0° C. under nitrogen atmosphere and the resulting mixture was stirred overnight at 80° C. After cooled at rt, the reaction was quenched with water and extracted with EtOAc. The combined organic layers were washed with water and brine, dried over anhydrous Na$_2$SO$_4$ and concentrated. The residue was purified by Prep-HPLC to afford the title compound (70 mg, 43.6%).

Step 7: 13-amino-1-methyl-1,10-diazadispiro[4.1.57.25]tetradecan-2-one

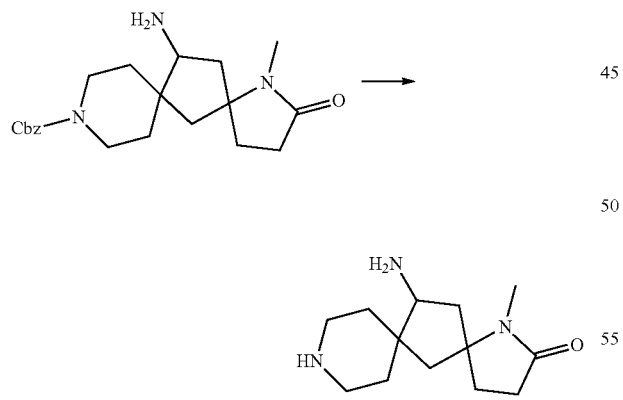

To a benzyl 13-amino-1-methyl-2-oxo-1,10-diazadispiro[4.1.57.25]tetradecane-10-carboxylate (25 mg, 0.067 mmol, 1.0 equiv) in dioxane (0.30 mL) was added HCl solution (0.05 mL, 0.494 mmol, 8.80 equiv) dropwise at 0° C. and the resulting mixture was stirred for 1 h at 100° C. The reaction mixture was then concentrated under reduced pressure and the residue was triturated with of Et$_2$O to give the title crude product (18 mg).

Step 8: 13-amino-10-(5-((2-amino-3-chloropyridin-4-yl)thio)-3-(hydroxymethyl)pyrazin-2-yl)-1-methyl-1,10-diazadispiro[4.1.57.25]tetradecan-2-one

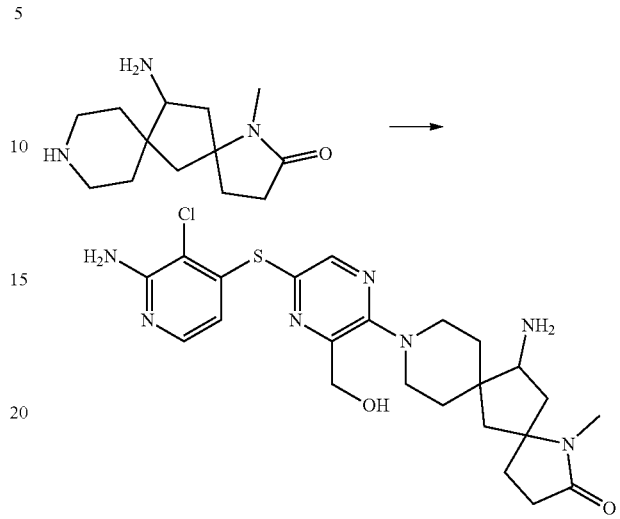

A solution of [6-[(2-amino-3-chloropyridin-4-yl)sulfanyl]-3-chloropyrazin-2-yl]methanol (20 mg, 0.066 mmol, 1.0 equiv), 13-amino-1-methyl-1,10-diazadispiro[4.1.57.25]tetradecan-2-one dihydrochloride (18 mg, 0.066 mmol, 1.0 equiv) and DIEA (43 mg, 0.33 mmol, 5 equiv) in CH$_3$CN (0.20 mL) was stirred overnight at 60° C. The reaction was diluted with water and extracted with EtOAc. The combined organic layers were washed with water and brine, dried over anhydrous Na$_2$SO$_4$ and concentrated. The crude product was purified by Prep-HPLC to afford the title compound (5.2 mg, 15.7%). MS (ES, m/z): [M+1]$^+$=504.3.

Example 37

Synthesis of (S)-(6-((2-amino-3-chloropyridin-4-yl)thio)-3-(5-amino-5,7-dihydrospiro-[cyclopenta[b]pyridine-6,4'-piperidin]-1'-yl)pyrazin-2-yl)methanol

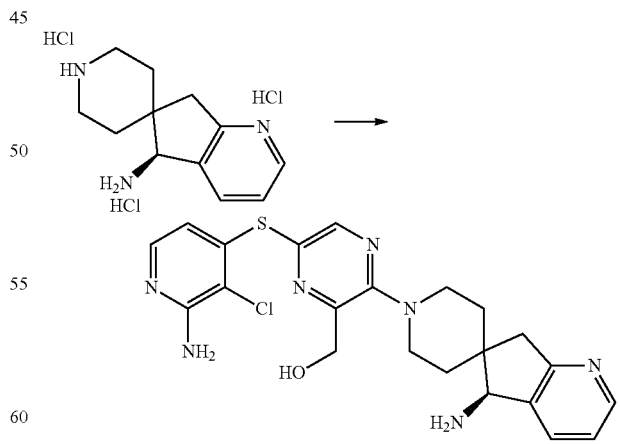

A solution of (5S)-5,7-dihydrospiro[cyclopenta[b]pyridine-6,4-piperidin]-5-amine trihydrochloride (24.00 mg, 0.077 mmol, 1.00 equiv), [6-[(2-amino-3-chloropyridin-4-yl)sulfanyl]-3-chloropyrazin-2-yl]methanol (31.61 mg, 0.104 mmol, 1.35 equiv) and DIEA (33.69 mg, 0.261 mmol, 3.40 equiv) in DMA (0.50 mL) was stirred for 4 h at 100° C. under nitrogen atmosphere. The mixture was cooled at rt and purified directly by Prep-HPLC to give the title compound (7 mg, 17.62%). MS (ES, m/z): [M+1]$^+$=470.2.

Example 38

Synthesis of (3-((3S,4S)-4-amino-3-methyl-2-oxa-8-azaspiro[4.5]decan-8-yl)-6-((2-chloro-8-methoxy-6,7,8,9-tetrahydro-5H-pyrido[3,2-b]indol-3-yl)thio)pyrazin-2-yl)methanol

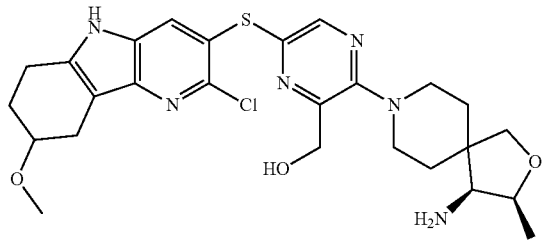 [SMILES: COC1CCc2[nH]c3cc(Sc4cnc(N5CCC6(CC5)CO[C@@H](C)[C@H]6N)c(CO)n4)c(Cl)nc3c2C1]

Step 1: 3-bromo-2-chloro-5-hydrazineylpyridine hydrochloride

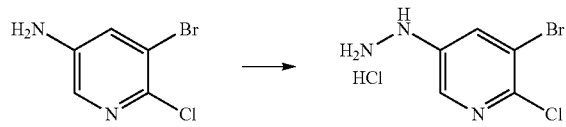

To a stirred solution of 5-bromo-6-chloropyridin-3-amine (2.00 g, 9.640 mmol, 1.00 equiv) in 10 M HCl (aq.) (20.00 mL, 200.00 mmol, 20.75 equiv) was added NaNO$_2$ (798.17 mg, 11.568 mmol, 1.20 equiv) in H$_2$O (6 mL) dropwise at −5° C. under nitrogen atmosphere. The resulting mixture was stirred for 1 h at 0° C. under nitrogen atmosphere. To the above mixture was added SnCl$_2$.2H$_2$O (8.70 g, 38.555 mmol, 4.00 equiv) in 10 M HCl (aq) (20.00 mL) dropwise over 10 min at 0° C. The resulting mixture was stirred for additional 3 h at room temperature. The precipitated solids were collected by filtration and washed with PE to afford the title compound (3 g, crude) as an off-white solid, which was used for next step without further purification.

Step 2: 3-bromo-2-chloro-8-methoxy-6,7,8,9-tetrahydro-5H-pyrido[3,2-b]indole

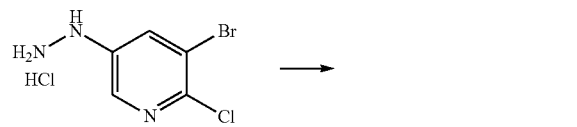

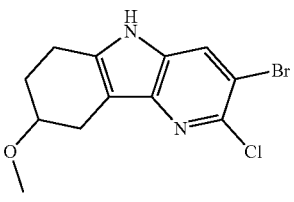

A solution of 3-bromo-2-chloro-5-hydrazineylpyridine hydrochloride (1100 mg, 4.248 mmol, 1.00 equiv) and 4-methoxycyclohexan-1-one (1089 mg, 8.497 mmol, 2.00 equiv) in EtOH (30.00 mL) was stirred for 16 h at 80° C. under nitrogen atmosphere. The organic solvent was removed under vacuum. The residue was diluted with water. The resulting mixture was extracted with EtOAc. The combined organic layers were washed with brine, dried over anhydrous Na$_2$SO$_4$. After filtration, the filtrate was concentrated under reduced pressure. The residue was purified by silica gel column chromatography, eluted with PE/EtOAc (3/1) to afford the title compound (360 mg, 26.85%) as a yellow solid.

Step 3: (3-((3S,4S)-4-amino-3-methyl-2-oxa-8-azaspiro[4.5]decan-8-yl)-6-((2-chloro-8-methoxy-6,7,8,9-tetrahydro-5H-pyrido[3,2-b]indol-3-yl)thio)pyrazin-2-yl)methanol

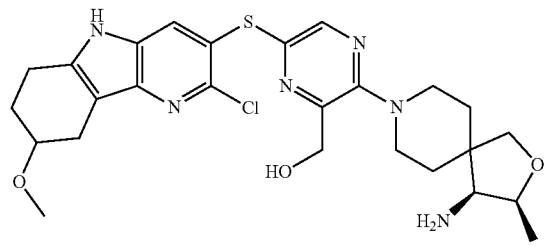 [SMILES: COC1CCc2[nH]c3cc(Sc4cnc(N5CCC6(CC5)CO[C@@H](C)[C@H]6N)c(CO)n4)c(Cl)nc3c2C1]

The title compound was synthesized from 3-bromo-2-chloro-8-methoxy-6,7,8,9-tetrahydro-5H-pyrido[3,2-b]indole by proceeding analogously as described in Example 14, Steps 7-8. MS (ES, m/z): [M+1]$^+$=545.2;

Example 39

Synthesis of 3-((5-((3S,4S)-4-amino-3-methyl-2-oxa-8-azaspiro[4.5]decan-8-yl)-6-(hydroxymethyl)pyrazin-2-yl)thio)-2-chloro-6,7,8,9-tetrahydro-5H-pyrido[3,2-b]indol-8-ol formate

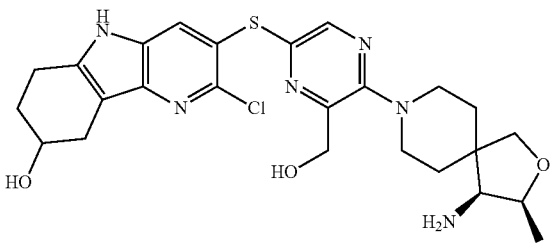

Step 1: 3-bromo-2-chloro-6,7,8,9-tetrahydro-5H-pyrido[3,2-b]indol-8-ol

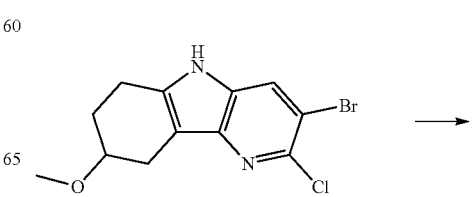

189
-continued

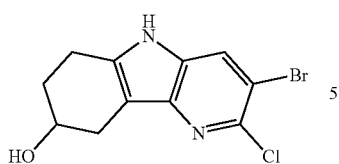

To a stirred mixture of 3-bromo-2-chloro-8-methoxy-6,7,8,9-tetrahydro-5H-pyrido[3,2-b]indole (70 mg, 0.222 mmol, 1.00 equiv) and NaI (110 mg, 0.732 mmol, 3.3 equiv) in CH₃CN (2 mL) was added SiCl₄ (124 mg, 0.732 mmol, 3.3 equiv) dropwise at room temperature under nitrogen atmosphere. The resulting mixture was stirred for 2 h at 80° C. under nitrogen atmosphere. The mixture was neutralized to pH 7 with saturated Na₂CO₃ (aq.). The resulting mixture was extracted with EtOAc. The combined organic layers were washed with water, dried over anhydrous Na₂SO₄. After filtration, the filtrate was concentrated under vacuum to give the title compound (100 mg, crude) as a yellow oil, which was used for next step without further purification.

Step 2: 3-bromo-8-((tert-butyldimethylsilyl)oxy)-2-chloro-6,7,8,9-tetrahydro-5H-pyrido[3,2-b]indole

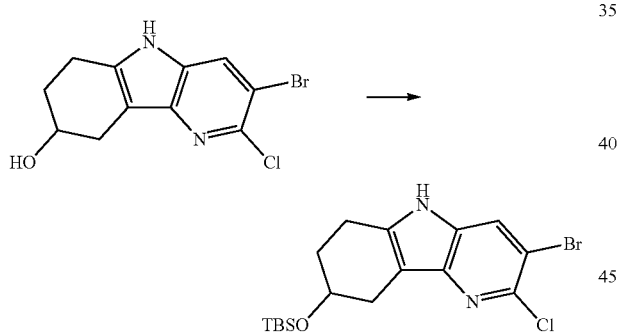

To a stirred mixture of 3-bromo-2-chloro-6,7,8,9-tetrahydro-5H-pyrido[3,2-b]indol-8-ol (100 mg, 0.332 mmol, 1.00 equiv) and 1H-imidazole (34 mg, 0.497 mmol, 1.50 equiv) in DMF (2 mL) was added TBSCl (75 mg, 0.497 mmol, 1.50 equiv) at room temperature. The resulting mixture was stirred for 16 h at room temperature. The resulting mixture was diluted with water and extracted with EtOAc. The combined organic layers were washed with water, dried over anhydrous Na₂SO₄. After filtration, the filtrate was concentrated under reduced pressure. The residue was purified by silica gel column chromatography, eluted with PE/EtOAc (3/1) to afford the title compound (15 mg, 10.88%) as a yellow solid.

190

Step 3: Tert-Butyl ((3S,4S)-8-(5-((8-((tert-butyldimethylsilyl)oxy)-2-chloro-6,7,8,9-tetrahydro-5H-pyrido[3,2-b] indol-3-yl)thio)-3-(hydroxymethyl) pyrazin-2-yl)-3-methyl-2-oxa-8-azaspiro[4.5]decan-4-yl)carbamate

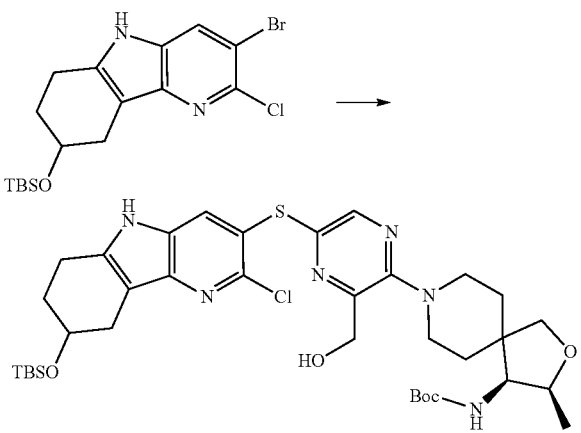

To a stirred mixture of 3-bromo-8-((tert-butyldimethylsilyl)oxy)-2-chloro-6,7,8,9-tetrahydro-5H-pyrido [3,2-b]indole (15 mg, 0.036 mmol, 1.00 equiv), tert-butyl ((3S,4S)-8-(3-(hydroxymethyl)-5-mercaptopyrazin-2-yl)-3-methyl-2-oxa-8-azaspiro[4.5]decan-4-yl)carbamate (15 mg, 0.036 mmol, 1.00 equiv) and DIPEA (19 mg, 0.144 mmol, 4.00 equiv) in 1,4-dioxane (1 mL) were added XantPhos (6 mg, 0.011 mmol, 0.3 equiv) and Pd₂(dba)₃ (10 mg, 0.011 mmol, 0.3 equiv) at room temperature under nitrogen atmosphere. The mixture was stirred for 1 h at 100° C. under nitrogen atmosphere. The resulting mixture was filtered. The filtrate was concentrated under reduced pressure. The residue was purified by silica gel column chromatography, eluted with DCM/MeOH (20/1) to afford the title compound (15 mg, 55.78%) as a yellow solid.

Step 4: formic acid; 3-((5-((3S,4S)-4-amino-3-methyl-2-oxa-8-azaspiro[4.5]decan-8-yl)-6-(hydroxymethyl) pyrazin-2-yl)thio)-2-chloro-6,7,8,9-tetrahydro-5H-pyrido[3,2-b]indol-8-ol

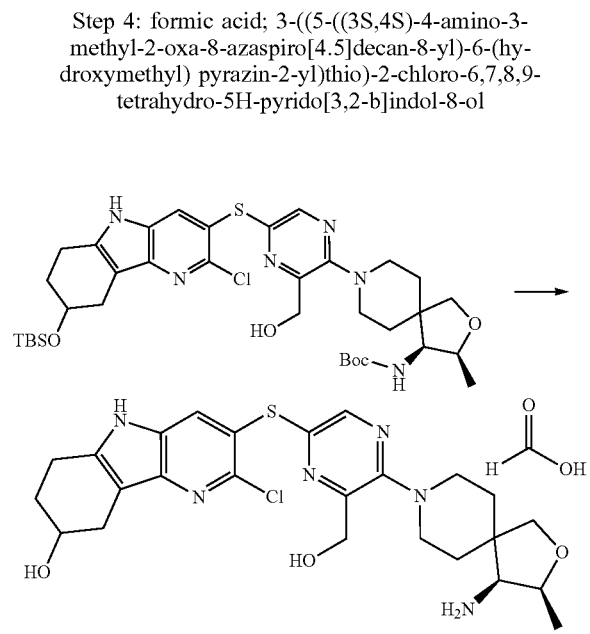

A stirred mixture of tert-butyl ((3S,4S)-8-(5-((8-((tert-butyldimethylsilyl)oxy)-2-chloro-6,7,8,9-tetrahydro-5H-pyrido[3,2-b]indol-3-yl)thio)-3-(hydroxymethyl)pyrazin-2-yl)-3-methyl-2-oxa-8-azaspiro[4.5]decan-4-yl)carbamate (10 mg, 0.013 mmol, 1.00 equiv) and 2 M HCl in EA (1.00 mL) was stirred for 1 h at room temperature. The mixture was neutralized to pH 7 with NH$_3$.H$_2$O. The resulting mixture was concentrated under vacuum. The residue was purified by Prep-HPLC to afford the title compound (3.6 mg, 46.50%) as a white solid. MS (ES, m/z): [M+1]$^+$=531.3.

Example 40

Synthesis of 3-((5-((3S,4S)-4-amino-3-methyl-2-oxa-8-azaspiro[4.5]decan-8-yl)-6-(hydroxymethyl)pyrazin-2-yl)thio)-2-chloro-6,7,8,9-tetrahydro-5H-pyrido[3,2-b]indol-6-ol

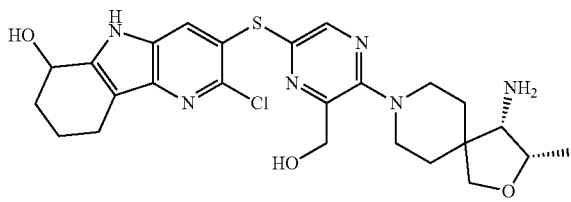 [SMILES: C[C@@H]1OCC2(CCN(c3ncc(Sc4cc5[nH]c6c(c5nc4Cl)CCCC6O)nc3CO)CC2)[C@@H]1N]

Step 1: 3-bromo-6-((tert-butyldimethylsilyl)oxy)-2-chloro-6,7,8,9-tetrahydro-5H-pyrido[3,2-b]indole

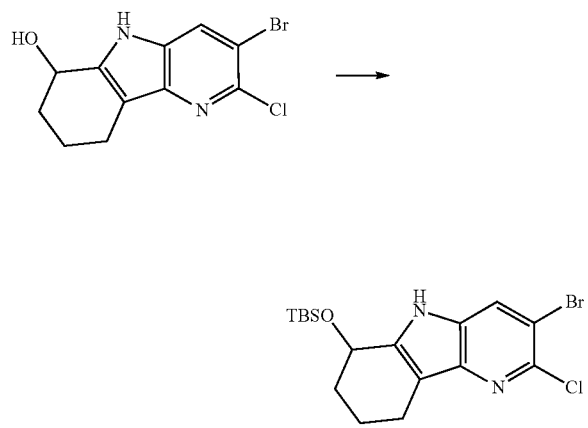

Into a 8-mL vial, was placed 3-bromo-2-chloro-6,7,8,9-tetrahydro-5H-pyrido[3,2-b]indol-6-ol (100 mg, 0.332 mmol, 1.00 equiv), imidazole (34 mg, 0.497 mmol, 1.50 equiv), DMF (2.00 mL), TBDMSCl (65 mg, 0.431 mmol, 1.30 equiv). The resulting solution was stirred for 2 h at room temperature. The resulting mixture was diluted with water. The resulting solution was extracted with EtOAc. The organic layers were dried over anhydrous sodium sulfate and concentrated under vacuum. The residue was applied onto a silica gel column with EtOAc/PE (1/4) to afford the title compound (112 mg, 81.5%) as a yellow solid.

Step 2: Tert-Butyl ((3S,4S)-8-(5-((6-((tert-butyldimethylsilyl)oxy)-2-chloro-6,7,8,9-tetrahydro-5H-pyrido[3,2-b]indol-3-yl)thio)-3-(hydroxymethyl)pyrazin-2-yl)-3-methyl-2-oxa-8-azaspiro[4.5]decan-4-yl)carbamate

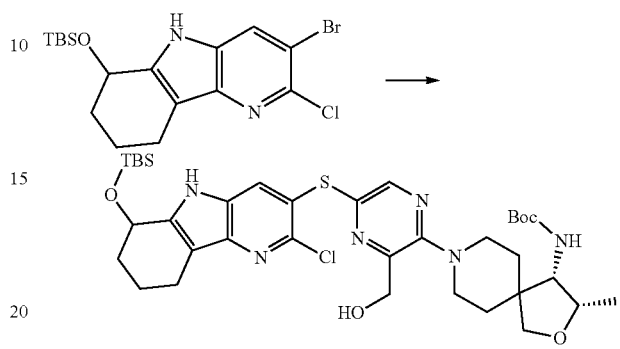

Into a 8-mL vial purged and maintained with an inert atmosphere of nitrogen, was placed 3-bromo-6-((tert-butyldimethylsilyl)oxy)-2-chloro-6,7,8,9-tetrahydro-5H-pyrido[3,2-b]indole (60 mg, 0.144 mmol, 1.00 equiv), sodium 5-((3S,4S)-4-((tert-butoxycarbonyl)amino)-3-methyl-2-oxa-8-azaspiro[4.5]decan-8-yl)-6-(hydroxymethyl)pyrazine-2-thiolate (62 mg, 0.144 mmol, 1.00 equiv), Pd$_2$(dba)$_3$ (40 mg, 0.043 mmol, 0.3 equiv), XantPhos (25 mg, 0.043 mmol, 0.3 equiv), DIEA (56 mg, 0.433 mmol, 3 equiv), 1,4-dioxane (3.00 mL). The resulting solution was stirred for 4 h at 80° C. The resulting mixture was concentrated under vacuum. The residue was applied onto a silica gel column with ethyl acetate/petroleum ether (1/1) to afford the title compound (101 mg, 82.27%) as a yellow solid.

Step 3: 3-((5-((3S,4S)-4-amino-3-methyl-2-oxa-8-azaspiro[4.5]decan-8-yl)-6-(hydroxy-methyl)pyrazin-2-yl)thio)-2-chloro-6,7,8,9-tetrahydro-5H-pyrido[3,2-b]indol-6-ol

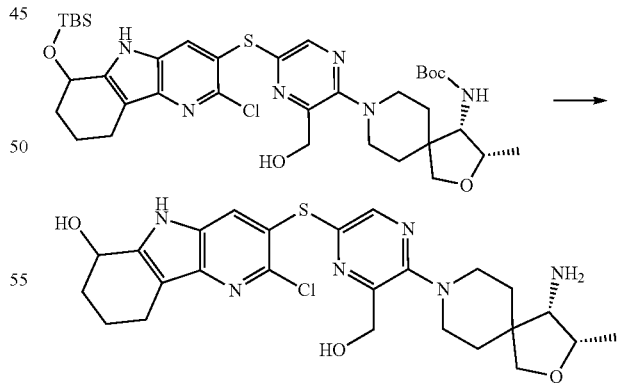

Into a 30-mL vial, was placed tert-butyl ((3S,4S)-8-(5-((6-((tert-butyldimethylsilyl)oxy)-2-chloro-6,7,8,9-tetrahydro-5H-pyrido[3,2-b]indol-3-yl)thio)-3-(hydroxymethyl)pyrazin-2-yl)-3-methyl-2-oxa-8-azaspiro[4.5] decan-4-yl) carbamate (110 mg, 1.00 equiv), DCM (6.00 mL) and TFA (2.00 mL). The resulting solution was stirred for 3 h at room temperature. The resulting mixture was concentrated under vacuum. The residue was purified by Prep-HPLC with the following conditions: (2 #SHIMADZU (HPLC-01)): Column, XBridge Prep C18 OBD Column, 19*150 mm Sum; mobile phase: Water (0.05% $NH_3H_2O$) and ACN (30% PhaseB up to 50% in 7 min) to afford the title compound (10 mg, 13.29%) as an off-white solid. MS (ES, m/z): $[M+1]^+$ =531.3.

Biological Assays

SHP2 Allosteric Inhibition Assay

SHP2 possesses two N-terminal Src homology 2 (SH2) domains, a central protein-tyrosine phosphatase (PTP) domain, and C-terminal tail. At the basal state, SHP2 is auto-inhibited and access of substrates to the catalytic site is blocked by the intermolecular interactions between the SH2 domains and the PTP domain. When bis-tyrosyl-phosphorylated peptides bind to SH2 domain of SHP2, the PTP domain becomes available for substrate recognition and reaction catalysis and SHP2 is allosterically activated. SHP2 catalytic activity can be measured using a fluorogenic artificial substrate DiFMUP.

The phosphatase reactions were carried out at room temperature in 384-well black polystyrene plates (Greiner Bio-One, Cat #784076) using assay buffers containing 60 mM HEPES, pH 7.2, 75 mM NaCl, 75 mM KCl, 1 mM EDTA, 0.05% P-20, and 5 mM DTT.

0.33 nM of STIP2 was co-incubated with of 0.5 μM of bisphos-IRS 1 peptide (sequence: H2N-LN(pY)IDLDLV (dPEG8)LST(pY)ASINFQK-amide) and various concentrations of compounds for 30-60 min at room temperature. Then the reaction was initiated by addition of the surrogate substrate DiFMUP (Invitrogen, Cat #D6567, 100 uM final).

The real-time conversion of DiFMUP to DiFMU (6,8-difluoro-7-hydroxyl-4-methyl-coumarin) was measured every 5 min for 30 min using a microplate reader (CLARIOstar, BMG Labtech) with excitation and emission wavelengths of 340 nm and 450 nm, respectively. Initial reaction rates were determined by linear fitting of the data and the inhibitor dose response curves were analyzed using normalized $IC_{50}$ regression curve fitting with control based normalization.

The $IC_{50}$'s for compounds as numbered in compound Table 1 are provided below.

| Compound # | Structure | Shp2 $IC_{50}$(nM) |
|---|---|---|
| 1 | 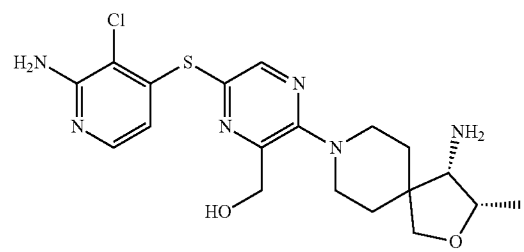 | 0.9 |
| 2 | 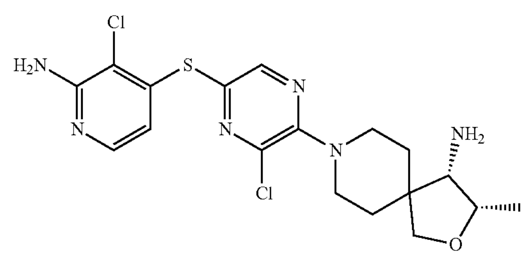 [SMILES: C[C@@H]1OCC2(CCN(c3ncc(Sc4ccnc(N)c4Cl)nc3Cl)CC2)[C@@H]1N] | 12 |
| 3 | 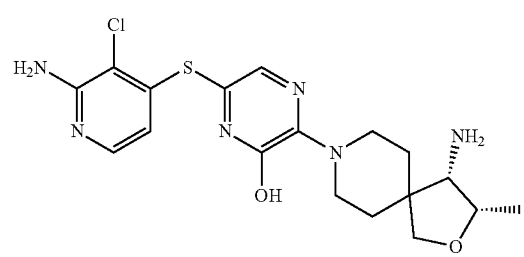 [SMILES: C[C@@H]1OCC2(CCN(c3ncc(Sc4ccnc(N)c4Cl)nc3O)CC2)[C@@H]1N] | 13 |
| 4 | 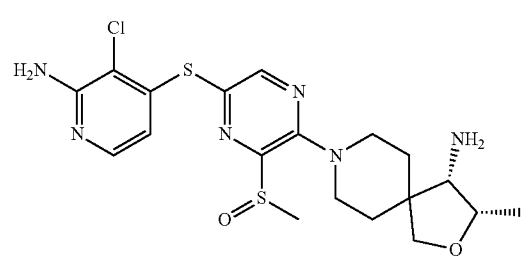 [SMILES: C[C@@H]1OCC2(CCN(c3ncc(Sc4ccnc(N)c4Cl)nc3S(C)=O)CC2)[C@@H]1N] | 13 |

-continued

| Compound # | Structure | Shp2 IC$_{50}$(nM) |
|---|---|---|
| 5 | 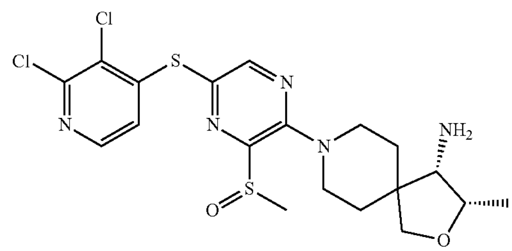 [SMILES: C[C@@H]1OCC2(CCN(c3ncc(Sc4ccnc(Cl)c4Cl)nc3S(C)=O)CC2)[C@@H]1N] | 6 |
| 6 | 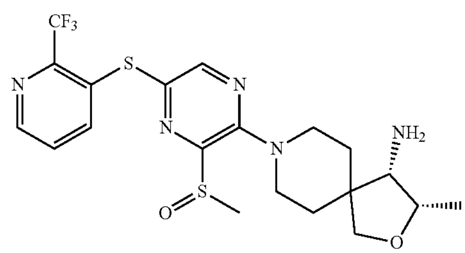 [SMILES: C[C@@H]1OCC2(CCN(c3ncc(Sc4cccnc4C(F)(F)F)nc3S(C)=O)CC2)[C@@H]1N] | 85 |
| 7 | 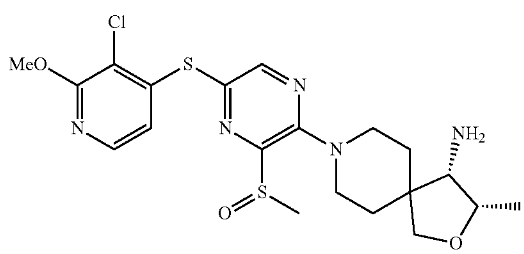 [SMILES: COc1nccc(Sc2cnc(N3CCC4(CC3)CO[C@@H](C)[C@H]4N)c(S(C)=O)n2)c1Cl] | 18 |
| 8 | 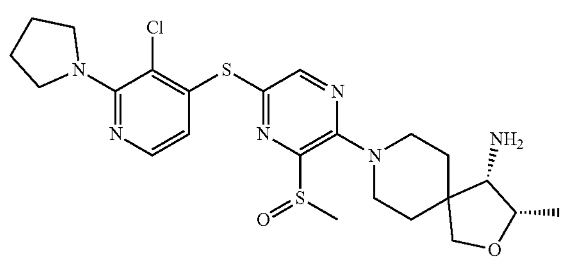 [SMILES: C[C@@H]1OCC2(CCN(c3ncc(Sc4ccnc(N5CCCC5)c4Cl)nc3S(C)=O)CC2)[C@@H]1N] | 13 |
| 9 | 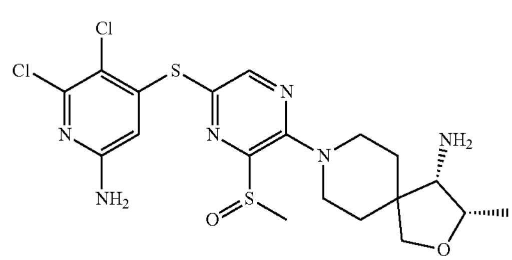 [SMILES: C[C@@H]1OCC2(CCN(c3ncc(Sc4cc(N)nc(Cl)c4Cl)nc3S(C)=O)CC2)[C@@H]1N] | 3 |
| 10 | 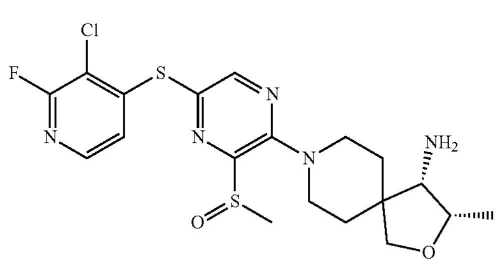 [SMILES: C[C@@H]1OCC2(CCN(c3ncc(Sc4ccnc(F)c4Cl)nc3S(C)=O)CC2)[C@@H]1N] | 21 |

-continued

| Compound # | Structure | Shp2 IC$_{50}$(nM) |
|---|---|---|
| 11 | 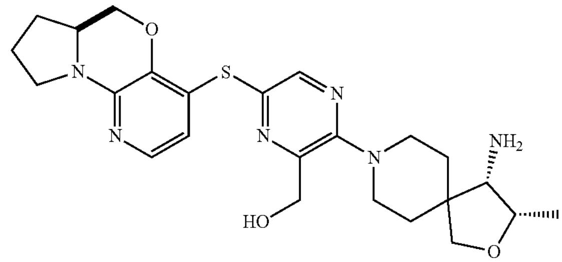 | 3 |
| 12 | 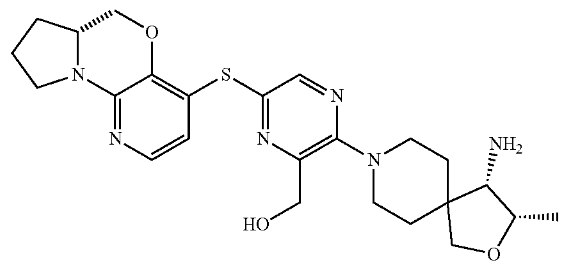 | 4 |
| 14 | 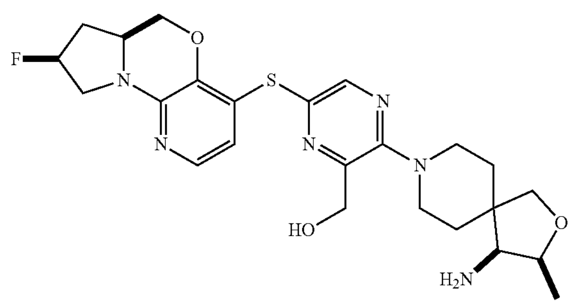 | 13 |
| 15 | 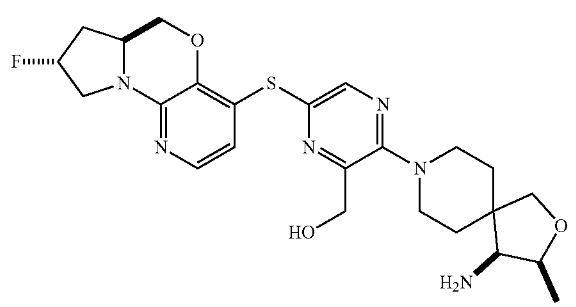 | 5 |
| 16 | 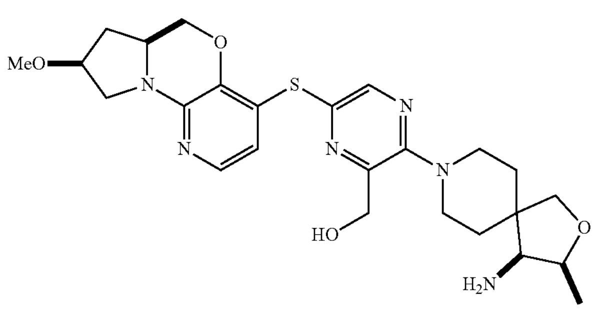 | 8 |

-continued

| Compound # | Structure | Shp2 IC$_{50}$(nM) |
|---|---|---|
| 17 | 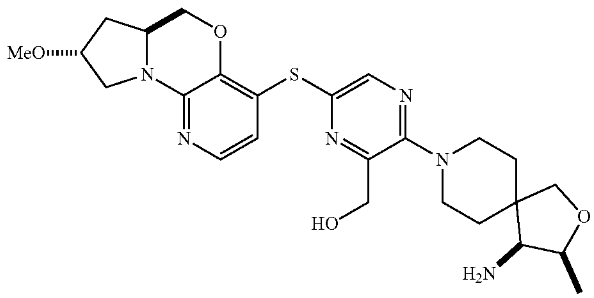 | 6 |
| 18 | 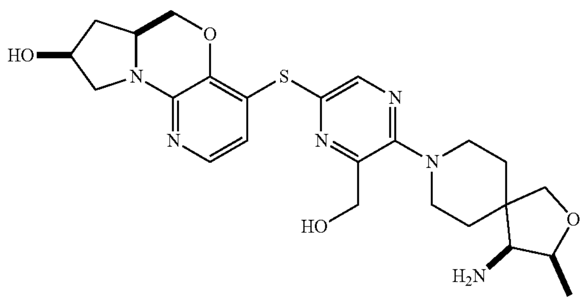 | 6 |
| 19 | 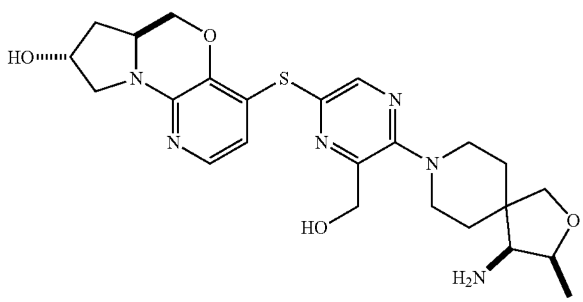 | 8 |
| 20 | 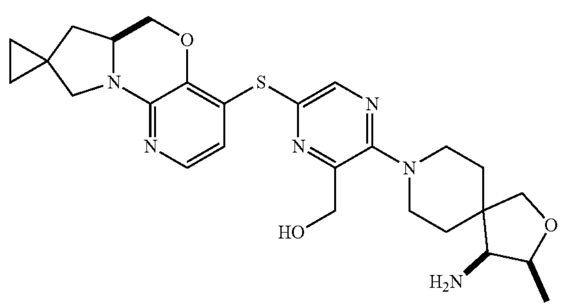 | 2 |
| 21 | 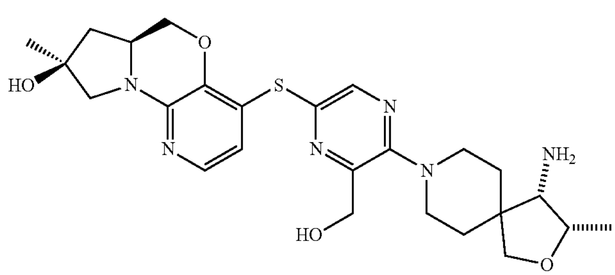 [SMILES: C[C@@H]1OCC2(CCN(c3ncc(Sc4ccnc5c4OC[C@@H]4C[C@](C)(O)CN54)nc3CO)CC2)[C@@H]1N] | One of 21 and 22 is 13 and the other is 8 |

| Compound # | Structure | Shp2 IC$_{50}$(nM) |
|---|---|---|
| 22 | 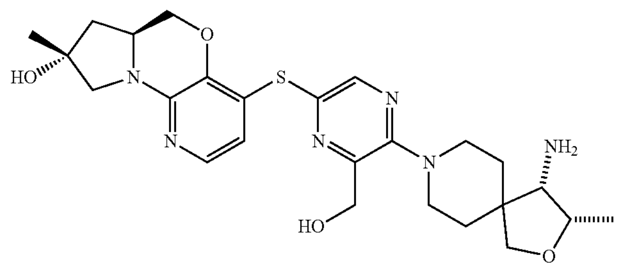 [SMILES: C[C@@H]1OCC2(CCN(c3ncc(Sc4ccnc5c4OC[C@@H]4C[C@@](C)(O)CN54)nc3CO)CC2)[C@@H]1N] | |
| 23 | 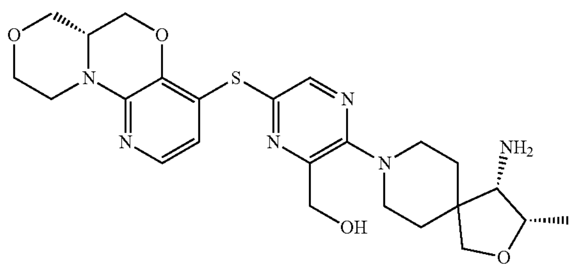 [SMILES: C[C@@H]1OCC2(CCN(c3ncc(Sc4ccnc5c4OC[C@H]4COCCN54)nc3CO)CC2)[C@@H]1N] | One of 23 and 24 is 8 and the other is 10 |
| 24 | 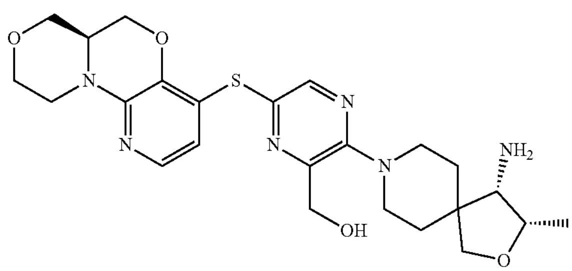 [SMILES: C[C@@H]1OCC2(CCN(c3ncc(Sc4ccnc5c4OC[C@@H]4COCCN54)nc3CO)CC2)[C@@H]1N] | |
| 25 | 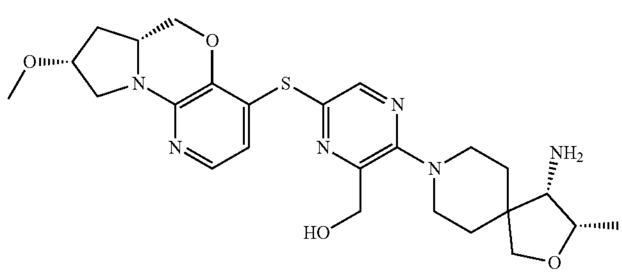 | 8 |
| 26 | 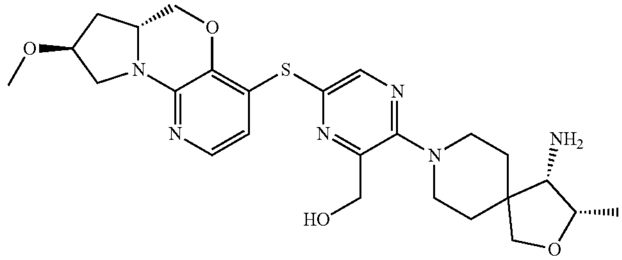 | 10 |

-continued

| Compound # | Structure | Shp2 IC$_{50}$(nM) |
|---|---|---|
| 27 | 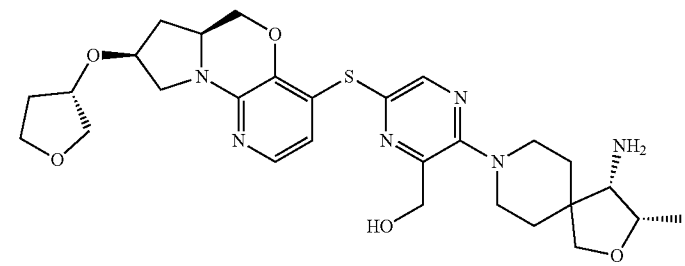 [SMILES: C[C@@H]1OCC2(CCN(c3ncc(Sc4ccnc5c4OC[C@@H]4C[C@H](O[C@H]6CCOC6)CN54)nc3CO)CC2)[C@@H]1N] | 14 |
| 28 | 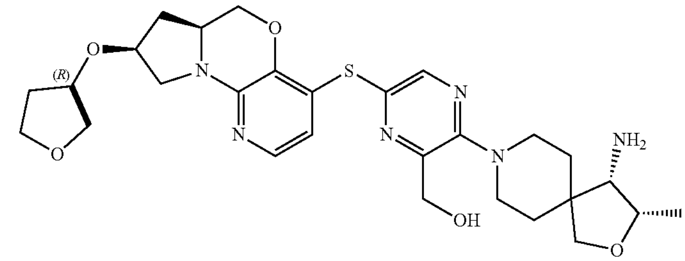 | 12 |
| 29 | 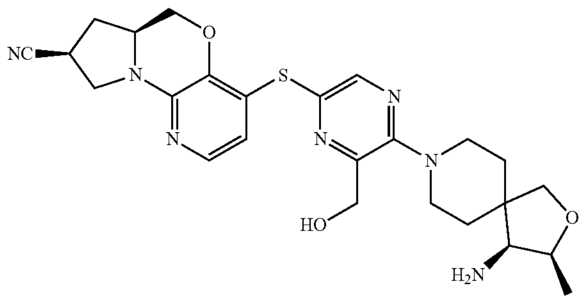 [SMILES: C[C@@H]1OCC2(CCN(c3ncc(Sc4ccnc5c4OC[C@@H]4C[C@H](C#N)CN54)nc3CO)CC2)[C@@H]1N] | 11 |
| 30 | 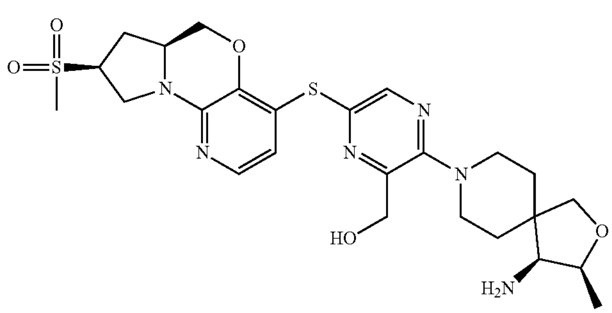 [SMILES: C[C@@H]1OCC2(CCN(c3ncc(Sc4ccnc5c4OC[C@@H]4C[C@H](S(C)(=O)=O)CN54)nc3CO)CC2)[C@@H]1N] | 13 |
| 31 | 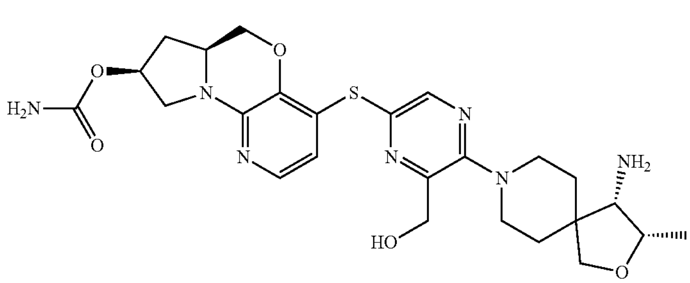 [SMILES: C[C@@H]1OCC2(CCN(c3ncc(Sc4ccnc5c4OC[C@@H]4C[C@H](OC(N)=O)CN54)nc3CO)CC2)[C@@H]1N] | 6 |

-continued

| Compound # | Structure | Shp2 IC$_{50}$(nM) |
|---|---|---|
| 32 | 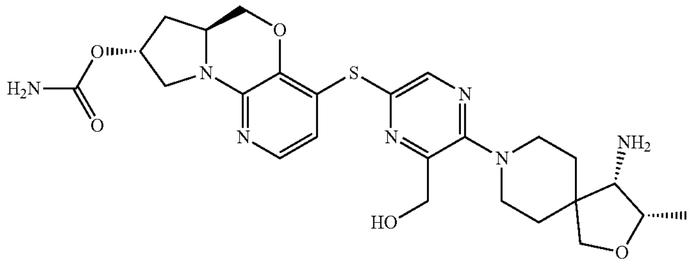 [SMILES: C[C@@H]1OCC2(CCN(c3ncc(Sc4ccnc5c4OC[C@@H]4C[C@@H](OC(N)=O)CN54)nc3CO)CC2)[C@@H]1N] | 8 |
| 33 | 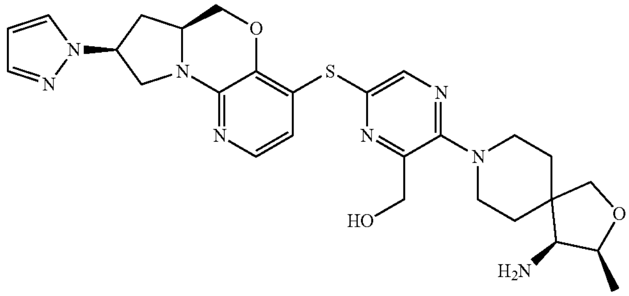 [SMILES: C[C@@H]1OCC2(CCN(c3ncc(Sc4ccnc5c4OC[C@@H]4C[C@H](n6cccn6)CN54)nc3CO)CC2)[C@@H]1N] | 10 |
| 34 | 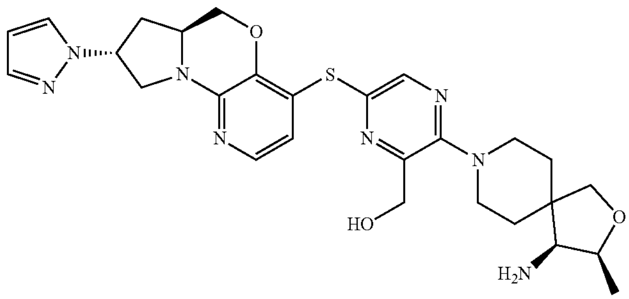 [SMILES: C[C@@H]1OCC2(CCN(c3ncc(Sc4ccnc5c4OC[C@@H]4C[C@@H](n6cccn6)CN54)nc3CO)CC2)[C@@H]1N] | 11 |
| 35 | 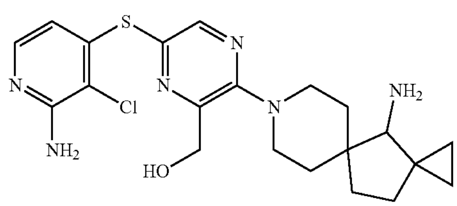 [SMILES: Nc1nccc(Sc2cnc(N3CCC4(CC3)CCC3(CC3)C4N)c(CO)n2)c1Cl] | 3 |
| 36 | 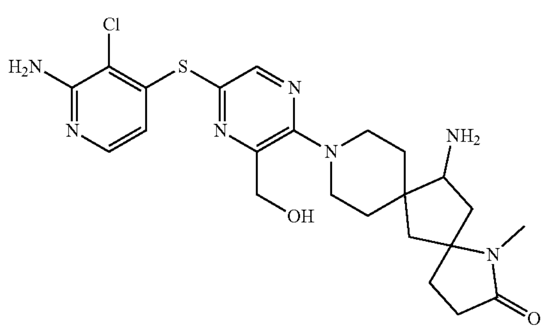 [SMILES: CN1C(=O)CCC12CC(N)C1(CCN(c3ncc(Sc4ccnc(N)c4Cl)nc3CO)CC1)C2] | 269 |

-continued

| Compound # | Structure | Shp2 IC$_{50}$(nM) |
|---|---|---|
| 37 | 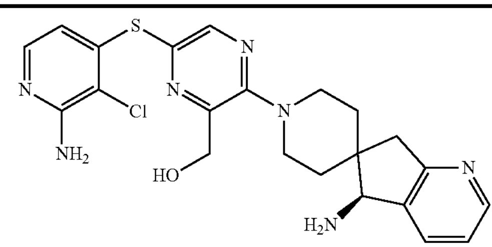 | 0.6 |
| 38 | 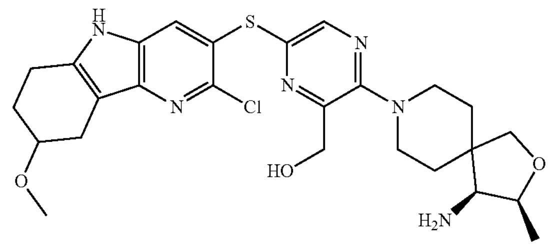 [SMILES: COC1CCc2[nH]c3cc(Sc4cnc(N5CCC6(CC5)CO[C@@H](C)[C@H]6N)c(CO)n4)c(Cl)nc3c2C1] | 5.5 |
| 39 | 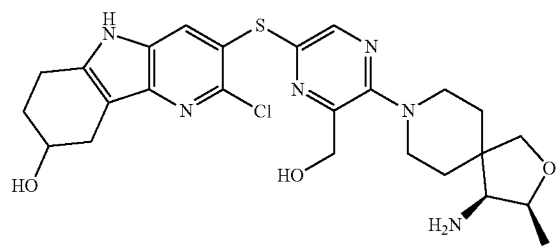 [SMILES: C[C@@H]1OCC2(CCN(c3ncc(Sc4cc5[nH]c6c(c5nc4Cl)CC(O)CC6)nc3CO)CC2)[C@@H]1N] | 3.5 |
| 40 | | 4.8 | p-ERK Cellular Assay

Detroit562 cells were seeded in 96-well plate and cultured overnight (30,000 cells per well, 200 ul total volume). Following morning, cells were treated with compounds of the disclosure, with starting concentration at 10 uM and ½ log dilution down to 1 nM for 2 hours at 37° C. DMSO treatment serves as control. p-ERK was then measured using AlphaLISA® SureFire® Ultra™ p-ERK 1/2 (Thr202/Tyr204) Assay Kit (PerkinElmer, ALSU-PERK-A500) following instruction. Briefly, medium was removed and add 50 ul 1× lysis buffer was added, followed by 10 minutes incubation on a plate shaker at room temperature. Then 10 ul of lysate was transferred to a white 384-well plate, and 5 ul Acceptor mix, and 5 ul Donor mix were added (both prepared according to manufacturer's instruction). The plate was wrapped with foil, shaken for 1-2 minutes on a plate reader and incubated for >2 hours. Signal was then measured on a CLARIOstar® plate reader. Percentage inhibition was calculated with DMSO treatment as 100% of signal, and IC$_{50}$ is calculated by Graphpad Prism 7.

Formulation Examples

The following are representative pharmaceutical formulations containing a compound of Formula (I'A), (I'), (I), (IA), (II), or (IIA).

Tablet Formulation

The following ingredients are mixed intimately and pressed into single scored tablets.

| Ingredient | Quantity per tablet mg |
|---|---|
| compound of disclosure | 400 |
| cornstarch | 50 |
| croscarmellose sodium | 25 |
| lactose | 120 |
| magnesium stearate | 5 |

Capsule Formulation

The following ingredients are mixed intimately and loaded into a hard-shell gelatin capsule.

| Ingredient | Quantity per capsule (mg) |
|---|---|
| compound of this disclosure | 200 |
| lactose spray dried | 148 |
| magnesium stearate | 2 |

Injectable Formulation

Compound of the disclosure (e.g., compound 1) in 2% HPMC, 1% Tween 80 in DI water, pH 2.2 with MSA, q.s. to at least 20 mg/mL Inhalation Composition To prepare a pharmaceutical composition for inhalation delivery, 20 mg of a compound disclosed herein is mixed with 50 mg of anhydrous citric acid and 100 mL of 0.9% sodium chloride solution. The mixture is incorporated into an inhalation delivery unit, such as a nebulizer, which is suitable for inhalation administration.

Topical Gel Composition

To prepare a pharmaceutical topical gel composition, 100 mg of a compound disclosed herein is mixed with 1.75 g of hydroxypropyl cellulose, 10 mL of propylene glycol, 10 mL of isopropyl myristate and 100 mL of purified alcohol USP. The resulting gel mixture is then incorporated into containers, such as tubes, which are suitable for topical administration.

Ophthalmic Solution Composition

To prepare a pharmaceutical ophthalmic solution composition, 100 mg of a compound disclosed herein is mixed with 0.9 g of NaCl in 100 mL of purified water and filtered using a 0.2 micron filter. The resulting isotonic solution is then incorporated into ophthalmic delivery units, such as eye drop containers, which are suitable for ophthalmic administration.

Nasal Spray Solution

To prepare a pharmaceutical nasal spray solution, 10 g of a compound disclosed herein is mixed with 30 mL of a 0.05M phosphate buffer solution (pH 4.4). The solution is placed in a nasal administrator designed to deliver 100 ul of spray for each application.

What is claimed:

1. A compound of Formula (I'):

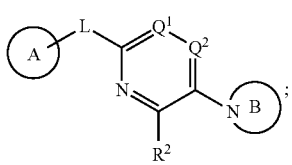

wherein:
ring A is a heteroaryl of formula (d):

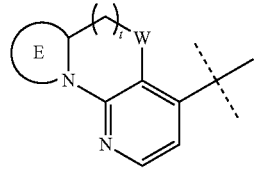

where:
t is 0, or 2;
ring E is 4 to 7 membered heterocycle containing 1 or 2 heteroatoms independently selected from O, N, S, and $SO_2$ and the remaining atoms are carbon; and W is O, $CH_2$, or N; substituted with $R^a$, $R^b$, and/or $R^c$ wherein $R^a$ and $R^b$ are independently selected from hydrogen, amino, alkyl, alkenyl, halo, haloalkyl, alkoxy, alkoxyalkyl, haloalkoxy, hydroxy, hydroxyalkyl, cyano, aminoalkyl, carboxy, and alkoxycarbonyl and $R^c$ is hydrogen, alkyl, halo, hydroxy, or alkoxy; or
when $R^a$ and $R^c$ are attached to the same carbon atom, $R^a$ and $R^c$ together with the carbon atom to which they are attached can form cycloalkylene or heterocyclylene;
$Q^1$ is N or $CR^1$ wherein $R^1$ is hydrogen or deuterium;
$Q^2$ is N or CH, or CD;
$R^2$ is alkyl, halo, hydroxy, hydroxyalkyl, —$CD_2OH$, alkylsulfoxide, alkylsulfonyl, aminosulfonyl, aminocarbonyl, carboxy, cyano, or alkoxycarbonyl;
L is bond, O, S, S(O), $S(O)_2$, or $CR^5R^6$ where $R^5$ and $R^6$ are independently hydrogen or alkyl;
and

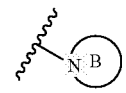

is a ring of formula (a):

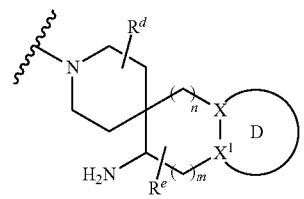

wherein:
m is 0, 1, or 2;
n is 0, 1, or 2 wherein when n is 2 then one of the $CH_2$ can be replaced with O, S, or $SO_2$; provided m+n is 1, 2, or 3;
$R^d$ is hydrogen, alkyl, or halogen;
$R^e$ is hydrogen, alkyl; halogen, haloalkyl, alkoxy, haloalkoxy, hydroxy, hydroxyalkyl, cyano or oxo;
ring D is phenyl or a 5 or 6 membered heteroaryl ring which, including X and $X^1$, contains one to three heteroatoms independently selected from N, O, and S and ring D can optionally be substituted with one or two groups independently selected from alkyl, halo, haloalkyl, alkoxy, haloalkoxy, hydroxy, hydroxyalkyl, cyano, amino, aminoalkyl, carboxy, cycloalkyl, heterocyclyl, heteroaryl, and acylamino; X and $X^1$ are independently N or C; provided that only one of X and $X^1$ is N;

with the proviso that

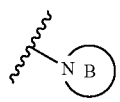

is not

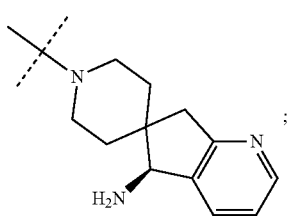

or a pharmaceutically acceptable salt thereof.

2. The compound of claim 1, or a pharmaceutically acceptable salt thereof having a structure of any one of formula (III)-(VI):

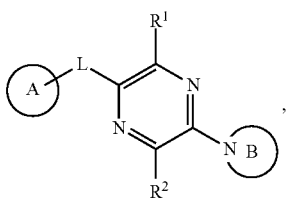
(III)

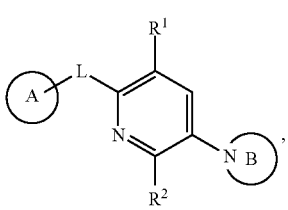
(IV)

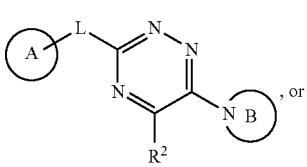
(V)

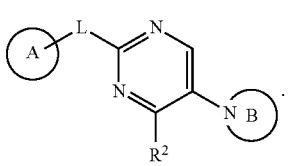
(VI)

3. The compound of claim 1, or a pharmaceutically acceptable salt thereof wherein L is S, S(O), or $S(O)_2$.

4. The compound of claim 1, or a pharmaceutically acceptable salt thereof wherein $R^2$ is hydroxyalkyl, alkyl, or halo.

5. The compound of claim 1, or a pharmaceutically acceptable salt thereof wherein $R^2$ is hydroxymethyl or —$CD_2OH$.

6. The compound of claim 1, or a pharmaceutically acceptable salt thereof wherein

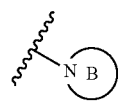

is:

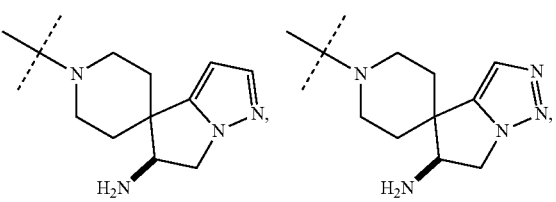

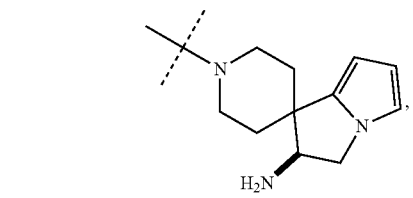

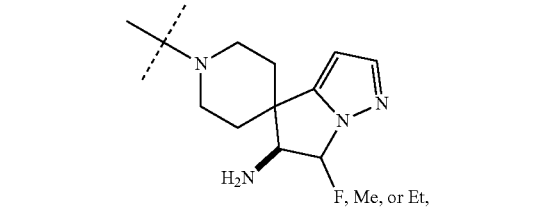

F, Me, or Et,

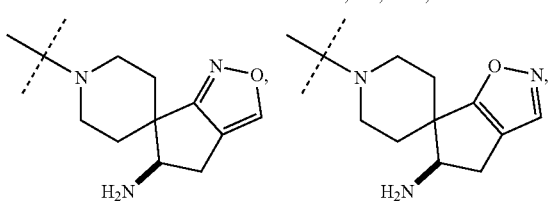

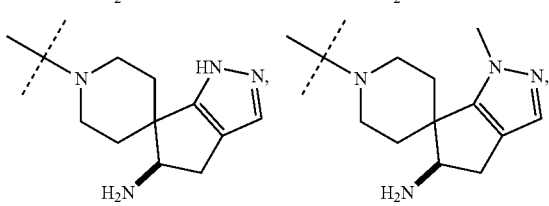

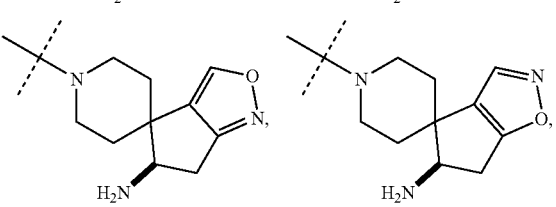

213
-continued
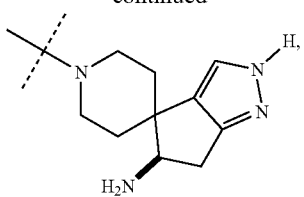
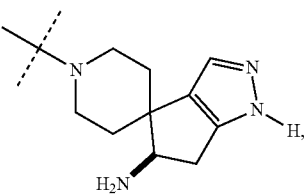
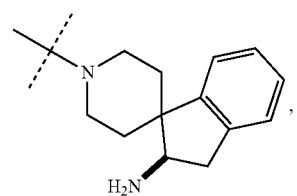
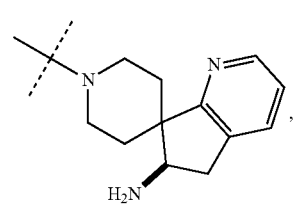
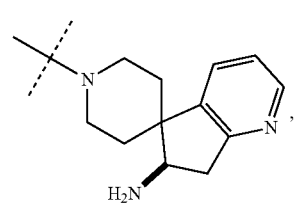
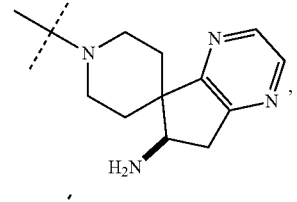
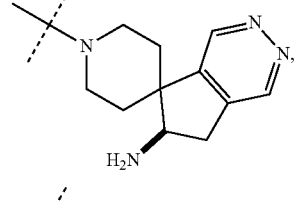
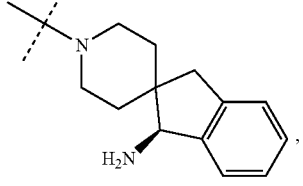
214
-continued
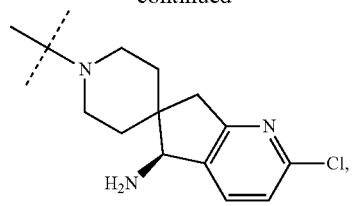
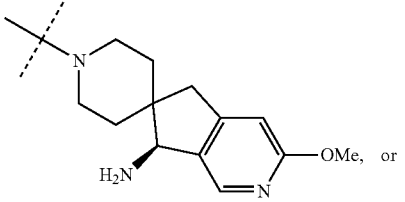
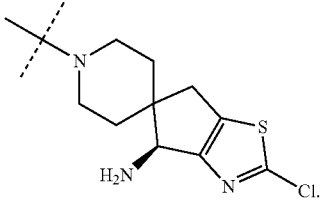
7. The compound of claim 1, or a pharmaceutically acceptable salt thereof wherein ring A is:
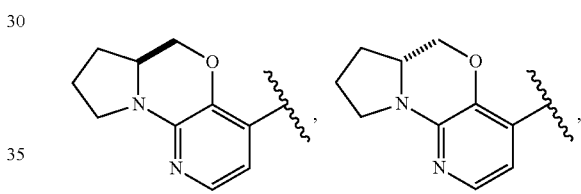
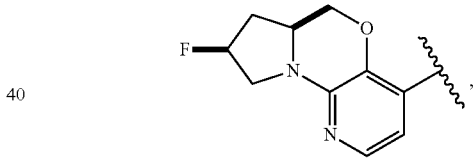
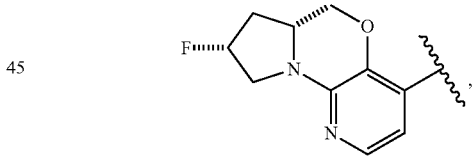
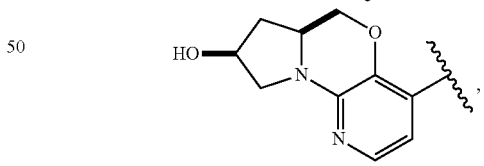
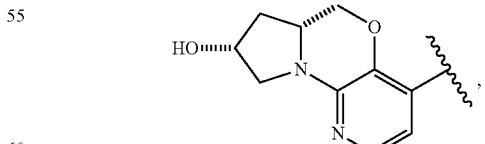
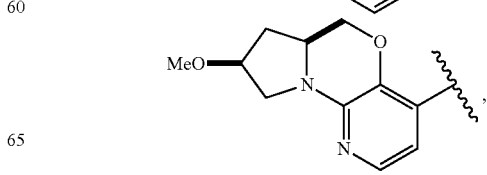

-continued
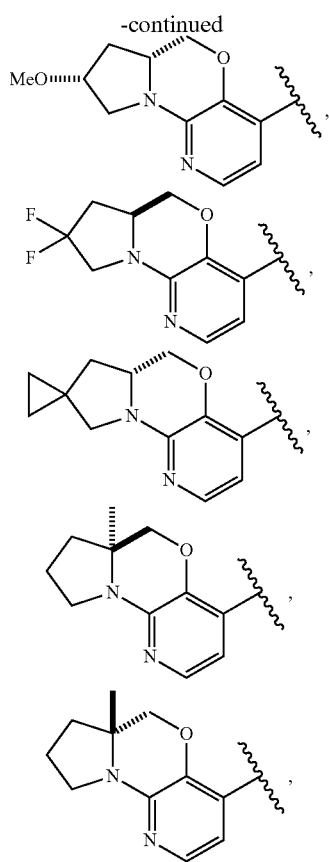
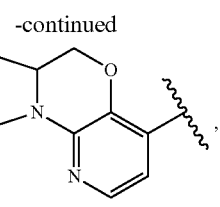
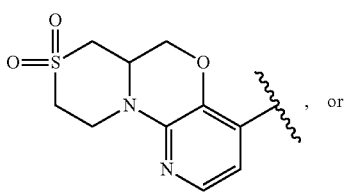
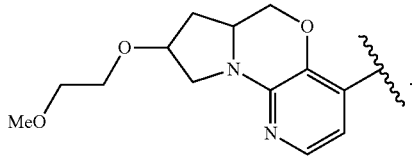
, or
-continued
8. A pharmaceutical composition comprising a compound of claim 1, or a pharmaceutically acceptable salt thereof and a pharmaceutically acceptable excipient.
* * * * *

UNITED STATES PATENT AND TRADEMARK OFFICE
CERTIFICATE OF CORRECTION

PATENT NO. : 11,459,340 B2  
APPLICATION NO. : 17/277293  
DATED : October 4, 2022  
INVENTOR(S) : Fu et al.

Page 1 of 1

It is certified that error appears in the above-identified patent and that said Letters Patent is hereby corrected as shown below:

In the Claims

Column 216, Lines 20-29 In Claim 1, replace 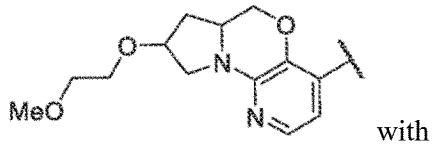 with 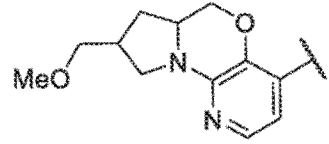

Signed and Sealed this  
Fourth Day of July, 2023

Katherine Kelly Vidal  
*Director of the United States Patent and Trademark Office*